US010174307B2

(12) United States Patent
Feist et al.

(10) Patent No.: US 10,174,307 B2
(45) Date of Patent: Jan. 8, 2019

(54) PERFORMANCE ENHANCING GENETIC VARIANTS OF *E. COLI*

(71) Applicant: THE REGENTS OF THE UNIVERSITY OF CALIFORNIA, Oakland, CA (US)

(72) Inventors: Adam M. Feist, San Diego, CA (US); Bernhard O. Palsson, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/326,264

(22) PCT Filed: Jul. 14, 2015

(86) PCT No.: PCT/US2015/040368
§ 371 (c)(1),
(2) Date: Jan. 13, 2017

(87) PCT Pub. No.: WO2016/011021
PCT Pub. Date: Jan. 21, 2016

(65) Prior Publication Data
US 2017/0198276 A1    Jul. 13, 2017

Related U.S. Application Data

(60) Provisional application No. 62/024,765, filed on Jul. 15, 2014.

(51) Int. Cl.
| *C12N 1/21*    | (2006.01) |
| *C12N 15/01*   | (2006.01) |
| *C12R 1/19*    | (2006.01) |
| *C07K 14/245*  | (2006.01) |
| *C12N 1/20*    | (2006.01) |
| *C12N 9/04*    | (2006.01) |
| *C12N 9/12*    | (2006.01) |
| *C12N 9/48*    | (2006.01) |

(52) U.S. Cl.
CPC .......... *C12N 15/01* (2013.01); *C07K 14/245* (2013.01); *C12N 1/20* (2013.01); *C12N 9/0006* (2013.01); *C12N 9/1217* (2013.01); *C12N 9/1247* (2013.01); *C12N 9/485* (2013.01); *C12R 1/19* (2013.01); *C12Y 207/07006* (2013.01); *C12N 2510/02* (2013.01)

(58) Field of Classification Search
None
See application file for complete search history.

(56) References Cited

U.S. PATENT DOCUMENTS

| 2009/0104667 | A1 | 4/2009 | Asakura et al. | 435/107 |
| 2011/0111458 | A1 | 5/2011 | Masuda et al. | 435/69.1 |
| 2013/0011874 | A1 | 1/2013 | Campbell et al. | 435/69.1 |
| 2014/0038296 | A1 | 2/2014 | Palsson et al. | 435/471 |

OTHER PUBLICATIONS

Adadi, et al., "Prediction of Microbial Growth Rate Versus Biomass Yield by a Metabolic Network with Kinetic Parameters." *PLoS Comput Biol*, 8(7):e1002575 (2012).
Atsumi, et al., "Evolution, Genomic Analysis, and Reconstruction of Isobutanol Tolerance in *Escherichia coli*." *Mol Syst Biol*, 6:449 (2010).
Ayers, et al., "Promoter Recognition by *Escherichia coli* RNA Polymerase. Role of the Spacer DNA in Functional Complex Formation." *J Mol Biol*, 207(4):749-756 (1989).
Barker, et al., "Mechanism of Regulation of Transcription Initiation by ppGpp. I. Effects of ppGpp on Transcription Initiation in Vivo and in Vitro." *J Mol Biol*, 305(4):673-688 (2001).
Barker, et al., "Increased Motility of *Escherichia coli* by Insertion Sequence Element Integration into the Regulatory Region of the f/hD Operon." *J Bacteriol*, 186(22):7529-7537 (2004).
Bar-Nahum, et al., "A Ratchet Mechanism of Transcription Elongation and Its Control." *Cell*, 120(2):183-193 (2005).
Barrick, et al., "Genome Evolution and Adaptation in a Long-Term Experiment with *Escherichia coli*." *Nature*, 461(7268):1243-1247 (2009).
Barrick, et al., "*Escherichia coli* rpoB Mutants Have Increased Evolvability in Proportion to Their Fitness Defects." *Mol Biol Evol*, 27(6):1338-1347 (2010).
Beg, et al., "Intracellular Crowding Defines the Mode and Sequence of Substrate Uptake by *Escherichia coli* and Constrains Its Metabolic Activity." *Proceedings of the National Academy of Sciences of the United States of America*, 104(31):12663-12668 (2007).
Best, et al., "Optimization of the Additive Charmm All-Atom Protein Force Field Targeting Improved Sampling of the Backbone Φ, Ψ and Side-Chain X1 and X2 Dihedral Angles." *Journal of Chemical Theory and Computation*, 8(9):3257-3273 (2012).
Charusanti, et al., "Genetic Basis of Growth Adaptation of *Escherichia coli* after Deletion of pgi, a Major Metabolic Gene." *PLoS Genet*, 6(11):e1001186 (2010).
Chaudhury, et al., "Pyrosetta: A Script-Based Interface for Implementing Molecular Modeling Algorithms Using Rosetta." *Bioinformatics*, 26(5):689-691 (2010).
Cheng, et al., "Global Metabolic Network Reorganization by Adaptive Mutations Allows Fast Growth of *Escherichia coli* on Glycerol." *Nature Communications*, 5:3233 (2014).

(Continued)

Primary Examiner — James S Ketter
(74) Attorney, Agent, or Firm — Medlen & Carroll, LLP

(57) ABSTRACT

The invention provides mutant *Escherichia coli* cells that contain one or more mutations in one or more of the rpoB, hns/tdk, cor A, ygaZ, iap, metL, ygeW, and pyrE/rph genes (exemplified in Table 2A and 2B), which confer on the mutant in M9-glucose minimal media the phenotype of increased level of growth and/or increased glucose uptake rate and/or increased acetate production rate and/or increased biomass yield, compared to a control *E. coli* (such as wild type *E. coli*) that lacks the one or more mutations in the one or more genes.

8 Claims, 75 Drawing Sheets
Specification includes a Sequence Listing.

(56) References Cited

OTHER PUBLICATIONS

Cho, et al., "Genome-Scale Reconstruction of the Sigma Factor Network in *Escherichia coli*: Topology and Functional States." *BMC Biol*, 12:4 (2014).
Conrad, et al., "Whole-Genome Resequencing of *Escherichia coli* K-12 MG1655 Undergoing Short-Term Laboratory Evolution in Lactate Minimal Media Reveals Flexible Selection of Adaptive Mutations." *Genome Biol*, 10(10):R118 (2009).
Conrad, et al., "RNA Polymerase Mutants Found through Adaptive Evolution Reprogram *Escherichia coli* for Optimal Growth in Minimal Media." *Proceedings of the National Academy of Sciences of the United States of America*, 107(47):20500-20505 (2010).
Conrad, et al., "Microbial Laboratory Evolution in the Era of Genome-Scale Science." *Mol Syst Biol*, 7:509 (2011).
Cookson, et al., "Mapping Complex Disease Traits with Global Gene Expression." *Nat Rev Genet*, 10(3):184-194 (2009).
Cooper and Helmstetter, "Chromosome Replication and the Division Cycle of *Escherichia coli* B/R." *J Mol Biol*, 31(3):519-540 (1968).
Cooper and Lenski, "The Population Genetics of Ecological Specialization in Evolving *Escherichia coli* Populations." *Nature*, 407(6805):736-739 (2000).
Cox, "Bacterial Mutator Genes and the Control of Spontaneous Mutation." *Annu Rev Genet*, 10:135-156 (1976).
Datsenko and Wanner, "One-Step Inactivation of Chromosomal Genes in *Escherichia coli* K-12 Using PCR Products." *Proceedings of the National Academy of Sciences of the United States of America*, 97(12):6640-6645 (2000).
Deatherage and Barrick, "Identification of Mutations in Laboratory-Evolved Microbes from Next-Generation Sequencing Data Using Breseq." *Methods Mol Biol*, 1151:165-188 (2014).
Deng and Fong, "Laboratory Evolution and Multi-Platform Genome Re-Sequencing of the Cellulolytic Actinobacterium Thermobifida Fusca." *The Journal of biological chemistry*, 286(46):39958-39966 (2011).
Dragosits and Mattanovich, "Adaptive Laboratory Evolution—Principles and Applications for Biotechnology." *Microb Cell Fact*, 12:64 (2013).
Dragosits, et al., "Evolutionary Potential, Cross-Stress Behavior and the Genetic Basis of Acquired Stress Resistance in *Escherichia coli*." *Mol Syst Biol*, 9:643 (2013).
Enard, et al., "Genome-Wide Signals of Positive Selection in Human Evolution." *Genome Research*, 24(6):885-895 (2014).
Farida Vasi, et al., "Long-Term Experimental Evolution in *Escherichia coli*. II. Changes in Life-History Traits During Adaptation to a Seasonal Environment." *American Naturalist*, 144(3):432-456 (1994).
Feist and Palsson, "The Growing Scope of Applications of Genome-Scale Metabolic Reconstructions Using *Escherichia coli*." *Nat Biotechnol*, 26(6):659-667 (2008).
Feist, et al., "Reconstruction of Biochemical Networks in Microorganisms." *Nat Rev Microbiol*, 7(2):129-143 (2009).
Feist and Palsson, "The Biomass Objective Function." *Curr Opin Microbiol*, 13(3):344-349 (2010).
Ferenci, "The Spread of a Beneficial Mutation in Experimental Bacterial Populations: The Influence of the Environment and Genotype on the Fixation of rpos Mutations." *Heredity (Edinb)*, 100(5):446-452 (2008).
Fischer and Sauer, "Metabolic Flux Profiling of *Escherichia coli* Mutants in Central Carbon Metabolism Using GC-MS." *Eur J Biochem*, 270(5):880-891 (2003).
Flamholz, et al., "Glycolytic Strategy as a Tradeoff between Energy Yield and Protein Cost." *Proceedings of the National Academy of Sciences of the United States of America*, 110(24):10039-10044 (2013).
Fong and Palsson, "Metabolic Gene-Deletion Strains of *Escherichia coli* Evolve to Computationally Predicted Growth Phenotypes." *Nat Genet*, 36(10):1056-1058 (2004).
Fong, et al., "Parallel Adaptive Evolution Cultures of *Escherichia coli* Lead to Convergent Growth Phenotypes with Different Gene Expression States." *Genome Res*, 15(10):1365-1372 (2005).

Fraser "Gene Expression Drives Local Adaptation in Humans." *Genome Res*, 23(7):1089-1096 (2013).
Futuyma and Moreno, "The Evolution of Ecological Specialization." *Annual Review of Ecology and Systematics*, 19(1):207-233 (1988).
Gavenonis, et al., "Comprehensive Analysis of Loops at Protein-Protein Interfaces for Macrocycle Design." *Nature chemical biology*, 10(9):716-722 (2014).
Grossman, et al., "Identifying Recent Adaptations in Large-Scale Genomic Data." *Cell*, 152(4):703-713 (2013).
Hall, "Transposable Elements as Activators of Cryptic Genes in *E. coli*." *Genetica*, 107(1-3):181-187 (1999).
Hauryliuk, et al., "Recent Functional Insights into the Role of (P)ppGpp in Bacterial Physiology." *Nat Rev Microbiol*, 13(5):298-309 (2015).
Herring, et al., "Gene Replacement without Selection: Regulated Suppression of Amber Mutations in *Escherichia coli*." *Gene*, 311:153-163 (2003).
Herring, et al., "Comparative Genome Sequencing of *Escherichia coli* Allows Observation of Bacterial Evolution on a Laboratory Timescale." *Nat Genet*, 38(12):1406-1412 (2006).
Hill and Little, "Allele Replacement in *Escherichia coli* by Use of a Selectable Marker for Resistance to Spectinomycin: Replacement of the Lexa Gene." *J Bacteriol*, 170(12):5913-5915 (1988).
Horinouchi, et al., "Transcriptome Analysis of Parallel-Evolved *Escherichia coli* Strains under Ethanol Stress." *BMC Genomics*, 11:579 (2010).
Huang, et al., "Industrial Production of Recombinant Therapeutics in *Escherichia coli* and Its Recent Advancements." *J Ind Microbiol Biotechnol*, 39(3):383-399 (2012).
Humphrey, et al., "VMD: Visual Molecular Dynamics." *J Mol Graph*, 14(1):33-38, 27-38 (1996).
Ibarra, et al., "*Escherichia coli* K-12 Undergoes Adaptive Evolution to Achieve in Silico Predicted Optimal Growth." *Nature*, 420(6912):186-189 (2002).
Innocenti and Chenoweth, "Interspecific Divergence of Transcription Networks Along Lines of Genetic Variance in *Drosophila*: Dimensionality, Evolvability, and Constraint." *Molecular Biology and Evolution*, 30(6):1358-1367 (2013).
Ishino, et al., "Nucleotide Sequence of the Iap Gene, Responsible for Alkaline Phosphatase Isozyme Conversion in *Escherichia coli*, and Identification of the Gene Product." *J Bacteriol*, 169(12):5429-5433 (1987).
Jansen, et al., "Experimental Evolution as an Efficient Tool to Dissect Adaptive Paths to Antibiotic Resistance. Lid—S1368-7646(14)00004-1 [Pii] Lid—10.1016/J.Drup.2014.02.002 [Doi]." (1532-2084 (Electronic)).
Janssen, et al., "Genome Coverage, Literally Speaking. The Challenge of Annotating 200 Genomes with 4 Million Publications." *EMBO Rep*, 6(5):397-399 (2005).
Jensen, "The *Escherichia coli* K-12 "Wild Types" W3110 and MG1655 Have an rph Frameshift Mutation That Leads to Pyrimidine Starvation Due to Low Pyre Expression Levels." *J Bacteriol*, 175(11):3401-3407 (1993).
Jishage, et al., "Regulation of Sigma Factor Competition by the Alarmone ppGpp." *Genes Dev*, 16(10):1260-1270 (2002).
Jones, et al., "The Genomic Basis of Adaptive Evolution in Threespine Sticklebacks." *Nature*, 484:55 (2012).
Joyce and Palsson, "The Model Organism as a System: Integrating 'Omics' Data Sets." *Nat Rev Mol Cell Biol*, 7(3):198-210 (2006).
Keseler, et al., "Ecocyc: Fusing Model Organism Databases with Systems Biology." *Nucleic Acids Res*, 41(Database issue):D605-612 (2013).
King and Wilson, "Evolution at Two Levels in Humans and Chimpanzees." *Science*, 188(4184):107-116 (1975).
King, et al., "A Regulatory Trade-Off as a Source of Strain Variation in the Species *Escherichia coli*." *Journal of Bacteriology*, 186(17):5614-5620 (2004).
Klumpp and Hwa, "Bacterial Growth: Global Effects on Gene Expression, Growth Feedback and Proteome Partition." *Curr Opin Biotechnol*, 28:96-102 (2014).

(56) References Cited

OTHER PUBLICATIONS

Kobayashi, et al., "Promoter Selectivity of *Escherichia coli* RNA Polymerase: Effect of Base Substitutions in the Promoter-35 Region on Promoter Strength." *Nucleic Acids Res*, 18(24):7367-7372 (1990).
Korch, et al., "Characterization of the HipA7 Allele of *Escherichia coli* and Evidence That High Persistence Is Governed by (P)ppGpp Synthesis." *Mol Microbiol*, 50(4):1199-1213 (2003).
Kortemme and Baker, "A Simple Physical Model for Binding Energy Hot Spots in Protein-Protein Complexes." *Proceedings of the National Academy of Sciences*, 99(22):14116-14121 (2002).
Kuznedelov, et al., "A Role for Interaction of the RNA Polymerase Flap Domain with the Sigma Subunit in Promoter Recognition. "*Science*, 295(5556):855-857 (2002).
LaCroix, et al., "Use of Adaptive Laboratory Evolution to Discover Key Mutations Enabling Rapid Growth of *Escherichia coli* K-12 MG1655 on Glucose Minimal Medium." *Appl Environ Microbiol*, 81(1):17-30 (2015).
Langmead, "Aligning Short Sequencing Reads with Bowtie." *Curr Protoc Bioinformatics*, Chapter 11:Unit 11 17 (2010).
Langmead and Salzberg, "Fast Gapped-Read Alignment with Bowtie 2." *Nat Methods*, 9(4):357-359 (2012).
Latif, et al., "The Genome Organization of *Thermotoga maritima* Reflects Its Lifestyle." *PLoS Genet*, 9(4):e1003485 (2013).
Lee and Palsson, "Adaptive Evolution of *Escherichia coli* K-12 MG1655 During Growth on a Nonnative Carbon Source, L-1,2-Propanediol." *Appl Environ Microbiol*, 76(13):4158-4168 (2010).
Lee, et al., "Cumulative Number of Cell Divisions as a Meaningful Timescale for Adaptive Laboratory Evolution of *Escherichia coli.*" *PLoS one*, 6(10):e26172 (2011).
Leiby and Marx, "Metabolic Erosion Primarily through Mutation Accumulation, and Not Tradeoffs, Drives Limited Evolution of Substrate Specificity in *Escherichia coli.*" *PLoS Biol*, 12(2):e1001789 (2014).
Lenski, et al., "Long-Term Experimental Evolution in *Escherichia coli*. I. Adaptation and Divergence During 2,000 Generations." *The American Naturalist*, 138(6):1315-1341 (1991).
Lerman, et al., "In Silico Method for Modelling Metabolism and Gene Product Expression at Genome Scale." *Nat Commun*, 3:929 (2012).
McCarthy, et al., "Genome-Wide Association Studies for Complex Traits: Consensus, Uncertainty and Challenges." *Nat Rev Genet*, 9(5):356-369 (2008).
McCloskey, et al., "Basic and Applied Uses of Genome-Scale Metabolic Network Reconstructions of *Escherichia coli.*" *Mol Syst Biol*, 9:661 (2013).
McCloskey, et al., "Fast Swinnex Filtration (FSF): A Fast and Robust Sampling and Extraction Method Suitable for Metabolomics Analysis of Cultures Grown in Complex Media." *Metabolomics*, 11(1):198-209 (2015).
Mozhayskiy and Tagkopoulos, "Microbial Evolution in Vivo and in Silico: Methods and Applications." *Integr Biol (Camb)*, 5(2):262-277 (2013).
Nedialkov, et al., "The RNA Polymerase Bridge Helix YFI Motif in Catalysis, Fidelity and Translocation." *Biochimica et biophysica acta*, 1829(2):187-198 (2013).
Newton, et al., "Analysis of Any Point Mutation in DNA. The Amplification Refractory Mutation System (Arms)." *Nucleic Acids Res*, 17(7):2503-2516 (1989).
O'Brien, et al., "Genome-Scale Models of Metabolism and Gene Expression Extend and Refine Growth Phenotype Prediction." *Mol Syst Biol*, 9:693 (2013).
Opolka, et al., "Complete Structural Model of *Escherichia coli* RNA Polymerase from a Hybrid Approach." *PLoS Biol*, 8(9) (2010).
Osterberg, et al., "Regulation of Alternative Sigma Factor Use." *Annu Rev Microbiol*, 65:37-55 (2011).
Palsson, "Adaptive Laboratory Evolution." *Microbe*, 6(2):6 (2011).
Park, et al., "Application of Systems Biology for Bioprocess Development." *Trends Biotechnol*, 26(8):404-412 (2008).
Phillips, et al., "Scalable Molecular Dynamics with Namd." *J Comput Chem*, 26(16):1781-1802 (2005).
Pirt, "Maintenance Energy: A General Model for Energy-Limited and Energy-Sufficient Growth." *Arch Microbiol*, 133(4):300-302 (1982).
Portnoy, et al., "Aerobic Fermentation of D-Glucose by an Evolved Cytochrome Oxidase-Deficient *Escherichia coli* Strain." *Appl Environ Microbiol*, 74(24):7561-7569 (2008).
Prud'homme, et al., "Emerging Principles of Regulatory Evolution." *Proceedings of the National Academy of Sciences*, 104(suppl 1):8605-8612 (2007).
Quan, et al., "Adaptive Evolution of the Lactose Utilization Network in Experimentally Evolved Populations of *Escherichia coli.*" *PLoS Genet*, 8(1):e1002444 (2012).
Remold, "Understanding Specialism When the Jack of All Trades Can Be the Master of All." *Proceedings of the Royal Society B: Biological Sciences*, 279(1749):4861-4869 (2012).
Reyes, et al., "Visualizing Evolution in Real Time to Determine the Molecular Mechanisms of N-Butanol Tolerance in *Escherichia coli.*" *Metab Eng*, 14(5):579-590 (2012).
Riley, et al., "*Escherichia coli* K-12: A Cooperatively Developed Annotation Snapshot—2005." *Nucleic Acids Res*, 34(1):1-9 (2006).
Salgado, et al., "Regulondb V8.0: Omics Data Sets, Evolutionary Conservation, Regulatory Phrases, Cross-Validated Gold Standards and More." *Nucleic Acids Research*, 41(Database issue):D203-D213 (2013).
Sandberg, et al., "Evolution of *Escherichia coli* to 42° C and Subsequent Genetic Engineering Reveals Adaptive Mechanisms and Novel Mutations." *Molecular Biology and Evolution* (2014).
Saxer, et al., "Mutations in Global Regulators Lead to Metabolic Selection During Adaptation to Complex Environments." *PLoS Genetics*, 10(12):e1004872 (2014).
Schmidt, et al., "GIM3E: Condition-Specific Models of Cellular Metabolism Developed from Metabolomics and Expression Data." *Bioinformatics*, 29(22):2900-2908 (2013).
Schuetz, et al., "Multidimensional Optimality of Microbial Metabolism." *Science*, 336(6081):601-604 (2012).
Scott, et al., "Interdependence of Cell Growth and Gene Expression: Origins and Consequences." *Science*, 330(6007):1099-1102 (2010).
Sethi, et al., "Dynamical Networks in tRNA:Protein Complexes." *Proceedings of the National Academy of Sciences of the United States of America*, 106(16):6620-6625 (2009).
Shachrai, et al., "Cost of Unneeded Proteins in *E. coli* Is Reduced after Several Generations in Exponential Growth." *Mol Cell*, 38(5):758-767 (2010).
Shin, et al., "Production of Bulk Chemicals Via Novel Metabolic Pathways in Microorganisms." *Biotechnology Advances*, 31(6):925-935 (2013).
Solopova, et al., "Bet-Hedging During Bacterial Diauxic Shift." *Proceedings of the National Academy of Sciences of the United States of America*, 111(20):7427-7432 (2014).
Tatusov, et al., "The Cog Database: An Updated Version Includes Eukaryotes." *BMC Bioinformatics*, 4:41 (2003).
Tenaillon, et al., "The Molecular Diversity of Adaptive Convergence." *Science*, 335(6067):457-461 (2012).
Thiele, et al., "Genome-Scale Reconstruction of *Escherichia coli's* Transcriptional and Translational Machinery: A Knowledge Base, Its Mathematical Formulation, and Its Functional Characterization." *PLoS Comput Biol*, 5(3):e1000312 (2009).
Totemeyer, et al., "From Famine to Feast: The Role of Methylglyoxal Production in *Escherichia coli.*" *Mol Microbiol*, 27(3):553-562 (1998).
Trapnell, et al., "Transcript Assembly and Quantification by RNA-Seq Reveals Unannotated Transcripts and Isoform Switching During Cell Differentiation." *Nat Biotechnol*, 28(5):511-515 (2010).
Tremblay, et al., "A C-Type Cytochrome and a Transcriptional Regulator Responsible for Enhanced Extracellular Electron Transfer in Geobacter Sulfurreducens Revealed by Adaptive Evolution." *Environ Microbiol*, 13(1):13-23 (2011).
Tucker, et al., "Genes of the Gadx-Gadw Regulon in *Escherichia coli.*" *J Bacteriol*, 185(10):3190-3201 (2003).
Umeda and Ohtsubo, "Mapping of Insertion Elements IS1, IS2 and IS3 on the *Escherichia coli* K-12 Chromosome. Role of the Inser-

(56) References Cited

OTHER PUBLICATIONS tion Elements in Formation of Hfrs and F' Factors and in Rearrangement of Bacterial Chromosomes." *J Mol Biol*, 208(4):601-614 (1989).
Vasi and Lenski, "Ecological Strategies and Fitness Tradeoffs in *Escherichia coli* Mutants Adapted to Prolonged Starvation." *Journal of Genetics*, 78(1):43-49 (1999).
Vassylyev, et al., "Structural Basis for Substrate Loading in Bacterial RNA Polymerase." *Nature*, 448(7150):163-168 (2007).
Venturelli, et al., "Population Diversification in a Yeast Metabolic Program Promotes Anticipation of Environmental Shifts." *PLoS Biol*, 13(1):e1002042 (2015).
Wagner, et al., "The Road to Modularity." *Nature Reviews Genetics*, 8:921 (2007).
Wang, et al., "Programming Cells by Multiplex Genome Engineering and Accelerated Evolution." *Nature*, 460(7257):894-898 (2009).
Wang, et al., "Chromosome Organization by a Nucleoid-Associated Protein in Live Bacteria." *Science*, 333(6048):1445-1449 (2011).
Wang, et al., "Natural Variation in Preparation for Nutrient Depletion Reveals a Cost-Benefit Tradeoff." *PLoS Biol*, 13(1):e1002041 (2015).
Weinzierl, "The Nucleotide Addition Cycle of RNA Polymerase Is Controlled by Two Molecular Hinges in the Bridge Helix Domain." *BMC Biology*, 8:134-134 (2010).
Weinzierl, "The Bridge Helix of RNA Polymerase Acts as a Central Nanomechanical Switchboard for Coordinating Catalysis and Substrate Movement." *Archaea*, 2011(Article ID 608385):1-7 (2011).
Wiser, et al., "Long-Term Dynamics of Adaptation in Asexual Populations." *Science*, 342(6164):1364-1367 (2013).
Wray "The Evolutionary Significance of cis-Regulatory Mutations." *Nat Rev Genet*, 8(3):206-216 (2007).
Xu, et al., "Genome-Scale Metabolic Model in Guiding Metabolic Engineering of Microbial Improvement." *Appl Microbiol Biotechnol*, 97(2):519-539 (2013).
Zhou and Jin, "The Rpob Mutants Destabilizing Initiation Complexes at Stringently Controlled Promoters Behave Like "Stringent" RNA Polymerases in *Escherichia coli*." *Proceedings of the National Academy of Sciences of the United States of America*, 95(6):2908-2913 (1998).
Cramer, et al., "Structural basis of transcription: RNA polymerase II at 2.8 angstrom resolution." Science 292:1863-1876 (2001).

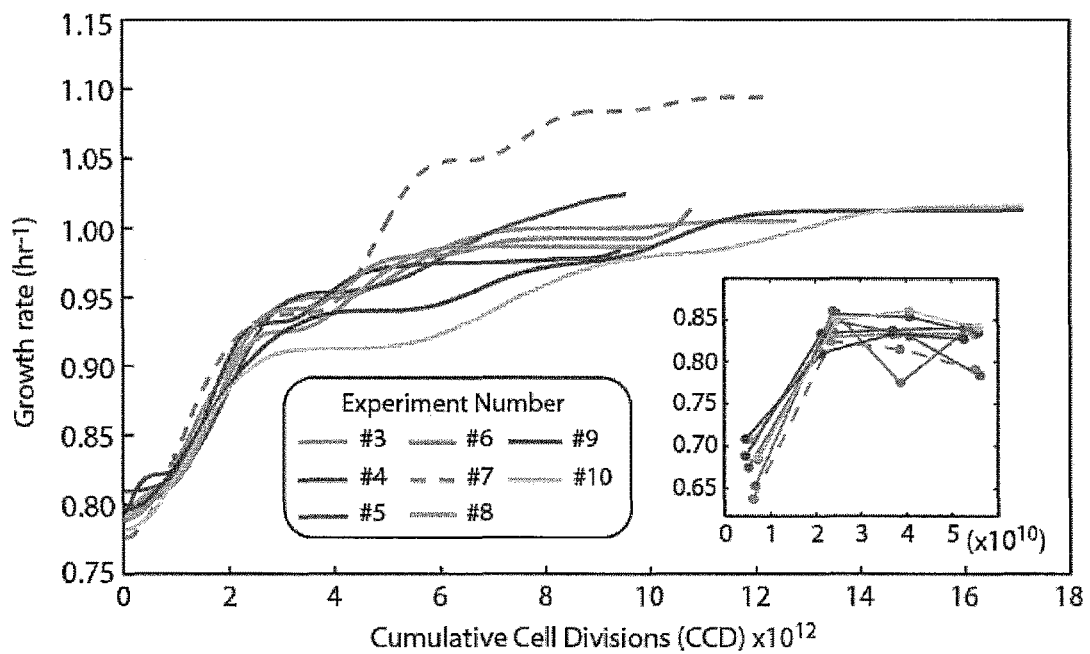

Figure 1: **Fitness trajectories for *E. coli* populations evolved on glucose minimal media.** Shown is a plot of the fitness (i.e., the growth rate) of the independently evolved experiments versus the number of cumulative cell divisions (CCD). The strain indicated with a dashed line was classified as a hypermutator. The insert shows the growth rates of the initial four flasks of batch growth in each experiment. Overall, the fitness of the hypermutator population outpaced the non-mutators.

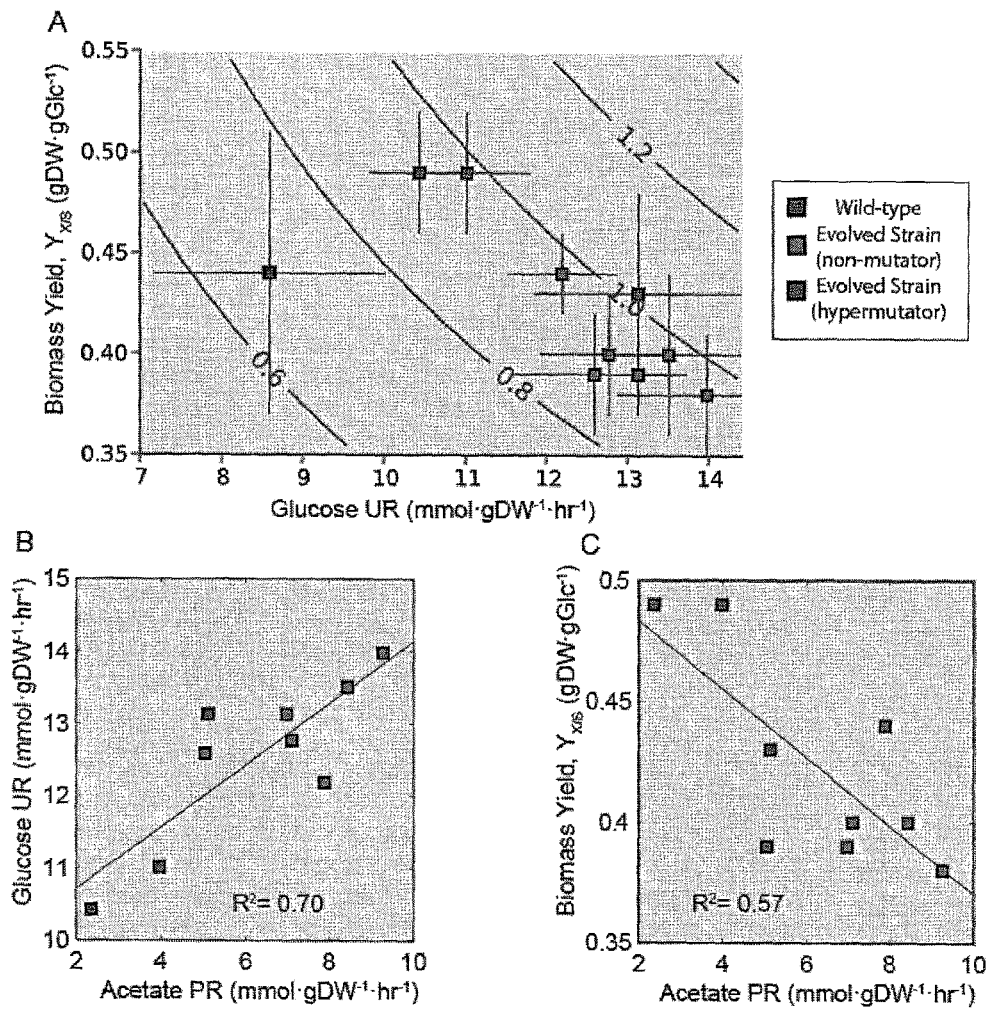

Figure 2: Phenotypic properties of evolved strains. Clones isolated from the last flask of the experiments (i.e., endpoint strains of non-mutators) and three hypermutator strains were characterized phenotypically. (A) A plot of biomass yield versus glucose uptake rate (UR). The isoclines indicate different growth rates. Of all measured phenotypic traits, the correlations between (B) glucose uptake rate and acetate production rate (PR), and (C) biomass yield and acetate production rate were the strongest. The percent of carbon from glucose being secreted in the form of acetate increased in all of the non-mutator endpoint strains (18-22%) except for one (13%), as compared to wild-type (15%). This percent decreased for all of the hypermutator strains (8-13%).

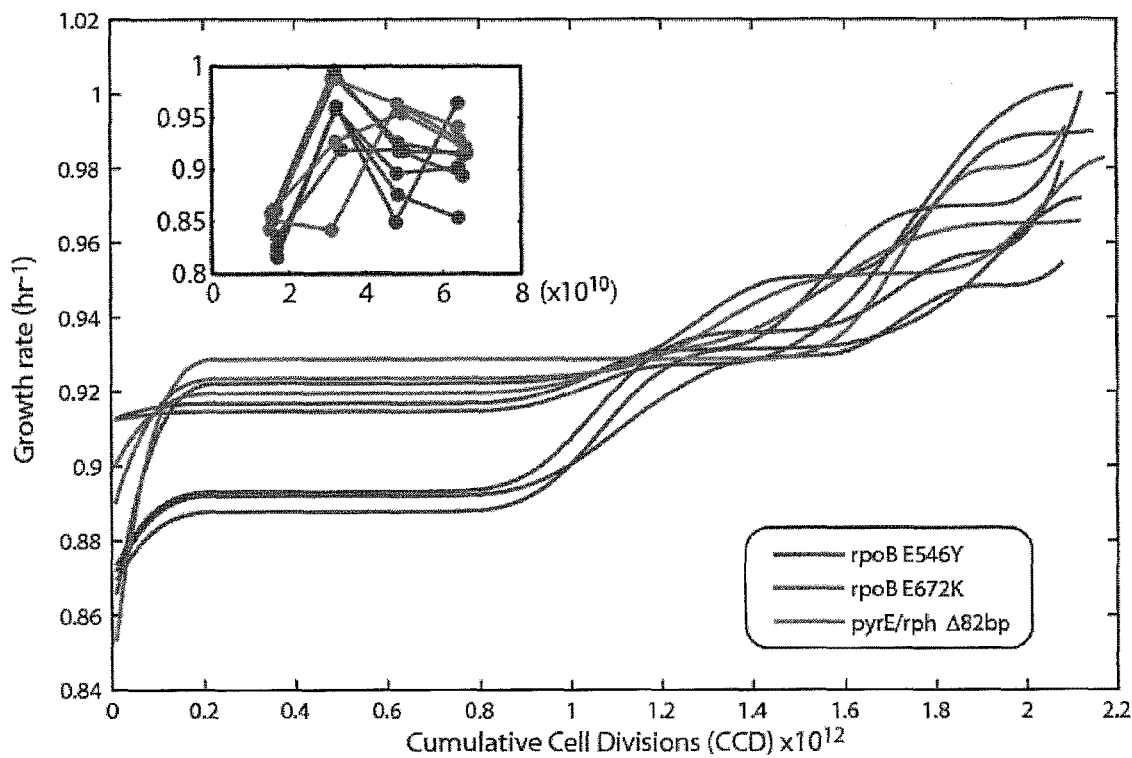

Figure 4: Fitness Trajectory for the Validation ALE
Shown is a plot of the validation ALE where three unique starting strains were evolved in biological triplicate, each harboring one of the following mutations: *rpoB* E546V, *rpoB* E672K, and *pyrE/rph* Δ82bp. The increase in fitness is shown as a function of the cumulative cell divisions (CCD). The insert shows the unsmoothed and filtered growth rates of the beginning of the experiment to show any possible physiological adaptation that is characteristic of ALE experiments. A smoothing spline will often obscure such abrupt changes.

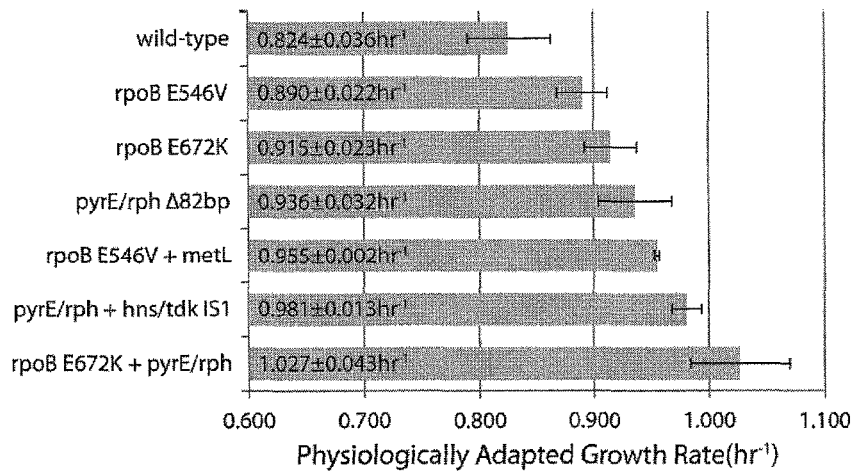

Figure 5: Casual Mutation Analysis
Shown is a bar graph of the physiologically adapted growth rates of strains harboring key mutations identified in this work. The error bars represent 95% confidence intervals. This shows that the mutation in *metL* and the IS1 insertion between *hns/tdk* are causal in the presence of the additional mutations shown. The strain with *metL* also had one additional mutation, but this was not observed in any other sequenced *metL* mutant from the ALE experiment. It is clear from the fastest growing mutant, with growth 1.3 fold higher than the wild-type, how significantly the *pyrE/rph* and *rpoB* mutations can affect growth rate.

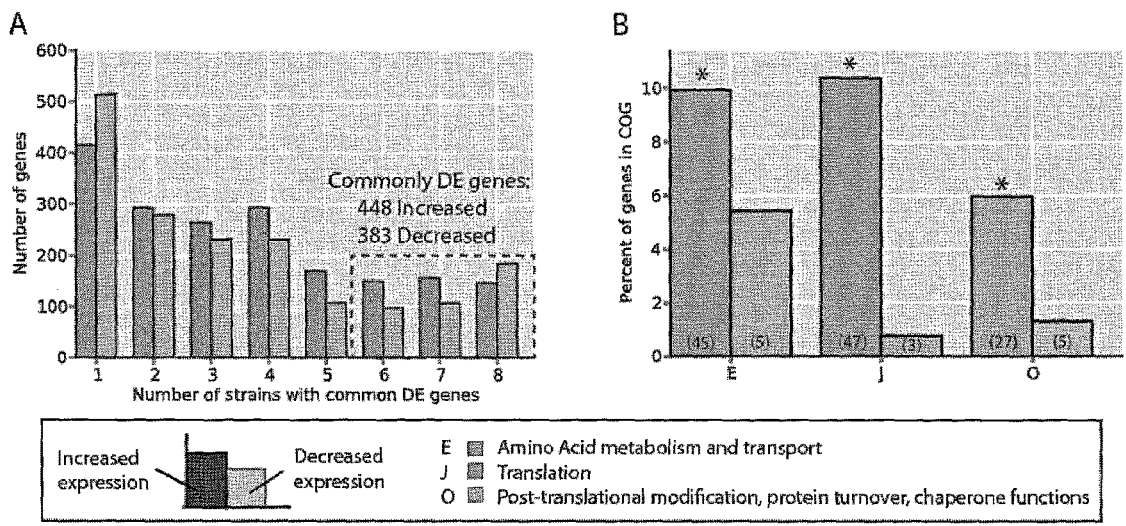

Figure 6: Commonly differentially expressed genes. (A) The number of differentially expressed genes (with respect to the wild-type strain) common across evolved strains is indicated. Increased and decreased expression genes are counted separately to ensure the direction of change is conserved across strains. The y-axis indicates the number of genes differentially expressed in exactly the number of strains indicated on the x-axis. From this, 448 increased and 383 decreased genes are identified as common to at least 6 strains, whereas one would expect no genes in common to all six by random chance (see Supplementary Figure 6, Methods). (B) The commonly differentially expressed genes' functions are interrogated using annotated Clusters of Orthologous Groups (COGs). COGs over-represented in either the up-regulated or down-regulated gene sets were identified with a hypergeometric test (p<0.05; see Methods). The percentage and number of genes for the identified COGs is indicated in the bar chart. Asterisk indicates over-represented.

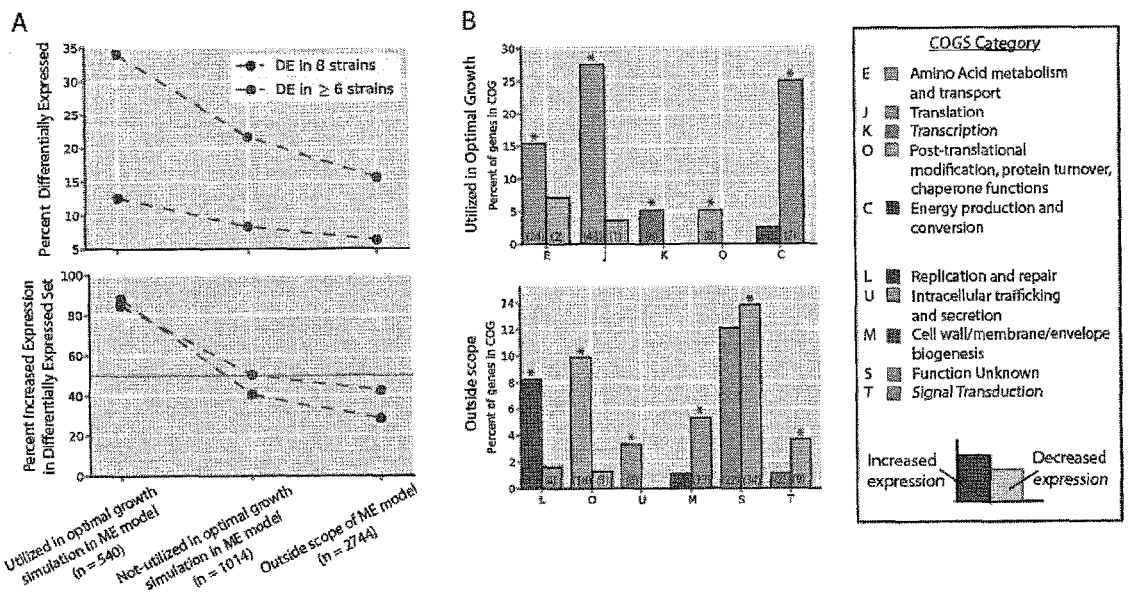

Figure 7: Comparison of genome-scale modeling predictions and categorization of commonly differentially expressed genes.

(A) The commonly differentially expressed genes were compared to a gene classification obtained by a genome-scale model of E. coli (38). Growth rate is optimized in the same glucose aerobic batch conditions as used in the ALE experiment. Simulation results can be used as an additional characterization of gene content (x-axis). Overall, differentially expressed genes are more enriched in the set of genes predicted to enable an optimal growth phenotype (top). Furthermore, within the differentially expressed set of genes, those which increased in expression versus wild-type are enriched within the predicted set of genes which enable an optimal growth phenotype (bottom). (B) Using the combination of in silico predicted genes and COGS for categorization, subsets of genes could be identified which enabled the observed optimal states of the evolved strains on the pathway level.

Mapping mutations in protein structure

- rpoB E672K (genome 4,181,281 G→A)

- External 1 region
- no function assigned

- rpoB E546V (genome 4,180,904 A→T)
- Domain 3 also know as the fork domain, possible involved in transcription regulation

Figure 8 rpoB E672K
mapping in RNAP model

E672K mutation rpoB E546V
mapping in RNAP model
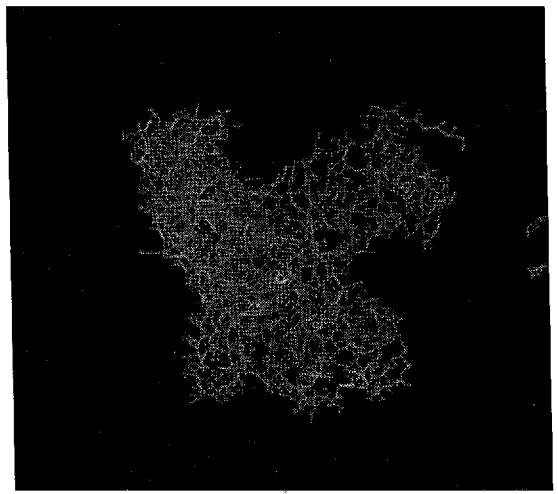
E546V mutation
only Beta subunit
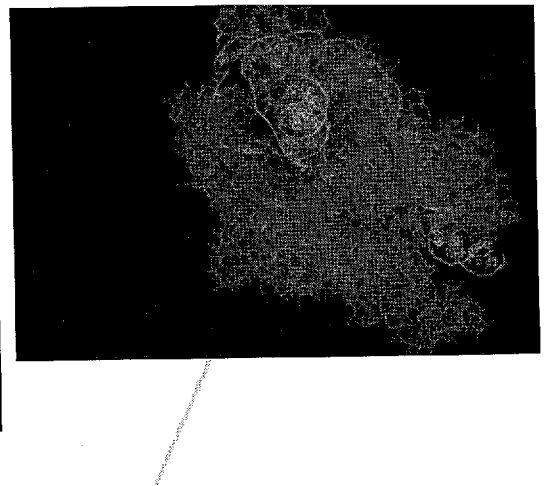
E546V mutation
complete RNAP
Figure 10

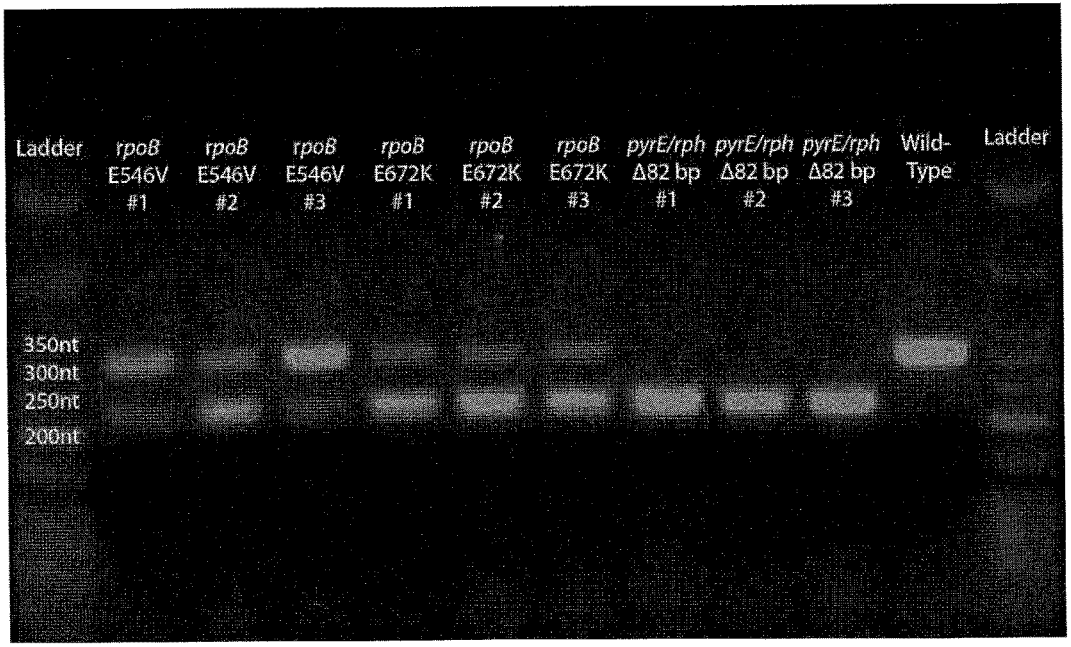

Δ82bp deletion in pyrE/rph penetration by PCR - Populations from the final flask of the validation ALE were probed for the presence of the Δ82bp deletion in pyrE/rph. The upper band shows wild-type genotype and the lower band shows a deletion in pyrE/rph. Low molecular weight ladders were run on the outermost lanes (N0474S from Bio Labs). When clones were sequenced from these populations, rpoB E546V #1 showed no mutations in pyrE/rph and rpoB E546V #3 showed only a Δ1bp deletion in pyrE/rph which would not be resolved from the wild-type band in the gel. Though not observed in all the clones, the PCR results clearly show that a ~Δ82bp deletion in pyrE/rph exists in all the final populations. Based on the relative intensities of the bands, the degree to which the 82bp deletion has penetrated the culture varies. Specifically, in the populations where the clones did not show the Δ82bp deletion, the wild-type band shows greater intensity than the mutant band, thus corroborating why we did not see the Δ82bp deletion in the clone sequences.

Figure 14

Transcriptomic Data: Enriched Differentially Expressed Protein coding Genes from Evolved Strains. (A) The Differentially expressed genes from each strain. (B) Distribution of differentially expressed genes if expression was randomized.

SEQ ID NO:1 rpoB_4181281

ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGAAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCT
GAAACACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTGTCTCTGGGTGAACCGGTTG
AACGTGGCGACGTGCTGGCAGACGGTCCGTCCACCGACCTCGGTGAACTGGCGCTTGGTCAGAACATGCGCGTAGCGTT
CATGCCGTGGAATGGTTACAACTTCGAAGACTCCATCCTCGTATCCGAGCGTGTTGTTCAGGAAGACCGTTTCACCACCAT
CCACATTCAGGAACTGGCGTGTGTGTCCCGTGACACCAAGCTGGGTCCGGAAGAGATCACCGCTGACATCCCGAACGTG
GGTGAAGCTGCGCTCTCCAAACTGGATGAATCCGGTATCGTTTACATTGGTGCGGAAGTGACCGGTGGCGACATTCTGGT
TGGTAAGGTAACGCCGAAAGGTGAAACTCAGCTGACCCCAGAAGAAAAACTGCTGCGTGCGATCTTCGGTGAGAAAGCC
TCTGACGTTAAAGACTCTTCTCTGCGCGTACCAAACGGTGTATCCGGTACGGTTATCGACGTTCAGGTCTTTACTCGCGAT

FIG 16

```
GGCGTAGAAAAAGACAAACGTGCGCTGGAAATCGAAGAAATGCAGCTCAAACAGGCGAAGAAAGACCTGTCTGAAGAA
CTGCAGATCCTCGAAGCGGGTCTGTTCAGCCGTATCCGTGCTGTGCTGGTAGCCGGTGGCGTTGAAGCTGAGAAGCTCGA
CAAACTGCCGCGCGATCGCTGGCTGGAGCTGGGCCTGACAGACGAAGAGAAACAAAATCAGCTGGAACAGCTGGCTGA
GCAGTATGACGAACTGAAACACGAGTTCGAGAAGAAACTCGAAGCGAAACGCCGCAAAATCACCCAGGGCGACGATCTG
GCACCGGGCGTGCTGAAGATTGTTAAGGTATATCTGGCGGTTAAACGCCGTATCCAGCCTGGTGACAAGATGGCAGGTC
GTCACGGTAACAAGGGTGTAATTTCTAAGATCAACCCGATCGAAGATATGCCTTACGATGAAAACGGTACGCCGGTAGAC
ATCGTACTGAACCCGCTGGGCGTACCGTCTCGTATGAACATCGGTCAGATCCTCGAAACCCACCTGGGTATGGCTGCGAA
AGGTATCGGCGACAAGATCAACGCCATGCTGAAACAGCAGCAAGAAGTCGCGAAACTGCGCGAATTCATCCAGCGTGCG
TACGATCTGGGCGCTGACGTTCGTCAGAAAGTTGACCTGAGTACCTTCAGCGATGAAGAAGTTATGCGTCTGGCTGAAAA
CCTGCGCAAAGGTATGCCAATCGCAACGCCGGTGTTCGACGGTGCGAAAGAAGCAGAAATTAAAGAGCTGCTGAAACTT
GGCGACCTGCCGACTTCCGGTCAGATCCGCCTGTACGATGGTCGCACTGGTGAACAGTTCGAGCGTCCGGTAACCGTTGG
TTACATGTACATGCTGAAACTGAACCACCTGGTCGACGACAAGATGCACGCGCGTTCCACCGGTTCTTACAGCCTGGTTAC
TCAGCAGCCGCTGGGTGGTAAGGCACAGTTCGGTGGTCAGCGTTTCGGGGAGATGGAAGTGTGGGCGCTGGAAGCATA
CGGCGCAGCATACACCCTGCAGGAAATGCTCACCGTTAAGTCTGATGACGTGAACGGTCGTACCAAGATGTATAAAAACA
TCGTGGACGGCAACCATCAGATGGAGCCGGGCATGCCAGAATCCTTCAACGTATTGTTGAAAGAGATTCGTTCGCTGGGT
ATCAACATCGAACTGGAAGACGAGTAA
```

FIG 16 CONT

SEQ ID NO:2 rpoB_4182566

ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCTGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGAAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCT
GGAACACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTGTCTCTGGGTGAACCGGTTG
AACGTGGCGACGTGCTGGCAGACGGTCCGTCCACCGACCTCGGTGAACTGGCGCTTGGTCAGAACATGCGCGTAGCGTT
CATGCCGTGGAATGGTTACAACTTCGAAGACTCCATCCTCGTATCCGAGCGTGTTGTTCAGGAAGACCGTTTCACCACCAT
CCACATTCAGGAACTGGCGTGTGTGTCCCGTGACACCAAGCTGGGTCCGGAAGAGATCACCGCTGACATCCCGAACGTG
GGTGAAGCTGCGCTCTCCAAACTGGATGAATCCGGTATCGTTTACATTGGTGCGGAAGTGACCGGTGGCGACATTCTGGT
TGGTAAGGTAACGCCGAAAGGTGAAACTCAGCTGACCCCAGAAGAAAAACTGCTGCGTGCGATCTTCGGTGAGAAAGCC
TCTGACGTTAAAGACTCTTCTCTGCGCGTACCAAACGGTGTATCCGGTACGGTTATCGACGTTCAGGTCTTTACTCGCGAT

FIG 17

```
GGCGTAGAAAAAGACAAACGTGCGCTGGAAATCGAAGAAATGCAGCTCAAACAGGCGAAGAAAGACCTGTCTGAAGAA
CTGCAGATCCTCGAAGCGGGTCTGTTCAGCCGTATCCGTGCTGTGCTGGTAGCCGGTGGCGTTGAAGCTGAGAAGCTCGA
CAAACTGCCGCGCGATCGCTGGCTGGAGCTGGGCCTGACAGACGAAGAGAAACAAAATCAGCTGGAACAGCTGGCTGA
GCAGTATGACGAACTGAAACACGAGTTCGAGAAGAAACTCGAAGCGAAACGCCGCAAAATCACCCAGGGCGACGATCTG
GCACCGGGCGTGCTGAAGATTGTTAAGGTATATCTGGCGGTTAAACGCCGTATCCAGCCTGGTGACAAGATGGCAGGTC
GTCACGGTAACAAGGGTGTAATTTCTAAGATCAACCCGATCGAAGATATGCCTTACGATGAAAACGGTACGCCGGTAGAC
ATCGTACTGAACCAGCTGGGCGTACCGTCTCGTATGAACATCGGTCAGATCCTCGAAACCCACCTGGGTATGGCTGCGAA
AGGTATCGGCGACAAGATCAACGCCATGCTGAAACAGCAGCAAGAAGTCGCGAAACTGCGCGAATTCATCCAGCGTGCG
TACGATCTGGGCGCTGACGTTCGTCAGAAAGTTGACCTGAGTACCTTCAGCGATGAAGAAGTTATGCGTCTGGCTGAAAA
CCTGCGCAAAGGTATGCCAATCGCAACGCCGGTGTTCGACGGTGCGAAAGAAGCAGAAATTAAAGAGCTGCTGAAACTT
GGCGACCTGCCGACTTCCGGTCAGATCCGCCTGTACGATGGTCGCACTGGTGAACAGTTCGAGCGTCCGGTAACCGTTGG
TTACATGTACATGCTGAAACTGAACCACCTGGTCGACGACAAGATGCACGCGCGTTCCACCGGTTCTTACAGCCTGGTTAC
TCAGCAGCCGCTGGGTGGTAAGGCACAGTTCGGTGGTCAGCGTTTCGGGGAGATGGAAGTGTGGGCGCTGGAAGCATA
CGGCGCAGCATACACCCTGCAGGAAATGCTCACCGTTAAGTCTGATGACGTGAACGGTCGTACCAAGATGTATAAAAACA
TCGTGGACGGCAACCATCAGATGGAGCCGGGCATGCCAGAATCCTTCAACGTATTGTTGAAAGAGATTCGTTCGCTGGGT
ATCAACATCGAACTGGAAGACGAGTAA
```

FIG 17 CONT

SEQ ID NO:3 rpoB_4180904

ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCTGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGTAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCT
GGAACACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTGTCTCTGGGTGAACCGGTTG
AACGTGGCGACGTGCTGGCAGACGGTCCGTCCACCGACCTCGGTGAACTGGCGCTTGGTCAGAACATGCGCGTAGCGTT
CATGCCGTGGAATGGTTACAACTTCGAAGACTCCATCCTCGTATCCGAGCGTGTTGTTCAGGAAGACCGTTTCACCACCAT
CCACATTCAGGAACTGGCGTGTGTGTCCCGTGACACCAAGCTGGGTCCGGAAGAGATCACCGCTGACATCCCGAACGTG
GGTGAAGCTGCGCTCTCCAAACTGGATGAATCCGGTATCGTTTACATTGGTGCGGAAGTGACCGGTGGCGACATTCTGGT
TGGTAAGGTAACGCCGAAAGGTGAAACTCAGCTGACCCCAGAAGAAAAACTGCTGCGTGCGATCTTCGGTGAGAAAGCC
TCTGACGTTAAAGACTCTTCTCTGCGCGTACCAAACGGTGTATCCGGTACGGTTATCGACGTTCAGGTCTTTACTCGCGAT
GGCGTAGAAAAGACAAACGTGCGCTGGAAATCGAAGAAATGCAGCTCAAACAGGCGAAGAAAGACCTGTCTGAAGAA
TGCAGATCCTCGAAGCGGGTCTGTTCAGCCGTATCCGTGCTGTGCTGGTAGCCGGTGGCGTTGAAGCTGAGAAGCTCGAC

FIG 18

AAACTGCCGCGCGATCGCTGGCTGGAGCTGGGCCTGACAGACGAAGAGAAACAAAATCAGCTGGAACAGCTGGCTGA
GCAGTATGACGAACTGAAACACGAGTTCGAGAAGAAACTCGAAGCGAAACGCCGCAAAATCACCCAGGGCGACGATCTG
GCACCGGGCGTGCTGAAGATTGTTAAGGTATATCTGGCGGTTAAACGCCGTATCCAGCCTGGTGACAAGATGGCAGGTC
GTCACGGTAACAAGGGTGTAATTTCTAAGATCAACCCGATCGAAGATATGCCTTACGATGAAAACGGTACGCCGGTAGAC
ATCGTACTGAACCCGCTGGGCGTACCGTCTCGTATGAACATCGGTCAGATCCTCGAAACCCACCTGGGTATGGCTGCGAA
AGGTATCGGCGACAAGATCAACGCCATGCTGAAACAGCAGCAAGAAGTCGCGAAACTGCGCGAATTCATCCAGCGTGCG
TACGATCTGGGCGCTGACGTTCGTCAGAAAGTTGACCTGAGTACCTTCAGCGATGAAGAAGTTATGCGTCTGGCTGAAAA
CCTGCGCAAAGGTATGCCAATCGCAACGCCGGTGTTCGACGGTGCGAAAGAAGCAGAAATTAAAGAGCTGCTGAAACTT
GGCGACCTGCCGACTTCCGGTCAGATCCGCCTGTACGATGGTCGCACTGGTGAACAGTTCGAGCGTCCGGTAACCGTTGG
TTACATGTACATGCTGAAACTGAACCACCTGGTCGACGACAAGATGCACGCGCGTTCCACCGGTTCTTACAGCCTGGTTAC
TCAGCAGCCGCTGGGTGGTAAGGCACAGTTCGGTGGTCAGCGTTTCGGGGAGATGGAAGTGTGGGCGCTGGAAGCATA
CGGCGCAGCATACACCCTGCAGGAAATGCTCACCGTTAAGTCTGATGACGTGAACGGTCGTACCAAGATGTATAAAAACA
TCGTGGACGGCAACCATCAGATGGAGCCGGGCATGCCAGAATCCTTCAACGTATTGTTGAAAGAGATTCGTTCGCTGGGT
ATCAACATCGAACTGGAAGACGAGTAA

FIG 18 CONT

SEQ ID NO:4 rpoB_4181284

ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCTGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGAAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCT
GGAATACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTGTCTCTGGGTGAACCGGTTG
AACGTGGCGACGTGCTGGCAGACGGTCCGTCCACCGACCTCGGTGAACTGGCGCTTGGTCAGAACATGCGCGTAGCGTT
CATGCCGTGGAATGGTTACAACTTCGAAGACTCCATCCTCGTATCCGAGCGTGTTGTTCAGGAAGACCGTTTCACCACCAT
CCACATTCAGGAACTGGCGTGTGTGTCCCGTGACACCAAGCTGGGTCCGGAAGAGATCACCGCTGACATCCCGAACGTG
GGTGAAGCTGCGCTCTCCAAACTGGATGAATCCGGTATCGTTTACATTGGTGCGGAAGTGACCGGTGGCGACATTCTGGT
TGGTAAGGTAACGCCGAAAGGTGAAACTCAGCTGACCCCAGAAGAAAAACTGCTGCGTGCGATCTTCGGTGAGAAAGCC
TCTGACGTTAAAGACTCTTCTCTGCGCGTACCAAACGGTGTATCCGGTACGGTTATCGACGTTCAGGTCTTTACTCGCGAT
GGCGTAGAAAAAGACAAACGTGCGCTGGAAATCGAAGAAATGCAGCTCAAACAGGCGAAGAAAGACCTGTCTGAAGAA
CTGCAGATCCTCGAAGCGGGTCTGTTCAGCCGTATCCGTGCTGTGCTGGTAGCCGGTGGCGTTGAAGCTGAGAAGCTCGA

FIG 19

```
CAAACTGCCGCGCGATCGCTGGCTGGAGCTGGGCCTGACAGACGAAGAGAAACAAAATCAGCTGGAACAGCTGGCTGA
GCAGTATGACGAACTGAAACACGAGTTCGAGAAGAAACTCGAAGCGAAACGCCGCAAAATCACCCAGGGCGACGATCTG
GCACCGGGCGTGCTGAAGATTGTTAAGGTATATCTGGCGGTTAAACGCCGTATCCAGCCTGGTGACAAGATGGCAGGTC
GTCACGGTAACAAGGGTGTAATTTCTAAGATCAACCCGATCGAAGATATGCCTTACGATGAAAACGGTACGCCGGTAGAC
ATCGTACTGAACCCGCTGGGCGTACCGTCTCGTATGAACATCGGTCAGATCCTCGAAACCCACCTGGGTATGGCTGCGAA
AGGTATCGGCGACAAGATCAACGCCATGCTGAAACAGCAGCAAGAAGTCGCGAAACTGCGCGAATTCATCCAGCGTGCG
TACGATCTGGGCGCTGACGTTCGTCAGAAAGTTGACCTGAGTACCTTCAGCGATGAAGAAGTTATGCGTCTGGCTGAAAA
CCTGCGCAAAGGTATGCCAATCGCAACGCCGGTGTTCGACGGTGCGAAAGAAGCAGAAATTAAAGAGCTGCTGAAACTT
GGCGACCTGCCGACTTCCGGTCAGATCCGCCTGTACGATGGTCGCACTGGTGAACAGTTCGAGCGTCCGGTAACCGTTGG
TTACATGTACATGCTGAAACTGAACCACCTGGTCGACGACAAGATGCACGCGCGTTCCACCGGTTCTTACAGCCTGGTTAC
TCAGCAGCCGCTGGGTGGTAAGGCACAGTTCGGTGGTCAGCGTTTCGGGGAGATGGAAGTGTGGGCGCTGGAAGCATA
CGGCGCAGCATACACCCTGCAGGAAATGCTCACCGTTAAGTCTGATGACGTGAACGGTCGTACCAAGATGTATAAAAACA
TCGTGGACGGCAACCATCAGATGGAGCCGGGCATGCCAGAATCCTTCAACGTATTGTTGAAAGAGATTCGTTCGCTGGGT
ATCAACATCGAACTGGAAGACGAGTAA
```

FIG 19 CONT

SEQ ID NO:5 rpoB_4181279

ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCTGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGAAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCC
GGAACACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTGTCTCTGGGTGAACCGGTTG
AACGTGGCGACGTGCTGGCAGACGGTCCGTCCACCGACCTCGGTGAACTGGCGCTTGGTCAGAACATGCGCGTAGCGTT
CATGCCGTGGAATGGTTACAACTTCGAAGACTCCATCCTCGTATCCGAGCGTGTTGTTCAGGAAGACCGTTTCACCACCAT
CCACATTCAGGAACTGGCGTGTGTGTCCCGTGACACCAAGCTGGGTCCGGAAGAGATCACCGCTGACATCCCGAACGTG
GGTGAAGCTGCGCTCTCCAAACTGGATGAATCCGGTATCGTTTACATTGGTGCGGAAGTGACCGGTGGCGACATTCTGGT
TGGTAAGGTAACGCCGAAAGGTGAAACTCAGCTGACCCCAGAAGAAAAACTGCTGCGTGCGATCTTCGGTGAGAAAGCC
TCTGACGTTAAAGACTCTTCTCTGCGCGTACCAAACGGTGTATCCGGTACGGTTATCGACGTTCAGGTCTTTACTCGCGAT
GGCGTAGAAAAAGACAAACGTGCGCTGGAAATCGAAGAAATGCAGCTCAAACAGGCGAAGAAAGACCTGTCTGAAGAA

FIG 20

```
CTGCAGATCCTCGAAGCGGGTCTGTTCAGCCGTATCCGTGCTGTGCTGGTAGCCGGTGGCGTTGAAGCTGAGAAGCTCGA
CAAACTGCCGCGCGATCGCTGGCTGGAGCTGGGCCTGACAGACGAAGAGAAACAAAATCAGCTGGAACAGCTGGCTGA
GCAGTATGACGAACTGAAACACGAGTTCGAGAAGAAACTCGAAGCGAAACGCCGCAAAATCACCCAGGGCGACGATCTG
GCACCGGGCGTGCTGAAGATTGTTAAGGTATATCTGGCGGTTAAACGCCGTATCCAGCCTGGTGACAAGATGGCAGGTC
GTCACGGTAACAAGGGTGTAATTTCTAAGATCAACCCGATCGAAGATATGCCTTACGATGAAAACGGTACGCCGGTAGAC
ATCGTACTGAACCCGCTGGGCGTACCGTCTCGTATGAACATCGGTCAGATCCTCGAAACCCACCTGGGTATGGCTGCGAA
AGGTATCGGCGACAAGATCAACGCCATGCTGAAACAGCAGCAAGAAGTCGCGAAACTGCGCGAATTCATCCAGCGTGCG
TACGATCTGGGCGCTGACGTTCGTCAGAAAGTTGACCTGAGTACCTTCAGCGATGAAGAAGTTATGCGTCTGGCTGAAAA
CCTGCGCAAAGGTATGCCAATCGCAACGCCGGTGTTCGACGGTGCGAAAGAAGCAGAAATTAAAGAGCTGCTGAAACTT
GGCGACCTGCCGACTTCCGGTCAGATCCGCCTGTACGATGGTCGCACTGGTGAACAGTTCGAGCGTCCGGTAACCGTTGG
TTACATGTACATGCTGAAACTGAACCACCTGGTCGACGACAAGATGCACGCGCGTTCCACCGGTTCTTACAGCCTGGTTAC
TCAGCAGCCGCTGGGTGGTAAGGCACAGTTCGGTGGTCAGCGTTTCGGGGAGATGGAAGTGTGGGCGCTGGAAGCATA
CGGCGCAGCATACACCCTGCAGGAAATGCTCACCGTTAAGTCTGATGACGTGAACGGTCGTACCAAGATGTATAAAAACA
TCGTGGACGGCAACCATCAGATGGAGCCGGGCATGCCAGAATCCTTCAACGTATTGTTGAAAGAGATTCGTTCGCTGGGT
ATCAACATCGAACTGGAAGACGAGTAA
```

FIG 20 CONT

SEQ ID NO:6 rpoB_4181620

```
ATGGTTTACTCCTATACCGAGAAAAAACGTATTCGTAAGGATTTTGGTAAACGTCCACAAGTTCTGGATGTACCTTATCTCC
TTTCTATCCAGCTTGACTCGTTTCAGAAATTTATCGAGCAAGATCCTGAAGGGCAGTATGGTCTGGAAGCTGCTTTCCGTTC
CGTATTCCCGATTCAGAGCTACAGCGGTAATTCCGAGCTGCAATACGTCAGCTACCGCCTTGGCGAACCGGTGTTTGACGT
CCAGGAATGTCAAATCCGTGGCGTGACCTATTCCGCACCGCTGCGCGTTAAACTGCGTCTGGTGATCTATGAGCGCGAAG
CGCCGGAAGGCACCGTAAAAGACATTAAAGAACAAGAAGTCTACATGGGCGAAATTCCGCTCATGACAGACAACGGTAC
CTTTGTTATCAACGGTACTGAGCGTGTTATCGTTTCCCAGCTGCACCGTAGTCCGGGCGTCTTCTTTGACTCCGACAAAGGT
AAAACCCACTCTTCGGGTAAAGTGCTGTATAACGCGCGTATCATCCCTTACCGTGGTTCCTGGCTGGACTTCGAATTCGAT
CCGAAGGACAACCTGTTCGTACGTATCGACCGTCGCCGTAAACTGCCTGCGACCATCATTCTGCGCGCCCTGAACTACACC
ACAGAGCAGATCCTCGACCTGTTCTTTGAAAAAGTTATCTTTGAAATCCGTGATAACAAGCTGCAGATGGAACTGGTGCC
GGAACGCCTGCGTGGTGAAACCGCATCTTTTGACATCGAAGCTAACGGTAAAGTGTACGTAGAAAAAGGCCGCCGTATCA
CTGCGCGCCACATTCGCCAGCTGGAAAAAGACGACGTCAAACTGATCGAAGTCCCGGTTGAGTACATCGCAGGTAAAGT
GGTTGCTAAAGACTATATTGATGAGTCTACCGGCGAGCTGATCTGCGCAGCGAACATGGAGCTGAGCCTGGATCTGCTGG
CTAAGCTGAGCCAGTCTGGTCACAAGCGTATCGAAACGCTGTTCACCAACGATCTGGATCACGGCCCATATATCTCTGAAA
CCTTACGTGTCGACCCAACTAACGACCGTCTGAGCGCACTGGTAGAAATCTACCGCATGATGCGCCCTGGCGAGCCGCCG
ACTCGTGAAGCAGCTGAAAGCCTGTTCGAGAACCTGTTCTTCTCCGAAGACCGTTATGACTTGTCTGCGGTTGGTCGTATG
AAGTTCAACCGTTCTCTGCTGCGCGAAGAAATCGAAGGTTCCGGTATCCTGAGCAAAGACGACATCATTGATGTTATGAA
AAAGCTCATCGATATCCGTAACGGTAAAGGCGAAGTCGATGATATCGACCACCTCGGCAACCGTCGTATCCGTTCCGTTG
GCGAAATGGCGGAAAACCAGTTCCGCGTTGGCCTGGTACGTGTAGAGCGTGCGGTGAAAGAGCGTCTGTCTCTGGGCGA
TCTGGATACCCTGATGCCACAGGATATGATCAACGCCAAGCCGATTTCCGCAGCAGTGAAAGAGTTCTTCGGTTCCAGCC
AGCTGTCTCAGTTTATGGACCAGAACAACCCGCTGTCTGAGATTACGCACAAACGTCGTATCTCCGCACTCGGCCCAGGCG
GTCTGACCCGTGAACGTGCAGGCTTCGAAGTTCGAGACGTACACCCGACTCACTACGGTCGCGTATGTCCAATCGAAACC
CCTGAAGGTCCGAACATCGGTCTGATCAACTCTCTGTCCGTGTACGCACAGACTAACGAATACGGCTTCCTTGAGACTCCG
TATCGTAAAGTGACCGACGGTGTTGTAACTGACGAAATTCACTACCTGTCTGCTATCGAAGAAGGCAACTACGTTATCGCC
CAGGCGAACTCCAACTTGGATGAAGAAGGCCACTTCGTAGAAGACCTGGTAACTTGCCGTAGCAAAGGCGAATCCAGCTT
GTTCAGCCGCGACCAGGTTGACTACATGGACGTATCCACCCAGCAGGTGGTATCCGTCGGTGCGTCCCTGATCCCGTTCCT
GGAACACGATGACGCCAACCGTGCATTGATGGGTGCGAACATGCAACGTCAGGCCGTTCCGACTCTGCGCGCTGATAAG
CCGCTGGTTGGTACTGGTATGGAACGTGCTGTTGCCGTTGACTCCGGTGTAACTGCGGTAGCTAAACGTGGTGGTGTCGT
TCAGTACGTGGATGCTTCCCGTATCGTTATCAAAGTTAACGAAGACGAGATGTATCCGGGTGAAGCAGGTATCGACATCT
ACAACCTGACCAAATACACCCGTTCTAACCAGAACACCTGTATCAACCAGATGCCGTGTGTCTCTGGGTGAACCGGTTG
AACGTGGCGACGTGCTGGCATACGGTCCGTCCACCGACCTCGGTGAACTGGCGCTTGGTCAGAACATGCGCGTAGCGTTC
ATGCCGTGGAATGGTTACAACTTCGAAGACTCCATCCTCGTATCCGAGCGTGTTGTTCAGGAAGACCGTTTCACCACCATC
CACATTCAGGAACTGGCGTGTGTCCCGTGACACCAAGCTGGGTCCGGAAGAGATCACCGCTGACATCCCGAACGTGG
GTGAAGCTGCGCTCTCCAAACTGGATGAATCCGGTATCGTTTACATTGGTGCGGAAGTGACCGGTGGCGACATTCTGGTT
GGTAAGGTAACGCCGAAAGGTGAAACTCAGCTGACCCCAGAAGAAAAACTGCTGCGTGCGATCTTCGGTGAGAAAGCCT
CTGACGTTAAAGACTCTTCTCTGCGCGTACCAAACGGTGTATCCGGTACGGTTATCGACGTTCAGGTCTTTACTCGCGATG
```

FIG 21

GCGTAGAAAAAGACAAACGTGCGCTGGAAATCGAAGAAATGCAGCTCAAACAGGCGAAGAAAGACCTGTCTGAAGAAC
TGCAGATCCTCGAAGCGGGTCTGTTCAGCCGTATCCGTGCTGTGCTGGTAGCCGGTGGCGTTGAAGCTGAGAAGCTCGAC
AAACTGCCGCGCGATCGCTGGCTGGAGCTGGGCCTGACAGACGAAGAGAAACAAAATCAGCTGGAACAGCTGGCTGAG
CAGTATGACGAACTGAAACACGAGTTCGAGAAGAAACTCGAAGCGAAACGCCGCAAAATCACCCAGGGCGACGATCTGG
CACCGGGCGTGCTGAAGATTGTTAAGGTATATCTGGCGGTTAAACGCCGTATCCAGCCTGGTGACAAGATGGCAGGTCGT
CACGGTAACAAGGGTGTAATTTCTAAGATCAACCCGATCGAAGATATGCCTTACGATGAAAACGGTACGCCGGTAGACAT
CGTACTGAACCCGCTGGGCGTACCGTCTCGTATGAACATCGGTCAGATCCTCGAAACCCACCTGGGTATGGCTGCGAAAG
GTATCGGCGACAAGATCAACGCCATGCTGAAACAGCAGCAAGAAGTCGCGAAACTGCGCGAATTCATCCAGCGTGCGTA
CGATCTGGGCGCTGACGTTCGTCAGAAAGTTGACCTGAGTACCTTCAGCGATGAAGAAGTTATGCGTCTGGCTGAAAACC
TGCGCAAAGGTATGCCAATCGCAACGCCGGTGTTCGACGGTGCGAAAGAAGCAGAAATTAAAGAGCTGCTGAAACTTGG
CGACCTGCCGACTTCCGGTCAGATCCGCCTGTACGATGGTCGCACTGGTGAACAGTTCGAGCGTCCGGTAACCGTTGGTT
ACATGTACATGCTGAAACTGAACCACCTGGTCGACGACAAGATGCACGCGCGTTCCACCGGTTCTTACAGCCTGGTTACTC
AGCAGCCGCTGGGTGGTAAGGCACAGTTCGGTGGTCAGCGTTTCGGGGAGATGGAAGTGTGGGCGCTGGAAGCATACG
GCGCAGCATACACCCTGCAGGAAATGCTCACCGTTAAGTCTGATGACGTGAACGGTCGTACCAAGATGTATAAAAACATC
GTGGACGGCAACCATCAGATGGAGCCGGGCATGCCAGAATCCTTCAACGTATTGTTGAAAGAGATTCGTTCGCTGGGTAT
CAACATCGAACTGGAAGACGAGTAA

FIG 21 CONT

SEQ ID NO:7

>gi|49175990:1292145-1292750 Escherichia coli str. K-12 substr. MG1655, complete genome TTGTAGTAATCTCAAACTTATATTGGGGTGGTTTGTTGAGGTAATAATAGAGCCTTAAATTCAGTTGTGC
AATAGCCAGGAATGTAAGGAATTCAAAATTGTTCTTTATTTTGTGCCGC gattccacta atttattcca
tgtcacactt ttcgcatctt tgttatgcta tggttatttc
atacctggat ttgcccctat atttccagac atctgttatc acttaaccca ttacaagccc
gctgccgcag atattcccgt ggcgagcgat aacccagcgc actatgcgga tgccattcgt
tataatgctc gaacgcctct gcaaggttct ttgctgccgt taacccgtct ggtttgggca
tgatactgat gtagtcacgc tttatcgttt tcacgaagct ctctgctatt ccgttactct
ccggactccg caccgccgtg ttcttcggtt caagtcccaa catccgggcg aactggcgtg
tttcattagc ccggtagcat gaaccattat ccgtcagcca ctccactgga gacgacggaa
gatcgttgcc gaagcggcgt tccaccgctc cagcatgac gtcctgtact gtttcactgt
tgaagccgcc ggtagtgacc gcccagtgca gtgcctcacg atcacagcag tccagcgcga
acgtgacacg cagtctctct ccgttatcac agcagaactc gaacccgtca gagcaccatc
gctgattgct ttcttcacg gccactctgc ctgtatgtgc ccgtttcgat ggcggtacag
caggttttcg ctcaagcaac agcgcattct ggcgcatgat ccggtaaaca cgtttggcat
tgatcgcagg cataccatca agttctgcct gtctgcgaag cagcgcccat acccgacgat
aaccatacgt tggcagctct ccgataacat ggtgtatacg gagaagcaca tccgtatcat
cagtgtgacg actgcggcgg ccatccatcc agtcatcggt tgtctgaga atgacgtgca
actgcgcacg cgacacccgg agacaacggc tgactaagct tactccccat ccccgggcaa
taagggcgcg tgcgctatcc acttttttgc ccgtccatat tcaacggctt ctttgaggag
ttcattttcc atcgtttct tgccagcag gcgctggagt tctttaatct gcttcatggc
ggcagcaagt tcagaggcag gaacaacctg ttctccggcg gcgacagcag taagacttcc
ttcctggtat tgcttacgcc agagaaataa ctggctggct gctacaccat gttgccgggc
aacgagggag accgtcatcc ccggttcaaa gctctgctga acaattgcga tcttttcctg
tgtggtacgc cgtctgcgtt tctccggccc taagacatca atcatctgtt ctccaatgac
tagtctaaaa actagtatta agactatcac ttatttaagt gatattggtt gtctggagat
tcaggggcc agtctaatac cataagccta atggagcgaa ttatgagagt tctggttacc
gg GCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 22

SEQ ID NO:8

>gi|49175990:1292145-1292750 Escherichia coli str. K-12 substr. MG1655, complete genome TTGTAGTAATCTCAAACTTATATTGGGGTGGTTTGTTGAGGTAATAATAGAGCCTTAAATTCAGTTGTGC
AATAGCCAGGAATGTAAGGAATTCAAAATTGTTCTTTATTTTGTGCCG aataaataga ggaatctgat
tacttccttc atggggatgc tgaaaagagt agtaattgct
ggtaatgact ccaacttatt gatagtgttt tatgttcaga taatgcccga tgactttgtc
atgcagctcc accgattttg agaacgacag cgacttccgt cccagccgtg ccaggtgctg
cctcagattc aggttatgcc gctcaattcg ctgcgtatat cgcttgctga ttacgtgcag
cttcccttc aggcgggatt catacagcgg ccagccatcc gtcatccata tcaccacgtc
aaagggtgac agcaggctca taagacgccc cagcgtcgcc atagtgcgtt caccgaatac
gtgcgcaaca accgtcttcc ggagactgtc atacgcgtaa aacagccagc gctggcgcga
tttagccccg acatagcccc actgttcgtc catttccgcg cagacgatga cgtcactgcc
cggctgtatg cgcgaggtta ccgactgcgg cctgagtttt ttaagtgacg taaaatcgtg
ttgaggccaa cgcccataat gcgggctgtt gccggcatc caacgccatt catggccata
tcaatgattt tctggtgcgt accggggtga gaagcggtgt aagtgaactg cagttgccat
gttttacggc agtgagagca gagatagcgc tgatgtccgg cggtgctttt gccgttacgc
accaccccgt cagtagctga acaggaggga cagctgatag aaacagaagc cactggagca
cctcaaaaac accatcatac actaaatcag taagttggca gcatcaccta cctcaatgtg
tatcacaata tccatattct ttgtggggga gtctggagat tgagtagata ttcttgttca
ga TTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 23

SEQ ID NO:9

>gi|49175990:1292145-1292750 Escherichia coli str. K-12 substr. MG1655,
complete genome TTGTAGTAATCTCAAACTTATATTGGGGTGGTTTGTTGAGGTAATAATAGAGCCTTAAATTCAGTTGTGC
AATAGCCAGGAATGTAAGGAATTCAAAATTGTTCTTTATTTTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAG
ggaaggtgcg aataagcggg gaaattcttc tcggctgact cagtcatttc atttcttcat
gtttgagccg attttttctc ccgtaaatgc cttgaatcag cctatttaga ccgtttcttc
gccatttaag gcgttatccc cagtttttag tgagatctct cccactgacg tatcattgg
tccgcccgaa acaggttggc cagcgtgaat aacatcgcca gttggttatc gttttcagc
aacccttgt atctggcttt cacgaagccg aactgtcgct tgatgatgcg aaatgggtgc
tccaccctgg cccggatgct ggctttcatg tattcgatgt tgatggccgt tttgttcttg
cgtggatgct gtttcaaggt tcttaccttg ccggggcgct cggcgatcag ccagtccaca
tccacctcgg ccagctcctc gcgctgtggc gcccttggt agccggcatc ggctgagaca
aattgctcct ctccatgcag cagattaccc agctgattga ggtcatgctc gttggccgcg
gtggtgacca ggctgtgggt caggccactc ttggcatcga caccaatgtg ggccttcatg
ccaaagtgcc actgattgcc tttcttggtc tgatgcatct ccggatcgcg ttgctgctct
ttgttcttgg tcgagctggg tgcctcaatg atggtggcat cgaccaaggt gccttgagtc
atcatgacgc ctgcttcggc cagccagcga ttgatggtct tgaacaattg gcgggccagt
tgatgctgct ccagcaggtg gcggaaattc atgatggtgg tgcggtccgg caaggcgcta
tccagggata accgggcaaa cagacgcatg gaggcgattt cgtacagagc atcttccatc
gcgccatcgc tcaggttgta ccaatgctgc atgcagtgaa tgcgtagcat ggtttccagc
ggataaggtc gccggccatt accagccttg gggtaaaacg gctcgatgac ttccaccatg
ttttgccatg gcagaatctg ctccatgcgg gacaagaaaa tctctttct ggtctgacgg
cgcttactgc tgaattcact gtcggcgaag gtaagttgat gactcatgat gaaccctgtt
ctatggctcc agatgacaaa catgatctca tatcagggac ttgttcgcac cttccttag
TTAGTTGTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCACAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 24

SEQ ID NO:10

>gi|49175990:1292145-1292750 Escherichia coli str. K-12 substr. MG1655, complete genome

```
TTGTAGTAATCTCAAACTTATATTGGGGTGGTTTGTTGAGGTAATAATAGAGCCTTAAATTCAGTTGTGC
AATAGCCAGGAATGTAAGGAATTCA aataaataga ggaatctgat tacttccttc atggggatgc
tgaaaagagt agtaattgct
ggtaatgact ccaacttatt gatagtgttt tatgttcaga taatgcccga tgactttgtc
atgcagctcc accgattttg agaacgacag cgacttccgt cccagccgtg ccaggtgctg
cctcagattc aggttatgcc gctcaattcg ctgcgtatat cgcttgctga ttacgtgcag
cttcccttc aggcgggatt catacagcgg ccagccatcc gtcatccata tcaccacgtc
aaagggtgac agcaggctca taagacgccc cagcgtcgcc atagtgcgtt caccgaatac
gtgcgcaaca accgtcttcc ggagactgtc atacgcgtaa acagccagc gctggcgcga
tttagccccg acatagcccc actgttcgtc catttccgcg cagacgatga cgtcactgcc
cggctgtatg cgcgaggtta ccgactgcgg cctgagtttt ttaagtgacg taaaatcgtg
ttgaggccaa cgcccataat gcgggctgtt gcccggcatc aacgccatt catggccata
tcaatgattt tctggtgcgt accgggttga gaagcggtgt aagtgaactg cagttgccat
gttttacggc agtgagagca gagatagcgc tgatgtccgg cggtgctttt gccgttacgc
accaccccgt cagtagctga acaggaggga cagctgatag aaacagaagc cactggagca
cctcaaaaac accatcatac actaaatcag taagttggca gcatcaccta cctcaatgtg
tatcacaata tccatattct ttgtggggga gtctggagat tgagtagata ttcttgttca
ga AGGAATTCAAAATTGTTCTTTATTTTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA
```

Figure 25

SEQ ID NO:11

>gi|49175990:1292145-1292750 Escherichia coli str. K-12 substr. MG1655, complete genome TTGTAGTAATCTCAAACTTATATTGGGGTGGTTTGTTGAGGTAATAATAGAGCCTTAAATTCAGTTG**TGC
AATAG** aataaataga ggaatctgat tacttccttc atggggatgc tgaaaagagt agtaattgct
ggtaatgact ccaacttatt gatagtgttt tatgttcaga taatgcccga tgactttgtc
atgcagctcc accgattttg agaacgacag cgacttccgt cccagccgtg ccaggtgctg
cctcagattc aggttatgcc gctcaattcg ctgcgtatat cgcttgctga ttacgtgcag
ctttcccttc aggcgggatt catacagcgg ccagccatcc gtcatccata tcaccacgtc
aaagggtgac agcaggctca taagacgccc cagcgtcgcc atagtgcgtt caccgaatac
gtgcgcaaca accgtcttcc ggagactgtc atacgcgtaa aacagccagc gctggcgcga
tttagccccg acatagcccc actgttcgtc catttccgcg cagacgatga cgtcactgcc
cggctgtatg cgcgaggtta ccgactgcgg cctgagtttt ttaagtgacg taaaatcgtg
ttgaggccaa cgcccataat gcgggctgtt gcccggcatc caacgccatt catggccata
tcaatgattt tctggtgcgt accgggttga gaagcggtgt aagtgaactg cagttgccat
gttttacggc agtgagagca gagatagcgc tgatgtccgg cggtgctttt gccgttacgc
accacccgt cagtagctga acaggaggga cagctgatag aaacagaagc cactggagca
cctcaaaaac accatcatac actaaatcag taagttggca gcatcaccta cctcaatgtg
tatcacaata tccatattct ttgtggggga gtctggagat tgagtagata ttcttgttca
ga TGCAATAGCCAGGAATGTAAGGAATTCAAAATTGTTCTTTATTTTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 26

SEQ ID NO:12

>gi|49175990:1292145-1292750 Escherichia coli str. K-12 substr. MG1655, complete genome TTGTAGTAATCTCAAACTTATATTGGGGTGGTTTGTTGAGGTAATAATAGAGCCCTTAAATTCAGTTGTGC
AATAGCCAGGAATGTAAGGAATTCAAAATTG ggaaggtgcg aataagcggg gaaattcttc tcggctgact
cagtcatttc atttcttcat
gtttgagccg attttttctc ccgtaaatgc cttgaatcag cctatttaga ccgtttcttc
gccatttaag gcgttatccc cagttttttag tgagatctct cccactgacg tatcatttgg
tccgcccgaa acaggttggc cagcgtgaat aacatcgcca gttggttatc gtttttcagc
aacccttgt atctggcttt cacgaagccg aactgtcgct tgatgatgcg aaatgggtgc
tccaccctgc cccggatgct ggctttcatg tattcgatgt tgatggccgt tttgttcttg
cgtggatgct gtttcaaggt tcttaccttg ccggggcgct cggcgatcag ccagtccaca
tccacctcgg ccagctcctc gcgctgtggc gccccttggt agccggcatc ggctgagaca
aattgctcct ctccatgcag cagattaccc agctgattga ggtcatgctc gttggccgcg
gtggtgacca ggctgtgggt caggccactc ttggcatcga caccaatgtg ggccttcatg
ccaaagtgcc actgattgcc tttcttggtc tgatgcatct ccggatcgcg ttgctgctct
ttgttcttgg tcgagctggg tgcctcaatg atggtggcat cgaccaaggt gccttgagtc
atcatgacgc ctgcttcggc cagccagcga ttgatggtct tgaacaattg gcgggccagt
tgatgctgct ccagcaggtg gcggaaattc atgatggtgg tgcggtccgg caaggcgcta
tccagggata accgggcaaa cagacgcatg gaggcgattt cgtacagagc atcttccatc
gcgccatcgc tcaggttgta ccaatgctgc atgcagtgaa tgcgtagcat ggtttccagc
ggataaggtc gccggccatt accagccttg gggtaaaacg gctcgatgac ttccaccatg
ttttgccatg gcagaatctg ctccatgcgg gacaagaaaa tctcttttct ggtctgacgg
cgcttactgc tgaattcact gtcggcgaag gtaagttgat gactcatgat gaaccctgtt
ctatggctcc agatgacaaa catgatctca tatcagggac ttgttcgcac cttccttag
CAAAATTGTTCTTTATTTTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 27

SEQ ID NO:13

>gi|49175990:1292145-1292750 Escherichia coli str. K-12 substr. MG1655, complete genome TTGTAGTAATCTCAAACTTATATTGGGGTGGTTTGTTGACGTAATAATAGAGCCTTAAATTCAGTTGTGC
AATAGCCAGGAATGTAAGGAATTCAAAATTGTTCTTTATTTTGTGCCGCCAATAAATATCTTTTCATAAA
ATTAGCCAGAAAAGACGCGGCATATAGCCCTATTTACACCGATGATTTCGCAGCACGTGAGGTTAAAACT
TCCTGATTCATGTCACATTTTATGGGGAGATTATCGTAGGCTGACGACCTTT ggaaggtgcg aataagcggg
gaaattcttc tcggctgact cagtcatttc atttcttcat
gtttgagccg attttttctc ccgtaaatgc cttgaatcag cctatttaga ccgtttcttc
gccatttaag gcgttatccc cagtttttag tgagatctct cccactgacg tatcatttgg
tccgcccgaa acaggttggc cagcgtgaat aacatcgcca gttggttatc gtttttcagc
aacccctttgt atctggcttt cacgaagccg aactgtcgct tgatgatgcg aaatgggtgc
tccaccctgg cccggatgct ggctttcatg tattcgatgt tgatggccgt tttgttcttg
cgtggatgct gtttcaaggt tcttaccttg ccggggcgct cggcgatcag ccagtccaca
tccacctcgg ccagctcctc gcgctgtggc gccccttggt agccggcatc ggctgagaca
aattgctcct ctccatgcag cagattaccc agctgattga ggtcatgctc gttggccgcg
gtggtgacca ggctgtgggt caggccactc ttggcatcga caccaatgtg ggccttcatg
ccaaagtgcc actgattgcc tttcttggtc tgatgcatct ccggatcgcg ttgctgctct
ttgttcttgg tcgagctggg tgcctcaatg atggtggcat cgaccaaggt gccttgagtc
atcatgacgc ctgcttcggc cagccagcga ttgatggtct tgaacaattg gcgggccagt
tgatgctgct ccagcaggtg gcggaaattc atgatggtgg tgcggtccgg caaggcgcta
tccagggata accgggcaaa cagacgcatg gaggcgattt cgtacagagc atcttccatc
gcgccatcgc tcaggttgta ccaatgctgc atgcagtgaa tgcgtagcat ggtttccagc
ggataaggtc gccggccatt accagccttg gggtaaaacg gctcgatgac ttccaccatg
ttttgccatg gcagaatctg ctccatgccg gacaagaaaa tctctttctct ggtctgacgg
cgcttactgc tgaattcact gtcggcgaag gtaagttgat gactcatgat gaaccctgtt
ctatggctcc agatgacaaa catgatctca tatcagggac ttgttcgcac cttccttag
CTTTCAGTCTTCTGTATTAGTT
GTGTTTACGAGAATTCCCTATTAAGCGAATGATGAAAAGTAGAACAGTCGCAATAAGAGCATGGACTTAG
TATTGCACTATCTCCTGGAGGTCAACAGAGGGCTATTACTTGCGCAACAGGTTAAAGATTGTGAATAGTT
ACCAGCAGTCATTTACCCGCTTATAACAAGCGAGGCAGTTGTAATGATAGCTCAGAAGGATTATGCAAGG
CTTCGTAAGGGAGAACGCATATACCCACTTCTGTGCATACTGTTGAGCTGAAAAACTGACGAATTATGAT
AAACTCCAGCCAACTTTATTTCATATCATTGAGGGCCTGTGGCTGA

Figure 28

SEQ ID NO:14

>gi|49175990:3999449-4000399 Escherichia coli str. K-12 substr. MG1655, complete genome ATGCTGAGCGCATTTCAACTGGAAAATAACCGACTGACCCGGCTGGAAGTCGAAGAGTCACAACCCCTTG
TAAATGCAGTATGGATTGATCTTGTCGAACCGGACGACGACGAGCGACTGCGCGTACAATCTGAACTTGG
CCAGAGCCTGGCAACCCGCCCGGAACTGGAAGACATCGAAGCATCGGCACGTTTCTTTGAAGACGACGAC
GGCCTGCATATTCACTCCTTCTTCTTCTTTGAAGATGCGGAAGATCACGCCGGTAACTCCACTGTGGCAT
TTACCATCCGTGATGGTCGTCTGTTTACTCTGCGTGAGCGTGAACTGCCCGCTTTTCGTCTGTATCGTAT
GCGTGCCCGTAGCCAGTCGATGGTAGACGGTAACGCCTACGAGTTGCTGCTGGATCTGTTCGAAACCAAA
ATCGAACAGTTGGCAGATGAAATTGAAAATATCTATAGCGACCTGGAGCAGTTGAGCCGGGTGATTATGG
AAGGGCATCAGGGCGATGAGTACGACGAGGCGCTCTCCACTCTGGCGGAACTGGAAGATATCGGCTGGAA
AGTTCGCCTGTGTCTGATGGATACCCAGCGCGCGCTCAACTTCCTGGTGCGTAAAGCGCGTTTACCGGGT
GGGCAACTGGAGCAGGCGCGTGAAATCCTGCGAGATATCGAATCCCTGCTGCCGCATAACGAATCCCTGT
TCCAGAAGGTGAACTTCCTGATGCAGGCAATGGGTTTTATCAACATCGAGCAGAACCGCATCATCAA
AATCTTCTCGGTGGTATCCGTGGTATTCCTGCCGCCGACGCTCGTTGCTTCCAGCTATGGCATGAACTTT
GAGTTTATGCCAGAACTGAAGTGGAGCTTCGGCTACCCTGGCGCGATTATCTTTATGATCCTCGCGGGCC
TGGCACCGTATCTGTACTTTAAGCGGAAGAACTGGTTGTAA

Figure 29

SEQ ID NO:15

>gi|49175990:3999449-4000399 Escherichia coli str. K-12 substr. MG1655, complete genome ATGCTGAGCGCATTTCAACTGGAAAATAACCGACTGACCCGGCTGGAAGTCGAAGAGTCACAACCCCTTG
TAAATGCAGTATGGATTGATCTTGTCGAACCGGACGACGACGAGCGACTGCGCGTACAATCTGAACTTGG
CCAGAGCCTGGCAACCCGCCCGGAACTGGAAGACATCGAAGCATCGGCACGTTTCTTTGAAGACGACGAC
GGCCTGCATCTCCTTCTTCTTCTTTGAAGATGCGGAAGATCACGCCGGTAACTCCACTGTGGCAT
TTACCATCCGTGATGGTCGTCTGTTTACTCTGCGTGAGCGTGAACTGCCCGCTTTTCGTCTGTATCGTAT
GCGTGCCCGTAGCCAGTCGATGGTAGACGGTAACGCCTACGAGTTGCTGCTGGATCTGTTCGAAACCAAA
ATCGAACAGTTGGCAGATGAAATTGAAAATATCTATAGCGACCTGGAGCAGTTGAGCCGGGTGATTATGG
AAGGGCATCAGGGCGATGAGTACGACGAGGCGCTCTCCACTCTGGCGGAACTGGAAGATATCGGCTGGAA
AGTTCGCCTGTGTCTGATGGATACCCAGCGCGCGCTCAACTTCCTGGTGCGTAAAGCGCGTTTACCGGGT
GGGCAACTGGAGCAGGCGCGTGAAATCCTGCGAGATATCGAATCCCTGCTGCCGCATAACGAATCCCTGT
TCCAGAAGGTGAACTTCCTGATGCAGGCGGCAATGGGTTTTATCAACATCGAGCAGAACCGCATCATCAA
AATCTTCTCGGTGGTATCCGTGGTATTCCTGCCGCCGACGCTCGTTGCTTCCAGCTATGGCATGAACTTT
GAGTTTATGCCAGAACTGAAGTGGAGCTTCGGCTACCCTGGCGCGATTATCTTTATGATCCTCGCGGGCC
TGGCACCGTATCTGTACTTTAAGCGGAAGAACTGGTTGTAA

Figure 30

SEQ ID NO:16

>gi|49175990:3999449-4000399 Escherichia coli str. K-12 substr. MG1655, complete genome ATGCTGAGCGCATTTCAACTGGAAAATAACCGACTGACCCGGCTGGAAGTCGAAGAGTCACAACCCCTTG
TAAATGCAGTATGGATTGATCTTGTCGAACCGGACGACGACGAGCGACTGCGCGTACAATCTGAACTTGG
CCAGAGCCTGGCAACCCGCCCGGAACTGGAAGACATCGAAGCATCGGCACGTTTCTTTGAAGACGACGAC
GGCCTGCATATTCACTCCTTCTTCTTCTTTGAAGATGCGGAAGATCACGCCGGTAACTCCACTGTGGCAT
TTACCATCCGTGATGGTCGTCTGTTTACTCTGCGTGAGCGTGAACTGCCCGCTTTTCGTCTGTATCGTAT
GCGTGCCCGTAGCCAGTCGATGGTAGACGGTAACGCCTACGAGTTGCTGCTGGATCTGTTCGAAACCAAA
ATCGAACAGTTGGCAGATGAAATTGAAATATCTATAGCGACCTGGAGCAGTTGAGCCGGGTGATTATGG
AAGGGCATCAGGGCGATGAGTACGACGAGGCGCTCTCCACTCTGGCGGAACTGGAAGATATCGGCTGGAA
AGTTCGCCTGTGTCTGATGGATACCCAGCGCGCGCTCAACTTCCTGGTGCGTAAAGTGCGTTTACCGGGT
GGGCAACTGGAGCAGGCGCGTGAAATCCTGCGAGATATCGAATCCCTGCTGCCGCATAACGAATCCCTGT
TCCAGAAGGTGAACTTCCTGATGCAGGCGGCAATGGGTTTTATCAACATCGAGCAGAACCGCATCATCAA
AATCTTCTCGGTGGTATCCGTGGTATTCCTGCCGCCGACGCTCGTTGCTTCCAGCTATGGCATGAACTTT
GAGTTTATGCCAGAACTGAAGTGGAGCTTCGGCTACCCTGGCGCGATTATCTTTATGATCCTCGCGGGCC
TGGCACCGTATCTGTACTTTAAGCGGAAGAACTGGTTGTAA

Figure 31

SEQ ID NO:17

>gi|49175990:3999449-4000399 Escherichia coli str. K-12 substr. MG1655,
complete genome ATCCTGAGCGCATTTCAACTGGAAAATAACCGACTGACCCGGCTGGAAGTCGAAGAGTCACAACCCCTTG
TAAATGCAGTATGGATTGATCTTGTCGAACCGGACGACGACGGCCTGCATATTCACTCCTTCTTCTTCTTTGAAGAT
GCGGAAGATCACGCCGGTAACTCCACTGTGGCAT
TTACCATCCGTGATGGTCGTCTGTTTACTCTGCGTGAGCGTGAACTGCCCGCTTTTCGTCTGTATCGTAT
GCGTGCCCGTAGCCAGTCGATGGTAGACGGTAACGCCTACGAGTTGCTGCTGGATCTGTTCGAAACCAAA
ATCGAACAGTTGGCAGATGAAATTGAAAATATCTATAGCGACCTGGAGCAGTTGAGCCGGGTGATTATCG
AACGGCATCAGGGCGATGAGTACGACGAGGCGCTCTCCACTCTGGCGGAACTGGAAGATATCGGCTGGAA
AGTTCGCCTGTGTCTGATGGATACCCAGCGCGCGCTCAACTTCCTGGTGCGTAAAGCGCGTTTACCGGGT
GGGCAACTGGAGCAGGCGCGTGAAATCCTGCGAGATATCGAATCCCTGCTGCCGCATAACGAATCCCTGT
TCCAGAAGGTGAACTTCCTGATGCAGGCGGCAATGGGTTTTATCAACATCGAGCAGAACCGCATCATCAA
AATCTTCTCGGTGGTATCCGTGGTATTCCTGCCGCCGACGCTCGTTGCTTCCAGCTATGGCATGAACTTT
GAGTTTATGCCAGAACTGAAGTGGAGCTTCGGCTACCCTGGCGCGATTATCTTTATGATCCTCGCGGGCC
TGGCACCGTATCTGTACTTTAAGCGGAAGAACTGGTTCTAA

Figure 32

SEQ ID NO:18

>gi|49175990:3999449-4000399 Escherichia coli str. K-12 substr. MG1655, complete genome ATGCTGAGCGCATTTCAACTGGAAAATAACCGACTGACCCGGCTGGAAGTCGAAGAGTCACAACCCCTTG
TAAATGCAGTATGGATTGATCTTGTCGAACCGGACGACGACGAGCGACTGCGCGTACAATCTGAACTTGG
CCAGAGCCTGGCAACCCGCCCGGAACTGGAAGACATCGAAGCATCGGCACGTTTCTTTGAAGACGACGAC
GGCCTGCATATTCACTCCTTCTTCTTCTTTGAAGATGCGGAAGATCACGCCGGTAACTCCACTGTGGCAT
TTACCATCCGTGATGGTCGTCTGTTTACTCTGCGTGAGCGTGAACTGCCCGCTTTTCGTCTGTATCGTAT
GCGTGCCCGTAGCCAGTCGATGGTAGACGGTAACGCCTACGAGTTGCTGCTGGATCTGTTCGAAACCAAA
ATCGAACAGTTGGCAGATGAAATTGAAAATATCTATAGCGACCTGGAGCAGTTGAGCCGGGTGATTATGG
AAGGGCATCAGGGCGATGAGTACGACGAGGCGCTCTCCACTCTGGCGGAACTGGAAGATATCGGCTGGAA
AGTTCGCCTGTGTCTGATGGATACCCAGCGCGCGCTCAACTTCCTGGTGCGTAAAGCGCGTTTACCGGGT
GGGCAACTGGAGCAGGCGCGTGAAATCCTGCGAGATATCGAATCCCTGCTGCCGCATAACGAATCCCTGCTGCCGCA
TAACGAATCCCTGT
TCCAGAAGGTGAACTTCCTGATGCAGGCGGCAATGGGTTTTATCAACATCGAGCAGAACCGCATCATCAA
AATCTTCTCGGTGGTATCCGTGGTATTCCTGCCGCCGACGCTCGTTGCTTCCAGCTATGGCATGAACTTT
CAGTTTATGCCAGAACTGAAGTGGAGCTTCGGCTACCCTGGCGCGATTATCTTTATGATCCTCGCGGGCC
TGGCACCGTATCTGTACTTTAAGCGGAAGAACTGGTTGTAA

Figure 33

SEQ ID NO:19

>gi|49175990:2807639-2808376 Escherichia coli str. K-12 substr. MG1655, complete genome ATGGAAAGCCCTACTCCACAGCCTGCTCCTGGTTCGGCGACCTTCATGGAAGGATGCAAAGACA
GTTTACCGATTGTTATTAGTTATATTCCGGTGGCCTTTGCGTTCGGTCTGAATGCGACCCGTCT
GGGATTCTCTCCTCTCGAAAGCGTTTTTTTCTCCTGCATCATTTATGCAGGCGCGAGCCAGTTC
GTCATTACCGCGATGCTGGCAGCCGGGAGTAGTTTGTGGATTGCTGCACTGACCGTCATGGCAA
TGGATGTTCGCCATGTGTTGTATGGCCCGTCACTGCGTAGCCGTATTATTCAGCGTCTGCAAAA
ATCGAAAACCGCCCTGTGGGCGTTTGGCCTGACGGATGAGGTTTTTGCCGCCGCAACCGCAAAA
CTGGTACGCAATAATCGCCGCTGGAGCGAGAACTGGATGATCGGCATTGCCTTCAGTTCATGGT
CATCGTGGGTATTTGGTACGGTAATAGGGGCATTCTCCGGCAGCGGCTTGCTGCAAGGTTATCC
CGCCGTTGAAGCTGCATTAG ggaaggtgcg aataagcggg gaaattcttc tcggctgact
cagtcatttc atttcttcat
gtttgagccg attttttctc ccgtaaatgc cttgaatcag cctatttaga ccgtttcttc
gccatttaag gcgttatccc cagtttttag tgagatctct cccactgacg tatcatttgg
tccgcccgaa acaggttggc cagcgtgaat aacatcgcca gttggttatc gttttcagc
aacccettgt atctggcttt cacgaagccg aactgtcgct tgatgatgcg aaatgggtgc
tccaccctgg cccggatgct ggctttcatg tattcgatgt tgatggccgt tttgttcttg
cgtggatgct gtttcaaggt tcttaccttg ccggggcgct cggcgatcag ccagtccaca
tccacctcgg ccagctcctc gcgctgtggc gccccttggt agccggcatc ggctgagaca
aattgctcct ctccatgcag cagattaccc agctgattga ggtcatgctc gttggccgcg
gtggtgacca ggctgtgggt caggccactc ttggcatcga caccaatgtg ggccttcatg
ccaaagtgcc actgattgcc tttcttggtc tgatgcatct ccggatcgcg ttgctgctct
ttgttcttgg tcgagctggg tgcctcaatg atggtggcat cgaccaaggt gccttgagtc
atcatgacgc ctgcttcggc cagccagcga ttgatggtct tgaacaattg gcgggccagt
tgatgctgct ccagcaggtg gcggaaattc atgatggtgg tgcggtccgg caaggcgcta
tccagggata accgggcaaa cagacgcatg gaggcgattt cgtacagagc atcttccatc
gcgccatcgc tcaggttgta ccaatgctgc atgcagtgaa tgcgtagcat ggtttccagc
ggataaggtc gccggccatt accagccttg gggtaaaacg gctcgatgac ttccaccatg
ttttgccatg gcagaatctg ctccatgcgg gacaagaaaa tctcttttct ggtctgacgg
cgcttactgc tgaattcact gtcggcgaag gtaagttgat gactcatgat gaaccctgtt
ctatggctcc agatgacaaa catgatctca tatcagggac ttgttcgcac cttccttag
TTAGGTTTTATGCTTCCGGCACTCTTTATGAGTTTCCTGCTCGCCTCTTTCCAGCGCAAACAAT
CTCTTTGCGTTACCGCAGCGTTAGTTGGTGCCCTTGCAGGCGTAACGCTATTTTCTATTCCCGT
CGCCATTCTGGCAGGCATTGTCTGTGGCTGCCTCACTGCGTTAATCCAGGCATTCTGGCAAGGA
GCGCCCGATGAGCTATGA

Figure 34

SEQ ID NO:20

>gi|49175990:2807639-2808376 Escherichia coli str. K-12 substr.
MG1655, complete genome ATGGAAAGCCCTACTCCACAGCCTGCTCCTGGTTCGGCGACCTTCATGGAAGGATGCAAAGACA
GTTTACCGATTGTTATTAGTTATATTCCGGTGGCCTTTGCGTTCGGTCTGAATGCGACCCGTCT
GGGATTCTCTCCTCTCGAAAGCGTTTTTTTCTCCTGCATCATTTATGCAGGCGCGAGCCAGTTC
GTCATTACCGCGATGCTGGCAGCCGGGAGTAGTTTGTGGATTGCTGCACTGACCGTCATGGCAA
TGGATGTTCGCCATGTGTTGTATGGCCCGTCACTGCGTAGCCGTATTATTAAAAATCGAAAACC
GCCCTGTGGGCGTTTGGCCTGACGGATGAGGTTTTTGCCGCCGCAACCGCAAAACTGGTACGCA
ATAATCGCCGCTGGAGCGAGAACTGGATGATCGGCATTGCCTTCAGTTCATGGTCATCGTGGGT
ATTTGGTACGGTAATAGGGGCATTCTCCGGCAGCGGCTTGCTGCAAGGTTATCCCGCCGTTGAA
GCTGCATTAGGTTTTATGCTTCCGGCACTCTTTATGAGTTTCCTGCTCGCCTCTTTCCAGCGCA
AACAATCTCTTTGCGTTACCGCAGCGTTAGTTGGTGCCCTTGCAGGCGTAACGCTATTTTCTAT
TCCCGTCGCCATTCTGGCAGGCATTGTCTGTGGCTGCCTCACTGCGTTAATCCAGGCATTCTGG
CAAGGAGCGCCCGATGAGCTATGA

Figure 35

SEQ ID NO:21

>gi|49175990:2807639-2808376 Escherichia coli str. K-12 substr. MG1655, complete genome ATGGAAAGCCCTACTCCACAGCCTGCTCCTGGTTCGGCGACCTTCATGGAAGGATGCAAAGACA
GTTTACCGATTGTTATTAGTTATATTCCGGTGGCCTTTGCGTTCGGTCTGAATGCGACCCGTCT
GGGATTCTCTCCTCTCTAAAGCGTTTTTTTCTCCTGCATCATTTATGCAGGCGCGAGCCAGTTC
GTCATTACCGCGATGCTGGCAGCCGGGAGTAGTTTGTGGATTGCTGCACTGACCGTCATGGCAA
TGGATGTTCGCCATGTGTTGTATGGCCCGTCACTGCGTAGCCGTATTATTCAGCGTCTGCAAAA
ATCGAAAACCGCCCTGTGGGCGTTTGGCCTGACGGATGAGGTTTTTGCCGCCGCAACCGCAAAA
CTGGTACGCAATAATCGCCGCTGGAGCGAGAACTGGATGATCGGCATTGCCTTCAGTTCATGGT
CATCGTGGGTATTTGGTACGGTAATAGGGGCATTCTCCGGCAGCGGCTTGCTGCAAGGTTATCC
CGCCGTTGAAGCTGCATTAGGTTTTATGCTTCCGGCACTCTTTATGAGTTTCCTGCTCGCCTCT
TTCCAGCGCAAACAATCTCTTTGCGTTACCGCAGCGTTAGTTGGTGCCCTTGCAGGCGTAACGC
TATTTTCTATTCCCGTCGCCATTCTGGCAGGCATTGTCTGTGGCTGCCTCACTGCGTTAATCCA
GGCATTCTGGCAAGGAGCGCCCGATGAGCTATGA

Figure 36

SEQ ID NO:22

>gi|49175990:2807639-2808376 Escherichia coli str. K-12 substr. MG1655, complete genome ATGGAAAGCCCTACTCCACAGCCTGCTCCTGGTTCGGCGACCTTCATGGAAGGATGCAAAGACA
GTTTACCGATTGTTATTAGTTATATTCCGGTGGCCTTTGCGTTCGGTCTGAATGCGACCCGTCT
GGGATTCTCTCCTCTCGAAAGCGTTTTTTTCTCCTGCATCATTTATGCAGGCGCGAGCCAGTTC
GTCATTACCGCGATGCTGGCAGCCGGGAGTAGTTTGTGGATTGCTGCACTGACCGTCATGGCAA
TGGATGTTCGCCATGTGTTGTATGGTTCGCCATGTGTTGTATGGCCCGTCACTGCGTAGCCGTA
TTATTCAGCGTCTGCAAAAATCGAAAACCGCCCTGTGGGCGTTTGGCCTGACGGATGAGGTTTT
TGCCGCCGCAACCGCAAAACTGGTACGCAATAATCGCCGCTGGAGCGAGAACTGGATGATCGGC
ATTGCCTTCAGTTCATGGTCATCGTGGGTATTTGGTACGGTAATAGGGGCATTCTCCGGCAGCG
GCTTGCTGCAAGGTTATCCCGCCGTTGAAGCTGCATTAGGTTTTATGCTTCCGGCACTCTTTAT
GAGTTTCCTGCTCGCCTCTTTCCAGCGCAAACAATCTCTTTGCGTTACCGCAGCGTTAGTTGGT
GCCCTTGCAGGCGTAACGCTATTTCTATTCCCGTCGCCATTCTGGCAGGCATTGTCTGTGGCT
GCCTCACTGCGTTAATCCAGGCATTCTGGCAAGGAGCGCCCGATGAGCTATGA

Figure 37

SEQ ID NO:23

>gi|49175990:2874603-2875640 Escherichia coli str. K-12 substr. MG1655, complete genome ATGTTTTCCGCATTGCGCCACCGTACCGCTGCCCTGGCGCTCGGCGTATGCTTTATTCTCCCCGTACACG
CCTCGTCACCTAAACCTGGCGATTTTGCTAA ggaaggtgcg aataagcggg gaaattcttc tcggctgact
cagtcatttc atttcttcat
gtttgagccg attttttctc ccgtaaatgc cttgaatcag cctatttaga ccgtttcttc
gccatttaag gcgttatccc cagttttag tgagatctct cccactgacg tatcatttgg
tccgcccgaa acaggttggc cagcgtgaat aacatcgcca gttggttatc gttttcagc
aacccttgt atctggcttt cacgaagccg aactgtcgct tgatgatgcg aaatgggtgc
tccaccctgg cccggatgct ggctttcatg tattcgatgt tgatggccgt tttgttcttg
cgtggatgct gtttcaaggt tcttaccttg ccggggcgct cggcgatcag ccagtccaca
tccacctcgg ccagctcctc gcgctgtggc gcccttggt agccggcatc ggctgagaca
aattgctcct ctccatgcag cagattaccc agctgattga ggtcatgctc gttggccgcg
gtggtgacca ggctgtgggt caggccactc ttggcatcga caccaatgtg ggccttcatg
ccaaagtgcc actgattgcc tttcttggtc tgatgcatct ccggatcgcg ttgctgctct
ttgttcttgg tcgagctggg tgcctcaatg atggtggcat cgaccaaggt gccttgagtc
atcatgacgc ctgcttcggc cagccagcga ttgatggtct tgaacaattg gcgggccagt
tgatgctgct ccagcaggtg gcggaaattc atgatggtgg tgcggtccgg caaggcgcta
tccagggata accgggcaaa cagacgcatg gaggcgattt cgtacagagc atcttccatc
gcgccatcgc tcaggttgta ccaatgctgc atgcagtgaa tgcgtagcat ggtttccagc
ggataaggtc gccggccatt accagccttg gggtaaaacg gctcgatgac ttccaccatg
ttttgccatg gcagaatctg ctccatgcgg gacaagaaaa tctcttttct ggtctgacgg
cgcttactgc tgaattcact gtcggcgaag gtaagttgat gactcatgat gaaccctgtt
ctatggctcc agatgacaaa catgatctca tatcagggac ttgttcgcac cttccttag
CTAATACTCAGGCACGACATATTGCTACTTTCTTTCCGGGACG
CATGACCGGAACTCCTGCAGAAATGTTATCTGCCGATTATATTCGCCAACAGTTTCAGCAAATGGGTTAT
CGCAGTGATATTCGGACATTTAATAGTCGGTATATTTATACCGCCCGCGATAATCGTAAGAGCTGGCATA
ACGTGACGGGAAGTACGGTGATTGCCGCTCATGAAGGCAAAGCGCCGCAGCAGATCATCATTATGGCGCA
TCTGGATACTTACGCCCCGCTGAGCGATGCTGACGCCGATGCCAATCTCGGCGGGCTGACGTTACAAGGA
ATGGATGATAACGCCGCAGGTTTAGGTGTCATGCTGGAATTGGCAGAACGCCTGAAAAATACGCCTACCG
AGTATGGTATTCGATTTGTGGCGACCAGCGGCGAAGAGGAAGGGAAATTAGGCGCTGAGAATTTACTCAA
GCGGATGAGTGACACCGAAAAGAAAAATACGCTGCTGGTGATTAATCTCGATAACTTAATTGTTGGCGAT
AAATTGTATTTCAACAGCGGTGTAAAAACCCCTGAGGCAGTAAGGAAATTAACGCGCGACAGGGCGCTGG
CAATTGCGCGCAGTCACGGAATAGCCGCAACGACCAATCCGGGTTTGAATAAAAATTATCCGAAAGGCAC
TGGGTGTTGTAATGACGCAGAAATATTCGACAAAGCGGGCATTGCTGTACTTTCGGTGGAAGCGACTAAC
TGGAATCTTGGGAATAAGGATGGTTATCAGCAACGCGCAAAAACACCTGCCTTCCCGGCGGGAAATAGCT
GGCATGACGTAAGACTGGATAATCACCAACATATTGATAAGGCTCTTCCTGGAAGAATAGAACGTCGCTG
CCGTGACGTTATGCGGATAATGCTACCTCTGGTGAAGGAGTTGGCGAAGGCGTCTTGA

Figure 38

SEQ ID NO:24 metL_4129195_1bpdel

>gi|49175990:4127858-4130290 Escherichia coli str. K-12 substr. MG1655, complete genome Mutated
ATGAGTGTGATTGCGCAGGCAGGGGCGAAAGGTCGTCAGCTGCATAAATTTGGTGGCAGTAGTCTGGCTG
ATGTGAAGTGTTATTTGCGTGTCGCGGGCATTATGGCGGAGTACTCTCAGCCTGACGATATGATGGTGGT
TTCCGCCGCCGGTAGCACCACTAACCAGTTGATTAACTGGTTGAAACTAAGCCAGACCGATCGTCTCTCT
GCGCATCAGGTTCAACAAACGCTGCGTCGCTATCAGTGCGATCTGATTAGCGGTCTGCTACCCGCTGAAG
AAGCCGATAGCCTCATTAGCGCTTTTGTCAGCGACCTTGAGCGCCTGGCGGCGCTGCTCGACAGCGGTAT
TAACGACGCAGTGTATGCGGAAGTGGTGGGCCACGGGGAAGTATGGTCGGCACGTCTGATGTCTGCGGTA
CTTAATCAACAAGGGCTGCCAGCGGCCTGGCTTGATGCCCGCGAGTTTTTACGCGCTGAACGCGCCGCAC
AACCGCAGGTTGATGAAGGGCTTTCTTACCCGTTGCTGCAACAGCTGCTGGTGCAACATCCGGGCAAACG
TCTGGTGGTGACCGGATTTATCAGCCGCAACAACGCCGGTGAAACGGTGCTGCTGGGGCGTAACGGTTCC
GACTATTCCGCGACACAAATCGGTGCGCTGGCGGGTGTTTCTCGCGTAACCATCTGGAGCGACGTCGCCG
GGGTATACAGTGCCGACCCGCGTAAAGTGAAAGATGCCTGCCTGCTGCCGTTGCTGCGTCTGGATGAGGC
CAGCGAACTGGCGCGCCTGGCGGCTCCCGTTCTTCACGCCCGTACTTTACAGCCGGTTTCTGGCAGCGAA
ATCGACCTGCAACTGCGCTGTAGCTACACGCCGGATCAAGGTTCCACGCGCATTGAACGCGTGCTGGCCT
CCGGTACTGGTGCGCGTATTGTCACCAGCCACGATGATGTCTGTTTGATTGAGTTTCAGGTGCCCGCCAG
TCAGGATTTCAAACTGGCGCATAAAGAGATCGACCAAATCCTGAAACGCGCGCAGGTACGCCCGCTGGCG
GTTGGCGTACATAACGATCGCCAGTTGCTGCAATTTTGCTACACCTCAGAAGTGGCCGACAGTGCGCTGA
AAATCCTCGACGAAGCGGGATTACCTGGCGAACTGCGCCTGCGTCAGGGGCTGGCGCTGGTGGCGATGGT
CGGTGCAGGCGTCACCCGTAACCCGCTGCATTGCCACCGCTTCTGGCAGCAACTGAAAGGCCAGCCGGTC
GAATTACCTGGCAGTCCGATGACGGCATCAGCCTGGTGGCAGTACTGCGCACCGGCCCGACCGAAAGCC
TGATTCAGGGCTGCATCAGTCCGTCTTCCGCGCAGAAAAACGCATCGGCCTGGTATTGTTCGGTAAGGG
CAATATCGGTTCCCGTTGGCTGGAACTGTTCGCCCGTGAGCAGAGCACGCTTTCGGCACGTACCGGCTTT
GAGTTTGTGCTGGCAGGTGTGGTGGACAGCCGCCGCAGCCTGTTGAGCTATGACGGGCTGGACGCCAGCC
GCGCGTTAGCCTTCTTCAACGATGAAGCGGTTGAGCAGGATGAAGAGTCGTTGTTCCTGTGGATGCGCGC
CCATCCGTATGATGATTTAGTGGTGCTGGACGTTACCGCCAGCCAGCAGCTTGCTGATCAGTATCTTGAT
TTCGCCAGCCACGGTTTCCACGTTATCAGCGCCAACAAACTGGCGGGAGCCAGCGACAGCAATAAATATC
GCCAGATCCACGACGCCTTCGAAAAACCGGGCGTCACTGGCTGTACAATGCCACCGTCGGTGCGGGCTT
GCCGATCAACCACACCGTGCGCGATCTGATCGACAGCGGCGATACTATTTTGTCGATCAGCGGGATCTTC
TCCGGCACGCTCTCCTGGCTGTTCCTGCAATTCGACGGTAGCGTGCCGTTTACCGAGCTGGTGGATCAGG
CGTGGCAGCAGGGCTTAACCGAACCTGACCCGCGTGACGATCTCTCTGGCAAAGACGTGATGCGCAAGCT
GGTGATTCTGGCGCGTGAAGCAGGTTACAACATCGAACCGGATCAGGTACGTGTGGAATCGCTGGTGCCT
GCTCATTGCGAAGGCGGCAGCATCGACCATTTCTTTGAAAATGGCGATGAACTGAACGAGCAGATGGTGC
AACGGCTGGAAGCGGCCCGCGAAATGGGGCTGGTGCTGCGCTACGTGGCGCGTTCGATGCCAACGGTAA
AGCGCGTGTAGGCGTGGAAGCGGTGCGTGAAGATCATCCGTTGGCATCACTGCTGCCGTGCGATAACGTC
TTTGCCATCGAAAGCCGCTGGTATCGCGATAACCCTCTGGTGATCCGCGGACCTGGCGCTGGGCGCGACG
TCACCGCCGGGGCGATTCAGTCGGATATCAACCGGCTGGCACAGTTGTTGTAA

Figure 39

SE ID NO:25 metL 4130250

>gi|49175990:4127858-4130290 Escherichia coli str. K-12 substr. MG1655, complete genome ATGAGTGTGATTGCGCAGGCAGGGGCGAAAGGTCGTCAGCTGCATAAATTTGGTGGCAGTAGTCTGGCTG
ATGTGAAGTGTTATTTGCGTGTCGCGGGCATTATGGCGGAGTACTCTCAGCCTGACGATATGATGGTGGT
TTCCGCCGCCGGTAGCACCACTAACCAGTTGATTAACTGGTTGAAACTAAGCCAGACCGATCGTCTCTCT
GCGCATCAGGTTCAACAAACGCTGCGTCGCTATCAGTGCGATCTGATTAGCGGTCTGCTACCCGCTGAAG
AAGCCGATAGCCTCATTAGCGCTTTTGTCAGCGACCTTGAGCGCCTGGCGGCGCTGCTCGACAGCGGTAT
TAACGACGCAGTGTATGCGGAAGTGGTGGGCCACGGGGAAGTATGGTCGGCACGTCTGATGTCTGCGGTA
CTTAATCAACAAGGGCTGCCAGCGGCCTGGCTTGATGCCCGCGAGTTTTACGCGCTGAACGCGCCGCAC
AACCGCAGGTTGATGAAGGGCTTTCTTACCCGTTGCTGCAACAGCTGCTGGTGCAACATCCGGGCAAACG
TCTGGTGGTGACCGGATTTATCAGCCGCAACAACGCCGGTGAAACGGTGCTGCTGGGGCGTAACGGTTCC
GACTATTCCGCGACACAAATCGGTGCGCTGGCGGGTGTTTCTCGCGTAACCATCTGGAGCGACGTCGCCG
GGGTATACAGTGCCGACCCGCGTAAAGTGAAAGATGCCTGCCTGCTGCCGTTGCTGCGTCTGGATGAGGC
CAGCGAACTGGCGCGCCTGGCGGCTCCCGTTCTTCACGCCCGTACTTTACAGCCGGTTTCTGGCAGCGAA
ATCGACCTGCAACTGCGCTGTAGCTACACGCCGGATCAAGGTTCCACGCGCATTGAACGCGTGCTGGCCT
CCGGTACTGGTGCGCGTATTGTCACCAGCCACGATGATGTCTGTTTGATTGAGTTTCAGGTGCCCGCCAG
TCAGGATTTCAAACTGGCGCATAAAGAGATCGACCAAATCCTGAAACGCGCGCAGGTACGCCCGCTGGCG
GTTGGCGTACATAACGATCGCCAGTTGCTGCAATTTTGCTACACCTCAGAAGTGGCCGACAGTGCGCTGA
AAATCCTCGACGAAGCGGGATTACCTGGCGAACTGCGCCTGCGTCAGGGGCTGGCGCTGGTGGCGATGGT
CGGTGCAGGCGTCACCCGTAACCCGCTGCATTGCCACCGCTTCTGGCAGCAACTGAAAGGCCAGCCGGTC
GAATTTACCTGGCAGTCCGATGACGGCATCAGCCTGGTGGCAGTACTGCGCACCGGCCCGACCGAAAGCC
TGATTCAGGGGCTGCATCAGTCCGTCTTCCGCGCAGAAAAACGCATCGGCCTGGTATTGTTCGGTAAGGG
CAATATCGGTTCCCGTTGGCTGGAACTGTTCGCCCGTGAGCAGAGCACGCTTTCGGCACGTACCGGCTTT
GAGTTTGTGCTGGCAGGTGTGGTGGACAGCCGCCGCAGCCTGTTGAGCTATGACGGGCTGGACGCCAGCC
GCGCGTTAGCCTTCTTCAACGATGAAGCGGTTGAGCAGGATGAAGAGTCGTTGTTCCTGTGGATGCGCGC
CCATCCGTATGATGATTTAGTGGTGCTGGACGTTACCGCCAGCCAGCAGCTTGCTGATCAGTATCTTGAT
TTCGCCAGCCACGGTTTCCACGTTATCAGCGCCAACAAACTGGCGGGAGCCAGCGACAGCAATAAATATC
GCCAGATCCACGACGCCTTCGAAAAAACCGGGCGTCACTGGCTGTACAATGCCACCGTCGGTGCGGGCTT
GCCGATCAACCACACCGTGCGCGATCTGATCGACAGCGGCGATACTATTTTGTCGATCAGCGGGATCTTC
TCCGGCACGCTCTCCTGGCTGTTCCTGCAATTCGACGGTAGCGTGCCGTTTACCGAGCTGGTGGATCAGG
CGTGGCAGCAGGGCTTAACCGAACCTGACCCGCGTGACGATCTCTCTGGCAAAGACGTGATGCGCAAGCT
GGTGATTCTGGCGCGTGAAGCAGGTTACAACATCGAACCGGATCAGGTACGTGTGGAATCGCTGGTGCCT
GCTCATTGCGAAGGCGGCAGCATCGACCATTTCTTTGAAAATGGCGATGAACTGAACGAGCAGATGGTGC
AACGGCTGGAAGCGGCCCGCGAAATGGGGCTGGTGCTGCGCTACGTGGCGCGTTTCGATGCCAACGGTAA
AGCGCGTGTAGGCGTGGAAGCGGTGCGTGAAGATCATCCGTTGGCATCACTGCTGCCGTGCGATAACGTC
TTTGCCATCGAAAGCCGCTGGTATCGCGATAACCCTCTGGTGATCCGCGGACCTGGCGCTGGGCGCGACG
TCACCGCCGGGGAGATTCAGTCGGATATCAACCGGCTGGCACAGTTGTTGTAA

Figure 40

SEQ ID NO:26

>gi|49175990:3004284-3005474 Escherichia coli str. K-12 substr. MG1655, complete genome ATGATGAAAACTGTTAATGAGCTGATTAAGGATATCAATTCGCTGACCTCTCACCTTCACGAGAAAGATT
TTTTGTTAACGTGGGAACAGACGCCAGATGAACTGAAACAAGTACTGGACGTTGCCGCAGCATTAAAAGC
ACTGCGTGCTGAAAACATCTCAACCAAAGTCTTTAATAGTGGATTAGGTATTTCCGTATTCCGCGACAAC
TCCACCCGTACCCGCTTCTCTTATGCTTCCGCGCTTAACCTGCTCGGCCTTGCACAACAAGATCTCGACG
AAGGCAAATCACAAATCGCTCACGGCGAAACCGTGCGTGAAACCGCCAATATGATCTCCTTCTGCGCCGA
CGCTATTGGTATTCGCGACGATATGTATCTGGGCGCAGGCAACGCCTATATGCGTGAAGTTGGCGCTGCA
CTTGATGACGGTTACAAGCAGGGTGTACTGCCACAGCGTCCGGCTTTAGTGAACCTGCAATGCGATATTG
ACCACCCGACTCAGTCAATGGCTGACCTCGCGTGGTTACGTGAACACTTTGGTTCACTGGAAAACCTGAA

AGGTAAAAAAATCGCCATGACCTGGGCCTACTCTCCAAGCTATGGCAAACCGCTCTCTGTACCACAAGGC

ATCATCGGTCTGATGACTCGCTTCGGTATGGATGTCACCCTGGCCCATCCGGAAGGCTACGACCTGATCC
CGGATGTGGTTGAAGTGGCGAAAAACAATGCTAAAGCCTCCGGTGGTAGCTTCCGTCAGGTCACCAGCAT
GGAAGAAGCCTTCAAAGACGCAGACATCGTTTATCCGAAGTCATGGGCACCTTACAAAGTGATGGAAGAG
CGTACTGAATTGCTGCGTGCGAACGATCACGAAGGCTTAAAAGCACTGGAAAAACAGTGTCTGGCACAGA
ACGCGCAACACAAAGACTGGCATTGTACTGAAGAGATGATGGAACTGACCCGTGATGGCGAAGCCCTGTA
CATGCACTGCCTGCCAGCTGATATCAGCGGCGTATCCTGTAAAGAAGGTGAAGTGACTGAAGGCGTATTC
GAAAAATACCGTATCGCTACCTACAAAGAAGCCAGCTGGAAGCCTTATATCATCGCCGCGATGATCCTGT
CCCGTAAATACGCCAAACCAGGTGCACTGCTCGAGCAACTGCTGAAAGAAGCGCAAGAACGCGTGAAATA
A

Figure 41

SEQ ID NO:27

>gi|49175990:3813791-3814572 Escherichia coli str. K-12 substr. MG1655, complete genome

```
TGCCTTCGCTCCTCATCTTACTTTTCTACAGACAAAAAAAAGGCGACTCATCAGTCGCCTTAAAAATCAG
TTTGCCAGCGCCGCCTTCTGCCGTCCCCTGCACTTCAATGATGCGCCCGTCTTCGGTC
ATCACTACGTTCATGTCGGTCTCTGCGGCAGAGTCTTCAACGTATTCCAGATCGCAAACCGCTTCGCCGT
TCACAATTCCGACAGAAACTGCGGCTACCATCCCTTTCATCGGATTGGTTTTCAGCTTGCCGTTTTCCAC
CAGCTTCTGTAGCGCATCTACCAGCGCCACGCAGGCACCCGTAATCGACGCGGTACGCGTGCCACCATCA
GCCTGAAGCACGTCGCAGTCCAGCGTAATGGTGAACTCACCCAGCGCTTTCAAATCTACTGCCGCGCGAA
GAGCACGGGCGATCAGACGCTGGATTTCCATTGTGCGTCCACCCTGCTTACCTTTCGCCGCTTCACGAGC
GTTACGGGTGTGGGTAGAACGTGGCAGCATGCCGTACTCTGCGGTGATCCAGCCCTGGCCCTGACCTTTC
AGGAAGCGCGGCACGCCTTCTTCAATAGAGGCGGTACACAACACTTTGGTATCGCCAAATTCGACCAGCA
CCGAGCCTTCTGCATGTTTTGTATAGTTACGAGTCAGGGTAACGGGACGCACCTGATTATTGCTACGGCC
TGCTGGACGCAT
```

Figure 42

SEQ ID NO:28

>gi|IS1 Sequence 902 BP

```
      aataaataga ggaatctgat tacttccttc atggggatgc tgaaaagagt agtaattgct    60
      ggtaatgact ccaacttatt gatagtgttt tatgttcaga taatgcccga tgactttgtc   120
      atgcagctcc accgattttg agaacgacag cgacttccgt cccagccgtg ccaggtgctg   180
      cctcagattc aggttatgcc gctcaattcg ctgcgtatat cgcttgctga ttacgtgcag   240
      ctttcccttc aggcgggatt catacagcgg ccagccatcc gtcatccata tcaccacgtc   300
      aaagggtgac agcaggctca taagacgccc cagcgtcgcc atagtgcgtt caccgaatac   360
      gtgcgcaaca accgtcttcc ggagactgtc atacgcgtaa aacagccagc gctggcgcga   420
      tttagccccg acatagcccc actgttcgtc catttccgcg cagacgatga cgtcactgcc   480
      cggctgtatg cgcgaggtta ccgactgcgg cctgagtttt ttaagtgacg taaaatcgtg   540
      ttgaggccaa cgcccataat gcgggctgtt gcccggcatc caacgccatt catggccata   600
      tcaatgattt tctggtgcgt accgggttga gaagcggtgt aagtgaactg cagttgccat   660
      gttttacggc agtgagagca gagatagcgc tgatgtccgg cggtgctttt gccgttacgc   720
      accacccgt cagtagctga acaggaggga cagctgatag aaacagaagc cactggagca   780
      cctcaaaaac accatcatac actaaatcag taagttggca gcatcaccta cctcaatgtg   840
      tatcacaata tccatattct ttgtggggga gtctggagat tgagtagata ttcttgttca   900
      ga
```

Figure 43

SEQ ID NO:29

>gi|IS2 Sequence 1442 BP;

```
     gattccacta atttattcca tgtcacactt ttcgcatctt tgttatgcta tggttatttc      60
     atacctggat ttgcccctat atttccagac atctgttatc acttaaccca ttacaagccc     120
     gctgccgcag atattcccgt ggcgagcgat aacccagcgc actatgcgga tgccattcgt     180
     tataatgctc gaacgcctct gcaaggttct ttgctgccgt taacccgtct ggtttgggca     240
     tgatactgat gtagtcacgc tttatcgttt tcacgaagct ctctgctatt ccgttactct     300
     ccggactccg caccgccgtg ttcttcggtt caagtcccaa catccgggcg aactggcgtg     360
     tttcattagc ccggtagcat gaaccattat ccgtcagcca ctccactgga gacgacggaa     420
     gatcgttgcc gaagcggcgt tccaccgctc ccagcatgac gtcctgtact gtttcactgt     480
     tgaagccgcc ggtagtgacc gcccagtgca gtgcctcacg atcacagcag tccagcgcga     540
     acgtgacacg cagtctctct ccgttatcac agcagaactc gaacccgtca gagcaccatc     600
     gctgattgct ttctttcacg gccactctgc ctgtatgtgc ccgtttcgat ggcggtacag     660
     caggttttcg ctcaagcaac agcgcattct ggcgcatgat ccggtaaaca cgtttggcat     720
     tgatcgcagg cataccatca agttctgcct gtctgcgaag cagcgcccat acccgacgat     780
     aaccatacgt tggcagctct ccgataacat ggtgtatacg gagaagcaca tccgtatcat     840
     cagtgtgacg actgcggcgg ccatccatcc agtcatcggt tcgtctgaga atgacgtgca     900
     actgcgcacg cgacacccgg agacaacggc tgactaagct tactccccat ccccgggcaa     960
     taagggcgcg tgcgctatcc acttttttgc ccgtccatat tcaacggctt ctttgaggag    1020
     ttcattttcc atcgtttttct tgccgagcag gcgctggagt tctttaatct gcttcatggc    1080
     ggcagcaagt tcagaggcag gaacaacctg ttctccggcg gcgacagcag taagacttcc    1140
     ttcctggtat tgcttacgcc agagaaataa ctggctggct gctacaccat gttgccgggc    1200
     aacgaggagg accgtcatcc ccggttcaaa gctctgctga acaattgcga tcttttcctg    1260
     tgtggtacgc cgtctgcgtt tctccggccc taagacatca atcatctgtt ctccaatgac    1320
     tagtctaaaa actagtatta agactatcac ttatttaagt gatattggtt gtctggagat    1380
     tcaggggggcc agtctaatac cataagccta atggagcgaa ttatgagagt tctggttacc    1440
     gg                                                                   1442
```

Figure 44

SEQ ID NO:30

>gi|IS5  Sequence 1199 BP;

```
    ggaaggtgcg aataagcggg gaaattcttc tcggctgact cagtcatttc atttcttcat      60
    gtttgagccg attttttctc ccgtaaatgc cttgaatcag cctatttaga ccgtttcttc     120
    gccatttaag gcgttatccc cagtttttag tgagatctct cccactgacg tatcatttgg     180
    tccgcccgaa acaggttggc cagcgtgaat aacatcgcca gttggttatc gttttttcagc    240
    aacccccttgt atctggcttt cacgaagccg aactgtcgct tgatgatgcg aaatgggtgc    300
    tccaccctgg cccggatgct ggctttcatg tattcgatgt tgatggccgt tttgttcttg    360
    cgtggatgct gtttcaaggt tcttaccttg ccggggcgct cggcgatcag ccagtccaca    420
    tccacctcgg ccagctcctc gcgctgtggc gcccccttggt agccggcatc ggctgagaca    480
    aattgctcct ctccatgcag cagattaccc agctgattga ggtcatgctc gttggccgcg    540
    gtggtgacca ggctgtgggt caggccactc ttggcatcga caccaatgtg ggccttcatg    600
    ccaaagtgcc actgattgcc tttcttggtc tgatgcatct ccggatcgcg ttgctgctct    660
    ttgttcttgg tcgagctggg tgcctcaatg atggtggcat cgaccaaggt gccttgagtc    720
    atcatgacgc ctgcttcggc cagccagcga ttgatggtct tgaacaattg gcgggccagt    780
    tgatgctgct ccagcaggtg gcggaaattc atgatggtgg tgcggtccgg caaggcgcta    840
    tccagggata accgggcaaa cagacgcatg gaggcgattt cgtacagagc atcttccatc    900
    gcgccatcgc tcaggttgta ccaatgctgc atgcagtgaa tgcgtagcat ggtttccagc    960
    ggataaggtc gccggccatt accagccttg gggtaaaacg gctcgatgac ttccaccatg   1020
    ttttgccatg gcagaatctg ctccatgcgg gacaagaaaa tctctttttct ggtctgacgg   1080
    cgcttactgc tgaattcact gtcggcgaag gtaagttgat gactcatgat gaaccctgtt   1140
    ctatggctcc agatgacaaa catgatctca tatcagggac ttgttcgcac cttccttag   1199
```

Figure 45

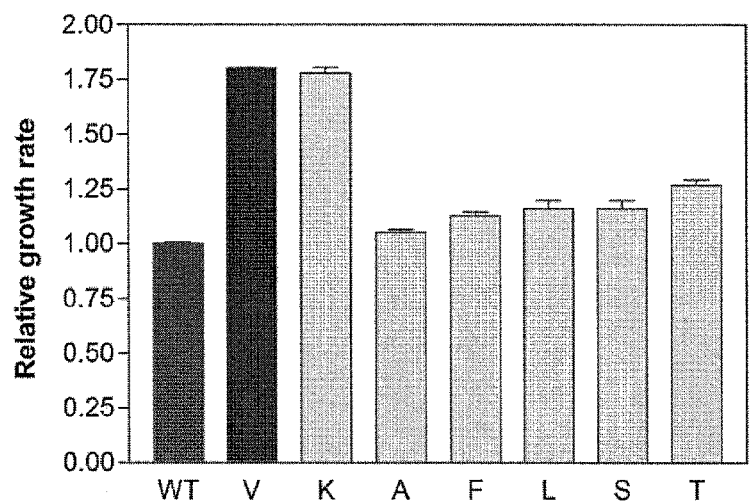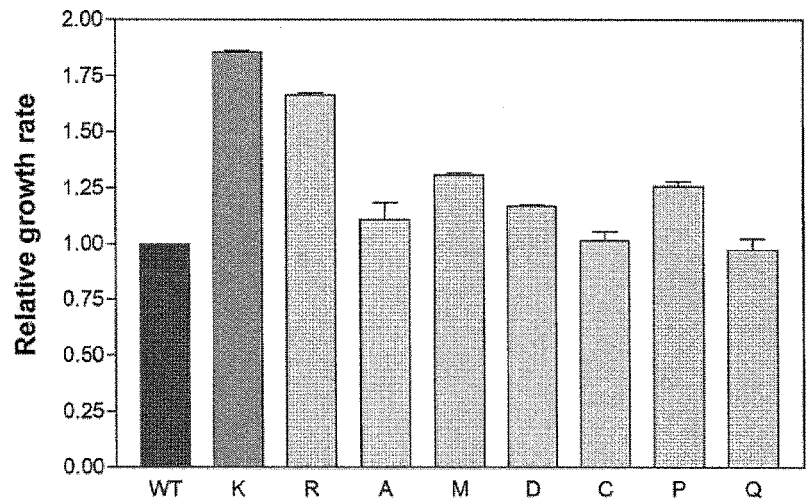
Figure 56

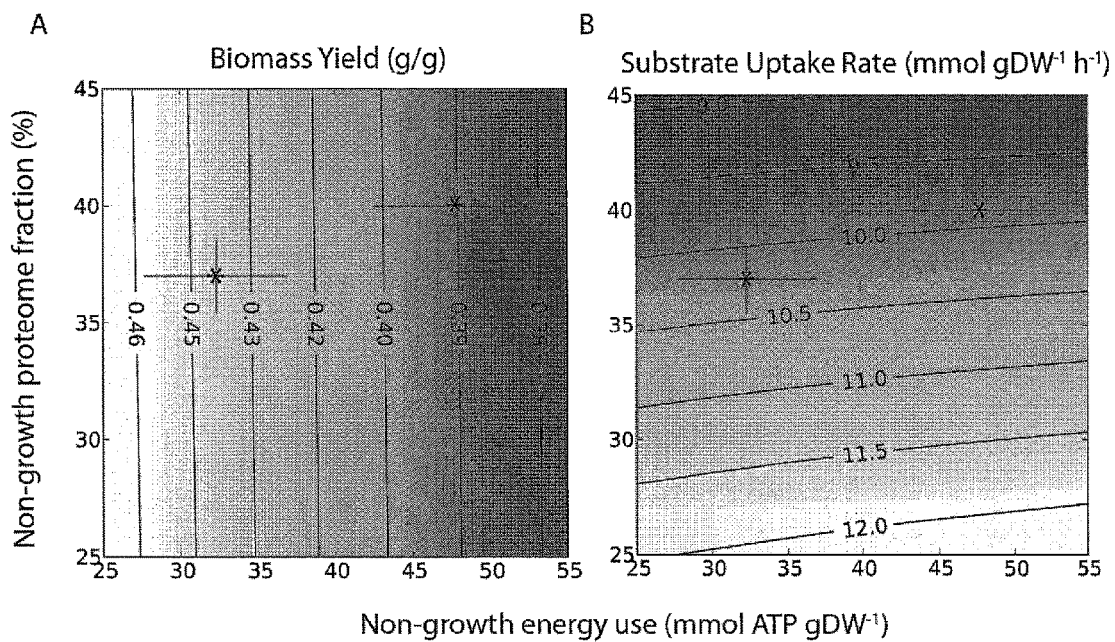
Figure 61: The effects of non-ME protein and energy use on biomass yield and substrate uptake rate. A) Biomass yield is primarily affected by non-growth energy use whereas B) substrate uptake rate is primarily affected by non-growth proteome fraction. The two points indicate wild-type and mutant strains.

US 10,174,307 B2

PERFORMANCE ENHANCING GENETIC VARIANTS OF *E. COLI*

CROSS-REFERENCE TO RELATED APPLICATIONS

This application claims priority to co-pending U.S. provisional Application Ser. No. 62/024,765 filed on Jul. 15, 2014, which is incorporated by reference.

A Sequence Listing has been submitted in an ASCII text file named "18001_ST25.txt," created on May 14, 2018, consisting of 80,252 bytes, the entire contents of which are herein incorporated by reference.

FIELD OF THE INVENTION

The invention provides mutant *Escherichia coli* cells that contain one or more mutations in one or more of the rpoB, hns/tdk, corA, ygaZ, iap, metL, ygeW, and pyrE/rph genes (exemplified in Table 2A and 2B), which confer on the mutant in minimal media the phenotype of increased level of growth and/or increased glucose uptake rate and/or increased acetate production rate and/or increased biomass yield, compared to a control *E. coli* (such as wild type *E. coli*) that lacks the one or more mutations in the one or more genes.

BACKGROUND

Evolution has shaped the biological world as we know and armed with whole genome sequencing, we can now obtain a deeper understand of how organisms adapt inside a laboratory.

What is needed in the art are *Escherichia coli* bacteria that are capable of growth on a commonly available sugar, such as glucose, for several generations.

SUMMARY OF THE INVENTION

The invention provides mutant *Escherichia coli* cells that contain one or more mutations in one or more of the rpoB, hns/tdk, corA, ygaZ, iap, metL, ygeW, and pyrE/rph genes (exemplified in Table 2A and 2B), which confer on the mutant in minimal media the phenotype of increased level of growth and/or increased glucose uptake rate and/or increased acetate production rate and/or increased biomass yield, compared to a control *E. coli* (such as wild type *E. coli*) that lacks the one or more mutations in the one or more genes.

Thus, in one embodiment, the invention provides a mutant *Escherichia coli* cell comprising at least one mutant nucleotide sequence listed as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27. In one embodiment, the mutant has an increased level of growth in minimal media compared to an *Escherichia coli* that lacks said at least one mutant sequence. In one embodiment, the mutant has an increased glucose uptake rate in minimal media compared to an *Escherichia coli* that lacks said at least one mutant sequence. In one embodiment, the mutant has an increased acetate production rate in minimal media compared to an *Escherichia coli* that lacks said at least one mutant sequence. In one embodiment, the mutant has an increased biomass yield in minimal media compared to an *Escherichia coli* that lacks said at least one mutant sequence. In one embodiment, the mutant has an increased production rate of one or more desired product as compared to an *Escherichia coli* that lacks said at least one mutant sequence.

In one embodiment, the invention provides a mutant *Escherichia coli* cell comprising at least one of the following mutations in the rpoB gene and/or at least one of the following mutations indicated in Table 2A and 2B:
  a) genome 4,181,281 G→A mutation,
  b) genome 4,180,904 A→T mutation,
  c) genome 4,181,620 G→T mutation, and
  d) genome 4,182,566 C→A mutation,
wherein said mutant *Escherichia coli* cell has increased growth rate and higher biomass yield per unit glucose in M9 minimal media with glucose as the substrate compared to wild-type *Escherichia coli*. In one embodiment, the mutant that comprises genome 4,181,281 G→A mutation is rpoB E672K. In one embodiment, the mutant that comprises genome 4,180,904 A→T mutation is rpoB E546V. In one embodiment, the mutant that comprises genome 4,181,620 G→T mutation is rpoB D785Y. In one embodiment, the mutant that comprises genome 4,182,566 C→A mutation is rpoB P1100Q.

The invention also provides a method for increasing the growth rate of *Escherichia coli* in minimal media, comprising producing any one or more of the mutant *Escherichia coli* cells described herein. In one embodiment, the method further comprises culturing said mutant in minimal media.

DEFINITIONS

A "Wild-type" cell is a cell found in nature without alteration by the hand of man (such as by chemical and/or molecular biological techniques, etc.).

A "mutant" when in reference to a cell, nucleotide sequence, and amino acid sequence refers to a cell, nucleotide sequence, and amino acid sequence cell, respectively that contains a mutation relative to a wild-type cell, nucleotide sequence, and amino acid sequence, respectively.

The terms "mutation" and "modification" refer to a deletion, insertion, or substitution.

A "deletion" is defined as a change in a nucleic acid sequence or amino acid sequence in which one or more nucleotides or amino acids, respectively, is absent.

An "insertion" or "addition" is that change in a nucleic acid sequence or amino acid sequence that has resulted in the addition of one or more nucleotides or amino acids, respectively.

A "substitution" in a nucleic acid sequence or an amino acid sequence results from the replacement of one or more nucleotides or amino acids, respectively, by a molecule that is a different molecule from the replaced one or more nucleotides or amino acids.

The terms "increase," "elevate," "raise," and grammatical equivalents (including "higher," "greater," etc.) when in reference to the level of any molecule (e.g., glucose, acetate, lactic acid, nucleic acid sequence, amino acid sequence, etc.), cell, and/or phenomenon (e.g., glucose uptake rate, acetate production rate, biomass yield, etc.) in a first sample relative to a second sample, mean that the quantity of the molecule, cell and/or phenomenon in the first sample is higher than in the second sample (or in a treated patient) by any amount that is statistically significant using any art-accepted statistical method of analysis. In one embodiment, the quantity of molecule, cell, and/or phenomenon in the first sample is higher by any numerical percentage, such as at least 10% greater than, at least 25% greater than, at least 50% greater than, at least 75% greater than, and/or at least 90% greater than the quantity of the same molecule, cell and/or phenomenon in a second sample. In yet a further embodiment, the quantity of molecule, cell, and/or phenomenon in the first sample is higher by any numerical amount from 5 fold to 1000 fold, including from 5 fold to 500 fold, 10 fold to 400 fold, from 20 fold to 300 fold, from 30 fold to 200 fold, from 40 fold to 200 fold, from 50 fold to 200 fold.

The terms "decrease," "reduce," "inhibit," "diminish," "suppress," and grammatical equivalents (including "lower," "smaller," etc.) when in reference to the level of any molecule (e.g., glucose, acetate, lactic acid, nucleic acid sequence, amino acid sequence, etc.), cell, and/or phenomenon (e.g., glucose uptake rate, acetate production rate, biomass yield, etc.) in a first sample relative to a second sample, mean that the quantity of molecule, cell, and/or phenomenon in the first sample is lower than in the second sample by any amount that is statistically significant using any art-accepted statistical method of analysis. In one embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in a second sample.

The term "substantially the same" when in reference to the level of any molecule (e.g., glucose, acetate, lactic acid, nucleic acid sequence, amino acid sequence, etc.), cell, and/or phenomenon (e.g., glucose uptake rate, acetate production rate, biomass yield, etc.) in a first sample relative to a second sample, means that the difference in quantity of measurement or phenomenon in the first sample compared to the second sample is not statistically significant.

"Minimal media" and "minimal essential media" are interchangeably used to refer to media for cell culture, which contains only salts and ions and lacks cell extracts, amino acids, nucleotides and other compounds. See Huang et al. (2012) J. Ind. Microbiol. Biotechnol. 39:383-399. Minimal media is exemplified by MOPS minimal media (Teknova, Inc., California) and M9 minimal media (described herein).

"Glucose minimal media" refers to minimal media that contains glucose as the sole carbon source.

"M9 minimal essential media" and "M9 minimal media" are used interchangeably to refer to a medium for culturing cells (Fischer E, Sauer U. "Metabolic flux profiling of *Escherichia coli* mutants in central carbon metabolism using GC-MS." *Eur J Biochem.* 2003 March; 270(5):880-91. PMID: 12603321; Sambrook, J., and D. W. Russell. 2001. Molecular Cloning: A Laboratory Manual 3ed, vol. A2.2. Cold Spring Harbor Laboratory Press, New York), and is commercially available from AMRESCO (Ohio, USA). M9 minimum medium contains salts and trace elements as follows (with exemplary commercial sources for individual components).

M9 Salts (Per Liter):

| 0.8 g | NH$_4$Cl (Sigma Aldrich) |
| 0.5 g | NaCl (Sigma Aldrich) |
| 7.52 g | Na$_2$HPO$_4$ (Sigma Aldrich) |
| 3.0 g | KH$_2$PO$_4$ (Sigma Aldrich) |
| 2 mL | MgSO$_4$ (1M) (Sigma Aldrich) |

-continued

| 1 mL | CaCl$_2$ (100 mM) (Sigma Aldrich) |
| 0.2-0.4% | Glucose (Sigma Aldrich) |

Trace Elements (Per Liter):

| 0.1667 g | FeCl$_3$•6H$_2$O (Sigma Aldrich) |
| 0.0018 g | ZnSO$_4$•7H$_2$O (Sigma Aldrich) |
| 0.0012 g | CuCl$_2$•2H$_2$O (Sigma Aldrich) |
| 0.0012 g | MnSO$_4$•H$_2$O (Sigma Aldrich) |
| 0.0018 g | CoCl$_2$•6H$_2$O (Sigma Aldrich) |
| 0.2225 g | Na$_2$EDTA•2H$_2$O (Sigma Aldrich) |
| 1 ml | Thiamine HCl (1 mg/ml) (Sigma Aldrich) |

In one embodiment, M9 minimal essential media lacks amino acids Ala, Arg, Asn, Asp, Cys, Glu, Gln, Gly, His, Ile, Leu, Lys, Met, Phe, Pro, Ser, Thr, Trp, Tyr, and Val.

"M9-glucose minimal media" refers to M9 minimal essential media that contains glucose as the sole carbon source.

A "control," such as when in reference to a cell, refers to a cell used for comparing to a test cell by maintaining the same conditions in the control cell and test cell, except in one or more particular variable in order to infer a causal significance of this varied one or more variable on a phenomenon.

"Desired product" refers to a chemical (such as commercial chemical, fine chemical, etc.), nutraceutical, and/or biofuel, and is exemplified by those produced in *E. coli*, such as those described in Shin et al., Biotechnology Advances 31 (2013) 925-935; Xu et al., Appl. Microbiol. Biotechnology. (2013) 97:519-539; and Park et al., Trends in Biotechnology (2008) 26(8): 404-412. "Desired product" includes, without limitation, 1,4-Butanediol, Catechol, D-Glucaric acid, L-Homoalanine, p-Hydroxybenzoate, cis,cis-Muconic acid, Phenol, Polylactic acid, Styrene, Bio-ethanol, Sesquiterpene, Vanillin, Formic acid, 2,3-Butanediol, Lycopene, Taxadiene, L-Valine, Polylactic acid, Malic acid, L-Threonine, Succinic acid, Lactic acid, Malonyl-CoA, 1,4-Butanediol, Malonyl-CoA, Isobutanol L-Lysine, L-Lysine, GFP, Triacylglycerol, Daptomycin, Succinic acid, Xylitol, Human antibody Fab fragment, Humanized antibody, Succinic acid, Poly(3-hydroxybutyrate), Human leptin, Lovastatin, and Pantothenate.

BRIEF DESCRIPTION OF THE DRAWINGS

FIG. 1: Fitness trajectories for *E. coli* populations evolved on glucose minimal media. Shown is a plot of the fitness (i.e., the growth rate) of the independently evolved experiments versus the number of cumulative cell divisions (CCD). The strain indicated with a dashed line was classified as a hypermutator. The insert shows the growth rates of the initial four flasks of batch growth in each experiment. Overall, the fitness of the hypermutator population outpaced the non-mutators.

FIG. 2: Phenotypic properties of evolved strains. Clones isolated from the last flask of the experiments (i.e., endpoint strains of non-mutators) and three hypermutator strains were characterized phenotypically. (A) A plot of biomass yield versus glucose uptake rate (UR). The isoclines indicate different growth rates. Of all measured phenotypic traits, the correlations between (B) glucose uptake rate and acetate production rate (PR), and (C) biomass yield and acetate production rate were the strongest. The percent of carbon from glucose being secreted in the form of acetate increased in all of the non-mutator endpoint strains (18-22%) except for one (13%), as compared to wild-type (15%). This percent decreased for all of the hypermutator strains (8-13%).

FIG. 4: Fitness Trajectory for the Validation ALE. Shown is a plot of the validation ALE where three unique starting strains were evolved in biological triplicate, each harboring one of the following mutations: rpoB E546V, rpoB E672K, and pyrE/rph Δ82 bp. The increase in fitness is shown as a function of the cumulative cell divisions (CCD). The insert shows the unsmoothed and filtered growth rates of the beginning of the experiment to show any possible physiological adaptation that is characteristic of ALE experiments. A smoothing spline will often obscure such abrupt changes.

FIG. 5: Casual Mutation Analysis. Shown is a bar graph of the physiologically adapted growth rates of strains harboring key mutations identified in this work. The error bars represent 95% confidence intervals. This shows that the mutation in metL and the IS1 insertion between hns/tdk are causal in the presence of the additional mutations shown. The strain with metL also had one additional mutation, but this was not observed in any other sequenced metL mutant from the ALE experiment. It is clear from the fastest growing mutant, with growth 1.3 fold higher than the wild-type, how significantly the pyrE/rph and rpoB mutations can affect growth rate.

FIG. 6: Commonly differentially expressed genes. (A) The number of differentially expressed genes (with respect to the wild-type strain) common across evolved strains is indicated. Increased and decreased expression genes are counted separately to ensure the direction of change is conserved across strains. The y-axis indicates the number of genes differentially expressed in exactly the number of strains indicated on the x-axis. From this, 448 increased and 383 decreased genes are identified as common to at least 6 strains, whereas one would expect no genes in common to all six by random chance. (B) The commonly differentially expressed genes' functions are interrogated using annotated Clusters of Orthologous Groups (COGs). COGs over-represented in either the up-regulated or down-regulated gene sets were identified with a hypergeometric test ($p<0.05$; see Methods). The percentage and number of genes for the identified COGs is indicated in the bar chart. Asterisk indicates over-represented.

FIG. 7: Comparison of genome-scale modeling predictions and categorization of commonly differentially expressed genes. (A) The commonly differentially expressed genes were compared to a gene classification obtained by a genome-scale model of *E. coli* (38). Growth rate is optimized in the same glucose aerobic batch conditions as used in the ALE experiment. Simulation results can be used as an additional characterization of gene content (x-axis). Overall, differentially expressed genes are more enriched in the set of genes predicted to enable an optimal growth phenotype (top). Furthermore, within the differentially expressed set of genes, those which increased in expression versus wild-type are enriched within the predicted set of genes which enable an optimal growth phenotype (bottom). (B) Using the combination of in silico predicted genes and COGS for categorization, subsets of genes could be identified which enabled the observed optimal states of the evolved strains on the pathway level.

FIG. 8: Mapping mutations in protein structure.

FIG. 10: rpoB E546V mapping in RNAP model.

FIG. 14: Δ82 bp deletion in pyrE/rph penetration by PCR—Populations from the final flask of the validation ALE were probed for the presence of the Δ82 bp deletion in pyrE/rph. The upper band shows wild-type genotype and the lower band shows a deletion in pyrE/rph. Low molecular weight ladders were run on the outermost lanes (N04745 from Bio Labs). When clones were sequenced from these populations, rpoB E546V #1 showed no mutations in pyrE/rph and rpoB E546V #3 showed only a Δ1 bp deletion in pyrE/rph which would not be resolved from the wild-type band in the gel. Though not observed in all the clones, the PCR results clearly show that a ~Δ82 bp deletion in pyrE/rph exists in all the final populations. Based on the relative intensities of the bands, the degree to which the 82 bp deletion has penetrated the culture varies. Specifically, in the populations where the clones did not show the 82 bp deletion, the wild-type band shows greater intensity than the mutant band, thus corroborating why we did not see the Δ82 bp deletion in the clone sequences.

FIG. 16 shows the nucleotide sequence (SEQ ID NO:1) of an exemplary rpoB gene mutation: E672K (GAA→AAA) (See Table 2B).

FIG. 17 shows the nucleotide sequence (SEQ ID NO:2) of an exemplary rpoB gene mutation: P1100Q (CCG→CAG) (See Table 2B).

FIG. 18 shows the nucleotide sequence (SEQ ID NO:3) of an exemplary rpoB gene mutation: E546V (GAA→GTA) (See Table 2B).

FIG. 19 shows the nucleotide sequence (SEQ ID NO:4) of an exemplary rpoB gene mutation: H673Y (CAC→TAC) (See Table 2B).

FIG. 20 shows the nucleotide sequence (SEQ ID NO:5) of an exemplary rpoB gene mutation: L671P (CTG→CCG) (See Table 2B).

FIG. 21 shows the nucleotide sequence (SEQ ID NO:6) of an exemplary rpoB gene mutation: D785Y (GAC→TAC) (See Table 2B).

FIG. 22 shows the nucleotide sequence (SEQ ID NO:7) of an exemplary hns/tdk gene mutation: intergenic (114/487) IS2 (See Table 2B). Note highlighted position 1,292,259 IS2 (+) +5 bp intergenic (−114/−487). These 5 bp (in bold) are duplicated and IS2 (SEQ ID NO:29) (underlined) of FIG. 44 is inserted between them.

FIG. 23 shows the nucleotide sequence (SEQ ID NO:8) of an exemplary hns/tdk gene mutation: intergenic (110/488) IS1 (See Table 2B). Note highlighted position 1,292,255 IS1 (−) +8 bp intergenic (−110/−488). These 8 bp (in bold) are duplicated and IS1 (SEQ ID NO:28) (underlined) of FIG. 43 is inserted in between them.

FIG. 24 shows the nucleotide sequence (SEQ ID NO:9) of an exemplary hns/tdk gene mutation: intergenic (274/328) IS5 (See Table 2B). Note highlighted position 1,292,419 IS5 (+) +4 bp intergenic (−274/−328). These 4 bp (in bold) are duplicated and IS5 (SEQ ID NO:30) (underlined) of FIG. 45 is inserted between the duplicates.

FIG. 25 shows the nucleotide sequence (SEQ ID NO:10) of an exemplary hns/tdk gene mutation: intergenic (86/511) IS1 (See Table 2B). Note highlighted position 1,292,231 IS1 (+) +9 bp intergenic (−86/−511). These 9 bp (in bold) are duplicated and IS1 (SEQ ID NO:28) (underlined) of FIG. 43 is inserted in between them.

FIG. 26 shows the nucleotide sequence (SEQ ID NO:11) of an exemplary hns/tdk gene mutation: intergenic (67/531) IS1 (See Table 2B). Note highlighted position 1,292,212 IS1 (+) +8 bp intergenic (−67/−531). These 8 bp (in bold) are duplicated and IS1 (SEQ ID NO:28) (underlined) of FIG. 43 is inserted between the duplicates.

FIG. 27 shows the nucleotide sequence (SEQ ID NO:12) of an exemplary hns/tdk gene mutation: intergenic (93/505) IS1 (See Table 2B). Note highlighted position 1,292,238 IS1 (−) +8 bp intergenic (−93/−505). These 8 bp (in bold) are duplicated and IS1 (SEQ ID NO:28) (underlined) of FIG. 43 is inserted in between them.

FIG. 28 shows the nucleotide sequence (SEQ ID NO:13) of an exemplary hns/tdk gene mutation: intergenic (258/344) IS5 (See Table 2B). Note highlighted position 1,292,403 IS5 (+) +4 bp intergenic (−258/−344). These 4 bp (in bold) are duplicated and IS5 (SEQ ID NO:30) (underlined) of FIG. 45 is inserted between them.

FIG. 29 shows the nucleotide sequence (SEQ ID NO:14) of an exemplary corA gene mutation: coding (726 728/951 nt) Δ3 bp (See Table 2B).

FIG. 30 shows the nucleotide sequence (SEQ ID NO:15) of an exemplary corA gene mutation: coding (220 224/951 nt) Δ5 bp (See Table 2B).

FIG. 31 shows the nucleotide sequence (SEQ ID NO:16) of an exemplary corA gene mutation: Δ206V (GCG→GTG) (See Table 2B).

FIG. 32 shows the nucleotide sequence (SEQ ID NO:17) of an exemplary corA gene mutation: coding (113 211/951 nt) Δ99 bp (See Table 2B).

FIG. 33 shows the nucleotide sequence (SEQ ID NO:18) of an exemplary corA gene mutation: coding (668/951 nt) duplication 21 bp (See Table 2B).

FIG. 34 shows the nucleotide sequence (SEQ ID NO:19) of an exemplary ygaZ gene mutation: coding (529 532/738 nt) IS5 (See Table 2B). Note highlighted position 2,808,167. These 4 bp (in bold) are duplicated and IS5 (SEQ ID NO:30) (underlined) of FIG. 45 is inserted between the duplicates.

FIG. 35 shows the nucleotide sequence (SEQ ID NO:20) of an exemplary ygaZ gene mutation: coding (307 316/738 nt) Δ10 bp (See Table 2B).

FIG. 36 shows the nucleotide sequence (SEQ ID NO:21) of an exemplary ygaZ gene mutation: E49* (GAA→TAA) (See Table 2B).

FIG. 37 shows the nucleotide sequence (SEQ ID NO:22) of an exemplary ygaZ gene mutation: coding (262/738 nt) 19 bp×2 (See Table 2B).

FIG. 38 shows the nucleotide sequence (SEQ ID NO:23) of an exemplary iap gene mutation: coding (98-101/1038 nt) IS5 (See Table 2B). These 4 bp (in bold) are duplicated and IS5 (SEQ ID NO:30) (underlined) of FIG. 45 is inserted in between them.

FIG. 39 shows the nucleotide sequence (SEQ ID NO:24) of an exemplary metL gene mutation: coding (1338/2433 nt) Δ1 bp (See Table 2B).

FIG. 40 shows the nucleotide sequence (SEQ ID NO:25) of an exemplary metL gene mutation: Δ798E (GCG→GAG) (See Table 2B).

FIG. 41 shows the nucleotide sequence (SEQ ID NO:26) of an exemplary ygeW gene mutation: S200R (AGC-→CGC) (See Table 2B).

FIG. 42 shows the nucleotide sequence (SEQ ID NO:27) of an exemplary pyrE/rph gene mutation: intergenic (−90/+5) Δ82 bp (See Table 2B).

FIG. 43 shows the nucleotide sequence (SEQ ID NO:28) of IS1 (See Table 2B).

FIG. 44 shows the nucleotide sequence (SEQ ID NO:29) of IS2 (See Table 2B).

FIG. 45 shows the nucleotide sequence (SEQ ID NO:30) of IS5 (See Table 2B).

FIG. 56: Relative growth rate change of ALE and MAGE selected mutations.

FIG. 61: The effects of non-ME protein and energy use on biomass yield and substrate uptake rate. A) Biomass yield is primarily affected by non-growth energy use whereas B) substrate uptake rate is primarily affected by non-growth proteome fraction. The two points indicate wild-type and mutant strains.

DETAILED DESCRIPTION OF THE INVENTION

Figure 3:
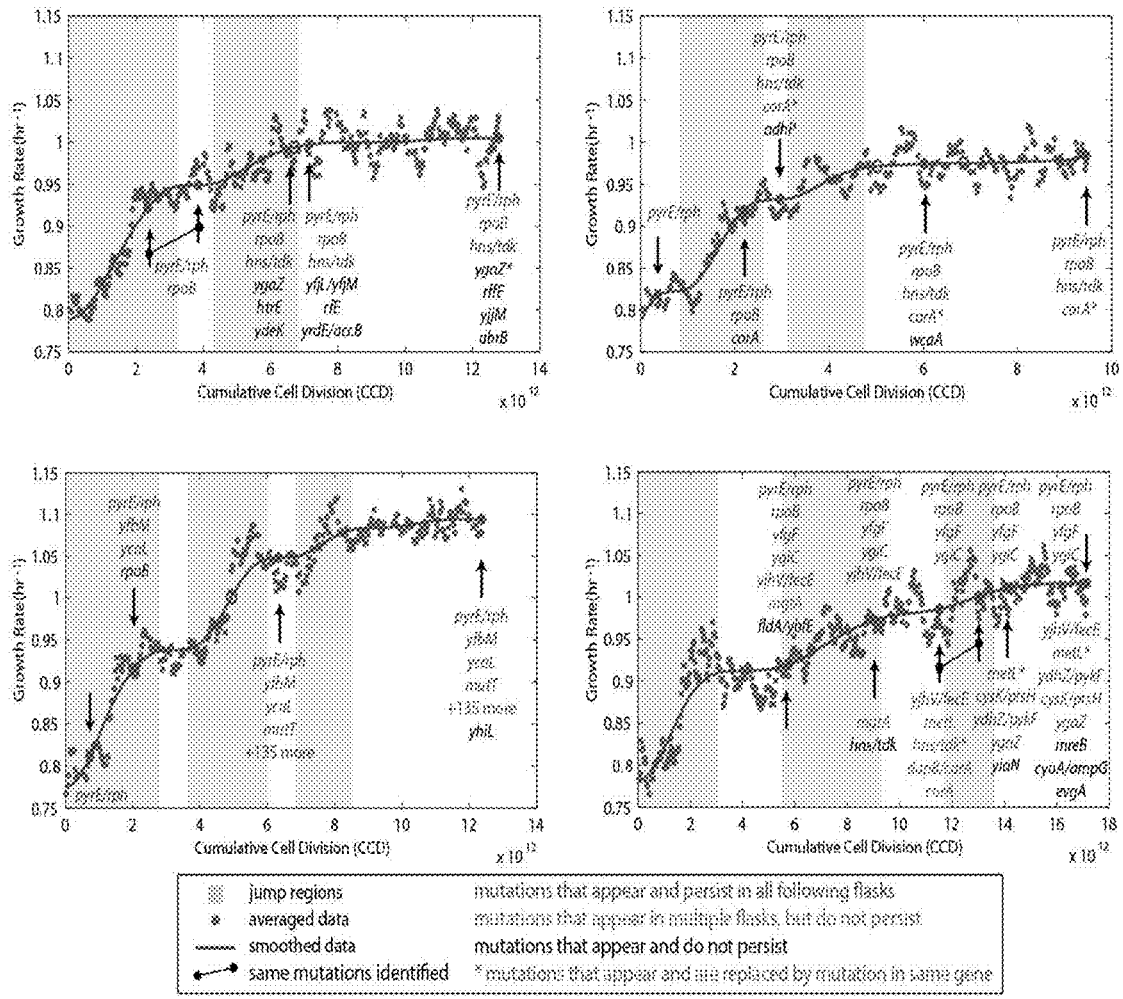
FIG. 3: The fitness trajectories of ALE experiments 3, 4, 7, and 10 along with identified jump regions and resequencing data. Shown is the fitness increases over the course of the evolution as a function of cumulative cell divisions (CCD) and the jump regions (grey boxes) identified using the outlined algorithm. Arrows indicate where colonies were isolated and resequenced. Mutations are categorized by color: those which occurred and were found in each subsequent colony resequencing (green), those which appear in colonies from multiple flasks but not consecutively (blue), and those which were only found in one particular clone and not in subsequent clones (black). Further, mutations that occur in genes that replace a mutation identified in the same gene are marked with an asterisk. All of the mutations from the hypermutator strain that arose in experiment 7 are not shown (more than 135 total mutations).
Figure 9:
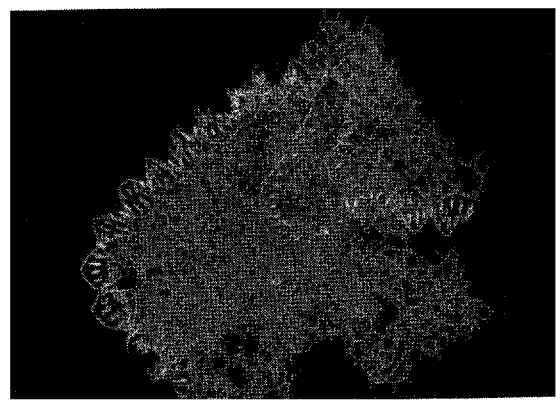
FIG. 9: rpoB E672K mapping in RNAP model.
Figure 11:
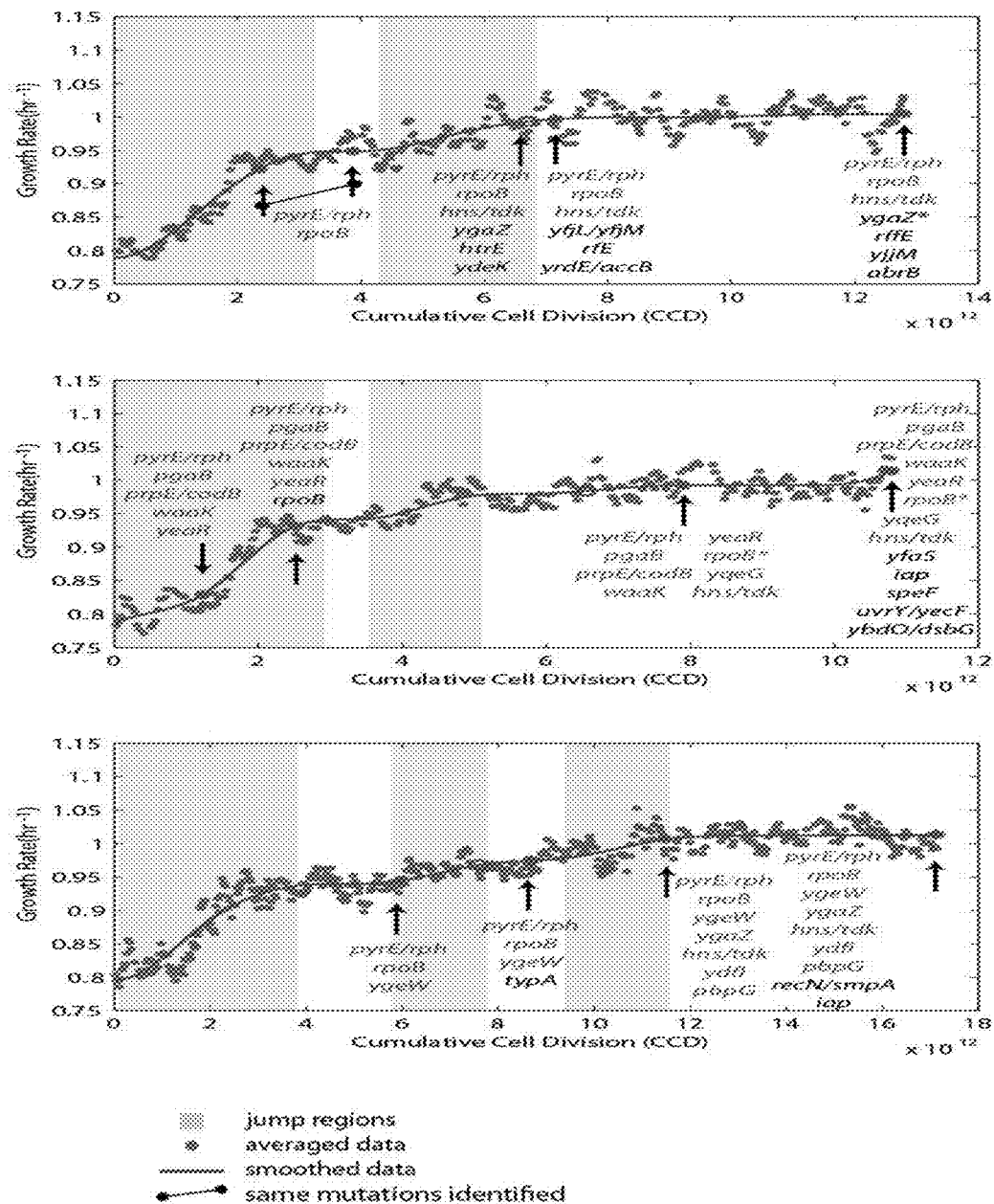
FIG. 11: Plots of the identified jump regions and mutations found in clones isolated at various points along the ALE experiments. Jump regions were identified by first smoothing the data using a cubic spline interpolation then finding regions where the derivative was above a certain threshold. Jumps identified that were not longer than 4 days were not accepted. Jumps were ranked according to their increase in growth rate and the length of jump, favoring short jumps with large increases. The green dots indicated locally averaged data before smoothing was applied.
Figure 11:
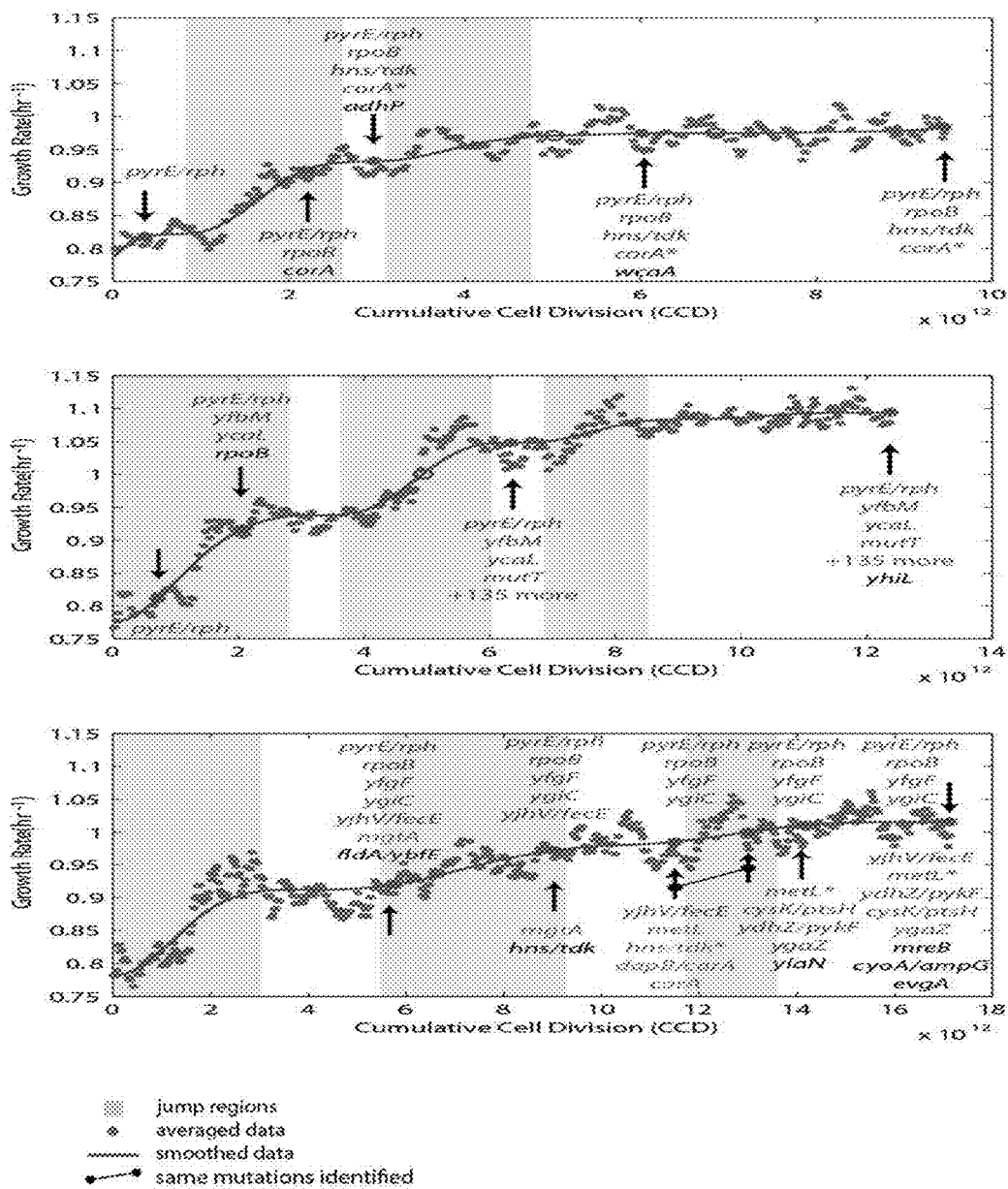
Figure 11:
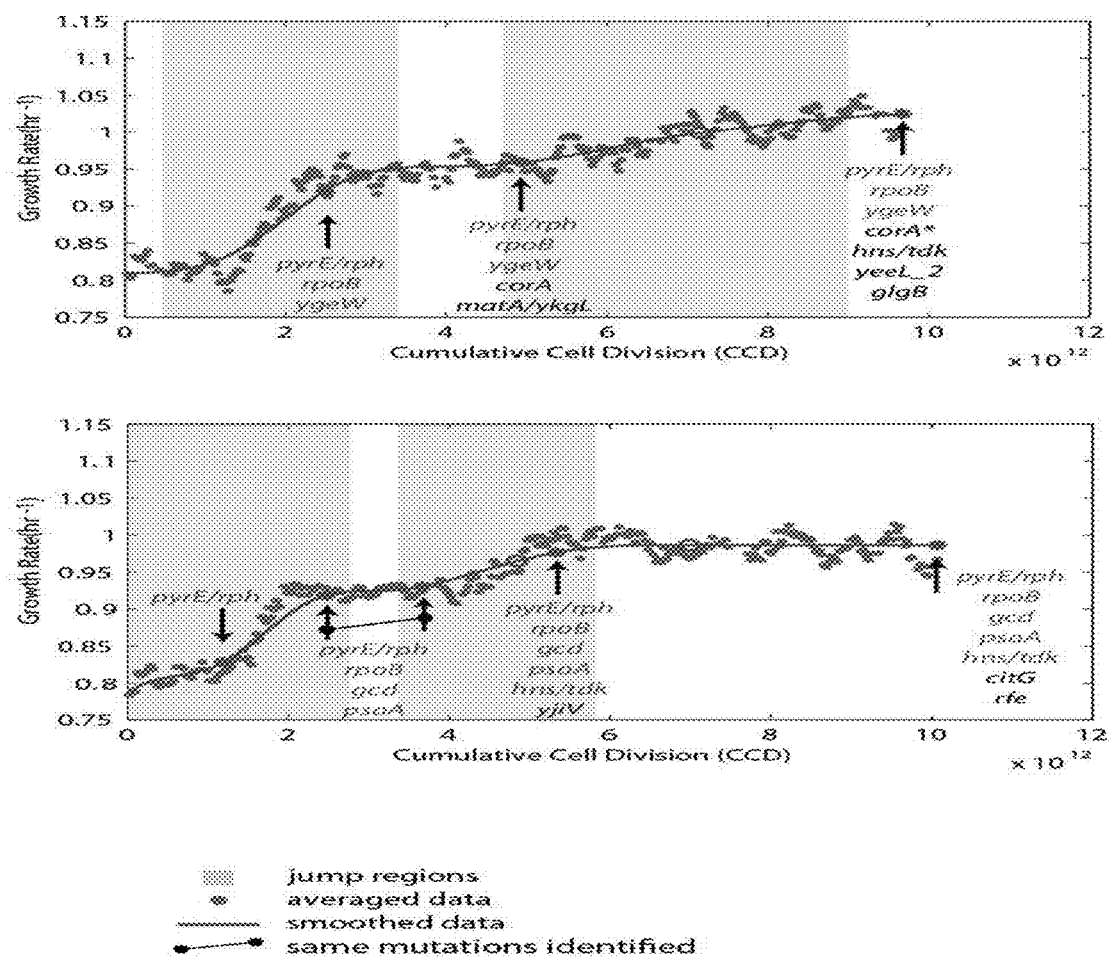
Figure 12:
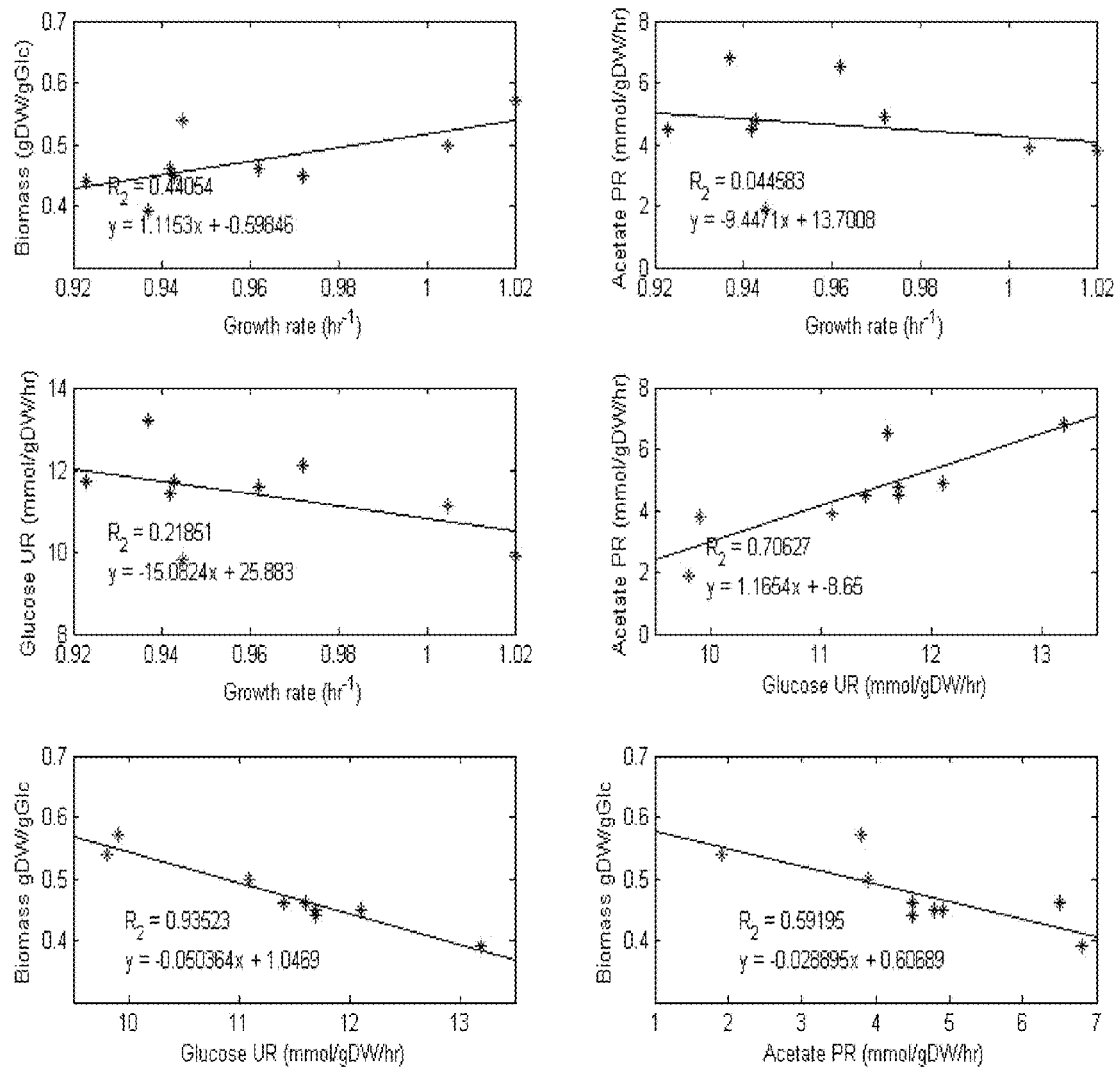
FIG. 12: Pairwise comparisons of all phenotypic data were made for each endpoint isolate. Biomass Yield vs Glucose uptake rate (GUR) and GUR vs Acetate production rate were the most highly correlated.
Figure 13:
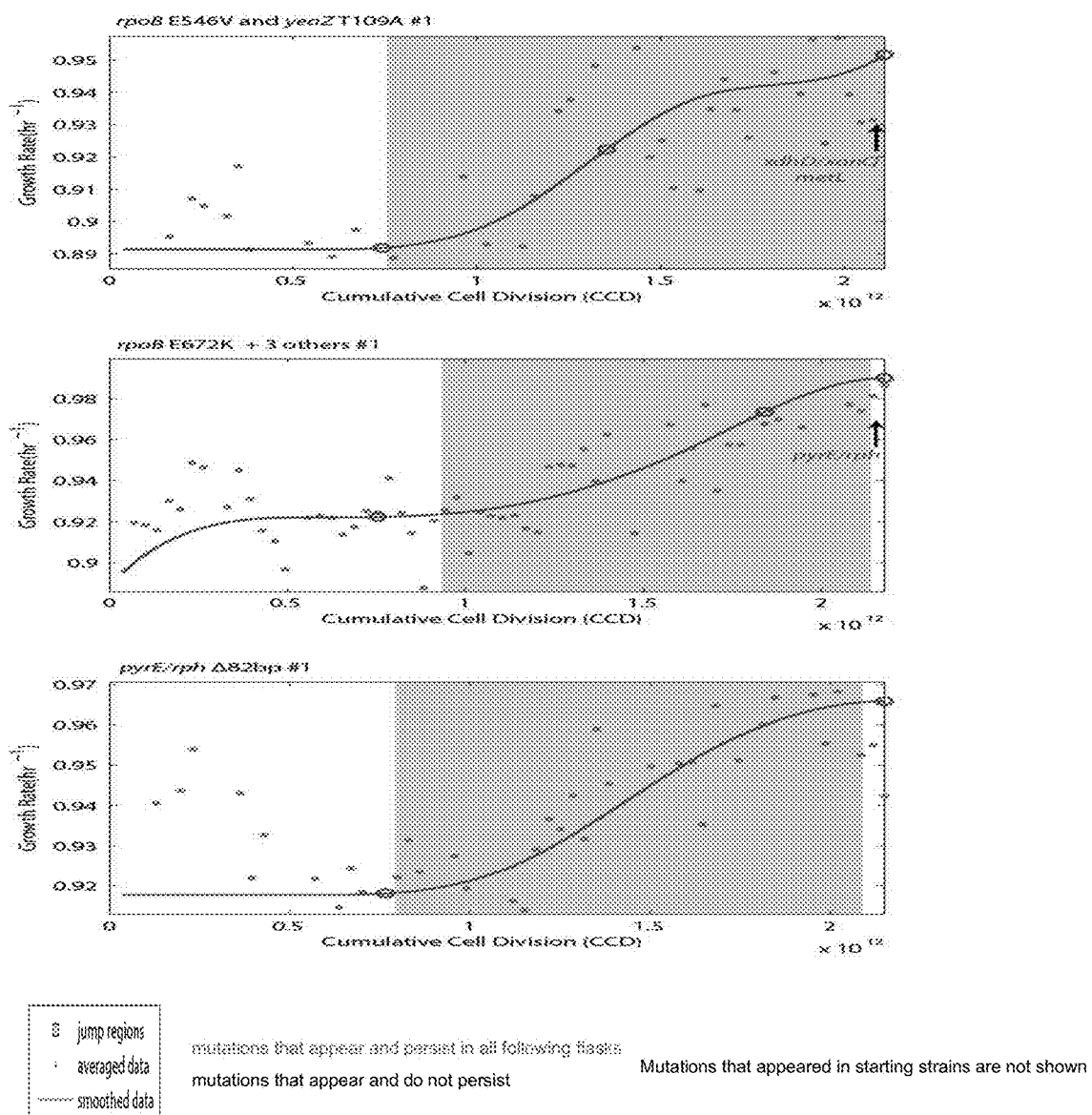
FIG. 13: Validation ALE Jumps and Sequences—Prepared in the same fashion as described but with the dataset from the validation ALE.
Figure 13:
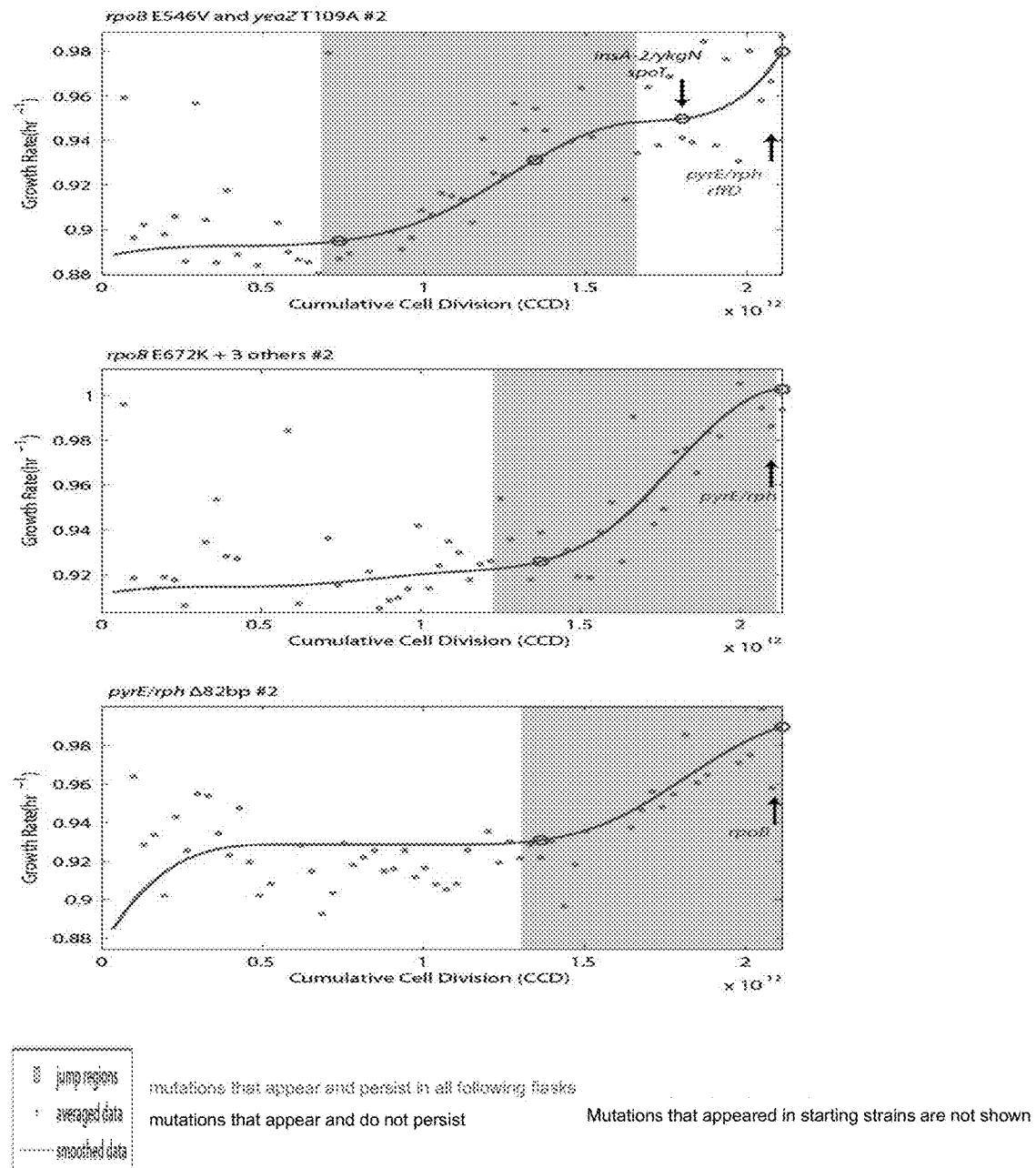
Figure 13:
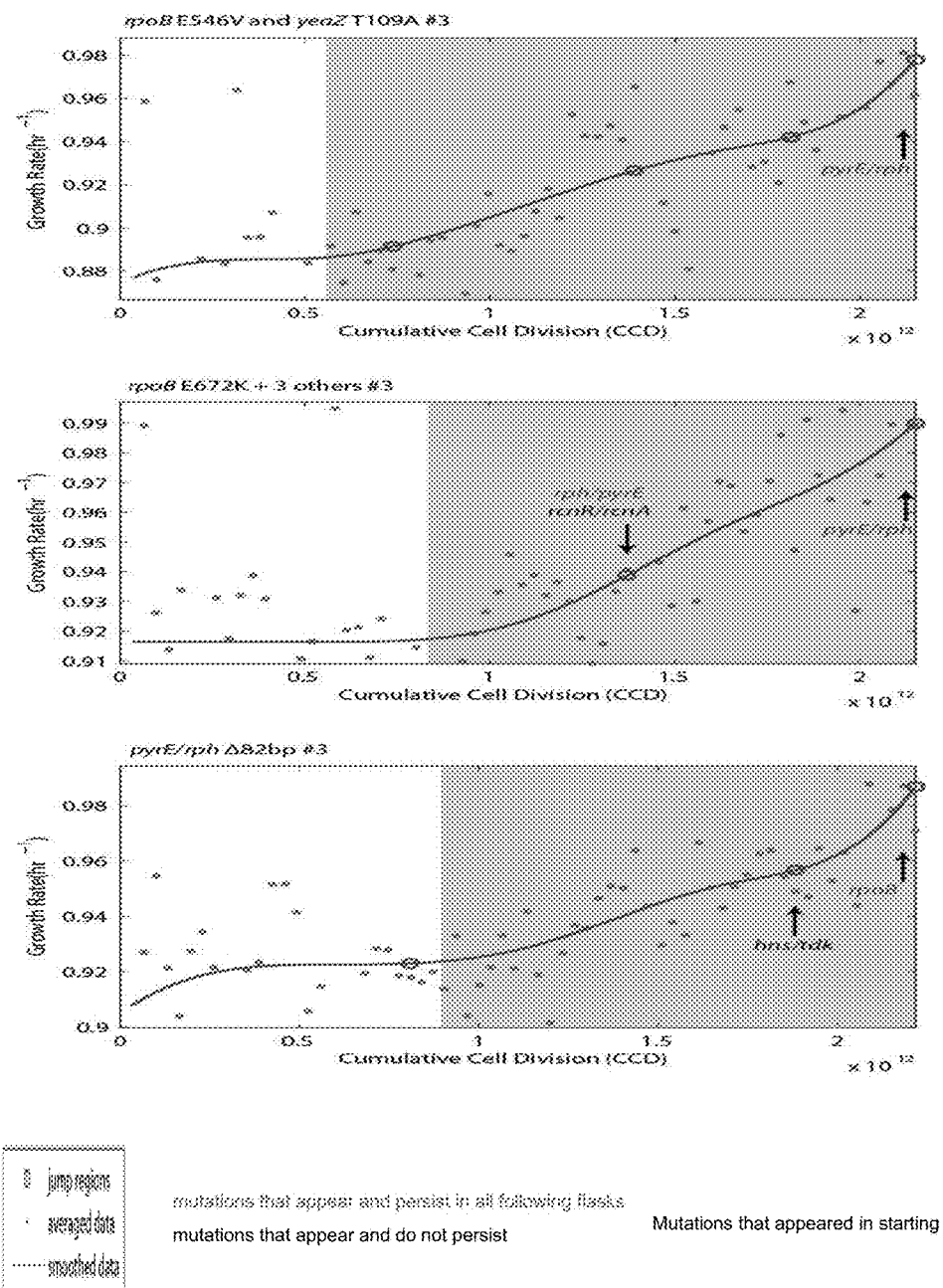
Figure 15:
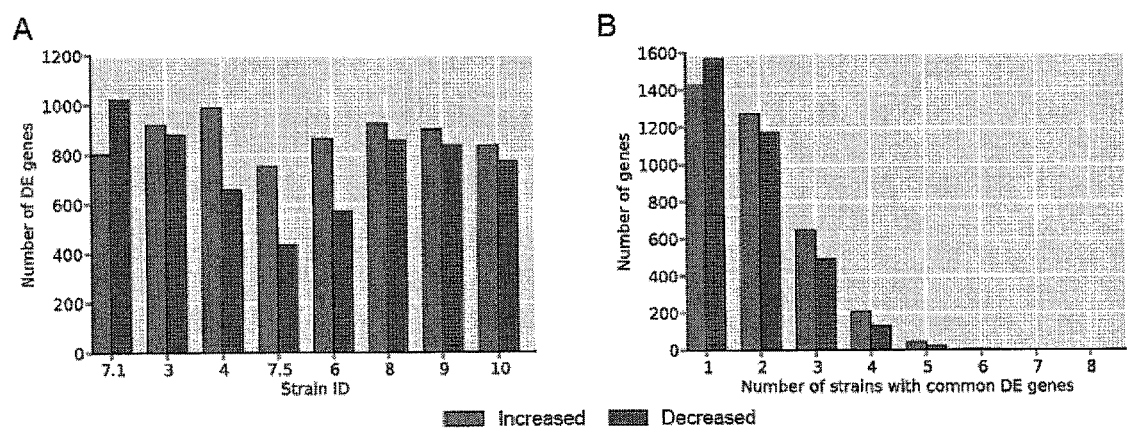
FIG. 15: Transcriptomic Data: Enriched Differentially Expressed Protein coding Genes from Evolved Strains. (A) The Differentially expressed genes from each strain. (B) Distribution of differentially expressed genes if expression was randomized.

The invention provides mutant *Escherichia coli* cells that contain one or more mutations in one or more of the rpoB, hns/tdk, corA, ygaZ, iap, metL, ygeW, and pyrE/rph genes (exemplified in Table 2A and 2B), which confer on the mutant in minimal media (exemplified by M9-minimal media) in the presence or absence of a carbon source such as glucose, the phenotype of increased level of growth and/or increased glucose uptake rate and/or increased acetate production rate and/or increased biomass yield, compared to a control *E. coli* (such as wild type *E. coli*) that lacks the one or more mutations in the one or more genes.

The invention provides a mutant *Escherichia coli* cell comprising at least one mutant nucleotide sequence listed as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27. The invention's mutants are further described in Table 2A, 2B and 2C.

The invention's mutants are useful for production of an increased number of *E. coli* cells for further genetic and/or metabolic modification and/or for generating *E. coli* that is capable of more efficient use of glucose in the culture medium and/or for generating *E. coli* that is capable of producing higher levels of acetate.

In one embodiment, the mutant has an increased level of growth in minimal media (exemplified by M9-minimal media) in the presence or absence of a carbon source such as glucose, compared to an *Escherichia coli* that lacks said at least one mutant sequence. Data herein shows that growth rates of *E. coli* were determined by the output of the interpolated cubic spline used, unless stated otherwise. Example 3 and Table 1 show that the growth rate of the mutants of Table 2 in minimal media (exemplified by M9-minimal media) in the presence or absence of a carbon source such as glucose, increased in the range from 1.42-1.59 compared to wild type *E. coli*. Example 3 and FIG. 2 show the increase in fitness (i.e., growth rate) of the mutants of Table 2 in minimal media (exemplified by M9-minimal media) in the presence or absence of a carbon source such as glucose, was 1.29-1.46 fold compared to wild type *E. coli*.

In one embodiment, the mutant has an increased glucose uptake rate in minimal media (exemplified by M9-minimal media) in the presence or absence of a carbon source such as glucose, compared to an *Escherichia coli* that lacks said at least one mutant sequence. Example 3 and FIG. 2 show that the mutants of Table 2 grown in minimal media (exemplified by M9-minimal media) in the presence or absence of a carbon source such as glucose, exhibited increased glucose uptake rates (GUR) compared to wild-type *E. coli* (except for one strain where the APR decreased), and that there was a correlation between the increase observed in the glucose uptake rate (GUR) and acetate production rate (APR) (FIG. 2B). Of all measured phenotypic traits, the correlation between glucose uptake rate and acetate production rate (PR) was one of the strongest.

In a further embodiment, the mutant has an increased acetate production rate in minimal media (exemplified by M9-minimal media) in the presence or absence of a carbon source such as glucose, compared to an *Escherichia coli* that lacks said at least one mutant sequence. Example 3 and FIG. 2 show that the mutants of Table 2 grown in minimal media (exemplified by M9-minimal media) in the presence or absence of a carbon source such as glucose, exhibited an increase in the acetate production rates (APR) compared to wild-type *E. coli* (except for one strain where the APR decreased), and that there was a correlation between the increase observed in the glucose uptake rate (GUR) and acetate production rate (APR) (FIG. 2B). Of all measured phenotypic traits, the correlation between glucose uptake rate and acetate production rate (PR) was one of the strongest.

In another embodiment, the mutant has an increased biomass yield in minimal media (exemplified by M9-minimal media) in the presence or absence of a carbon source such as glucose, compared to an *Escherichia coli* that lacks said at least one mutant sequence. Biomass yield ($Y_{X/S\_ss}$) is calculated as the quotient of the growth rate and glucose uptake rates during the exponential growth phase. Example 3 and FIG. 2C show that the mutants of Table 2 grown in minimal media (exemplified by M9-minimal media) in the presence or absence of a carbon source such as glucose, exhibited a correlation between biomass yield and acetate production rate (APR). Of all measured phenotypic traits, the correlation between biomass yield and acetate production rate was one of the strongest.

The invention also provides methods for increasing the growth rate of *Escherichia coli* in minimal media (exemplified by M9-minimal media) in the presence or absence of a carbon source such as glucose, comprising producing any one or more of the mutant *Escherichia coli* cells described herein. Methods for introducing mutations are known in the art, including, without limitation, homologous recombination, knockin of a nucleotide sequence, and/or knockout of a nucleotide sequence. In one embodiment, the method further comprises culturing said mutant in minimal media (exemplified by M9-minimal media) in the presence or absence of a carbon source such as glucose.

The invention is further described under the headings (1) Adaptive laboratory evolution (ALE) for generation of mutants, (2) *Escherichia coli* mutants described in Examples 1-7, and (3) Further characterization of exemplary mutants described in Examples 8-15.

(1) Adaptive Laboratory Evolution (ALE) for Generation of Mutants

Adaptive laboratory evolution (ALE) has emerged as an effective tool for answering basic scientific questions and addressing biotechnological needs. Much of ALE's utility is derived from fitness increases that can be reliably obtained, though the speed and extent of these gains depend on the protocol utilized. Identifying causal genetic changes and their combinatorial effects is challenging and time-consuming Understanding how these genetic changes enable increased fitness can be difficult. Here, a series of approaches that address each of these challenges was developed and demonstrated using Escherichia coli K-12 MG1655 on glucose minimal media at 37° C.—a canonical laboratory strain and growth condition. By keeping E. coli in constant substrate-excess and exponential growth, fitness increases up to 1.6-fold were obtained over wild-type. These increases are comparable to previously-reported maximum growth rates in similar conditions and were obtained over a relatively short experiment time (~30 days). Across the 8 replicate ALE experiments performed, putatively causal mutations were identified with two approaches: identifying mutations in the same gene/region across replicate independent experiments and sequencing strains before and after computationally-determined fitness jumps. Allelic replacement coupled with further targeted ALE of reconstructed strains was used to confirm casualty of Exemplary mutations. Three genetic regions were most often mutated: the global transcription gene rpoB, an 82 bp deletion between the metabolic pyrE gene and rph, and an IS element between the DNA structural gene has and tdk. A model-derived classification of gene expression revealed a number of processes important for increased growth that were missed using a gene classification system alone. The methods put forth here represent a powerful combination of approaches and technologies to increase the speed and efficiency of ALE studies. The identified mutations can be examined as genetic parts for increasing growth rate in a desired strain and for understanding rapid growth phenotypes.

Using sequencing, we were able to find a set of reproducibly occurring genetic changes that enabled E. coli to grow at an increased rate. The findings were further confirmed by re-introducing the specific mutations we found into the genomes of the un-evolved cells using cell engineering molecular biology techniques. We also found that although cells typically increased in growth rate to similar levels, they achieved this increased fitness through different means. Specifically, we identified sets of, as well as individual mutations that increased biomass yield and/or increased uptake rate of glucose significantly. Further, we were able to genome-scale models to understand which internal pathways enabled the faster growth rates. These mutations can be used as parts to be introduced into strains to enable similar phenotypes as those displayed here.

The specific mutations identified in the rpoB genes in E. coli:
rpoB E672K (genome 4,181,281 G→A)
rpoB E546V (genome 4,180,904 A→T)
enable an increased growth rate and higher biomass yield per unit glucose over wild-type in minimal media with glucose as the substrate.

A similar mutation have been identified, through knock-in and screening:
rpoB D785Y (genome 4,181,620 G→T)
rpoB P1100Q (genome 4,182,566 C→A)

The specific mutations have not been previously reported and they enable an increased growth rate and biomass efficiency, both desirable attributes for bioprocessing using E. coli.

The mutations have an effect on the growth rate of E. coli in glucose minimal media (M9 minimal media) by increasing the growth rate. Specifically, the mutations we have tested:
rpoB E672K (genome 4,181,281 G→A)
rpoB E546V (genome 4,180,904 A→T)
as compared to 'BOP27', which is wild-type E. coli K-12 MG1655. These mutations have the impact of increasing the growth rates and biomass yield. See, FIGS. 2 and 5.

The rpoB strains have been constructed in vivo and exist as a frozen stock at −80C. The strains can be recultured and grown from this stock and it has been demonstrated to retain its growth characteristics. The strain is a physical cell.

The rpoB mutation strains can be used as a platform strain to generate a number of products.

(2) Escherichia coli Mutants Described in Examples 1-7

Adaptive laboratory evolution was utilized to explore optimal growth of E. coli K-12 MG1655 on glucose minimal media. This combination of organism and media conditions is arguably the most widely-used in basic science and biotechnology applications (59). Multiple parallel experiments were performed to use as comparison points for the overall process. The ALE was performed by propagating batch cultures during exponential growth phase where the passage volume was intentionally kept at a relatively large amount and held constant throughout the experiment. This is different from previous ALE studies where passage volume was generally decreased as the growth rate increased (45). The intent was to isolate the growth rate as the only selection pressure and remove any bottlenecks associated with a lower passage size. The results show that the large increases in growth rates observed here are achieved over a significantly shorter time-frame (44). This finding can be put into context as with stationary phase batch culture propagation, any fixed mutated genetic regions could very well be causal for a secondary selection to growth rate (e.g., lag phase duration). The strains produced by this experiment were screened for their phenotype, genotype, and transcriptome. Genome-scale models were used to analyze the results of these screens. Accordingly, the major findings from this work are: i) passing larger volumes strictly in exponential phase batch culture can increase the rate of selection for improved fitness, ii.) the identification of Exemplary reproducibly-occurring mutations that enable higher growth rates for E. coli K-12 MG1655 under glucose minimal media conditions, iii.) apparent optimal phenotypes can be realized through modification of different mechanisms, and iv.) optimal phenotypic states, as probed through transcriptomic assays, are in good agreement with predicted cellular states from genome-scale modeling, and categorization with modeling results reveal drivers for the optimal phenotypes on a pathway level.

The growth rates achieved in this work surpass those from comparable studies. In a long-term evolution experiment (LTEE), in which E. coli have been evolving for over 50,000 generations in glucose minimal media, results at the 2,000 generation mark were used for comparison, as those were closest in evolutionary timeframe to the results of this work (60). It is important to note that in the LTEE, an E. coli B strain was used on glucose minimal media, as opposed to K-12 used here, and cells were always passed during stationary phase. Nonetheless, the LTEE observed a 1.29±0.10 (standard deviation) fold increase in growth rates of the populations, compared to the 1.42-1.59 fold increase achieved here. Further, the LTEE took 10,000-15,000 generations to reach an approximate 1.5 fold increase in growth rate, here this fold increase was achieved in approximately 2,000 generations. No identical mutations were seen between the LTEE and this work, and only three mutated genetic regions were found in both: rpoB, ygiC, and pykF. The differences can presumably be attributed to the serial passage of cultures and/or the different starting E. coli strain. As another point of comparison, a different evolution study was performed on glucose minimal media for 50 days using the same K-12 strain and media conditions used here (3). In that experiment, a 1.1-fold increase in growth rate was observed, drastically lower than the increase found here. The only major difference between the two K-12 studies was that in the previous work the passage size was adjusted (i.e., reduced as the fitness increased) to keep the cultures out of stationary phase. Thus, these findings point to the importance of methodology used in an ALE experiment as highlighted by the differences in phenotypic and genotypic outcomes.

Exemplary mutations were identified which enabled faster growth of E. coli K-12 MG1655 on glucose minimal media and these mutations did not appear in the identified hypermutating lineage. These Exemplary mutations were straightforward to identify as the given genetic regions were reproducibly mutated across multiple ALE experiments. The causality of select single and double mutants of these regions was shown. (FIG. 5). The reproducibility observed is likely due to the strict selection pressure that was maintained in the experiment, keeping the populations in constant exponential growth. However, in one experiment, a hypermutating population arose. The genotype of the hypermutator differed significantly from the non-mutators; the vast majority of the Exemplary mutations determined from the non-mutator set were not detected in the hypermutator clones sequenced. This indicated that there were multiple genetic changes capable of enabling a similar fitness increase, which is further supported by the similarities in the transcriptome across all strains. Furthermore, the rpoB and hns/tdk mutations in the non-mutator strains likely affect global transcriptional levels. This would allow for single mutations to affect a multitude of reactions in the network. Compared to the hypermutator that did not have either of these, it was able to confer a similar effect on the network by fixing numerous mutations that presumably have similar, perhaps more local, individual effects. It should be mentioned however, that while the hypermutator did not have mutation in rpoB, it did have one in the rpoC subunit of the RNA polymerase holoenzyme, which could have a similar board impact on transcriptional levels in the cellular network.

The occurrence of the identified Exemplary mutations was highly reproducible. This conclusion was supported by the results of the validation ALE experiment which was started using clones already harboring single causal mutations (FIG. 5, Table 4). Mutations in pyrE/rph, rpoB, hns/tdk, and metL all reappeared in these experiments, to varying extents. The ability of clonal analysis to capture population dynamics was also examined. Although clonal resequencing most often yielded agreement with the population-level analysis (analyzed with population PCR), it did not always capture the presence of a specific mutation shown to cause an increase in fitness (in this case, the 82 bp deletion between pyrE/rph). Thus, clonal analysis is useful and informative, but it has its limitations and ultimately ALE studies can benefit from a more population-centric analysis of mutations. Looking at the differences in mutations which occurred in a given gene, it appears that there are multiple specific mutations that can have a similar effect on fitness (Table 2A and 2B). Of the specific mutations observed in rpoB, all conferred a fitness advantage but to varying degrees (FIG. 5). More than one mutation in rpoB was never observed in a single strain, suggesting that there could be negative epistasis between the different identified SNPs; their effects are non-additive. Nonetheless, this study presents a number of reproducibly occurring and causal genes which enable rapid growth of E. coli on glucose minimal media.

The physiological characterization of evolved strains indicated that there were multiple mechanisms through which to realize an increased growth rate. The clones isolated from the endpoints of the primary ALE experiments all increased in fitness to a relatively similar degree, yet the GUR and $Y_{X/S\_ss}$ varied between them (FIG. 2). Of the three hypermutator clones isolated and characterized, two seemed to diverge from the others by having significantly lower GURs yet higher $Y_{X/S\_ss}$ (i.e., they are more efficient). The observed extremes in GUR, APR, and $Y_{X/S\_ss}$ show that the trajectory across the fitness landscape traversed by MG1655 on glucose minimal media is not a rigid, predetermined path. It should be noted that the growth rates of the two aforementioned hypermutators fell in between the range of growth rates of the other clones.

Furthermore, this study has shown that there is a clear and distinct physiologically adapted growth state which is realized after several generations of continuous exponential growth (differing from growth started directly from a stationary phase culture). This observed phenomenon was reproducible using the quantitative approach in this study and puts an emphasis on critically evaluating previously reported "maximum" growth rates of strains.

Genome-wide analysis of the evolved strains using transcriptomics revealed a consistent evolved expression shift, and further categorization using genome-scale modeling revealed pathway-level shifts underlying the increased growth phenotypes. Furthermore, transcriptomics was utilized to link genotype to phenotype when considering the effects of IS element mutations. The most apparent mutational effect was that of IS elements between hns/tdk, where the has gene product was significantly up-regulated in all of the strains harboring these mutations. These hns/tdk insertions were shown to be causal for an increased growth rate and could be further utilized, along with other Exemplary mutations, to improve efficiency in biomass yield or GUR. The most highly conserved changes in the transcriptomes across the evolved strains were in good agreement with the predicted gene products whose differential expression would enable rapid growth, as determined through genome-scale modeling. When considering the coordinated changes in the transcriptomes of the evolved strains solely with a classification like COGs, enriched pathways became apparent which contributed to the shift in the functional state of the cells. The results of the genome-scale modeling classification changed this enrichment significantly and allowed a deeper examination into the physiological state and mutation-induced pathway expression changes of the evolved strains. Thus, it was useful to interpret the outcome of evolution in the context of an in silico analysis of optimal performance in this particular condition.

In summary, we have shown that ALE can be utilized to find reproducible causal mutations that optimize for a selectable phenotype using a controlled experimental setup and strict selection pressure. Whole-genome resequencing enabled the mutational discovery, and transcriptomic analysis coupled with genome-scale modeling uncovered the metabolic pathways underlying the evolved phenotypes. These findings and the general experimental approach we have laid out can be extended to additional culture conditions, strains, and selection pressures for a variety of basic science and applied biotechnological purposes.

(3) Further Characterization of Exemplary Mutants Described in Examples 8-15.

Many causal genetic variants across all forms of life are found in regulatory regions[1-6]. In addition to cis regulatory variation, causal mutations are often found in trans-acting transcriptional regulators[7-11]. Here, we detail the multi-scale mechanism underlying several trans-acting adaptive regulatory mutations of E. coli's RNA polymerase (RNAP)[7,12,13]. Though these mutations are not physically close in sequence or structure, we find that they share a common molecular mechanism. Detailed phenotypic assays show consistent fitness benefits of the mutations in static environments and fitness detriments in variable environments (i.e., nutrient shifts and stress shocks). A multi-'omic' approach with key environmental controls reveals a systematic and consistent modulation of the transcriptional regulatory network (TRN) towards growth functions and away from functions that hedge against environmental change. 'Econometric' analysis using a genome-scale model reveals that the resulting resource re-allocation can quantitatively explain the fitness effects. Finally, structural dynamics of RNA polymerase (RNAP) provide insight as to how these mutations result in strikingly similar effects. Though RNAP is typically not considered a transcription factor, these results show that it lies at the top of the TRN hierarchy, regulating cellular growth and various hedging functions[14].

Thus, these mutations in RNAP result in a broad form of antagonistic pleiotropy (growth versus hedging) based on resource re-allocation. As protein synthesis and energy are limited resources, we can conclude that the pleiotropic effects reflect an inherent trade-off between growth and hedging functions. Similar antagonistic pleiotropy has been observed in other trans regulatory variants[15-18]. This study moves the field forward by detailing the multi-scale mechanism underlying the pleiotropic effects of adaptive regulatory mutations. It provides insight into the evolutionary constraints and the mechanisms that govern resource allocation in simple organisms.

Adaptive laboratory evolution (ALE) with genome re-sequencing of endpoint strains can identify the genetic basis for new phenotypes. Causation is established by introducing mutations found in endpoints into the starting strain. This approach, augmented with omics data and systems analysis, reveals multi-scale mechanistic genotype-phenotype relationships. This process is detailed for ALE-selected variants in Escherichia coli RNA polymerase. We show that these mutants perturb the transcriptional regulatory network to rebalance proteome and energy allocation towards growth and away from several hedging functions. These findings highlight the resource allocation constraints organisms face and suggests how regulatory structure enhances evolvability.

Here, we elucidate the mechanistic multi-scale basis of adaptive regulatory mutations. Single amino acid changes in the RNAP reprogram the TRN to re-allocate resources towards growth and away from hedging functions. The mutations result in antagonistic pleiotropy where the organism is more fit in stable environments but less fit in environmental shifts and shocks[35].

A. Antagonistic Pleiotropy Due to a Fundamental Trade-Off

Mutations that are beneficial or neutral in one environment often have negative fitness effects in other environments, referred to as pleiotropy. Pleiotropy shapes the evolution of organisms and is thought to underlie the evolution of specialist species[35]. Several mechanisms can give rise to pleiotropy and some have been demonstrated[36,37,38].

Fundamental biological constraints can result in antagonistic pleiotropy, though examples of these cases are lacking. Using a systems biology approach, we show that the growth rate difference in wild-type and mutant strains can be quantitatively explained by changes in proteome and energy allocation. These resources are limited, resulting in an inherent trade-off between growth and hedging functions. Such proteome and energy allocation constraints likely result in pervasive evolutionary trade-offs and likely underlie several recent examples of antagonistic pleiotropy[5,16,39].

B. Evolvability Through Regulatory Network Structure

Mounting evidence supports that much of the functional divergence between organisms occurs in regulatory regions[1-6]. The detailed example of the RNAP mutations here suggests why (in part) this may be the case.

As regulatory networks are 'aligned' with particular functional subsystems, mutations that perturb them change phenotypes in a functionally coherent manner[40-42]. The regulatory rebalancing detailed here occurs along a coherent growth versus hedging trajectory. On the other hand, mutations that are inconsistent or imbalanced in the molecular changes they cause would likely not be selected. Therefore, in addition to enabling proximal response to environmental change, the structure of the regulatory network also enables productive evolutionary change. Remarkably, single, but non-unique, point mutations allow such adaptation.

C. Multi-Scale Characterization of Genotype to Phenotype

Figure 51:
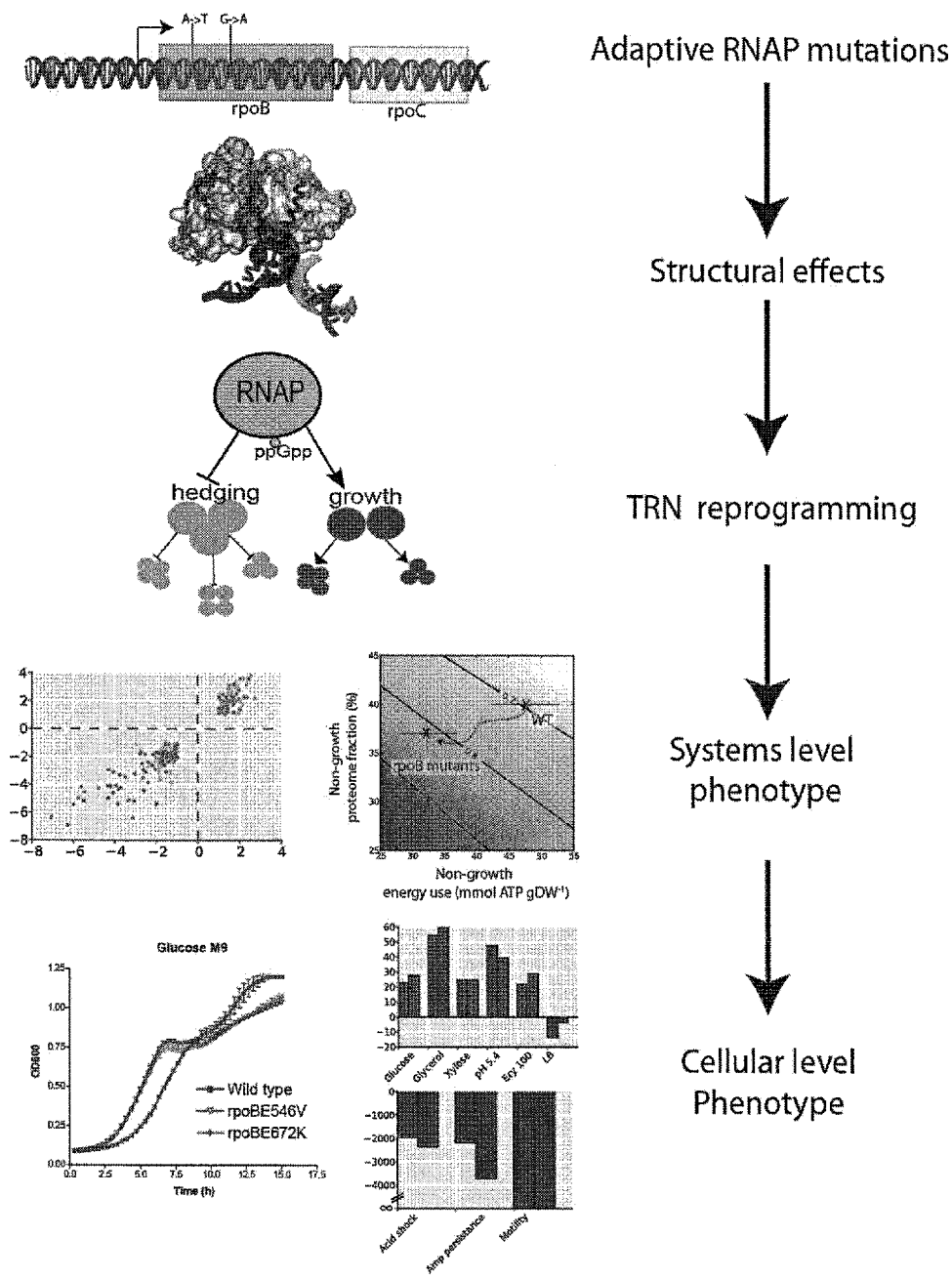
FIG. 51. Multi-scale characterization from genotype to phenotype. The multi-scale effects of the studied adaptive regulatory mutations in RNAP are summarized. The mutations alter the structural dynamics of the RNAP, perturbing the TRN through the action of key transcription factors. The decrease in expression of hedging functions lowers the proteome and energy allocation towards hedging functions and increases cellular growth. In turn, the cell can grow faster in conditions of steady-state growth, but is less fit under environmental shifts and shocks.
Figure 52A:
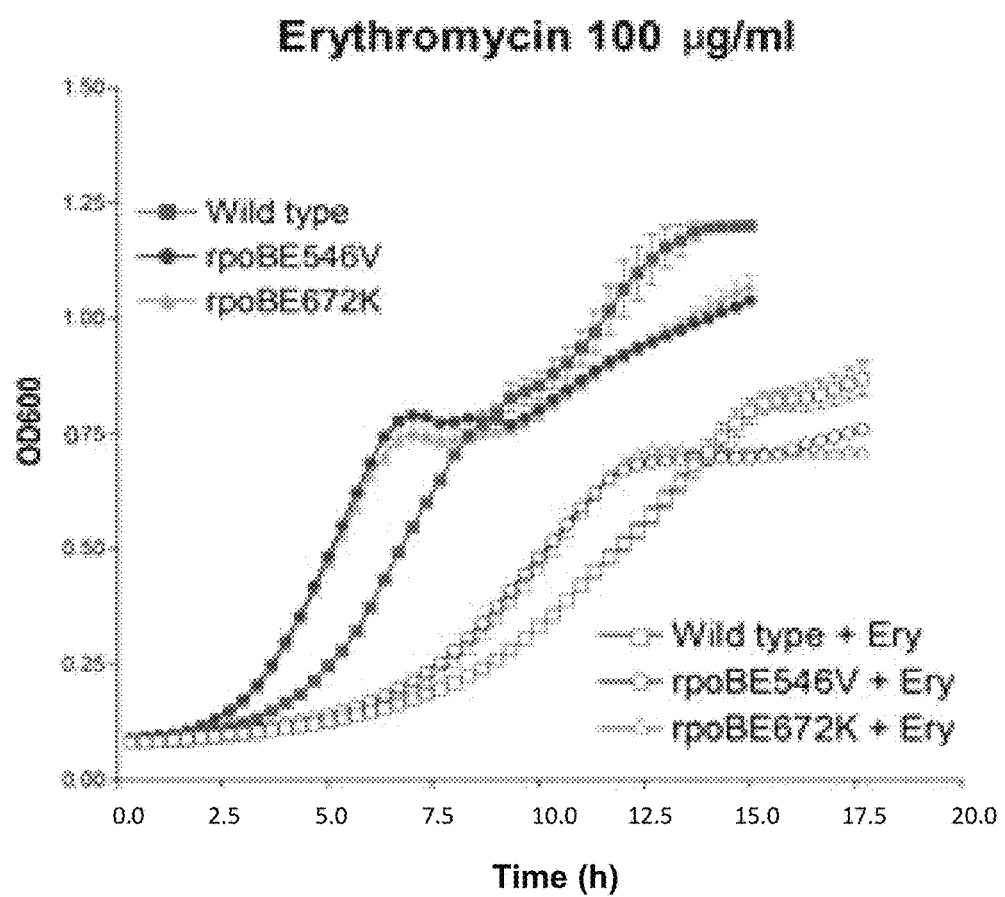
FIG. 52: Phenotypic assays. A) Comparison of the growth of the wild type and both ALE selected mutants with and without 100 μg/mL of erythromycin. ALE selected mutants grow faster than the wild type in the presence of erythromycin (MIC 512-1,024 μg/mL) B) both ALE selected mutants grow faster than the wild type at both neutral and low pH. C) Frequency of persisters after a treatment with ampicillin for 24 h. D) Survival counts after an acid shock of 3 hours at pH 2.6 (See methods for details).
Figure 52B:
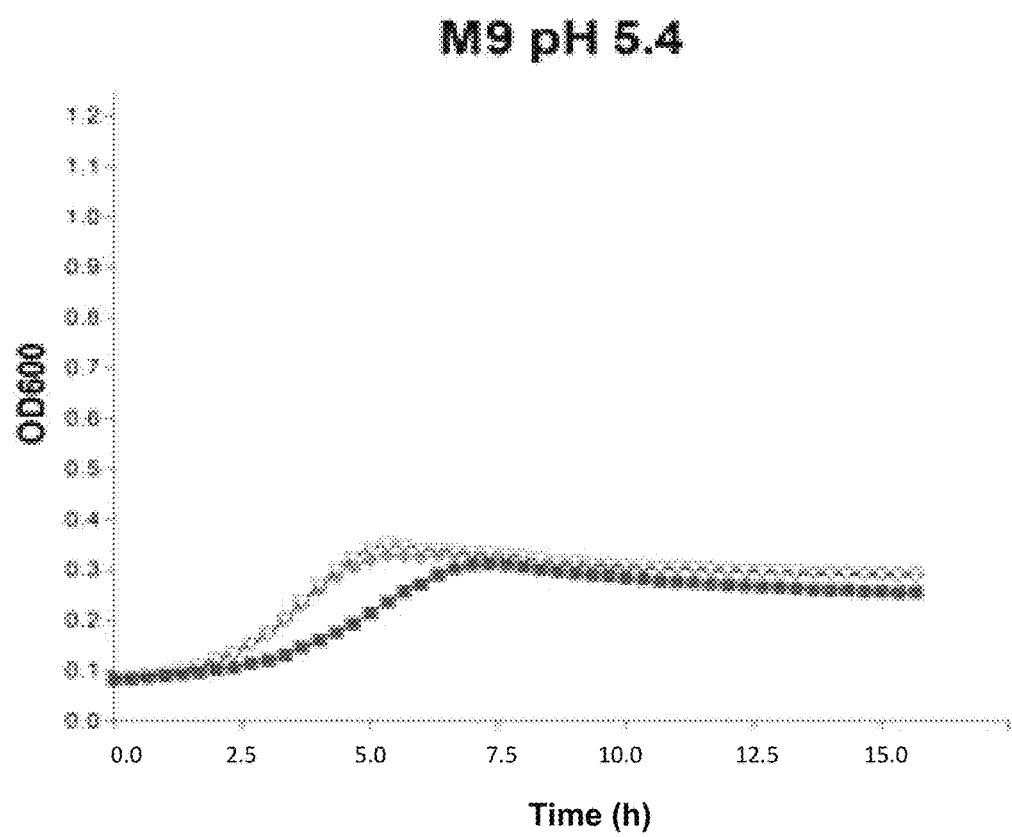
Figure 52C:
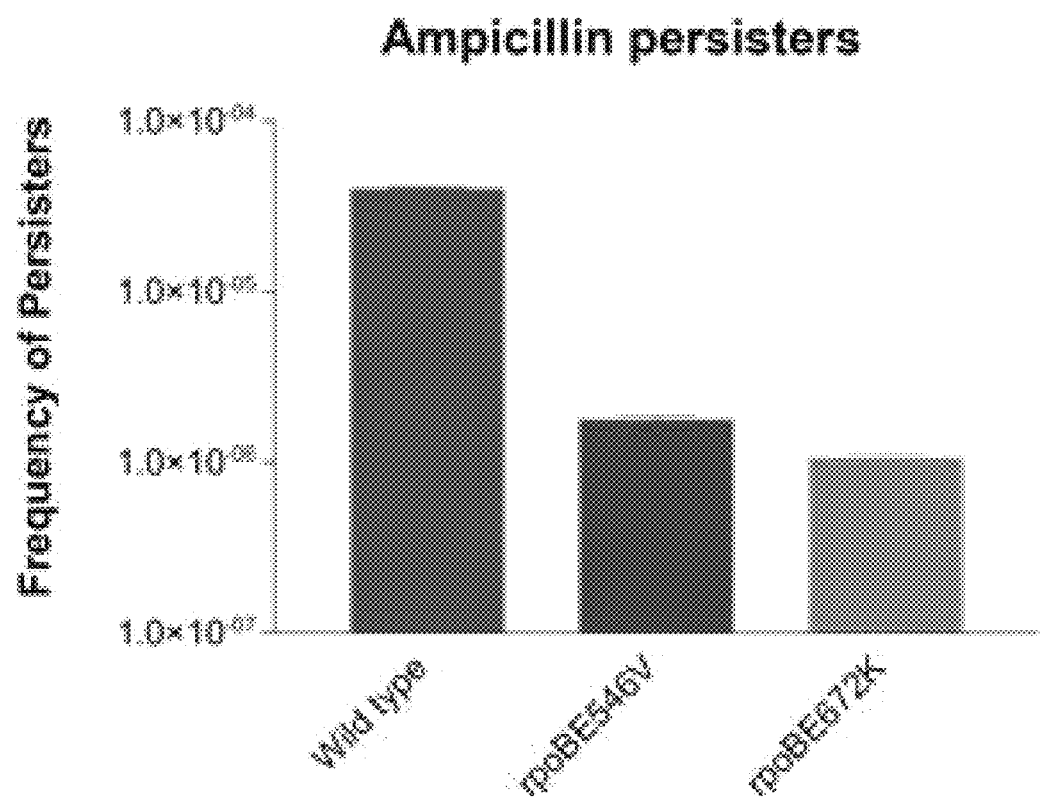
Figure 52D:
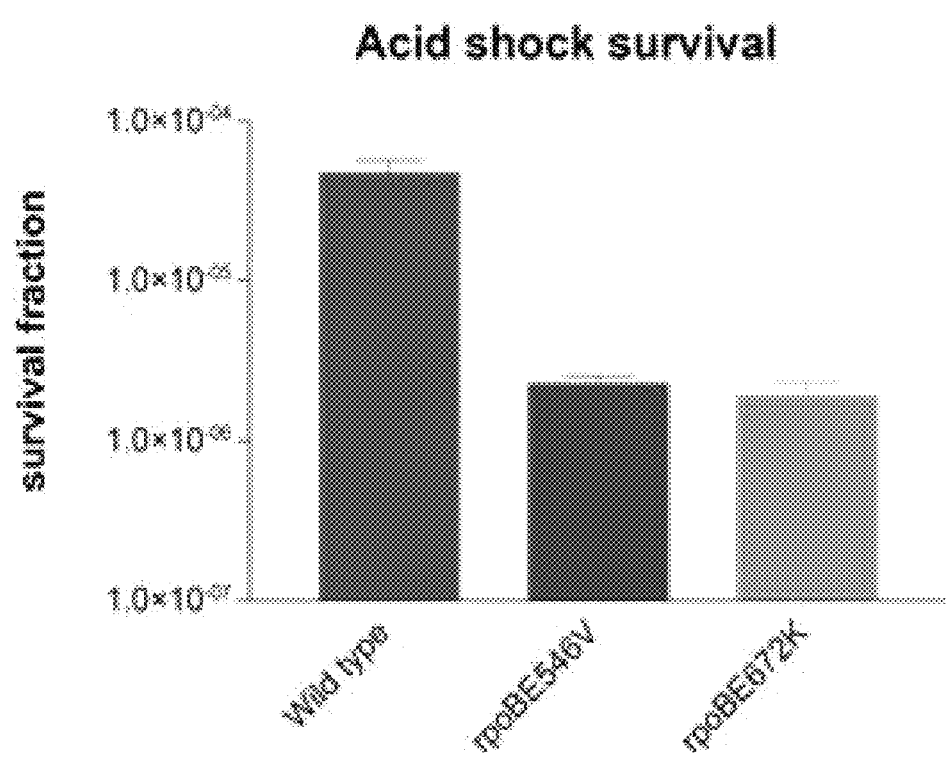
Figure 53:
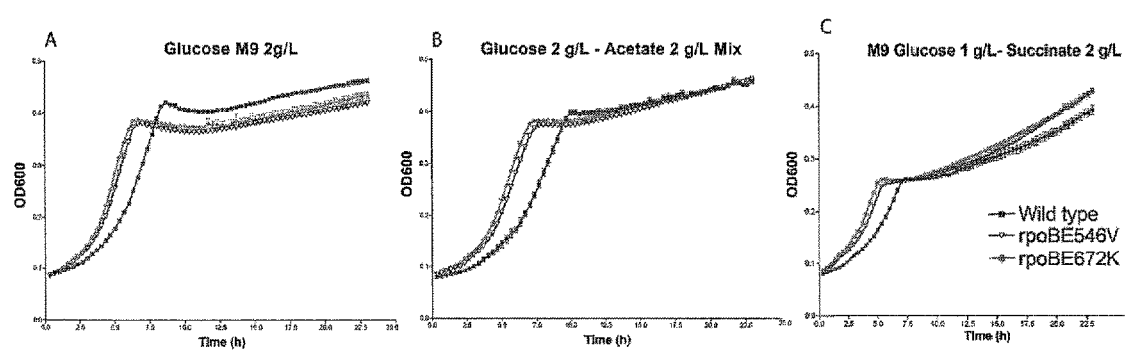
FIG. 53: Growth curves in A) glucose M9 2 g/L B) a mixture of 2 g/L glucose and 2 g/L acetate and C) a mixture of 1 g/L of glucose and 2 g/L of succinate.
Figure 54A:
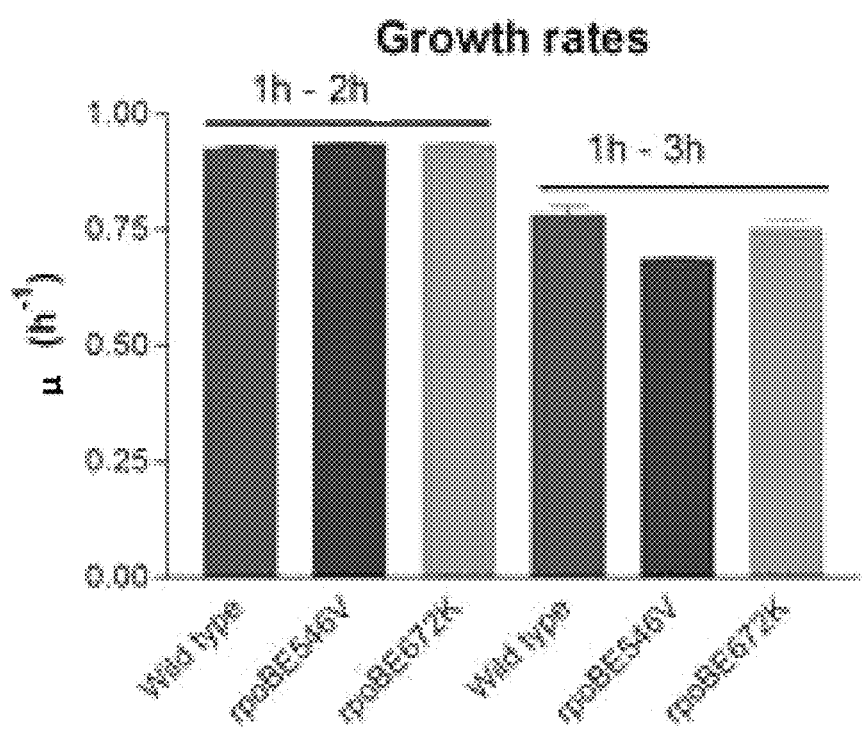
FIG. 54: Growth in rich media does not reach a steady state. A) Growth rates in LB rich media shows that the results of the calculation of growth rate depends on the period of time selected as the mutants grow at the same rate as the wild type for the first hour then they shift to a second slower growth phase as shown in B).
Figure 54B:
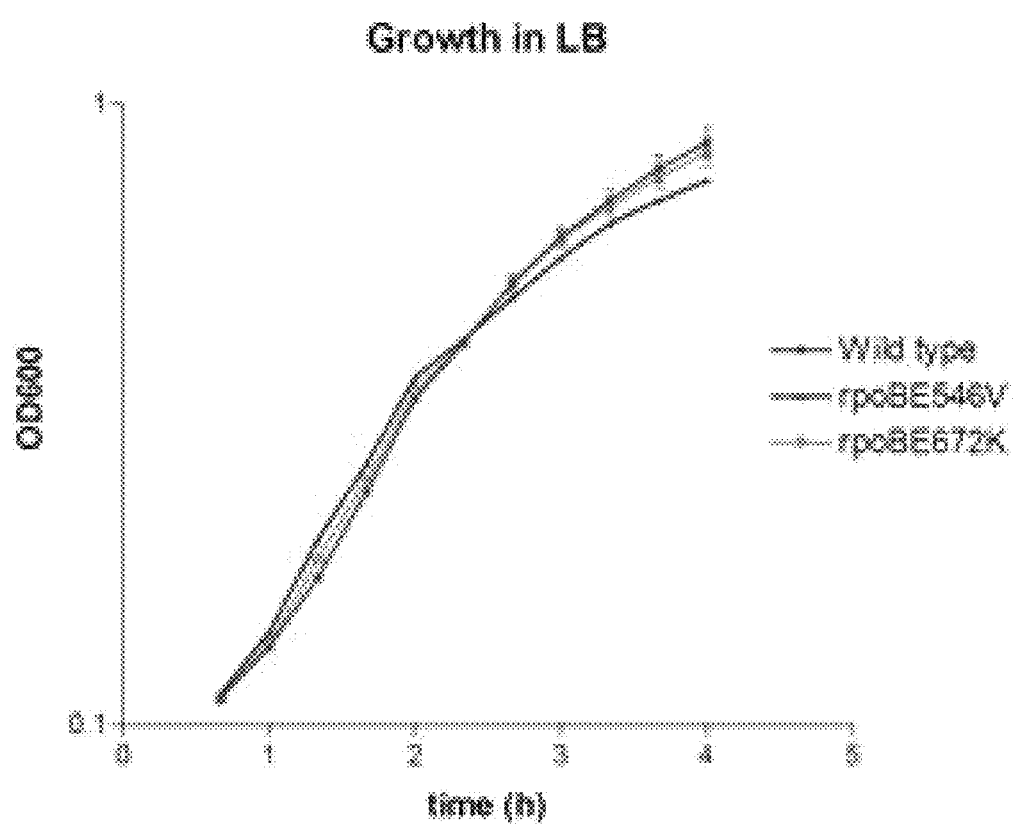

Sequencing of many individual genomes has led to the identification of genomic regions under selection[43] and enabled the association of variants with organismal[44] and molecular[45] phenotypes. However, there is a large gap between identifying causal variants and mechanistically understanding their phenotypic consequences. The mutations studied here are some of the most comprehensively phenotyped to date, with environmental controls to separate cause and effect. We employ state-of-the-art structural and systems biology modeling approaches to help bridge the gap between genotype and phenotype. Together, these analysis approaches enable us to step from mutation to biophysical effects on protein function to systems-level molecular and regulatory response, and finally to organismal phenotype (FIG. 51). Therefore, this study outlines how we might begin to understand the multi-scale genotype-phenotype relationship at a true systems level.

EXPERIMENTAL

The following is a brief description of the exemplary materials and methods used in the subsequent Examples.

Example 1

Methods Used in Examples 2-7

Adaptive Laboratory Evolution

Primary adaptive evolutions were started from wild type E. coli strain MG1655 (ATCC47076) frozen stock and grown up overnight in 500 mL Erlenmeyer flask with 200 mL of minimal media. 8 aliquots of 900 μL were passed into eight flasks containing 25 mL of media and magnetic stir discs for aeration. 800 μL of culture was serially passed during mid-exponential phase (3.2% of the culture size). Cultures were not allowed to reach stationary phase before passage. Four $OD_{600nm}$ measurements were taken between ODs of 0.05 and 0.30 to determine growth rates. Periodically, aliquots of samples were frozen in 25% glycerol solution and stored at −80° C. for future analysis. Glucose M9 minimal media consisted of 4 g/L Glucose, 0.1 mM $CaCl_2$, 2.0 mM $MgSO_4$, Trace Element Solution and M9 salts. 4000× Trace element solution consisted of 27 g/L $FeCl_3*6H_2O$, 2 g/L $ZnCl_2*4H_2O$, 2 g/L $CoCl_2*6H_2O$, 2 g/L $NaMoO_4*2H_2O$, 1 g/L $CaCl_2*H_2O$, 1.3 g/L $CuCl_2*6H_2O$, 0.5 g/L $H_3BO_3$, and Concentrated HCl dissolved in $ddH_2O$ and sterile filtered. 10× M9 Salts solution consisted of 68 g/L $Na_2HPO_4$ anhydrous, 30 g/L $KH_2PO_4$, 5 g/L NaCl, and 10 g/L $NH_4Cl$ dissolved $ddH_2O$ and autoclaved. The validation was performed under the same conditions as above except 0.7% of the culture was passed.

Physiological Characterizations

Growth rates of clones isolated from the primary ALE experiments were screened by inoculating cells from an overnight culture to a low optical density (OD) and sampling the $OD_{600nm}$ until stationary phase was reached. A linear regression of the log-linear region was computed using 'polyfit' in MATLAB and the growth rate (slope) was determined. Growth rates of clones isolated from the follow-up validation ALE were similarly started but passed serially three times in late exponential phase. The growth rates of each culture were computed as above and the average of the three cultures was taken. The first culture was omitted due to physiological characterization (32).

Growth rates of populations were determined by the output of the interpolated cubic spline used, unless stated otherwise.

Extra-Cellular by-products were determined by HPLC. Cell cultures were first sampled and then sterile filtered. The filtrate was injected into an HPLC column (Aminex HPX-87H Column #125-0140). Concentrations of detected compounds were determined by comparison to a normalized curve of known concentrations.

Biomass Yield ($Y_{X/S\_ss}$) was calculated as the quotient of the growth rate and glucose uptake rates during the exponential growth phase.

DNA Sequencing

Genomic DNA was isolated using Promega's Wizard DNA Purification Kit. The quality of DNA was assessed with UV absorbance ratios using a Nano drop. DNA was quantified using Qubit dsDNA High Sensitivity assay. Paired-end resequencing libraries were generated using Illumina's Nextera XT kit with 1 ng of input DNA total. Sequences were obtained using an Illumina Miseq with a PE500v2 kit. The breseq pipeline (33) version 0.23 with bowtie2 was used to map sequencing reads and identify mutations relative to the E. Coli K12 MG1655 genome (NCBI accession NC 000913.2). These runs were performed on the National Energy Research Scientific Computing Center carver supercomputer. The identified mutations were then entered into an SQL database to track mutations along each evolution. All samples had an average mapped coverage of at least 25×.

RNA-Sequencing

RNA-sequencing data was generated under conditions of exponential and aerobic growth in M9 minimal media with a glucose carbon source. Cells were washed with Qiagen RNA-protect Bacteria Reagent and pelleted for storage at −80° C. prior to RNA extraction. Cell pellets were thawed and incubated with Read-Lyse Lysozyme, SuperaseIn, Protease K, and 20% SDS for 20 minutes at 37° C. Total RNA was isolated and purified using the Qiagen RNeasy Mini Kit columns and following vendor procedures. An on-column DNase-treatment was performed for 30 minutes at room temperature. RNA was quantified using a Nano drop and quality assessed by running an RNA-nano chip on a bio-analyzer. Paired-end, strand-specific RNA-seq was performed following a modified dUTP method (34). A majority of rRNA was removed using Epicentre's Ribo-Zero rRNA removal kit for Gram Negative Bacteria.

Reads were mapped with bowtie2 (35). Expression levels in units fragments per kilobase per million fragments mapped (FPKM) were found with cufflinks 2.0.2 (36). Gene expression fold change (with respect to the wild-type strain) was found using cuffdiff; a q-value cutoff of 0.05 was used to call significant differential expression. Gene annotation from EcoCyc version 15.0 was used for all analysis (37).

Commonly Differentially Expressed Genes

A statistical model was used to determine how many genes are expected to be commonly differentially expressed in the same direction (up or down) across multiple strains. In the null model, each gene in each strain can have one of three states: up-regulated, down-regulated, or not significantly differentially expressed compared to the wild-type. For each gene in a given strain, the probability of the three states follows a multinomial distribution parameterized empirically by the differential expression calls in the processed RNA-seq data (see RNA-Sequencing). The genes that are differentially expressed in each strain are assumed independent in the null model, so the probability that a gene is differentially expressed in multiple strains is determined by the product rule of probability. Commonly differentially expressed genes are then called when no genes are expected to be differentially expressed in the same direction across that number of strains (i.e., expected value is less than 1). For this dataset, no genes are expected to be commonly differentially expressed (in either direction) across 6 or more strains.

ME-Model Simulation and Gene Classification

The ME-model as published in O'Brien et al. was used for all simulations (38). 20 distinct glucose uptake rates, evenly spaced between 0 and the optimal substrate uptake rate (when glucose is unbounded) were simulated as described in O'Brien et al. (38). Any gene predicted to be expressed in any of the 20 simulations are classified as 'Utilized ME'; genes within the scope of the ME-Model, but not expressed in any of the 20 simulations are classified as 'Non-utilized ME'; genes outside the scope of the ME-Model are classified as 'Outside scope ME'. These gene groups are then compared to COGs and the identified commonly differentially expressed genes in the end-point strains (see Commonly differentially expressed genes) (39).

Jump Finding

Growth rates were calculated for each batch during the course of evolution using a least-squares linear regression. The following criteria were used to determine whether to accept or reject the computed growth rate Number of OD samples ≥3

Range of OD measurements must be ≥0.02

Passage OD within 50% of targeted passage OD

The accepted growth rates were fit with a monotonically increasing piecewise cubic spline. Regions with a slope greater than $4.2 \times 10^{-15}$ $hr^{-1} CCD^{-1}$ were considered jumps with a few exceptions. The spline was created using 'slmtools' function in MATLAB available on the MATLAB file exchange. The number of spline segments (#knots-1) was varied to capture the upward trends in growth rates.

Knock-In Procedure

The single point mutation introduction in rpoB was done by 'gene gorging' as described previously (22). Briefly, the mutation in rpoB was amplified by PCR from the genomic DNA of the ALE clone where it was originally found. Amplification was done with primers approximately 500 bp upstream and downstream of the mutation and flanked by the 18 bp I-SceI site, and PCR product was cloned in a pCR-Blunt II-Topo vector (Invitrogen, Carlsbad, Calif.) to create a donor plasmid. The donor plasmid was co-transformed along with the pACBSR plasmid harboring an arabinose induced lamda-red system and the I-SceI endonuclease on a compatible replicon. A colony of the strain transformed with both plasmids was grown with arabinose as an inducer and after 7-12 h several dilutions of culture were plated with and without antibiotics to verify the loss of the donor plasmid. The initial screening of positive clones was carried out by PCR using a 3' specific primer to the introduced mutation (40). The positive colonies were confirmed by Sanger sequencing.

Example 2

Adaptive Laboratory Evolution

Adaptive laboratory evolution (ALE) is a growing field facilitated by whole genome sequencing. The process of ALE involves the continuous culturing of an organism over multiple generations. During an ALE experiment, mutations arise and those beneficial to the selection pressure are fixed over time in the population. Most ALE experiments analyze a perturbation from a reference state to another (e.g., environmental (1, 2) or genetic (3)). After adaptation, understanding what genetic changes enabled an increase in fitness is often desirable (4). Generally there are two methods of evolving microorganisms—batch cultures and chemostats. Each method has its own advantages and disadvantages, in terms of maintenance, growth environment, and selection pressures (5). Applications of ALE are numerous and include those for biotechnological goals, such as improving tolerance to a given compound of interest (6-8), or more progressive uses such as improving electrical current consumption in an organism (9). Additionally, there has been a significant focus on using ALE to understand antibiotic resistance to given compounds (i.e., drugs) in order to combat clinical resistance (10). A number of in depth reviews on ALE have appeared as the field continues to grow (5, 11, 12).

The methodology utilized for conducting an ALE experiment needs to be carefully considered. A critical characteristic of ALE experiments is that they have long timescales, on the order of months, and often require daily attention (1, 5). The timescale is typically determined by culture size, amount of cells propagated to the next culture (i.e., passage size), and the growth phase under which it is passed. When passing strictly in exponential phase (3, 13-15), the timescale becomes restrictive as there is only a small window of time in which to aliquot from the culture and propagate it. The amount passed significantly influences when the next window will occur. Thus, it is often the case that the passage size is adjusted according to the experimenter's schedule (3, 16). An unfortunate consequence of this is that as the growth rate increases, the passage size is generally decreased. This allows for fewer potentially beneficial mutations to advance to the next flask, possibly slowing evolution. An alternate approach is to pass a fixed amount at a regular time interval, generally once per day. This time frame allows the cells to reach stationary phase, where they remain for the majority of the time. This approach has been used in a notable study where E. coli B strains were evolved in glucose minimal media batch cultures for over 25 years (17). Passing cells after they have reached stationary phase creates a more complex selection pressure than strictly passing cells during exponential growth (18), favoring both growth rate increases and decreases in lag-phase duration (19). Thus, experimental setup should be tailored to the desired selection pressure of the experiment.

Next generation sequencing has eased the process of finding mutations in ALE studies, however tying specific components of the genotype to the phenotype remains difficult. Strains generated using ALE often have multiple mutations (20, 21) and if one wants to determine causality for a phenotype, it can require a significant effort (22-24). Despite the growing availability of genome engineering tools (22, 25, 26), determining causality is still a time consuming process. An alternative approach to speed in the discovery of causal mutations would be to perform multiple independent experiments and examine mutations that occur most frequently. Performing multiple experiments under strict identical conditions can help filter casual mutation candidates encountered during ALE.

Along with understanding causal genetic changes in ALE experiments, there is also a need to understand changes at the cellular pathway level. Omics characterization coupled with systems modeling approaches enable the mechanistic interpretation of data based on reconstructed metabolic network content (27). Constraint-based modeling, which is a bottom up approach based on network interactions and overall physiochemical constraints, has been shown to be a valuable systematic approach for analyzing omics data (28, 29). This approach has largely been pioneered using E. coli K-12 MG1655 as the organism of choice for validation and comparison of in silico predictions to experimental data (30, 31). In short, integration of omics data types with genome-scale constraint-based models has provided a context in which such data can be integrated and interpreted.

In an effort to demonstrate the power of using strict selection pressure to understand the process of ALE, E. coli K-12 MG1655 was adaptively evolved in minimal media at 37° C. with excess glucose in eight parallel experiments. At the end of the ALE experiments, clones from the final populations were characterized in terms of their growth rate, metabolic uptake and secretion rates, genome sequence, and transcriptome. These multi-omics data types were then integrated and further categorized with genome-scale models to examine how the cells adapted to the conditions and how their physiology and genomes changed.

Example 3

Characterization of the Evolution Process and the Endpoint Strains

Adaptive laboratory evolution was used to examine E. coli's physiological and genetic adaptation to simple media conditions under a strict selection pressure. Eight independent populations of wild-type E. coli K-12 MG1655 from the same seed culture were adaptively evolved in parallel under continuous exponential growth for a time period of 39-81 days. During this time, the cultures underwent approximately $8.3 \times 10^{12}$-$18.3 \times 10^{12}$ cumulative cell divisions (CCD) (Table 1) (41, 42). The use of CCD as a coordinate allows for incorporation of the number of cells passed in an ALE experiment along with generations of a culture (41). Variations in time courses and CCD are due to re-inoculations from frozen stocks (taken throughout the experiment) and occasional unexpected losses of cultures or suspected contamination as determined using 16S ribosomal sequencing. The fitness trajectories (i.e., population growth rates) as fit by a spline over the course of the evolution are given in FIG. 1. Each of the evolved populations increased in fitness from the starting strain (Table 1). The growth rate increases were 1.47±0.05 (standard deviation) fold faster than the starting strain and ranged from 1.42-1.59. One of the populations (determined to be a hypermutator strain, see below) was statistically faster than the rest and increased 1.59 fold (p-value ≤0.01). There was a significant increase in fitness from the first flask to the second in each of the independent experiments (FIG. 1, insert). This phenomenon has been previously observed and described through an examination of growth when cells are repeatedly passed during their exponential growth phase (32). An initial 'physiologically-adapted' growth rate was determined for the starting wild-type strain of 0.824±0.036 $hr^{-1}$ and was determined using growth rates recorded for flasks 2-4 across all of the independent ALE experiments. This repeated exponential phase growth rate is 19% faster than the average growth rate of flask 1 from each experiment (0.69±0.02 $hr^{-1}$). It should be noted that this increase in growth rate is not expected to be a result of a beneficial mutation.

Clones were isolated from the last flask of each of the evolved populations, phenotypically characterized (growth rates, glucose update rates (GUR) and acetate productions rates (APR)), and compared to the starting wild-type strain to understand how their behavior changed after evolution (FIG. 2). Nine clones isolated from the experiments were analyzed (six isolated from the non-hypermutator populations, and three isolated from the hypermutating linage were analyzed as it possessed a significantly higher population fitness). To quality control the data, the phenotype of the wild-type strain was compared with other studies and found to be in good agreement with previous characterizations (43). The clone growth rates were compared to the population from which they were derived, and the Pearson correlation coefficient between them was 0.16. The isolated hypermutator clones diverged more significantly from the population growth rates (1.10-1.20) than did the non-hypermutator strains (1.02-1.11). The physiological properties of each of the clones isolated from the independent ALE experiments were compared to examine if there were any conserved trends across the different experimental outcomes. There was a similar increase in growth rate across the isolates from different experiments, but a larger variation in the glucose uptake rates and biomass yields (FIG. 2A). The glucose uptake rates (GUR) and acetate production rates (APR) increased in the endpoint strains compared to wild-type (except for one strain where the APR decreased). There is a correlation ($r^2$=0.70) between the increase observed in the GUR and APR (FIG. 2B). Of the characterized strains, the hypermutators accounted for three of the four lowest APRs and highest steady-state biomass yields ($Y_{X/S\_ss}$). No other common fermentation products of *E. coli* K-12 MG1655 (i.e., formate, ethanol, succinate, lactate) were detected as secretion products in any of the endpoints, thus indicating that these the three hypermutator strains generally metabolized glucose more efficiently. A similar correlation was also seen between biomass yield and APR ($r^2$=0.57, FIG. 2C). Thus, clones in the independent ALE experiments converged to a similar optimal fitness by either becoming more efficient in their biomass yield or increasing GUR and overflow metabolism in the form of acetate secretion. A tradeoff between GUR and $Y_{X/S\_SS}$ was observed in that higher glucose uptake rates led to lower $Y_{X/S\_SS}$ (i.e., they are inversely correlated, $r^2$=0.93). However, it should be noted that the $Y_{X/S\_SS}$ calculation involves GUR as a factor.

Example 4

Analysis of Mutations Identified in the Evolved Strains

A persistent challenge and goal in ALE experiments is differentiating between causal mutations and genetic hitchhikers. In these set of experiments alone, 72 unique mutations were identified across non-mutator strains. To aid in determining causal mutations, jumps in fitness were identified using a jump finding algorithm (see methods). Clones were isolated that bracketed jump regions and sequenced in order to evaluate if jumps in growth rates could be linked to a genetic change which had been fixed in the population over the course of the jump (FIG. 3). An analysis of Exemplary mutations is given in Table 2A and 2B. The genes or genetic regions listed in Table 2A and 2B are those that were found mutated in multiple experiments, or which contained multiple unique mutations across the gene/genetic region. The mutations in Table 2A and 2B are contemplated as functioning in a similar fashion as shown herein for rpoB mutations. While rpoB mutations have been chosen as exemplary illustrations of some embodiments of the present invention, at least some of the alternative mutations in Table 2A and 2B are expected to have the same, or superior, effects.

FIG. 3 additionally shows if a given mutation persisted, was found in multiple points of clonal analysis, or was no longer detected but another mutation in the same gene was identified. Mutations that were linked to fitness jumps are identified in Table 2A and 2B.

Overall, 52 unique genetic regions (i.e., genes or intergenic regions between two genes) were mutated across all non-mutator clones sequenced, encompassing 72 total unique mutations. Of the 52 unique genetic regions, multiple unique mutations occurred in eight genetic regions (Table 2A and 2B). 57% (30 of 53) of all mutations persisted in every subsequent clone examined until the experiment ended (mutations only observed in the last clone examined for each experiment were not considered). Some mutations were found in multiple subsequent clones from an experiment, but did not persist after first being observed. There were two such instances in experiment 10, where three distinct genotype lineages were observed in the various clones sequenced. Of the genes containing the 30 persistent mutations, only three have been reported in a similar glucose minimal media ALE experiment: rpoB, ygiC, and ydhZ/pykF (44). When considering the hypermutator population clones, an additional pykF mutation was also observed. It should be noted that the exact mutations were different than those previously reported and only rpoB was included in our analysis of Exemplary mutations. Overall, there were 7-21 mutations identified in each experiment, with a median value of 13. Experiment 4 had the fewest genetic changes with seven unique mutations across all sequenced clones, and only four in the final clonal isolate. In comparison, experiment 10 had 21 unique mutations observed across all clones and 12 in the final clonal isolate. Similar continuous exponential growth-phase ALE experiments run for approximately $10^{11}$ CCDs (more than an order of magnitude fewer than in this study) on glycerol, lactic acid, and L-1,2-propanediol minimal media yielded 2-5, 1-8, and 5-6 mutations per independent experiment, respectively (23, 24, 45).

Several genes and genetic regions were identified that contained mutations across many of the independent ALE experiments, implying causality. A detailed analysis of each of the Exemplary mutations was performed, but the most frequent mutation targets were the intergenic region between pyrE and rph, the rpoB gene, and between hns/tdk via an insertion sequence (IS). An 82 bp pyrE/rph deletion was observed in every sequenced clone. A K-12 specific defect has been previously described which is ameliorated by this mutation (23, 46). A subunit of RNA polymerase, rpoB was found to be mutated in every experiment and likely has a genome-wide impact on transcription given its vital role in the transcription process (47, 48). All of the mutations were single amino acid changes. Multiple unique mutations were found singly across clones which harbored rpoB mutations after the first jump in fitness. IS element mediated mutations were found in all experiments, typically after the second jump in fitness, except where a hypermutating phenotype was dominant. Three different IS elements (IS1, IS2, and IS5) were inserted in seven different locations, and one identical IS5 mutation was detected using the described clonal analysis. IS1 is SEQ ID NO:28 shown in FIG. 43, IS2 is SEQ ID NO:29 shown in FIG. 44, and IS5 is SEQ ID NO:30 shown in FIG. 45.

The clones sequenced after the second jump in experiment 7 exhibited hypermutator behavior. This was readily apparent from the 139 mutations it possessed, an order of magnitude greater than any other strain for a given number of CCDs. Additionally there was an IS element inserted into the mutT gene of this strain. Due to the large size of the insertion (777 bp), it almost surely results in mutT loss-of-function. It has been shown, by knock-out, that defective MutT increases SNPs in the form of A:T to C:G conversions (49). Of all the mutations observed in the hypermutator strains, only 6 of 381 were not A:T to G:C conversions. When all four isolated and resequenced hypermutator clones were compared, 33 mutations were shared between all four.

The overlap in genes or genetic regions between the hypermutators and non-mutators was analyzed, and it was found that the only identical shared mutation was the 82 bp deletion in pyrE/rph. Only two (iap, ydeK) of the same genes or genetic regions were mutated in both the non-mutator and hypermutator lineages. Thus, these genes also indicate potential Exemplary mutations for the observed phenotypes.

Example 5

Analysis of Reproducibility for Exemplary Mutations which Enable

Increased Fitness Phenotypes

To analyze how reproducibly Exemplary mutations occur, the evolution process was repeated starting with strains that harbored three of the Exemplary mutations identified in this study: rpoB E546V, rpoB E672K, and pyrE/rph Δ82 bp. The hypothesis which was tested was the expectation that Exemplary mutations would again occur when starting another ALE experiment with one of the Exemplary mutations already present. Consequently, the fitness increase associated with each mutation could also be tested. Each of these single mutants were reconstructed in the starting strain background and validated (see Methods). The conditions of this 'validation' ALE experiment were essentially identical to the first ALE experimental setup, but with the dilution ratio changed to 0.67% of the total culture volume (as compared to 5.0% in the initial experiment) in order to reduce clonal interference and genetic drift. The fitness trajectories of the validation evolution experiment are shown in FIG. 4. The initial and physiologically-adapted growth rates of the three reconstructed strains demonstrated that their mutations were indeed causal for faster growth on minimal media. Exemplary mutations detected in the validation ALE are given in Table 4. It is interesting to note that a different mutation between pyrE/rph was detected (a 1bp deletion) besides the ubiquitous 82 bp deletion detected in the primary ALE. Furthermore, using PCR it was revealed that all populations showed evidence of obtaining the 82 bp deletion, though the entire population did not harbor the mutation. Additionally, metL and hns/tdk mutations were also detected in the validation ALE. metL mutations are not as widespread, but two out of three mutations that did appear in metL are consistently loss of function suggesting that inactivation of the gene can increase growth rate in the minimal media conditions tested.

To examine the increase in fitness from Exemplary mutations identified, growth screens were performed for relevant single and double mutants (FIG. 5). These strains were either reconstructed manually or were isolates of the validation ALE. The results show that the mutation observed in metL and the IS1 insertion into hns/tdk also conferred a fitness advantage. The metL and hns/tdk were both shown in the presence of additional mutations, so their potential for epistasis is unknown. However, for the mutant with the IS1 insertion into the region between hns/tdk, it only harbors the 82 bp deletion in pyrE/rph which has been previously shown to alleviate a known K-12 MG1655 specific defect (23, 46). Thus, it is highly likely that it is uniquely causal without epistasis. In the case of metL, mutations were only observed after a mutation in rpoB was present. This could either indicate epistasis between the two mutations or simply that rpoB confers a larger fitness advantage and thus was selected for before a mutation in metL. If the fitness advantage from the double mutant screens is assumed to be additive, the increase in fitness for the observed mutation in metL and between hns/tdk is $0.065 \pm 0.023$ hr$^{-1}$ and $0.045 \pm 0.035$ hr$^{-1}$, respectively. Furthermore, the double mutant harboring both the rpoB E672K and Δ82 bp pyrE/rph mutation follows this additive trend as each single mutant increased fitness $0.125 \pm 0.038$ hr$^{-1}$ and $0.146 \pm 0.044$ hr$^{-1}$, respectively, and when they were both present the increased fitness was $0.237 \pm 0.058$ hr$^{-1}$. It should be noted that the growth rate measured from just the rpoB E672K and Δ82 bp pyrE/rph mutations ($1.027 \pm 0.043$ hr$^{-1}$) matches the highest growth rate measured from the populations that harbored both of these mutations (1.01 hr$^{-1}$) in its 95% confidence interval.

Example 6

Transcriptomic Analysis of Evolved Strains

Expression profiling was performed on endpoint strains using RNA-seq to identify system-wide changes in gene expression after evolution. For the eight strains profiled using RNA-seq, out of 4298 protein-coding ORFs, reads aligned to a total of 4189 genes (109 have no reads) in at least one strain, and 2922 genes in all strains (see sequencing methods), indicating a comprehensive/deep coverage of the transcriptome. Genes were identified that were differentially expressed in endpoint strains compared to the wild-type (see sequencing methods). In all strains, hundreds of genes significantly increased and decreased in expression, indicating large shifts in the transcriptome.

The common changes in gene expression across strains were analyzed to examine the heterogeneity of the different independent ALE experiments. As a null model, it was assumed that the expression changes in each gene are independent of each other. Using this null model, the expectation would be that no genes should be commonly differentially expressed across 6 or more strains. However, 448 genes commonly increased in expression and 383 genes commonly decreased in expression across 6 or more strains (FIG. 6A), indicating largely consistent changes in expression (though there is also a significant amount of diversity in the expression changes). This commonly differentially expressed gene set was selected for further analysis to better understand the coordinated change in the transcriptomes of the evolved strains.

For a broad overview of the cellular processes with modulated expression, over-represented COG (Cluster of Orthologous Group) annotations (39) in the commonly differentially-expressed genes were identified. Overall, 79% (359) of the commonly increased and 65% (252) of the commonly decreased genes had annotated COGs (see Methods). While no COG annotation was enriched in the genes that decreased in expression, three categories were enriched in the increased genes. These up-regulated COGs are translation, protein folding, and amino acid metabolism (FIG. 6B). All of these COGs are related to protein synthesis, indicating that an increase in protein synthesis capacity is a common trend among evolved strains. These changes are consistent with previously described growth rate dependent increases in ribosomal and other protein synthesis machinery (50). At faster growth rates, the increased dilution of protein to daughter cells places a higher demand on protein synthesis, driving the increased expression.

A comparison was made between the identified common mutations (Table 4) and the expression level of the genes within or between where the mutations occurred, in order to connect genotype to molecular phenotype, where possible. Paired mutation and expression data for 6 endpoint strains (numbers 3, 4, 6, 8, 9, and 10) along with two hypermutator isolates, 7A and 7B, were used in the analysis. The same pyrE/rph mutation occurred in all 6 endpoint strains; pyrE was significantly up-regulated in all strains whereas rph was significantly down-regulated in 5 out of 6 strains (with no significant differential expression in strain 6). The up-regulation of pyrE is consistent with the previously identified mechanism of the mutation as relieving a pyrimidine pseudo-auxotrophy (23, 46); the rph down-regulation, on the other hand, is likely not directly beneficial for fitness as the gene contains a frameshift and lacks RNase PH activity (46). An intergenic hns/tdk mutation also occurred in all 6 endpoint strains, and in all strains, hns is significantly up-regulated and tdk is significantly down-regulated (though not significantly in strain 9). Histone-like nucleoid structuring protein (H-NS) is a global transcription factor, which represses a wide array of stress responses (51); the benefit of the hns/tdk mutation may therefore be due to the up-regulation of hns and subsequent down-regulation of many stress responses. Tdk down-regulation has no apparent benefit, but may ameliorate a potential imbalance in deoxyribonucleotide biosynthesis. A mutation occurred in rpoB in all 6 endpoint strains and rpoB was also up-regulated in all of these strains (though not significantly in strain 8). The mutation was intragenic within rpoB and likely does not directly affect its expression level, however rpoB was up-regulated (in addition to all other subunits of the sigma 70 holoenzyme) as a consequence of increases in growth rate (see section below). This growth-rate dependency is further corroborated in that the hypermutator clones did not have an rpoB mutation, but all of the RNAP holoenzyme subunits are upregulated in these strains as well. For the other Exemplary mutations that occurred repeatedly, there was no clear pattern between the occurrence of the mutation and differential expression of the related gene. Looking at an additional strain-specific intergenic IS element insertion between uvrY/yecF in endpoint strain 6, it was found that uvrY was significantly down-regulated, a shift experienced in three of the other strains as well (yecF expression was essentially the same as wild-type). Furthermore, there was an intragenic mutation in uvrY (W42G) in strain 7A, one of the other strains where it was differentially expressed. Thus, comparison of expression data and mutation data revealed potential links between genotype and molecular phenotype for the three intergenic IS element mutations identified in evolutions (those where one would most expect to see a change in transcription) (52-54).

Example 7

Integrated Genome-Scale Modeling

Constraint-based models are capable of predicting growth-optimizing phenotypes (15, 30, 55, 56). A recent genome-scale model of Metabolism and gene Expression for E. coli, a ME-Model, extends predictions beyond metabolism to also include growth-optimization of gene expression phenotypes (38). To test the predictions of gene expression, categorize the transcriptomic data, and provide further insight into the expression data, model predictions were compared to the commonly differentially expressed genes from the analysis of evolved strains. Utilizing the ME-Model of E. coli, growth rate optimizing phenotypes in glucose aerobic culture media conditions (i.e., the same conditions as the ALE experiments) were simulated. Based on these simulations, three groups of genes were identified: 1) genes utilized by the ME-Model in maximum growth rate conditions ('Utilized ME', n=540), 2) genes within the scope of the ME-Model, but not predicted to be utilized in a maximum growth phenotype ('Non-utilized ME' n=1014), and 3) genes outside the scope of the ME-Model ('Outside scope ME', n=2744) which have yet to be reconstructed in a constraint-based formalism (38).

If the in silico predicted Utilized ME genes are indeed important for an apparent optimal growth rate, one would expect them to be in the commonly differentially expressed set as determined through untargeted transcriptomics. To test this hypothesis, the three model-defined gene classes were compared to the commonly differentially expressed genes. Indeed, it was determined that the Utilized ME genes were more often commonly differentially expressed (FIG. 7A top). Furthermore, of the Utilized ME genes that are differentially expressed, 85% were up-regulated, indicating that the transcriptome generally shifts towards these optimal growth-supporting genes (FIG. 7A bottom). The Non-utilized ME genes form an intermediate category whose frequency of differential expression (and frequency of increased differential expression) is between that of Utilized ME genes and Outside scope ME genes. Non-utilized ME genes, although not predicted to be utilized for purely growth-optimizing phenotypes, still contribute to increased growth; whereas many Outside scope ME genes do not. While differentially expressed Non-utilized ME genes have increased expression about half of the time, Outside scope ME genes more often show decreased expression, indicating a shift away from the Outside scope ME genes.

The COG and model-based gene categorizations were combined to provide further insight into the processes commonly differentially expressed among the endpoint clonal isolate strains. By dividing up the genes into Utilized ME and Outside scope ME, new processes missed by just considering the COG annotations alone were identified, which also served to highlight important areas of model expansion.

As in the analysis of the transcriptomic data alone, amino acid metabolism, translation, and protein maturation were enriched in the commonly differentially expressed Utilized ME genes, indicating that the ME-Model correctly predicted a number of the genes in these processes that are important for increased growth rate. By further categorizing the COGs based on the Utilized ME genes, transcription was identified as an up-regulated process. This finding was missed by the categorization based on COGs alone as a result of the numerous genes annotated as related to Transcription. However, by further segmenting this COGs group by model-predicted genes essential for transcription, it is revealed as an up-regulated process.

Looking at the specific genes in the pared gene groups at the intersection of COGs annotations and modeling predictions revealed more details on the specific processes and complexes that change in expression (FIG. 7B). A detailed analysis of the pared groups was performed. However, there are some clear pathway-level shifts worth mentioning here. Energy production and conversion was identified as a down-regulated process (again, energy production and conversion (C) is a broad COG category), but when it is pared-down to only consider model-predicted Utilized ME genes, it is identified as a category with significant changes in expression. Interestingly, genes that decrease in expression all belong to the TCA and glyoxylate cycles (mdh, acnAB, aceAB, gltA, icd). This concerted down-regulation is likely related to the increase in fermentative metabolism and acetate secretion of the evolved strains (FIG. 2). Though aerobic respiration has higher energy yields than fermentative metabolism, it has been hypothesized that the flux through the respiratory reactions is limited by protein synthesis cost and capacity (38, 57, 58) (as TCA and the electron transport system require more proteins than glycolysis and acetate secretion) or limitations in membrane space (58) (for electron transport system enzymes). These gene expression and physiological changes may be driven by these Exemplary capacity constraints.

Many COG categories were revealed as enriched when combining this categorization with the Outside scope ME genes. COG categories with significantly increased expression indicate processes important for growth, but not yet encompassed by the ME-Model, whereas COG categories with decreased expression indicate processes important for growth, but not important for optimal growth in glucose-excess aerobic culture conditions (FIG. 7B). The up-regulated Outside scope ME genes involved in intracellular trafficking and secretion are all involved with protein translocation from the cytosol to the membranes and periplasm. These include genes in the Sec (secA, secE, yajC), Tat (tatB), and SRP (ffh, ftsY) translocation pathways. Similar to the common changes in gene expression and protein folding, this increased expression is likely driven by the increased need to synthesize a functional (and localized) proteome, as the dilution of these proteins to daughter cells increases their demand. Thus, categorization using both COGs and the ME-Model allows for an interpretation of the expression changes driving the observed growth increases in the evolved strains, and highlights areas of poor understanding to be further characterized and included in future genome-scale models.

Example 8

Methods Used in Examples 9-15

Strains and Cultivations

E. coli MG1655 was used as wild-type. The ALE selected rpoBE564V and rpoBE672K knock in strains were previously constructed by allelic replacement[7]. To generate additional variants of rpoB546 and 672 positions, MAGE was performed on the wild-type strain by first transformation of recombineering plasmid pKD46[46], then inactivation of mutS with two nonsense mutations at residues 189 and 191 using an oligo (mutS_MUT). Two oligos (rpoB_E546X and rpoB_E672X) that resulted in NNS codon mutations at rpoB residues 546 and 672 were introduced into the strain through 8-12 rounds of MAGE, followed by colony isolation of mutants, PCR verification, and Sanger sequencing. To perform each cycle of MAGE, the 1-Red system was induced with 0.5%-arabinose 45 minutes prior to generation of electrocompetent cells and oligo. Batch cultures were done in flask with M9 minimal media and 4 g/L of glucose at 37° C. or LB rich media. Glucose limited chemostats were carried out in a Bioflo 110 fermentor (New Brunswick Scientific, NJ). Glucose supplemented M9 was added to the reactor at 0.31 and 0.44 $h^{-1}$ dilution rates controlled by a peristaltic pump. Steady state was achieved after 3-5 residence times and was verified by biomass measurements. Phenotypic tests were performed by inoculation of media with an overnight pre-culture of glucose M9 media for all cases. Erythromycin was added to the media to the indicated concentration. The pH of M9 was adjusted to the indicated value with 6M HCl. Different substrates and mixtures were added to M9 to test growth in the indicated conditions. All growth curves were inoculated to a 0.02 OD and 200 µL were cultured by triplicate in a Bioscreen C device at 37° C. for 15-24 h Motility Test Cells were grown to mid log phase and 10 microliters of cell suspension were spotted onto 0.3% agar plate with glucose M9 media, plates were photographed motility was determined by halo expansion between 24 and 48 h Acid Shock Cells were harvested in mid log phase and normalized to $1 \times 10^8$ cells/mL, 50 µL of cells suspension were resuspended in 950 µL of pH 2.6 glucose M9 media. After 3 hours of incubation cells were diluted and plated in LB agar plates for cell counts[47].

Antibiotic Persistence

Cells were harvested in mid log phase and normalized to $1 \times 10^8$ cells/mL, different dilutions were plated in LB ampicillin plates after 24 h a sterile solution of 25 U of penicinillase was plated and plates were re-incubated for 24 h. Appearance of colonies was determined and persistence frequency determined in base of initial cell counts[48].

Analytics

Biomass was determined by measuring the absorbance of the culture at 600 nm using an equivalence of 0.429 g DW/L per $OD_{600}$ unit. Glucose, and acetate were measured by HPLC using refractive index (RI) detection by high-performance liquid chromatography (HPLC) (Waters, Mass.) with a Bio-Rad Aminex HPX87-H ion exclusion column (injection volume, 10 µl) and 5 mM $H_2SO_4$ as the mobile phase (0.5 ml/min, 45° C.). Metabolomic sampling, extraction and analysis was carried out as described earlier by our group[49].

RNA-Seq Libraries

Samples for RNA-sequencing were taken in mid log phase of batch cultures or during the steady-state in chemostats. Cells were collected with Qiagen RNA-protect Bacteria Reagent and pelleted for storage at −80° C. prior to RNA extraction. Cell pellets were thawed and incubated with Readylyse Lysozyme, SuperaseIn, Protease K, and 20% SDS for 20 minutes at 37° C. Total RNA was isolated and purified using the Qiagen RNeasy Mini Kit columns and following vendor procedures. An on-column DNase-treatment was performed for 30 minutes at room temperature. RNA was quantified using a Nano drop and quality assessed by running an RNA-nano chip on a bioanalyzer. Paired-end, strand-specific RNA-seq was performed following a modified dUTP method[50]. The rRNA was isolated using Epicentre's Ribo-Zero rRNA removal kit for Gram Negative Bacteria.RNA-seq was performed using a modified dUTP method 50

Transcriptome Analyses

The obtained reads were mapped to the E. coli MG1655 genome (NC_000913.2) using the short-read aligner Bowtie (http://bowtie-bio.sourceforge.net)[51] with two mismatches allowed per read alignment. To estimate gene expression FPKM values were calculated using cufflinks tool and differential expression analysis was carried out using cuffdiff feature of the same package using the upper quartile normalization[52]. Gene set enrichment analysis on differentially expressed genes was performed using GO annotations from EcoCyc[53]. A hypergeometric test and p-value cutoff of 0.01 was used.

Regulatory Network

Sigma factor use at promoters was obtained by combining annotations in Cho et al.[54] and EcoCyc[53]. The list of all transcription factors and sRNAs was obtained from RegulonDB[55]. A two-proportion z-test with two-tailed comparisons was used to determine significant differences in sigma factor usage among up-regulated and down-regulated genes.

Computation of Maximum Non-Growth Energy Use

The E. coli ME-Model with all parameters as published in O'Brien et al. was used[31]. For all replicate cultivations, the measured growth rate, glucose uptake rate, and acetate secretion rate were fixed in the model. The maximum unaccounted for energy use was then computed by maximizing the flux through ATP maintenance reaction, which hydrolyzes ATP. For a given strain, the unaccounted for energy use is reported as the average across biological replicates.

Computation of Non-ME Transcriptome

The (protein coding) ME and non-ME transcriptome fractions were estimated using FPKM and gene length. A gene's transcriptome fraction was taken to be the product of FPKM and the gene length, divided by the sum of this product over all genes. The ME and non-ME transcriptome fractions were then calculated by summing the transcriptome fractions of all ME and non-ME genes, respectively. Ranges are determined from the estimated lower and upper FPKM values across different samples.

Computation of the Effects of Changes in Resource Allocation

Figure 50:
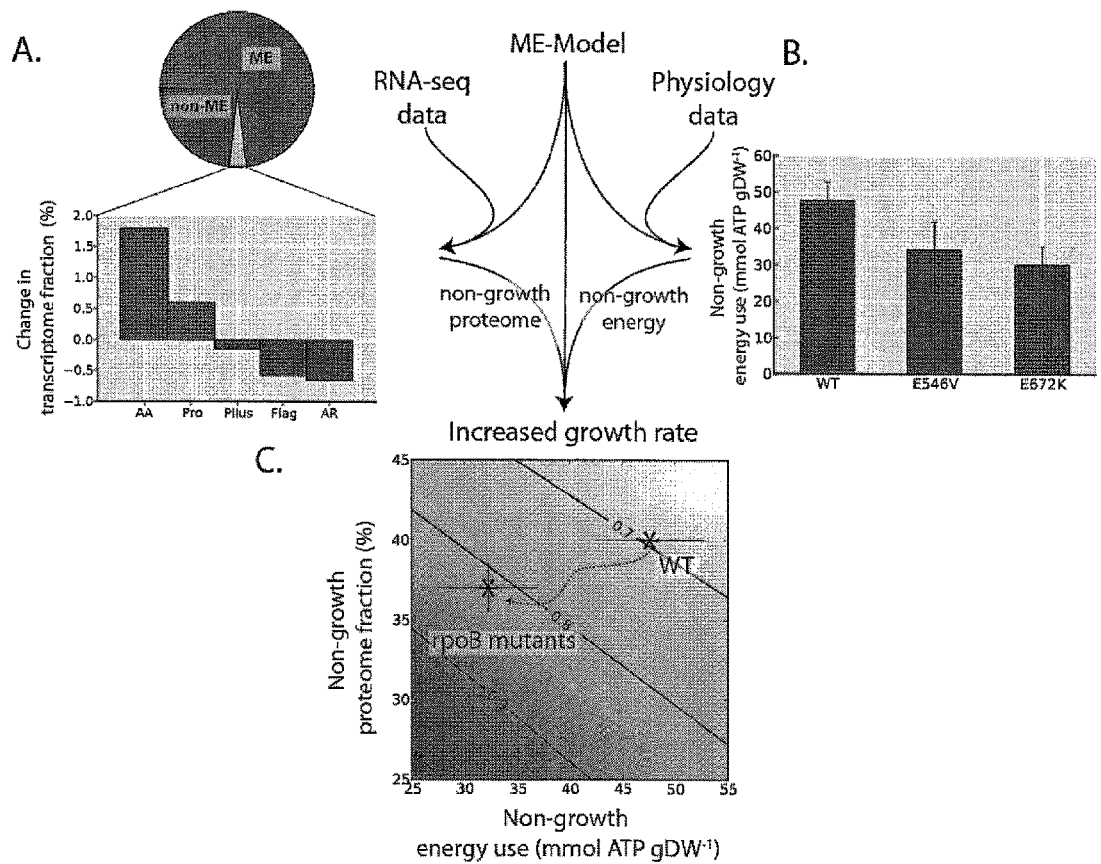
FIG. 50. The changes and effects of proteomic and energetic resource allocation A) A genome-scale model of Metabolism and gene Expression (ME-Model) is used to integrate the RNA-sequencing and physiological data. The transcriptome fraction devoted to ME and non-ME (i.e., not included in the ME-Model) genes is calculated for the wild-type and mutant strains. Grey area of the pie chart indicates the fraction of the transcriptome reallocated from non-ME to ME genes. Bar chart shows the functional categories that reduced or increased in expression by more than 0.1% of the total transcriptome. Abbreviations for the functional categories are: amino acid biosynthesis (AA), protein synthesis/folding (Pro), acid resistance (AR), and flagellar (Fla). All percentages are shown as the average for E546V and E672K. B) The physiological data was used to calculate the energy use not accounted for by the ME-Model (see Methods, Computation of maximum unaccounted for energy), showing a reduction in unaccounted for energy use in rpoB mutants compared to the wild-type. Error bars indicate standard error across biological replicates. C) The effects of non-ME protein and energy use on maximal growth rates in the ME-Model are computed and shown in the contour plot (see Methods). The wild-type and mutant strains are indicated on the plot, showing how lower non-ME protein and energy use can cause increased growth.

Protein and energy that are not used towards cell growth are changeable variables in the ME-Model. These are varied to determine the growth rate, biomass yield, and substrate uptake rate contours (FIG. 50C, FIG. 61). The points and error bars for wild-type and rpoB mutants are placed according to the unaccounted for energy (FIG. 50C) and change in non-ME transcriptome (FIG. 50B). As we do not explicitly know the proteome fraction devoted to growth in each strain, we determine these values with two assumptions. First, we assume the change in non-growth proteome is equal to the change in the non-ME transcriptome. Second, we infer the non-growth proteome in the wild-type strain based on its measured growth (which is why there is no y-axis error bar for the wild-type), resulting in a value consistent with previous estimates[56].

Molecular Dynamics Simulations

Molecular model of the E. coli RNAP elongation complex (EC) were created using the crystal structure of the E. coli RNAP core enzymes (PDB code: 3LU0[57]), the template and non-template DNA strands, and the DNA:RNA hybrid helix (PDB code: 2O5J[58]). The system were neutralized with $Mg^{2+}$ and $K^+$ ions, initially placed in positions occupied by metal ions in the crystal structure or according to the electrostatic potential. The complex was then solvated by well-equilibrated water molecules with periodic boundary conditions. 200 mM KCl was added to the final solution, Molecular dynamics simulations were run for 60 ns (1-fs time steps) under constant pressure (1 atm) and constant temperature (25° C.) using NAMD2.9[59] with the CHARMM36 force field[60] Community analysis and optimal path calculation were done using algorithms described in[22] with the software VMD[61].

Interaction Energy Calculation

Change in the interaction energy between the β and β' subunits upon mutations were calculated with the alanine scan script using PyRosetta[62], originally distributed by the Gray lab (http://graylab.jhu.edu/pyrosetta/downloads/scripts/demo/D090_Ala$_{13}$scan.py). We applied modifications of the score function parameterized according to recently reported protocols[63,64]. To reduce the bias introduced by a single static crystal structure, we performed the computational alanine scan every 25 ps through the entire trajectory, resulting in a broad distribution of the ddG values. Although such ddG value was taken to be qualitative conventionally (with ddG>1 kcal/mol to be destabilizing), we emphasized that it was the observed trend over the dynamical trajectory that correlated with phenotypic fitness of the MAGE mutants.

Example 9

Adaptive Mutations in RNA Polymerase Reveal Growth Versus Hedging Phenotypes

Figure 46:
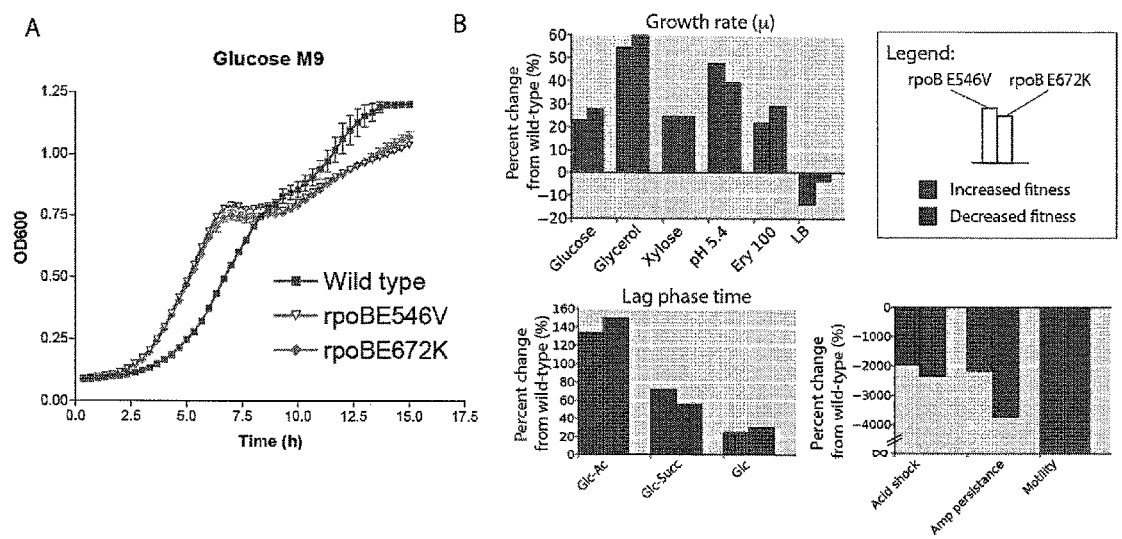
FIG. 46. Growth versus hedging antagonistic pleiotropy in organismal phenotypes A) Adaptive Laboratory Evolution (ALE)-selected rpoB mutations (E546V blue, E672K gray) grow faster in the glucose consumption phase but have a longer diauxic shift to grow on acetate than the wild type (red) (Table 5). B) In addition to growth on glucose (the environment in which the mutants were selected), several additional organismal phenotypes are affected by the rpoB mutations. Bar charts show the percent change in measured phenotypes compared to the wild type. Steady-state growth rates increases (cyan) and growth rate in LB medium as well as fitness in environmental shifts and shocks decreases (brown). LB: Luria Broth, Glc: Glucose, Succ: Succinate, Ac: Acetate, Ery 100: 100 μg/mL erythromycin, Amp: Ampicillin.
Figure 47:
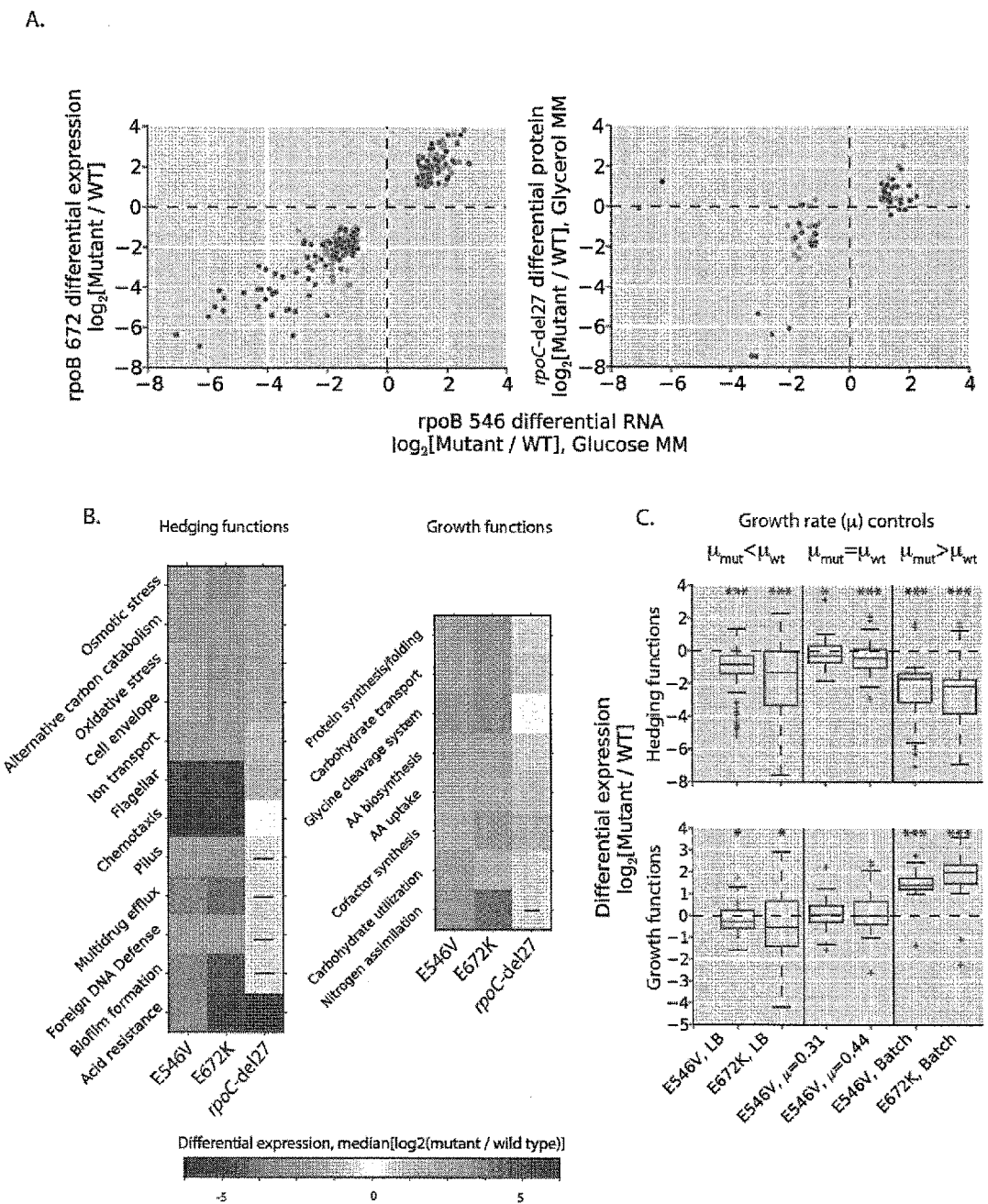
FIG. 47. Conserved molecular growth versus hedging response A) The differential RNA expression in the ALE-selected rpoB mutants (E546V, E672K) is conserved (left). The differential RNA expression in glucose is also concordant with the differential protein expression in glycerol of an ALE-selected 27 aa deletion in β' (rpoC-del27) (right). B) Functional classification of differentially expressed genes reveals that genes with common functions are often differentially expressed in the same direction, segregating growth (up-regulated, cyan) and hedging (down-regulated, brown) functions. Gray dots are genes with functions that are not consistently differentially expressed. Median differential expression of genes in the functional categories is shown in the heatmap; dashes indicate genes not detected in proteomics data[13]. C) Environmental controls disentangle direct effects of the mutations and indirect effects of changes in growth. Box plots show differential expression of identified growth and hedging functions across environments, showing that hedging functions are consistently down-regulated and the expression of growth functions depends on the growth rate. Stars indicate if the mean differential expression of the group of genes is significantly different than zero, based on a two-sided t-test (p<0.05, *; p<0.0001, ***).
Figure 48:
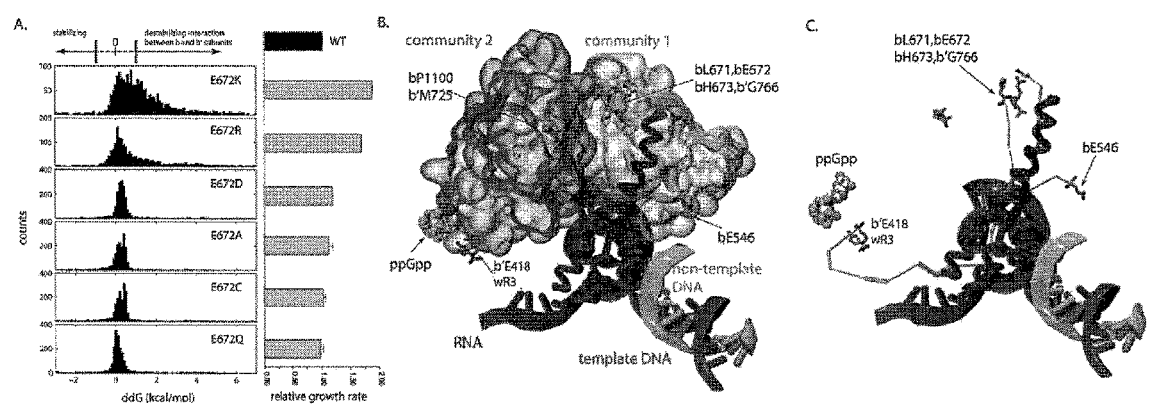
FIG. 48. ALE-selected rpoB mutations modulate structural dynamic of the *E. coli* RNAP. A) Change in interaction energy between the β & β' subunits across six different E672 mutations, compared with their corresponding growth rates. To reduce bias from a single static crystal structure, interaction energy is calculated every 25 ps over a 60 ns molecular dynamic trajectory starting from the RNAP open complex. B) Dynamical community structures encompassing the ALE-selected mutations. Community 1 (green), as discussed in the text, includes the bridge helix in β' subunit (purple), βE672, βE546, and a few other ALE-selected mutations in contact with βE672. Community 2 (brown) spans the interface between the β & β' subunits, interacting with community 1 on one side, and the (p)ppGpp binding site on the other. C) Effective allosteric communication between distantly located residues can be resolved from optimal path calculated based on a dynamical correlation network. The result shows that βE672 and βE546 share the same optimal dynamical path (orange) towards the ppGpp binding site in the ω subunit. Structural elements are shown from the same perspective, and color-coded the same as in B).

A recent adaptive laboratory evolution (ALE) experiment of E. coli in glucose minimal media (MM) identified recurring mutations in rpoB (the β subunit of RNAP), including rpoB E546V and rpoB E672K[7]. We introduced these two ALE-selected mutations into the starting strain (i.e., the 'wild type' strain) and observed consistent physiological effects. Growth rate increased (by ~25%) resulting from increases in both biomass yield (by ~11%) and substrate uptake rate (by ~14%). The use of an automated plate reader to obtain frequent measurements revealed a diauxic shift of the mutant strains in glucose M9 mineral media (FIG. 46A).

As mutations often have positive and negative fitness effects across several environments (referred to as pleiotropy), we then assessed the growth rate of the rpoB E546V and rpoB E672K mutants under a variety of single carbon sources, mixtures of carbon sources, rich media, and stress conditions. Additionally we performed, motility, acid shock, and antibiotic persistence phenotypic tests (FIG. 46B, Supplementary FIGS. 46-48, Table 5-6). These RNAP mutations show consistent fitness effects: they enable faster growth in several carbon sources, in low pH, and in the presence of erythromycin. However, they lead to lower motility, lower survival under acid shock, reduced antibiotic persistence, longer diauxic shifts, and lower growth rates in complex media.

Therefore, the mutants show increased fitness in conditions of steady-state growth, but a decreased fitness in changing environments. They show strong, consistent antagonistic pleiotropy for growth versus 'hedging' functions.

Example 10

Mutations in RNA Polymerase are Highly Specific

Figure 55:
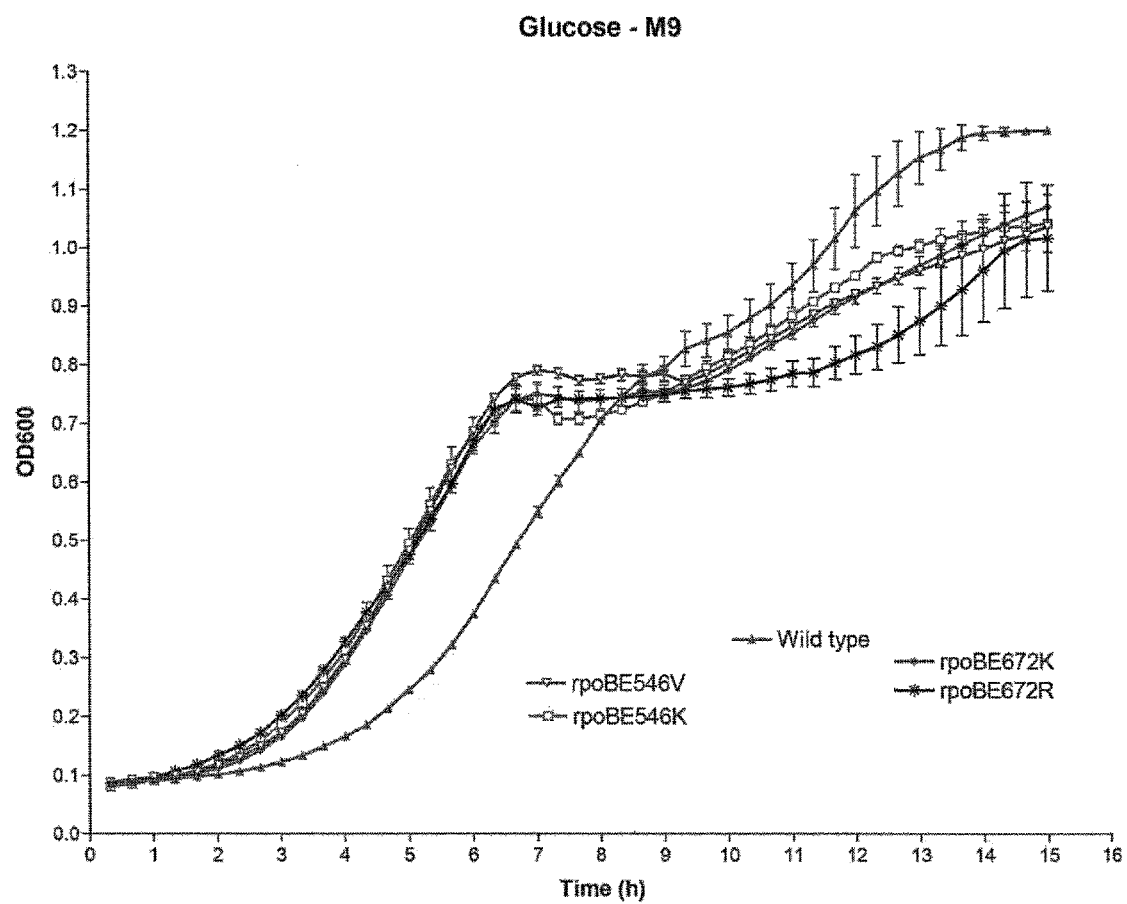
FIG. 55: MAGE introduced mutations. E546K and E672R show a faster growth than the wild-type and a similar growth phenotype as the ALE selected. A prolonged diauxic shift compared to the wild-type is shown when glucose is depleted and growth resumes on acetate.

To assess whether other amino acid substitutions in the RNAP ALE-selected loci affect growth phenotypes, we generated a series of additional variants using multiplex automated genome engineering (MAGE)[19]. Two amino acid substitutions with similar chemical properties as those discovered by ALE resulted in an increase in growth rate (i.e., E546K and E672R), whereas all other amino acid substitutions generated by MAGE did not affect growth rate significantly. MAGE selected mutants that grow faster than the wild type also exhibit longer diauxic shifts, showing similar pleiotropic effects as the ALE selected mutants (FIGS. 55-56).

Therefore, the mutations in RNAP affecting fitness are specific. All faster growing RNAP mutants showed antagonistic pleiotropy for growth versus 'hedging'.

Example 11

Figure 57:
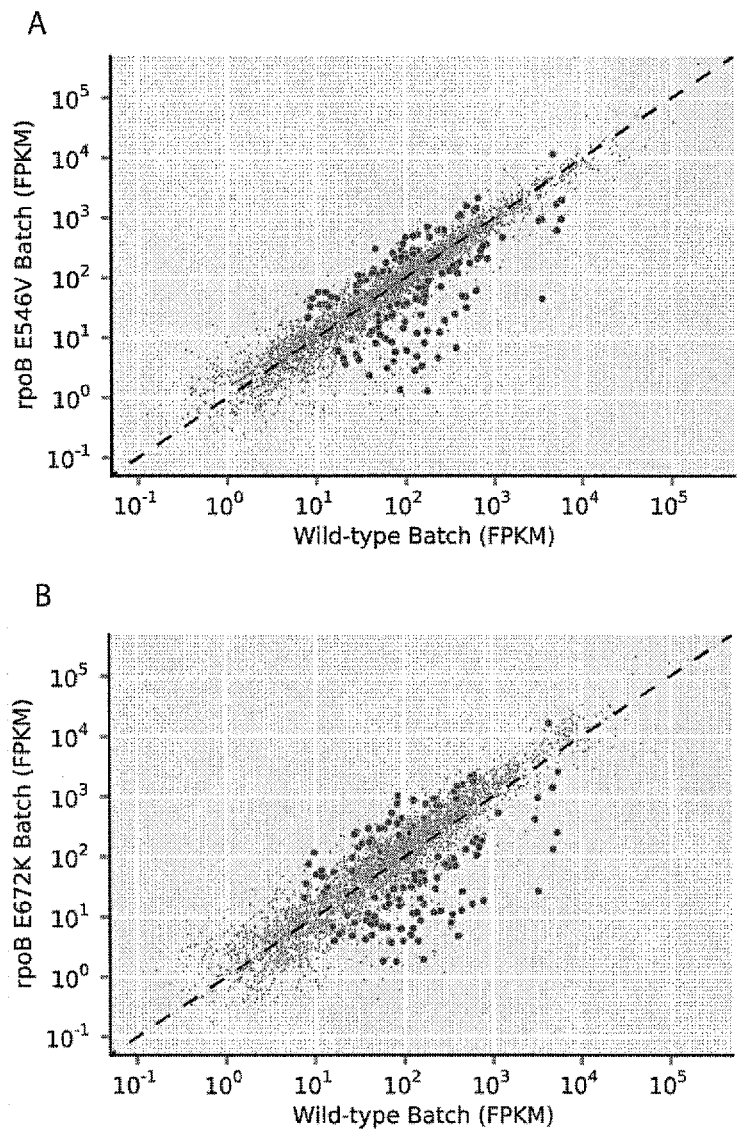
FIG. 57: Comparison of gene expression between the wild type strain and the A) rpoBE546V strain B) rpoBE672K strain. The brown dots are hedging functions and cyan dots growth functions according to the classification in Table 7
Figure 58:
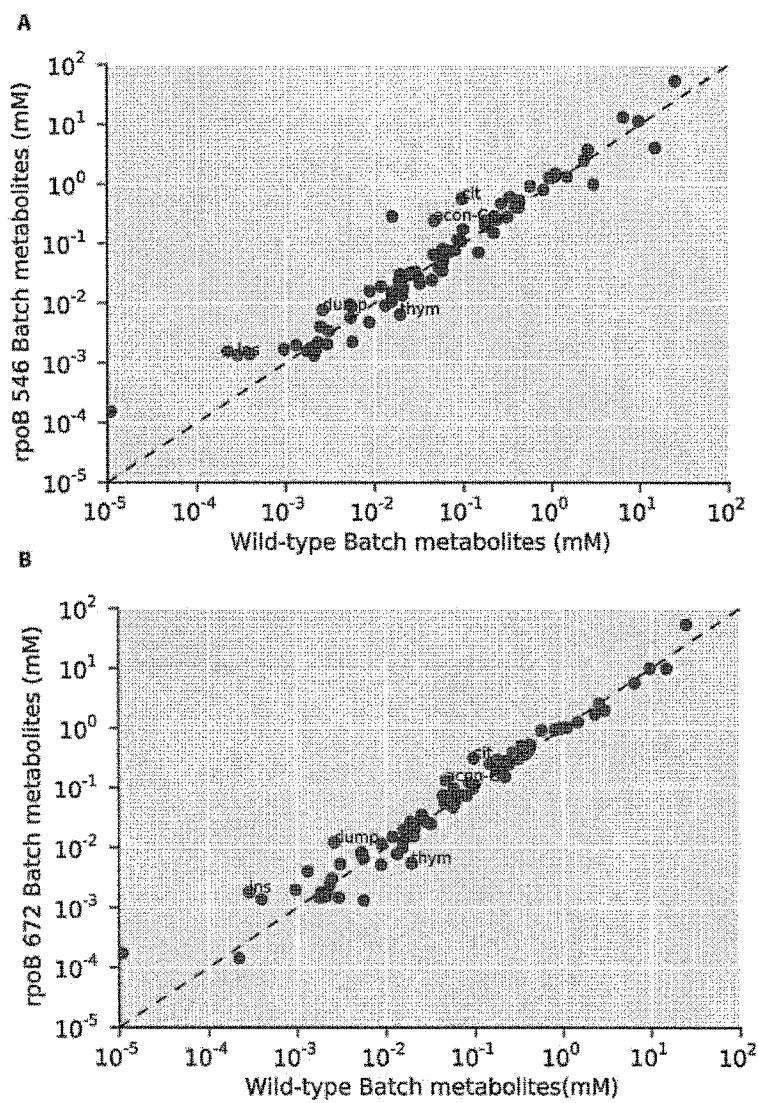
FIG. 58: Comparison of metabolite concentrations between the wild type strain and the A) rpoBE546V strain B) rpoBE672K strain. The blue dots are the metabolites that are significantly different (p<0.05, t-test). Labeled blue dots are those that are significantly different in both mutants. See supplementary data files for full information.

Genome-Scale Transcript Profiling Reveals Conserved Growth Versus Hedging Response To reveal the systems-level mechanism of the pleiotropic effects of the RNAP mutations, we obtained RNA-seq and metabolomics data from mid-logarithmic growth phase in glucose minimal media for the wild-type, rpoB E546V, and rpoB E672K mutant strains (FIG. 57). Metabolite concentrations that changed significantly compared to the wild-type include pyrimidine, glycolytic, and TCA intermediates, but overall, the metabolome remained fairly stable (FIG. 58). On the other hand, the expression profiling data revealed 243 consistently differentially expressed genes. Like the pleiotropic fitness effects of the mutants, the differential gene expression is strikingly conserved (FIG. 47A, left), indicating a common underlying mechanism at the systems level.

Interestingly, we also find that the differential expression of the two rpoB mutants is similar to a previously profiled 27 amino acid deletion mutant in the β' subunit of the RNAP (rpoC-del27, identified by ALE on glycerol)[12,13,20]. The changes in expression of the rpoC-del27 mutant[13] (compared to wild-type) grown in glycerol match those of the rpoB mutants grown in glucose (FIG. 47A, right).

To obtain insight into the processes perturbed by the RNAP mutations, we classified the 243 consistently differentially expressed genes by function (Table 7). We found that the genes in the same functional category are often differentially expressed in a consistent direction. We used this observation to define up-regulated and down-regulated functions. The up-regulated functions (defined as >80% of the genes being up-regulated) are broadly related to cellular growth, including protein synthesis and folding, amino acid biosynthesis and uptake, and carbohydrate transport and utilization. On the other hand, the down-regulated functions (defined as >80% of the genes being down-regulated) broadly hedge against environmental change and stress, including osmotic and oxidative stress, flagella, chemotaxis, acid resistance, and biofilm formation. Two categories of genes are not consistently up or down-regulated; these are DNA repair and genes with unknown function. Thus, at the molecular level, the differentially expressed genes reflect the growth versus hedging phenotypes observed at the organismal level.

Example 12

Environmental Controls Disentangles Cause Versus Effect of Mutations

As growth rate itself has a strong effect on gene expression[21], we sought to identify the differential expression caused only by the mutation from that indirectly caused by increased growth. To disentangle these effects we obtained RNA-seq data under conditions where the wild-type and mutant strains grow at the same rate (glucose limited chemostat culture) and under conditions where the mutants grow slower than the wild-type (LB rich media). Regardless of the growth rate and environment, the hedging functions are down-regulated in the mutant strain compared to the wild-type (FIG. 47C). Differential expression of the growth functions, however, is dependent on the growth rate: growth genes are not differentially expressed in chemostat and are down-regulated in LB. Thus, these environmental controls disentangle the cause and effect of the mutations: the mutations directly result in the down-regulation of hedging genes whereas the growth-related genes are coupled to the cell's growth rate.

Example 13

Structural Dynamics of RNAP Suggests a Common Allosteric Mechanism

Both mutations, rpoB E546V and E672K, are located approximately 25 Å away from the catalytic site of RNAP, and about 25 Å from each other. How do they result in such similar patterns in transcriptional reprogramming to down-regulate hedging functions?

To answer this question, we performed molecular dynamics simulations aiming to propose a common putative molecular mechanism for the pleiotropic fitness effects of the rpoB mutations. Interestingly, we found a strong correlation between the extent of increase in interaction energy between the β and β' subunits, and the increase in cell fitness for various E672 mutations generated by MAGE (both beneficial and neutral, FIG. 48A). Such destabilization of subunit interaction is consistent with a previous study that showed a decrease in open complex half-life of the rpoC-del27 mutation, which has similar growth and transcriptional effects[12].

Figure 59:
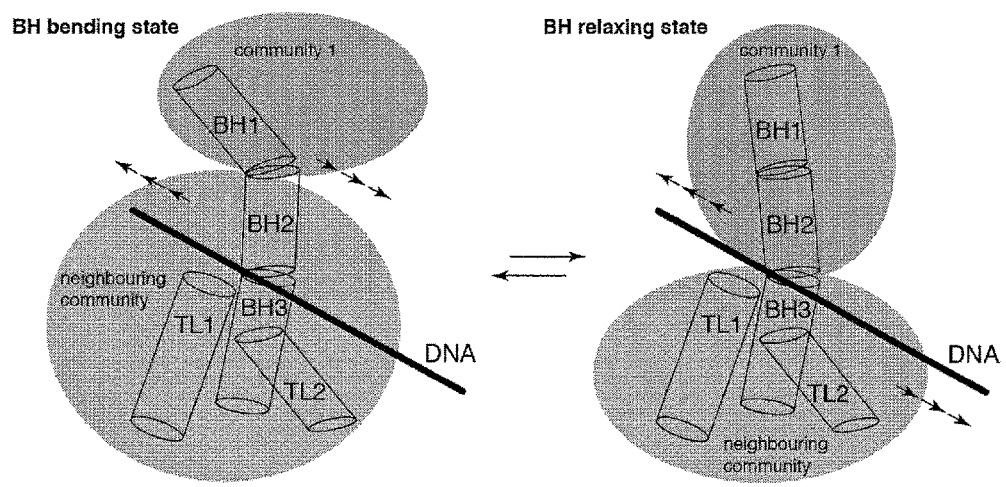
FIG. 59: A hypothesis for regulating nucleotide elongation by coordinated molecular motions of the RNAP. We calculated the bending angles between all pairs of helices in the bridge helix (BH1, BH2, BH3) and the trigger loops (TL1, TL2) along the 60 ns MD trajectory. As a result, each frame in the trajectory were represented by a ten-dimensional angle vector, based on which a distance could be calculated between all pairs of frames. Such a distance matrix was then used to cluster the dynamical RNAP structures into subtle functional states. In a similar manner, a second clustering was done using the relative motions between interacting communities the green and blue communities in the figure). These two metrics, although seemingly unrelated, give rise to over 90% identical clustering of the trajectory. In addition to this strong correlation observed between bridge helix bending and relative motion of structural communities, we also notice that community boundaries coincide with the kink in bridge helix. Therefore we hypothesize that relative motions between the communities facilitate the bending-relaxing cycle of bridge helix, which in turn generate a torque to move the nucleotide chain forward. The ALE-selected mutations are located in the critical community containing the moving top of the bridge helix, and affect such functional dynamics by modulating the interaction energy between the communities.

To further explore the functional correlation among different mutations, we decomposed the RNAP complex into 'structural communities' within which the molecular motions of residues are strongly correlated[22]. In spite of the large spatial separation between E672 and E546, they belong to the same dynamical community (FIG. 48B). Furthermore, many mutations detected in RNAP in other ALE experiments[7,10,23] can also be found in this and neighboring communities (FIG. 48B and Table 8). This structural community consists of ~250 residues in rpoB, the bridge helix in rpoC, and nucleotides on the template DNA strand. Because the bending motion of bridge helix has been shown to coordinate catalysis and DNA translocation in the nucleotide addition reaction[24-26], the collective motion of this community may be directly related to nucleotide elongation. In fact, we observe a strong correlation between the bending angle of the bridge helix (a motion known to be directly involved in elongation[24-26]) and the relative motion between neighboring communities along the direction of DNA translocation (FIG. 59). Again, the relation between the community dynamics and transcriptional elongation is consistent with the increased elongation rate observed in the related rpoC-de127 mutation.

The observed destabilization of subunit interaction and its role in elongation are both reminiscent of the effects of (p)ppGpp and dksA on the stringent response[27,28]. The allosteric regulator, (p)ppGpp, modulates transcription by destabilizing the intrinsically short lived open complexes[29] and affecting sigma factors use[30]. Interestingly, we observed a conserved optimal path linking E564/E672 and the (p)ppGpp binding site in the ω subunit (FIG. 48C), showing a common effective allosteric communication between these distantly located functional residues. The ALE-selected mutations may therefore modulate transcription in a similar manner as (p)ppGpp[14].

In summary, several features of RNAP structural dynamics and function suggest a common allosteric mechanism of these mutations. The ALE-selected mutations are capable of modulating RNAP complex interactions and nucleotide elongation at the molecular level, which in turn, modulates global transcriptional regulation.

Example 14

Figure 49:
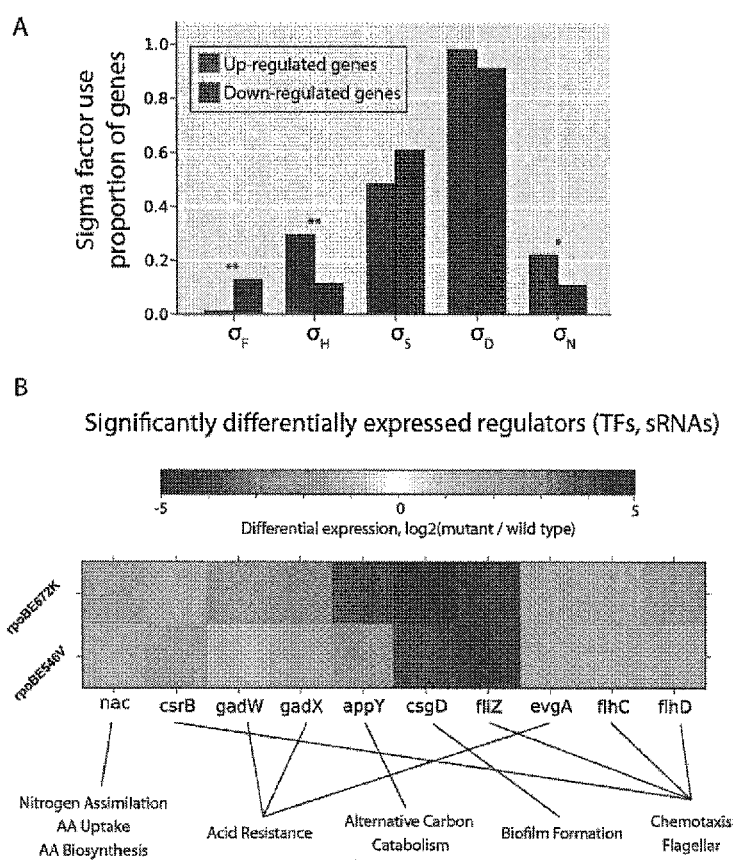
FIG. 49. Reprogramming of the regulatory network A) The σ factor usage of differentially expressed genes in mutant strains is shown. Bars indicate the fraction of up-regulated (cyan) and down-regulated (brown) genes that have a promoter that is regulated by a given σ factor. Only σ factors with greater than 10% of promoters regulated among either up-regulated or down-regulated genes are shown. Significant differences in the proportion between σ factor use in up-regulated and down-regulated genes are indicated with asterisks; one asterisk indicates p<0.05 and two asterisks indicate p<0.005. B) The fold change for transcription factors and sRNA that are significantly differentially expressed in both mutant strains compared to the wild type are shown.
Figure 60:
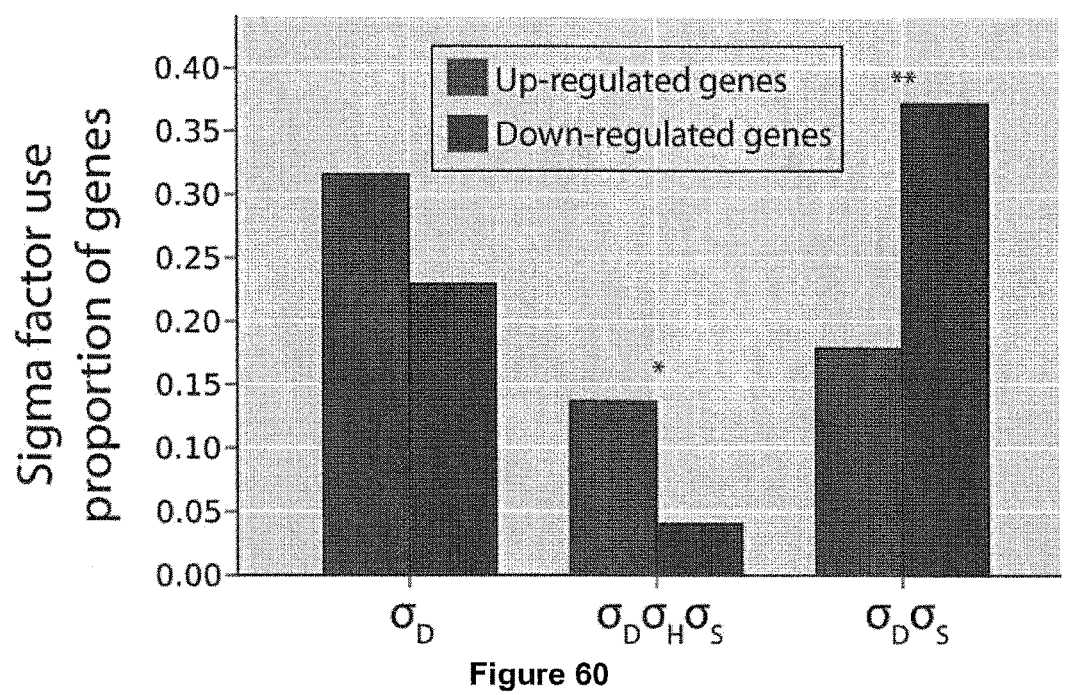
FIG. 60: Combinatorial Sigma Factor Use. The σ factor usage of differentially expressed genes in mutant strains is shown. Bars indicate the fraction of up-regulated (cyan) and down-regulated (brown) genes that have a promoter that is regulated by a given combination of σ factors. Only σ factor combinations with greater than 10% of promoters regulated among either up-regulated or down-regulated genes are shown. Significant differences in the proportion between σ factor use in up-regulated and down-regulated genes are indicated with asterisks; one asterisk indicate $p<0.05$ and two asterisks indicate $p<0.005$.

Transcriptional Regulatory Network Perturbation Explains Observed Molecular Response Consistent with the perturbed structural properties of the mutated RNAP, the differentially expressed growth and hedging functions have sigma factor biases. Even though the sigma factors are not detectably differentially expressed, the down-regulated (hedging) genes tend to have promoters utilizing stress related sigma factors ($\sigma^S$, $\sigma^F$) and the up-regulated (growth) genes tend to have promoters utilizing growth related sigma factors ($\sigma^D$, $\sigma^N$, $\sigma^H$) (FIG. 49A, FIG. 60).

However, the observed differential expression is more specific than that caused by sigma factors alone. There are 10 transcription factors (TFs) and regulatory small RNAs (sRNAs) that are differentially expressed in the mutant strains (FIG. 47C). Each of these regulators can be associated with one or more of the differentially expressed functional categories identified (Table 7). Furthermore, across all of the strains (wild-type, rpoB E546V, and rpoB E672K) and environments (glucose excess, glucose limitation, and rich media) examined with RNA-seq, the differential expression of the identified growth and hedging functions is in a direction consistent with the differential expression of their regulators (based on known activation or repression relationships; FIG. 47C, Table 7).

Thus, the balance between growth and hedging functions is achieved through global modulation of the TRN. The structure of the TRN enables *E. coli* to rebalance its proteome in response to evolutionary pressures with single point mutations in RNAP.

Example 15

'Econometric' Analysis of Proteome and Energy Resource Allocation Explains Fitness Trade-Off The molecular and regulatory effects of the rpoB mutations reveal that resource allocation underlies the observed growth versus hedging fitness effects. A recently developed genome-scale computer model of microbial growth[31], called a ME-model[31-33] (for metabolism and expression) can quantify the fitness effects associated with proteome and energy re-allocation (FIG. 48A).

The ME-model allows global energy accounting based on the physiological data from wild-type and RNAP mutant strains. The results show that the RNAP mutations eliminate about a third (28-37%) of the unaccounted for energy (i.e., processes not involved in metabolism and protein synthesis, often referred to as the 'maintenance energy'[34], FIG. 50B). Then, using the gene expression data we estimate a 2-5% reduction of the transcriptome allocated to non-ME genes (i.e., not included in the ME-model, non-growth functions) and a commensurate increase in ME gene (i.e., modeled, growth) allocation in the RNAP mutants (FIG. 50B). ME-model analysis thus shows a clear shift to a more growth-supporting proteome as a result of the observed RNAP mutations.

We used the ME-model to understand how these changes in resource allocation affect cellular physiology (i.e., growth rate, biomass yield, and uptake rate). The non-ME proteome and energy allocation are adjustable model variables. Indeed, when varied in the model, the measured changes in non-ME energy and transcriptome use can quantitatively account for the measured physiological changes (biomass yield and uptake rate) in the mutant strains (FIG. 48D, FIG. 61). Therefore, the growth increase can be accounted for by the measured change in resource allocation. The expression of hedging functions restrains growth rate in the wild-type strain.

The ME-model allows us to quantitatively elucidate the relationship between changes in overall physiological measures (i.e., growth rate, substrate uptake rate, and yield) and the changes in allocation of protein and energy (FIG. 48A). This quantitative relationship allows us to conclude that the pleiotropic effects of the rpoB mutation are due to a fundamental constraint of limited proteome and energy resources, leading to an inherent trade-off in resource allocation.

TABLE 1

Fitness properties of the evolved populations

| Experiment | Population Growth Rate ($hr^{-1}$) | Total CCD | Total Doublings | Ratio of Final Fitness to Wild Type | Total Number of Flasks |
|---|---|---|---|---|---|
| Wild-type K-12 MG1655 | 0.69 ± 0.02 | 0 | 0 | 1 | NA |
| 3 | 1.01 ± 0.16 | $13.5 \times 10^{12}$ | 1903 | 1.46 | 382 |
| 4 | 0.98 ± 0.10 | $10.2 \times 10^{12}$ | 1440 | 1.42 | 288 |
| 5 | 1.01 ± 0.08 | $8.3 \times 10^{12}$ | 1184 | 1.46 | 288 |
| 6 | 1.00 ± 0.16 | $11.3 \times 10^{12}$ | 1630 | 1.46 | 327 |
| 7 | 1.11 ± 0.10 | $13.6 \times 10^{12}$ | 1870 | 1.59 | 375 |
| 8 | 0.99 ± 0.11 | $10.5 \times 10^{12}$ | 1542 | 1.43 | 309 |
| 9 | 1.01 ± 0.09 | $18.1 \times 10^{12}$ | 2589 | 1.46 | 519 |
| 10 | 1.02 ± 0.12 | $18.3 \times 10^{11}$ | 2582 | 1.48 | 518 |

CCD - Cumulative cell divisions, 95% Confidence interval for the wild-type strain was determined from biological triplicates, population growth rate were taken from the endpoint of the fitted spline.

TABLE 2A

Exemplary Mutations

| Gene | Mutation | Appearance Location | Replacing Mutation (within same experiment) | Appearance Location | Occurrences | Experiment(s) |
|---|---|---|---|---|---|---|
| pyrE/rph | Δ82 bp | Jump 1<br>pre-Jump 1 | | | 8 | 3, 5, 9, 10<br>4, 6, 7, 8 |
| rpoB | E672K (GAA→AAA) | Jump 1 | | | 8 | 3, 5, 9 |
| | P1100Q (CCG→CAG) | Jump 1 | | | | 4, 8 |
| | E546V (GAA→GTA) | Jump 1 | | | | 10 |
| | H673Y (CAC→TAC) | Jump 1 | D785Y (GAC→TAC) | Jump 2 | | 6 |
| | L671P (CTG→CCG) | Jump 1 | hypermutator | Jump 2 | | 7 |
| hns/tdk | intergenic (−114/−487) IS2 | Jump 2 | | | 7 | 3 |
| | intergenic (−110/−488) IS1 | Jump 2 | | | | 4 |
| | intergenic (−274/−328) IS5 | Jump 2 | | | | 5 |
| | intergenic (−86/−511) IS1 | post Jump 2 | | | | 6 |
| | intergenic (−67/−531) IS1 | Jump 2 | | | | 8 |
| | intergenic (−93/−505) IS1 | Jump 3 | | | | 9 |
| | intergenic (−258/−344) IS5 | Jump 2 | intergenic (−274/−328) IS5 | post Jump 2 | | 10 |
| corA | coding (726-728/951 nt) Δ3 bp | Jump 1 | coding (220-224/951 nt) Δ5 bp | Jump 1 | 3 | 4 |
| | A206V (GCG→GTG) | Jump 1-2 | coding (113-211/951 nt) Δ99 bp | Jump 2 | | 5 |
| | coding (668/951 nt) duplication 21 bp | Jump 2-3 | wild type | Jump 3 | | 10 |
| ygaZ | coding (529-532/738 nt) IS5 | Jump 2 | coding (307-316/738 nt) Δ10 bp | post Jump 3 | 3 | 3 |
| | E49* (GAA→TAA) 2807900 19 bp × 2 | Jump 3 post Jump 3 | | | | 9 |
| iap | coding (98-101/1038 nt) IS5 | post Jump 2/3 | | | | 6, 9 |
| metL | coding (1338/2433 nt) Δ1 bp | Jump 2-3 | A798E (GCG→GAG) | Jump 3 | 1 | 10 |
| ygeW | S200R (AGC→CGC) | Jump 1 | | | 2 | 5, 9 |

TABLE 2B

Exemplary Mutations

| SEQ ID NO: | FIG. No. | Gene | Mutation | Position NC 000913.2 (version 2) | Mutation |
|---|---|---|---|---|---|
| 1 | 16 | rpoB | E672K (GAA→AAA) | 4,181,281 | G→A |
| 2 | 17 | | P1100Q (CCG→CAG) | 4,182,566 | C→A |
| 3 | 18 | | E546V (GAA→UTA) | 4,180,904 | A→T |
| 4 | 19 | | H673Y (CAC→TAC) | 4,181,284 | C→T |
| 5 | 20 | | L671P (CTG→CCG) | 4,181,279 | T→C |
| 6 | 21 | | D785Y (GAC→TAC) | 4,181,620 | G→T |
| 7 | 22 | hns/tdk | intergenic (−114/−487) IS2 | 1,292,259 | IS2 (+) |
| 8 | 23 | | intergenic (−110/−488) IS1 | 1,292,255 | IS1 (−) |
| 9 | 24 | | intergenic (−274/−328) IS5 | 1,292,419 | IS5 (+) |
| 10 | 25 | | intergenic (−86/−511) IS1 | 1,292,231 | IS1 (+) |
| 11 | 26 | | intergenic (−67/−531) IS1 | 1,292,212 | IS1 (+) |
| 12 | 27 | | intergenic (−93/−505) IS1 | 1,292,238 | IS5 (+) |
| 13 | 28 | | intergenic (−258/−344) IS5 | 1,292,403 | IS5 (+) |
| 14 | 29 | corA | coding (726-728/951 nt) Δ3 bp | 4,000,174 | Δ3 bp |
| 15 | 30 | | coding (220-224/951 nt) Δ5 bp | 3,999,668 | Δ5 bp |
| 16 | 31 | | A206V (GCG→GTG) | 4,000,065 | C→T |
| 17 | 32 | | coding (113-211/951 nt) Δ99 bp | 3,999,561 | Δ99 bp |
| 18 | 33 | | coding (668/951 nt) duplication 21 bp | 4,000,117 | 21 bp × 2 |
| 19 | 34 | ygaZ | coding (529-532/738 nt) IS5 | 2,808,167 | IS5 (+) |
| 20 | 35 | | coding (307-316/738 nt) Δ10 bp | 2,807,945 | Δ10 bp |
| 21 | 36 | | E49* (GAA→TAA) | 2,807,783 | G→T |
| 22 | 37 | | coding (262/738 nt) 19 bp × 2 | 2,807,900 | 19 bp × 2 |
| 23 | 38 | iap | coding (98-101/1038 nt) IS5 | 2,874,700 | ISS (+) |
| 24 | 39 | metL | coding (1338/2433 nt) Δ1 bp | 4,129,195 | Δ1 bp |
| 25 | 40 | | A798E (GCG→GAG) | 4,130,250 | C→A |

TABLE 2B-continued

Exemplary Mutations

| SEQ ID NO: | FIG. No. | Gene | Mutation | Position NC 000913.2 (version 2) | Mutation |
|---|---|---|---|---|---|
| 26 | 41 | ygeW | S200R (AGC→CGC) | 3,004,881 | A→C |
| 27 | 42 | pyrE/rph | intergenic (−90/+5) Δ82 bp | 3,813,882 | Δ82 bp |

TABLE 2C

The GenBank No. of the DNA sequence for each of wild type genes that were mutated per Table 2A and Table 2B. The GenBank No. Used for all of the coordinates below is NCBI Reference Sequence: NC_000913.2

| Gene | Gene | geneId | geneID | Start ... Stop NC_000913.2 | Start ... Stop NC_000913.2 |
|---|---|---|---|---|---|
| rpoB | | GeneID: 948488 | | 4179268 ... 4183296 | |
| corA | | GeneID: 949351 | | 3999449 ... 4000399 | |
| ygaZ | | GeneID: 945093 | | 2807639 ... 2808376 | |
| iap | | GeneID: 947215 | | 2874603 ... 2875640 | |
| metL | | GeneID: 948433 | | 4127858 ... 4130290 | |
| ygeW | | GeneID: 945826 | | 3004284 ... 3005474 | |
| pyrE | Rph | GeneID: 948157 | GeneID: 948156 | complement (3813150 ... 3813791) | complement (3813886 ... 3814572) |
| hns | tdk | GeneID: 945829 | GeneID: 945834 | complement (1291732 ... 1292145) | 1292750 ... 1293367 |

TABLE 3

Phenotypic data from clones isolated from the final flask of each experiment

| Strain | Growth Rate ($hr^{-1}$) | Glucose Uptake Rate (mmol $gDW^{-1}$ $hr^{-1}$) | Acetate Production Rate (mmol $gDW^{-1}$ $hr^{-1}$) | Biomass Yield (gDW $gGlc^{-1}$) | Fold Increase vs. wild-type | Population/Clone Growth Rate |
|---|---|---|---|---|---|---|
| Wild-type K-12 MG1655 | 0.69 ± 0.02 | 8.59 ± 1.42 | 3.91 ± 1.14 | 0.44 ± 0.07 | — | — |
| Exp. 3 | 0.98 ± 0.02 | 13.51 ± 1.15 | 8.43 ± 2.17 | 0.40 ± 0.04 | 1.42 | 1.03 |
| Exp. 4 | 0.96 ± <0.01 | 12.19 ± 0.68 | 7.89 ± 1.88 | 0.44 ± 0.02 | 1.39 | 1.02 |
| Exp. 6 | 0.93 ± 0.01 | 12.77 ± 0.85 | 7.11 ± 1.51 | 0.40 ± 0.03 | 1.34 | 1.07 |
| Exp. 7* | 1.01 ± 0.04 | 13.13 ± 1.29 | 5.12 ± 0.57 | 0.43 ± 0.06 | 1.46 | 1.10 |
| Exp. 7A* | 0.97 ± <0.01 | 11.01 ± 0.79 | 3.97 ± 0.98 | 0.49 ± 0.03 | 1.41 | 1.14 |
| Exp. 7B* | 0.92 ± 0.02 | 10.43 ± 0.62 | 2.36 ± 0.54 | 0.49 ± 0.03 | 1.33 | 1.20 |
| Exp. 8 | 0.89 ± 0.01 | 12.59 ± 1.01 | 5.05 ± 0.40 | 0.39 ± 0.03 | 1.29 | 1.11 |
| Exp. 9 | 0.92 ± 0.02 | 13.13 ± 0.59 | 6.99 ± 0.48 | 0.39 ± 0.02 | 1.33 | 1.10 |
| Exp. 10 | 0.95 ± 0.01 | 13.98 ± 1.11 | 9.27 ± 1.76 | 0.38 ± 0.03 | 1.38 | 1.07 |

*denotes hypermutator strain,
Exp. - experiment

TABLE 4

Exemplary Mutations in Validation ALE

| Genetic Region | Starting Strain | Mutation | Occurrences | Experiment(s) |
|---|---|---|---|---|
| pyrE/rph | rpoB E546V | Δ82 bp deletion | 1 | 2 |
| | | Δ1 bp deletion | 1 | 3 |
| | rpoB E672K | Δ82 bp deletion | 3 | 4, 5, 6 |
| rpoB | pyrE/rph | A679V (GCA→GTA) | 1 | 8 |
| | | V857E (GTG→GAG) | 1 | 9 |
| hns/tdk | pyrE/rph | intergenic (−75/−522) IS1 | 1 | 9 |
| metL | rpoB E546V | W424* (TGG→TAG) | 1 | 1 |

TABLE 5

Quantification of lag phases length (in hours) in diauxic shifts, lag phase was defined as the period of time where the change in biomass concentration goes from zero (or negative) to a positive number.

| | Wild type (h) | rpoBE546V (h) | rpoBE672K (h) |
|---|---|---|---|
| Glucose M9 4 g/L (FIG. 46A) | NA | 2.22 ± 0.77 | 2.56 ± 0.38 |
| Glucose 2 g/L M9 | 5.87 ± 0.37 | 7.33 ± 0.33 | 7.67 ± 1.76 |
| Glucose2 g/L + Acetate 2 g/L M9 | 1.33 ± 0.33 | 3.11 ± 0.19 | 3.33 ± 0.33 |
| Glucose 1 g/L + Succinate 2 g/L | 2 ± 0.33 | 3.44 ± 0.19 | 3.11 ± 0.51 |

TABLE 6

Physiological parameters of wild type and RNAP mutants

| | Wild type | rpoBE546V | rpoBE672K |
|---|---|---|---|
| Glucose Batch | | | |
| Growth rate ($h^{-1}$) | 0.69 ± 0.008 | 0.85 ± 0.014 | 0.88 ± 0.010 |
| GUR (mmol · $gDW^{-1}$ · $h^{-1}$) | 8.98 ± 0.407 | 10.23 ± 0.53 | 10.44 ± 0.61 |
| APR (mmol · $gDW^{-1}$ · $h^{-1}$) | 4.68 ± 0.060 | 4.75 ± 0.14 | 4.87 ± 0.22 |
| SS Yield (g/g) | 0.42 ± 0.018 | 0.46 ± 0.03 | 0.47 ± 0.02 |
| Glycerol Batch | | | |
| Growth rate ($h^{-1}$) | 0.23 ± 0.005 | 0.36 ± 0.021 | 0.38. ± 0.004 |
| GlyUR (mmol · $gDW^{-1}$ · $h^{-1}$) | 7.42 ± 0.17 | 9.50 ± 0.50 | 8.84 ± 0.46 |
| APR (mmol · $gDW^{-1}$ · $h^{-1}$) | N.D | N.D | N.D. |
| SS Yield (g/g) | 0.35 ± 0.013 | 0.41 ± 0.039 | 0.47 ± 0.028 |
| Xylose Batch | | | |
| Growth rate ($h^{-1}$) | 0.52 ± 0.010 | 0.65 ± 0.03 | 0.65 ± 0.01 |
| xylUR (mmol · $gDW^{-1}$ · $h^{-1}$) | 6.98 ± 0.40 | 9.10 ± 0.93 | 11.30 ± 0.15 |
| APR (mmol · $gDW^{-1}$ · $h^{-1}$) | 2.74 ± 0.33 | 2.22 ± 0.16 | 2.99 ± 0.56 |
| SS Yield (g/g) | 0.49 ± 0.04 | 0.48 ± 0.045 | 0.38 ± 0.009 |
| LB | | | |
| Growth rate ($h^{-1}$) | 1.42 ± 0.179 | 1.34 ± 0.068 | 1.40 ± 0.045 |
| Chemostat D = 0.31 $h^{-1}$ | | | |
| GUR (mmol · $gDW^{-1}$ · $h^{-1}$) | 4.02 ± 0.15 | 4.13 ± 0.27 | N.D. |
| APR (mmol · $gDW^{-1}$ · $h^{-1}$) | 1.28 ± 0.18 | 0.12 ± 0.04 | N.D. |
| Yield (g/g) | 0.43 ± 0.017 | 0.42 ± 0.001 | N.D. |
| Chemostat D = 0.44 $h^{-1}$ | | | |
| GUR (mmol · $gDW^{-1}$ · $h^{-1}$) | 5.62 ± 0.25 | 5.61 ± 0.03 | N.D. |
| APR (mmol · $gDW^{-1}$ · $h^{-1}$) | 1.48 ± 0.14 | 2.05 ± 0.11 | N.D. |
| Yield (g/g) | 0.39 ± 0.001 | 0.44 ± 0.02 | N.D. |

GUR: Glucose Uptake Rate
GlyUR: Glycerol Uptake Rate
XylUR: xylose Uptake Rate
APR: Acetate Production Rate

TABLE 7

Functional categories of differentially expressed genes, number of genes in each category, and growth or hedging annotation. Regulators associated with a functional category.

| Functional category | Number of genes down-regulated | Number of genes up-regulated | Growth or hedging annotation | Positive regulators | Negative regulators |
|---|---|---|---|---|---|
| AA biosynthesis | 0 | 11 | growth | nac | |
| AA uptake | 1 | 4 | growth | nac | |
| Acid resistance | 13 | 0 | hedging | | evgA, gadW, gadX |
| Alternative carbon catabolism | 11 | 0 | hedging | | appY |
| Biofilm formation | 5 | 0 | hedging | | csgD |
| Carbohydrate transport | 0 | 8 | growth | | |
| Carbohydrate utilization | 1 | 4 | growth | | |
| Cell envelope | 9 | 2 | hedging | | |
| Chemotaxis | 5 | 0 | hedging | fliZ, flhC, flhD | csrB |
| Cofactor synthesis | 0 | 7 | growth | | |
| DNA repair | 3 | 2 | | | |
| Flagellar | 17 | 0 | hedging | fliZ, flhC, flhD | csrB |
| Foreign DNA Defense | 3 | 0 | hedging | | |
| Glycine cleavage system | 0 | 3 | growth | | |
| Ion transport | 5 | 1 | hedging | | |
| Multidrug efflux | 2 | 0 | hedging | | |
| Nitrogen assimilation | 0 | 3 | growth | nac | |
| No classification | 30 | 17 | | | |
| No known function | 27 | 21 | | | |
| Osmotic stress | 6 | 0 | hedging | | |
| Oxidative stress | 3 | 0 | hedging | | |
| Pilus | 7 | 0 | hedging | | |
| Protein synthesis/folding | 0 | 12 | growth | | |

AA: Amino acid

TABLE 8

RNAP mutations in other ALE experiments, structural community localization and stability effect

| Experiment | Gene | Mutation | Community | ddG |
|---|---|---|---|---|
| Glucose ALE[7] 42.2C evolution[23] | rpoB | I(M*)1112L | #(1) | neutral |
| | rpoC | M725I | #2 | neutral |
| | rpoB | P806L | #2 | destabilizing* |
| | rpoB | K1078R | #2 | neutral |
| | rpoB | I572N(5)/L(5)/F(2)^ | #1 | /** |
| | rpoB | R151C | #(1) | $ / |
| | rpoB | N1236K | #1 | / |
| | rpoB | G664S | #1 | / |
| | rpoB | T539P (7) | #1 | / |
| | rpoB | T553I(2) | #1 | / |
| | rpoB | G556S(2) | #1 | / |
| | rpoB | E84G(2)/K | #(1) | / |
| | rpoB | P1081(3) | #2 | / |
| | rpoB | I1210N | #2 | / |
| | rpoB | N760H | #(1) | / |
| | rpoC | Y511S | #2 | / |
| Rif$^R$ [10] | rpoB | I572L | #1 | / |
| | rpoB | S574Y | #1 | / |
| | rpoB | D516Y | #1 | / |
| | rpoB | Q148L | #(1) | / |

TABLE 8-continued

RNAP mutations in other ALE experiments, structural community localization and stability effect

| Experiment | Gene | Mutation | Community | ddG |
|---|---|---|---|---|
| | rpoB | D516G | #1 | / |
| | rpoB | S512F | #(1) | / |
| | rpoB | Q513P | #(1) | / |
| | rpoB | d532-535 | #(1) | / |

*large destabilizing ddG comparing to E672R/K, possibly due to the highly hydrophobic local environment;
**not applicable for interaction energy calculation between rpoB and rpoC;
^number in the parenthesis indicates how many times this mutation is seen out of the total 115 lines in [23];
$ the residue is on the dynamical boarder of the community, so its inclusion into the community could change upon conformational change of the RNAP.

References Listed in Examples 1-7 and Under the Heading "*Escherichia Coli* Mutants Described in Examples 1-7."

1. Tenaillon O, Rodriguez-Verdugo A, Gaut R L, McDonald P, Bennett A F, Long A D, Gaut B S. 2012. The molecular diversity of adaptive convergence. Science 335:457-461.
2. Dragosits M, Mozhayskiy V, Quinones-Soto S, Park J, Tagkopoulos I. 2013. Evolutionary potential, cross-stress behavior and the genetic basis of acquired stress resistance in *Escherichia coli*. Mol Syst Biol 9:643.
3. Charusanti P, Conrad T M, Knight E M, Venkataraman K, Fong N L, Xie B, Gao Y, Palsson B O. 2010. Genetic basis of growth adaptation of *Escherichia coli* after deletion of pgi, a major metabolic gene. PLoS Genet 6:e1001186.
4. Palsson B. 2011. Adaptive Laboratory Evolution. Microbe 6:6.
5. Dragosits M, Mattanovich D. 2013. Adaptive laboratory evolution—principles and applications for biotechnology. Microb Cell Fact 12:64.
6. Reyes L H, Almario M P, Winkler J, Orozco M M, Kao K C. 2012. Visualizing evolution in real time to determine the molecular mechanisms of n-butanol tolerance in *Escherichia coli*. Metab Eng 14:579-590.
7. Atsumi S, Wu T Y, Machado I M, Huang W C, Chen P Y, Pellegrini M, Liao J C. 2010. Evolution, genomic analysis, and reconstruction of isobutanol tolerance in *Escherichia coli*. Mol Syst Biol 6:449.
8. Horinouchi T, Tamaoka K, Furusawa C, Ono N, Suzuki S, Hirasawa T, Yomo T, Shimizu H. 2010. Transcriptome analysis of parallel-evolved *Escherichia coli* strains under ethanol stress. BMC Genomics 11:579.
9. Tremblay P L, Summers Z M, Glaven R H, Nevin K P, Zengler K, Barrett C L, Qiu Y, Palsson B O, Lovley D R. 2011. A c-type cytochrome and a transcriptional regulator responsible for enhanced extracellular electron transfer in Geobacter sulfurreducens revealed by adaptive evolution. Environ Microbiol 13:13-23.
10. Jansen G, Barbosa C, Schulenburg H. Experimental evolution as an efficient tool to dissect adaptive paths to antibiotic resistance. LID-S1368-7646(14)00004-1 [pii] LID-10.1016/j.drup.2014.02.002 [doi].
11. Conrad T M, Lewis N E, Palsson B O. 2011. Microbial laboratory evolution in the era of genome-scale science. Mol Syst Biol 7:509.
12. Mozhayskiy V, Tagkopoulos I. 2013. Microbial evolution in vivo and in silico: methods and applications. Integr Biol (Camb) 5:262-277.
13. Fong S S, Joyce A R, Palsson B O. 2005. Parallel adaptive evolution cultures of *Escherichia coli* lead to convergent growth phenotypes with different gene expression states. Genome Res 15:1365-1372.
14. Ibarra R U, Edwards J S, Palsson B O. 2002. *Escherichia coli* K-12 undergoes adaptive evolution to achieve in silico predicted optimal growth. Nature 420:186-189.
15. Fong S S, Palsson B O. 2004. Metabolic gene-deletion strains of *Escherichia coli* evolve to computationally predicted growth phenotypes. Nat Genet 36:1056-1058.
16. Conrad T M, Frazier M, Joyce A R, Cho B K, Knight E M, Lewis N E, Landick R, Palsson B O. 2010. RNA polymerase mutants found through adaptive evolution reprogram *Escherichia coli* for optimal growth in minimal media. Proc Natl Acad Sci USA 107:20500-20505.
17. Wiser M J, Ribeck N, Lenski R E. 2013. Long-term dynamics of adaptation in asexual populations. Science 342:1364-1367.
18. Farida Vasi M T, Richard E. Lenski. 1994. Long-Term Experimental Evolution in *Escherichia coli*. II. Changes in life-history traits during adaptation to a seasonal environment. American Naturalist 144:432-456.
19. Vasi F K, Lenski R E. 1999. Ecological Strategies and Fitness Tradeoffs in *Escherichia coli* Mutants Adapted to Prolonged Starvation. Journal of Genetics 78:43-49.
20. Deng Y, Fong S S. 2011. Laboratory evolution and multi-platform genome re-sequencing of the cellulolytic actinobacterium *Thermobifida fusca*. J Biol Chem 286:39958-39966.
21. Quan S, Ray J C, Kwota Z, Duong T, Balazsi G, Cooper T F, Monds R D. 2012. Adaptive evolution of the lactose utilization network in experimentally evolved populations of *Escherichia coli*. PLoS Genet 8:e1002444.
22. Herring C D, Glasner J D, Blattner F R. 2003. Gene replacement without selection: regulated suppression of amber mutations in *Escherichia coli*. Gene 311:153-163.
23. Conrad T M, Joyce A R, Applebee M K, Barrett C L, Xie B, Gao Y, Palsson B O. 2009. Whole-genome resequencing of *Escherichia coli* K-12 MG1655 undergoing short-term laboratory evolution in lactate minimal media reveals flexible selection of adaptive mutations. Genome Biol 10:R118.
24. Lee D H, Palsson B O. 2010. Adaptive evolution of *Escherichia coli* K-12 MG1655 during growth on a Nonnative carbon source, L-1,2-propanediol. Appl Environ Microbiol 76:4158-4168.
25. Wang H H, Isaacs F J, Carr P A, Sun Z Z, Xu G, Forest C R, Church G M. 2009. Programming cells by multiplex genome engineering and accelerated evolution. Nature 460:894-898.
26. Hill S A, Little J W. 1988. Allele replacement in *Escherichia coli* by use of a selectable marker for resistance to spectinomycin: replacement of the lexA gene. J Bacteriol 170:5913-5915.
27. Feist A M, Herrgard M J, Thiele I, Reed J L, Palsson B O. 2009. Reconstruction of biochemical networks in microorganisms. Nat Rev Microbiol 7:129-143.
28. Joyce A R, Palsson B O. 2006. The model organism as a system: integrating 'omics' data sets. Nat Rev Mol Cell Biol 7:198-210.
29. Schmidt B J, Ebrahim A, Metz T O, Adkins J N, Palsson B O, Hyduke D R. 2013. GIM3E: condition-specific models of cellular metabolism developed from metabolomics and expression data. Bioinformatics 29:2900-2908.
30. McClosExemplary D, Palsson B O, Feist A M. 2013. Basic and applied uses of genome-scale metabolic network reconstructions of *Escherichia coli*. Mol Syst Biol 9:661.

31. Feist A M, Palsson B O. 2008. The growing scope of applications of genome-scale metabolic reconstructions using *Escherichia coli*. Nat Biotechnol 26:659-667.
32. Shachrai I, Zaslaver A, Alon U, Dekel E. 2010. Cost of unneeded proteins in *E. coli* is reduced after several generations in exponential growth. Mol Cell 38:758-767.
33. Deatherage D E, Barrick J E. 2014. Identification of Mutations in Laboratory-Evolved Microbes from Next-Generation Sequencing Data Using breseq. Methods Mol Biol 1151:165-188.
34. Latif H, Lerman J A, Portnoy V A, Tarasova Y, Nagarajan H, Schrimpe-Rutledge A C,
Smith R D, Adkins J N, Lee D H, Qiu Y, Zengler K. 2013. The genome organization of *Thermotoga maritima* reflects its lifestyle. PLoS Genet 9:e1003485.
35. Langmead B, Salzberg S L. 2012. Fast gapped-read alignment with Bowtie 2. Nat Methods 9:357-359.
36. Trapnell C, Williams B A, Pertea G, Mortazavi A, Kwan G, van Baren M J, Salzberg S L, Wold B J, Pachter L. 2010. Transcript assembly and quantification by RNA-Seq reveals unannotated transcripts and isoform switching during cell differentiation. Nat Biotechnol 28:511-515.
37. Keseler I M, Mackie A, Peralta-Gil M, Santos-Zavaleta A, Gama-Castro S, Bonavides-Martinez C, Fulcher C, Huerta A M, Kothari A, Krummenacker M, Latendresse M, Muniz-Rascado L, Ong Q, Paley S, Schroder I, Shearer A G, Subhraveti P, Travers M, Weerasinghe D, Weiss V, Collado-Vides J, Gunsalus R P, Paulsen I, Karp P D. 2013. EcoCyc: fusing model organism databases with systems biology. Nucleic Acids Res 41:D605-612.
38. O'Brien E J, Lerman J A, Chang R L, Hyduke D R, Palsson B O. 2013. Genome-scale models of metabolism and gene expression extend and refine growth phenotype prediction. Mol Syst Biol 9:693.
39. Tatusov R L, Fedorova N D, Jackson J D, Jacobs A R, Kiryutin B, Koonin E V, Krylov D M, Mazumder R, Mekhedov S L, Nikolskaya A N, Rao B S, Smirnov S, Sverdlov A V, Vasudevan S, Wolf Y I, Yin J, Natale D A. 2003. The COG database: an updated version includes eukaryotes. BMC Bioinformatics 4:41.
40. Newton C R, Graham A, Heptinstall L E, Powell S J, Summers C, Kalsheker N, Smith J C, Markham A F. 1989. Analysis of any point mutation in DNA. The amplification refractory mutation system (ARMS). Nucleic Acids Res 17:2503-2516.
41. Lee D H, Feist A M, Barrett C L, Palsson B O. 2011. Cumulative number of cell divisions as a meaningful timescale for adaptive laboratory evolution of *Escherichia coli*. PLoS One 6:e26172.
42. Sandberg T E, Pedersen M, LaCroix R A, Ebrahim A, Bonde M, Herrgard M J, Palsson B O, Sommer M, Feist A M. 2014. Evolution of *Escherichia coli* to 42° C. and Subsequent Genetic Engineering Reveals Adaptive Mechanisms and Novel Mutations. Molecular Biology and Evolution.
43. Portnoy V A, Herrgard M J, Palsson B O. 2008. Aerobic fermentation of D-glucose by an evolved cytochrome oxidase-deficient *Escherichia coli* strain. Appl Environ Microbiol 74:7561-7569.
44. Barrick J E, Yu D S, Yoon S H, Jeong H, Oh T K, Schneider D, Lenski R E, Kim J F. 2009. Genome evolution and adaptation in a long-term experiment with *Escherichia coli*. Nature 461:1243-1247.
45. Herring C D, Raghunathan A, Honisch C, Patel T, Applebee M K, Joyce A R, Albert T J, Blattner F R, van den Boom D, Cantor C R, Palsson B O. 2006. Comparative genome sequencing of *Escherichia coli* allows observation of bacterial evolution on a laboratory timescale. Nat Genet 38:1406-1412.
46. Jensen K F. 1993. The *Escherichia coli* K-12 "wild types" W3110 and MG1655 have an rph frameshift mutation that leads to pyrimidine starvation due to low pyrE expression levels. J Bacteriol 175:3401-3407.
47. Kobayashi M, Nagata K, Ishihama A. 1990. Promoter selectivity of *Escherichia coli* RNA polymerase: effect of base substitutions in the promoter−35 region on promoter strength. Nucleic Acids Res 18:7367-7372.
48. Ayers D G, Auble D T, deHaseth P L. 1989. Promoter recognition by *Escherichia coli* RNA polymerase. Role of the spacer DNA in functional complex formation. J Mol Biol 207:749-756.
49. Cox E C. 1976. Bacterial mutator genes and the control of spontaneous mutation. Annu Rev Genet 10:135-156.
50. Scott M, Gunderson C W, Mateescu E M, Zhang Z, Hwa T. 2010. Interdependence of cell growth and gene expression: origins and consequences. Science 330:1099-1102.
51. Wang W, Li G W, Chen C, Xie X S, Zhuang X. 2011. Chromosome organization by a nucleoid-associated protein in live bacteria. Science 333:1445-1449.
52. Barker C S, Pruss B M, Matsumura P. 2004. Increased motility of *Escherichia coli* by insertion sequence element integration into the regulatory region of the flhD operon. J Bacteriol 186:7529-7537.
53. Hall B G. 1999. Transposable elements as activators of cryptic genes in *E. coli*. Genetica 107:181-187.
54. Umeda M, Ohtsubo E. 1989. Mapping of insertion elements IS1, IS2 and IS3 on the *Escherichia coli* K-12 chromosome. Role of the insertion elements in formation of Hfrs and F' factors and in rearrangement of bacterial chromosomes. J Mol Biol 208:601-614.
55. Feist A M, Palsson B O. 2010. The biomass objective function. Curr Opin Microbiol 13:344-349.
56. Schuetz R, Zamboni N, Zampieri M, Heinemann M, Sauer U. 2012. Multidimensional optimality of microbial metabolism. Science 336:601-604.
57. Beg Q K, Vazquez A, Ernst J, de Menezes M A, Bar-Joseph Z, Barabasi A L, Oltvai Z N.
2007. Intracellular crowding defines the mode and sequence of substrate uptake by *Escherichia coli* and constrains its metabolic activity. Proc Natl Acad Sci USA 104:12663-12668.
58. Adadi R, Volkmer B, Milo R, Heinemann M, Shlomi T. 2012. Prediction of microbial growth rate versus biomass yield by a metabolic network with kinetic parameters. PLoS Comput Biol 8:e1002575.
59. Janssen P, Goldovsky L, Kunin V, Darzentas N, Ouzounis C A. 2005. Genome coverage, literally speaking. The challenge of annotating 200 genomes with 4 million publications. EMBO Rep 6:397-399.
60. Lenski R E, Rose M R, Simpson S C, Tadler S C. 1991. Long-Term Experimental Evolution in *Escherichia coli*. I. Adaptation and Divergence During 2,000 Generations. The American Naturalist 138:1315-1341.

References Listed in Examples 8-15 and Under the Heading "Further Characterization of Exemplary Mutants Described in Examples 8-15"

Jones, F. C. et al. The genomic basis of adaptive evolution in threespine sticklebacks. *Nature* 484, 55-61, doi: 10.1038/nature10944 (2012).

2 Fraser, H. B. Gene expression drives local adaptation in humans. *Genome Research* 23, 1089-1096, doi:10.1101/gr.152710.112 (2013).

3 Wray, G. A. The evolutionary significance of cis-regulatory mutations. *Nature reviews. Genetics* 8, 206-216, doi:10.1038/nrg2063 (2007).

4 Prud'homme, B., Gompel, N. & Carroll, S. B. Emerging principles of regulatory evolution. *P Natl Acad Sci USA* 104 Suppl 1, 8605-8612, doi:10.1073/pnas.0700488104 (2007).

5 Enard, D., Messer, P. W. & Petrov, D. A. Genome-wide signals of positive selection in human evolution. *Genome Research* 24, 885-895, doi:10.1101/gr.164822.113 (2014).

6 King, M. C. & Wilson, A. C. Evolution at two levels in humans and chimpanzees. *Science* 188, 107-116 (1975).

7 LaCroix, R. A., Sandberg, T. E., O'Brien, E. J., Utrilla, J., Ebrahim A., Guzman, G. I., Szubin, R., Palsson, B. O., Feist, A. M. Discovery of key mutations enabling rapid growth of *Escherichia coli* K-12 MG1655 on glucose minimal media using adaptive laboratory evolution. *Applied and Environmental Microbiology* AEM.02246-14, doi:10.1128/AEM.02246-14 (2014).

8 Ferenci, T. The spread of a beneficial mutation in experimental bacterial populations: the influence of the environment and genotype on the fixation of rpoS mutations. *Heredity* 100, 446-452, doi:10.1038/sj.hdy.6801077 (2008).

9 Sandberg, T. E. et al. Evolution of *Escherichia coli* to 42 degrees C. and Subsequent Genetic Engineering Reveals Adaptive Mechanisms and Novel Mutations. *Mol Biol Evol* 31, 2647-2662, doi:10.1093/molbev/msu209msu209 [pii] (2014).

10 Barrick, J. E., Kauth, M. R., Strelioff, C. C. & Lenski, R. E. *Escherichia coli* rpoB mutants have increased evolvability in proportion to their fitness defects. *Molecular biology and evolution* 27, 1338-1347, doi:10.1093/molbev/msq024 (2010).

11 Saxer, G. et al. Mutations in Global Regulators Lead to Metabolic Selection during Adaptation to Complex Environments. *PLoS Genetics* 10, e1004872-e1004872, doi:10.1371/journal.pgen.1004872 (2014).

12 Conrad, T. M. et al. RNA polymerase mutants found through adaptive evolution reprogram *Escherichia coli* for optimal growth in minimal media. *P Natl Acad Sci USA* 107, 20500-20505, doi:DOI 10.1073/pnas.0911253107 (2010).

13 Cheng, K. K. et al. Global metabolic network reorganization by adaptive mutations allows fast growth of *Escherichia coli* on glycerol. *Nat Commun* 5, 3233, doi:10.1038/ncomms4233ncomms4233 [pii] (2014).

14 Hauryliuk, V., Atkinson, G. C., Murakami, K. S., Tenson, T. & Gerdes, K. Recent functional insights into the role of (p)ppGpp in bacterial physiology. *Nat Rev Microbiol* 13, 298-309, doi:10.1038/nrmicro3448 (2015).

15 Wang, J. et al. Natural Variation in Preparation for Nutrient Depletion Reveals a Cost-Benefit Tradeoff. *PLOS Biology* 13, e1002041-e1002041, doi:10.1371/journal.pbio.1002041 (2015).

16 Solopova, A. et al. Bet-hedging during bacterial diauxic shift. *Proc Natl Acad Sci USA* 111, 7427-7432, doi:10.1073/pnas.1320063111 1320063111 [pii] (2014).

17 Venturelli, O. S., Zuleta, I., Murray, R. M. & El-Samad, H. Population Diversification in a Yeast Metabolic Program Promotes Anticipation of Environmental Shifts. *PLOS Biology* 13, e1002042-e1002042, doi:10.1371/journal.pbio.1002042 (2015).

18 King, T., Ishihama, A., Kori, A. & Ferenci, T. A Regulatory Trade-Off as a Source of Strain Variation in the Species *Escherichia coli* A Regulatory Trade-Off as a Source of Strain Variation in the Species *Escherichia coli* †. 186, 5614-5620, doi:10.1128/JB.186.17.5614 (2004).

19 Wang, H. H. et al. Programming cells by multiplex genome engineering and accelerated evolution. *Nature* 460, 894-898, doi:10.1038/nature08187 nature08187 [pii] (2009).

20 Herring, C. D. et al. Comparative genome sequencing of *Escherichia coli* allows observation of bacterial evolution on a laboratory timescale. *Nature genetics* 38, 1406-1412, doi:10.1038/ng1906 (2006).

21 Klumpp, S. & Hwa, T. Bacterial growth: global effects on gene expression, growth feedback and proteome partition. *Current opinion in biotechnology* 28C, 96-102, doi:10.1016/j.copbio.2014.01.001 (2014).

22 Sethi, A., Eargle, J., Black, A. A. & Luthey-Schulten, Z. Dynamical networks in tRNA:protein complexes. *Proc Natl Acad Sci USA* 106, 6620-6625, doi:10.1073/pnas.0810961106 (2009).

23 Tenaillon, O. et al. The molecular diversity of adaptive convergence. *Science* 335, 457-461, doi:10.1126/science.1212986 (2012).

24 Bar-Nahum, G. et al. A ratchet mechanism of transcription elongation and its control. *Cell* 120, 183-193, doi:10.1016/j.cell.2004.11.045 (2005).

25 Weinzierl, R. O. The nucleotide addition cycle of RNA polymerase is controlled by two molecular hinges in the Bridge Helix domain. *BMC Biol* 8, 134, doi:10.1186/1741-7007-8-134 (2010).

26 Weinzierl, R. O. The Bridge Helix of RNA polymerase acts as a central nanomechanical switchboard for coordinating catalysis and substrate movement. *Archaea* 2011, 608385, doi:10.1155/2011/608385 (2011).

27 Jishage, M., Kvint, K., Shingler, V. & Nystrom, T. Regulation of sigma factor competition by the alarmone ppGpp. *Genes Dev* 16, 1260-1270, doi:10.1101/gad.227902 (2002).

28 Zhou, Y. N. & Jin, D. J. The rpoB mutants destabilizing initiation complexes at stringently controlled promoters behave like "stringent" RNA polymerases in *Escherichia coli*. *P Natl Acad Sci USA* 95, 2908-2913 (1998).

29 Barker, M. M., Gaal, T., Josaitis, C. a. & Gourse, R. L. Mechanism of regulation of transcription initiation by ppGpp. I. Effects of ppGpp on transcription initiation in vivo and in vitro. *Journal of molecular biology* 305, 673-688, doi:10.1006/jmbi.2000.4327 (2001).

30 Osterberg, S., del Peso-Santos, T. & Shingler, V. Regulation of alternative sigma factor use. *Annu Rev Microbiol* 65, 37-55, doi:10.1146/annurev.micro.112408.134219 (2011).

31 O'Brien, E. J., Lerman, J. A., Chang, R. L., Hyduke, D. R. & Palsson, B. O. Genome-scale models of metabolism and gene expression extend and refine growth phenotype prediction. *Mol Syst Biol* 9, 693, doi:10.1038/msb.2013.52 (2013).

32 Lerman, J. A. et al. In silico method for modelling metabolism and gene product expression at genome scale. *Nature communications* 3, 929-929, doi:10.1038/ncomms1928 (2012).

33 Thiele, I., Jamshidi, N., Fleming, R. M. & Palsson, B. O. Genome-scale reconstruction of *Escherichia coli*'s transcriptional and translational machinery: a knowledge base, its mathematical formulation, and its functional characterization. *PLoS Comput Biol* 5, e1000312, doi:10.1371/journal.pcbi.1000312 (2009).

34 Pirt, S. J. Maintenance energy: a general model for energy-limited and energy-sufficient growth. *Arch Microbiol* 133, 300-302 (1982).
35 Futuyma, D. J. & Moreno, G. The Evolution of Ecological Specialization. *Annu Rev Ecol Syst* 19, 207-233, doi:Doi 10.1146/Annurev.Ecolsys.19.1.207 (1988).
36 Remold, S. Understanding specialism when the Jack of all trades can be the master of all. *Proc Biol Sci* 279, 4861-4869, doi:10.1098/rspb.2012.1990 (2012).
37 Cooper, V. S. & Lenski, R. E. The population genetics of ecological specialization in evolving *Escherichia coli* populations. *Nature* 407, 736-739, doi:10.1038/35037572 (2000).
38 Leiby, N. & Marx, C. J. Metabolic erosion primarily through mutation accumulation, and not tradeoffs, drives limited evolution of substrate specificity in *Escherichia coli*. *PLoS biology* 12, e1001789, doi:10.1371/journal.pbio.1001789 (2014).
39 Venturelli, O. S., Zuleta, I., Murray, R. M. & El-Samad, H. Population diversification in a yeast metabolic program promotes anticipation of environmental shifts. *PLoS biology* 13, e1002042, doi:10.1371/journal.pbio.1002042 (2015).
40 Innocenti, P. & Chenoweth, S. F. Interspecific divergence of transcription networks along lines of genetic variance in *Drosophila*: dimensionality, evolvability, and constraint. *Molecular biology and evolution* 30, 1358-1367, doi:10.1093/molbev/mst047 (2013).
41 Wagner, G. P., Pavlicev, M. & Cheverud, J. M. The road to modularity. *Nature reviews. Genetics* 8, 921-931, doi: 10.1038/nrg2267 (2007).
42 Saxer, G. et al. Mutations in global regulators lead to metabolic selection during adaptation to complex environments. *PLoS Genetics* 10, e1004872, doi:10.1371/journal.pgen.1004872 (2014).
43 Grossman, S. R. et al. Identifying recent adaptations in large-scale genomic data. *Cell* 152, 703-713, doi:10.1016/j.cell.2013.01.035 (2013).
44 McCarthy, M. I. et al. Genome-wide association studies for complex traits: consensus, uncertainty and challenges. *Nature reviews. Genetics* 9, 356-369, doi:10.1038/nrg2344 (2008).
45 Cookson, W., Liang, L., Abecasis, G., Moffatt, M. & Lathrop, M. Mapping complex disease traits with global gene expression. *Nature reviews. Genetics* 10, 184-194, doi:10.1038/nrg2537 (2009).
46 Datsenko, K. A. & Wanner, B. L. One-step inactivation of chromosomal genes in *Escherichia coli* K-12 using PCR products. *Proc Natl Acad Sci USA* 97, 6640-6645, doi:10.1073/pnas.120163297 120163297 [pii] (2000).
47 Tucker, D. L. et al. Genes of the GadX-GadW regulon in *Escherichia coli*. *J Bacteriol* 185, 3190-3201 (2003).
48 Korch, S. B., Henderson, T. A. & Hill, T. M. Characterization of the hipA7 allele of *Escherichia coli* and evidence that high persistence is governed by (p)ppGpp synthesis. *Mol Microbiol* 50, 1199-1213, doi:3779 [pii] (2003).
49 McCloskey, D., Utrilla, J., Naviaux, R. K., Palsson, B. O., & Feist, A. M. Fast Swinnex filtration (FSF): a fast and robust sampling and extraction method suitable for metabolomics analysis of cultures grown in complex media. *Metabolomics, doi:*10.1007/s11306-014-0686-2 (2014).
50 Latif, H. et al. The genome organization of *Thermotoga maritima* reflects its lifestyle. *PLoS Genet* 9, e1003485, doi:10.1371/journal.pgen.1003485 PGENETICS-D-12-01486 [pii] (2013).
51 Langmead, B. Aligning short sequencing reads with Bowtie. *Curr Protoc Bioinformatics* Chapter 11, Unit 11 17, doi:10.1002/0471250953.bi1107s32 (2010).
52 Trapnell, C. et al. Transcript assembly and quantification by RNA-Seq reveals unannotated transcripts and isoform switching during cell differentiation. *Nat Biotechnol* 28, 511-515, doi:10.1038/nbt.1621 nbt.1621 [pii] (2010).
53 Keseler, I. M. et al. EcoCyc: fusing model organism databases with systems biology. *Nucleic Acids Res* 41, D605-612, doi:10.1093/nar/gks1027 gks1027 [pii] (2013).
54 Cho, B. K., Kim, D., Knight, E. M., Zengler, K. & Palsson, B. O. Genome-scale reconstruction of the sigma factor network in *Escherichia coli*: topology and functional states. *BMC Biol* 12, 4, doi:10.1186/1741-7007-12-4 1741-7007-12-4 [pii] (2014).
55 Salgado, H. et al. RegulonDB v8.0: omics data sets, evolutionary conservation, regulatory phrases, cross-validated gold standards and more. *Nucleic Acids Res* 41, D203-213, doi:10.1093/nar/gks1201 gks1201 [pii] (2013).
56 Scott, M., Gunderson, C. W., Mateescu, E. M., Zhang, Z. & Hwa, T. Interdependence of cell growth and gene expression: origins and consequences. *Science* 330, 1099-1102, doi:10.1126/science.1192588 (2010).
57 Opalka, N. et al. Complete structural model of *Escherichia coli* RNA polymerase from a hybrid approach. *PLoS Biol* 8, doi:10.1371/journal.pbio.1000483 e1000483 [pii] (2010).
58 Vassylyev, D. G. et al. Structural basis for substrate loading in bacterial RNA polymerase. *Nature* 448, 163-168, doi:10.1038/nature05931 (2007).
59 Phillips, J. C. et al. Scalable molecular dynamics with NAMD. *J Comput Chem* 26, 1781-1802, doi:10.1002/jcc.20289 (2005).
60 Best, R. B. et al. Optimization of the additive CHARMM all-atom protein force field targeting improved sampling of the backbone phi, psi and side-chain chi(1) and chi(2) dihedral angles. *J Chem Theory Comput* 8, 3257-3273, doi:10.1021/ct300400x (2012).
61 Humphrey, W., Dalke, A. & Schulten, K. VMD: visual molecular dynamics *J Mol Graph* 14, 33-38, 27-38 (1996).
62 Chaudhury, S., Lyskov, S. & Gray, J. J. PyRosetta: a script-based interface for implementing molecular modeling algorithms using Rosetta. *Bioinformatics* 26, 689-691, doi:10.1093/bioinformatics/btq007 (2010).
63 Kortemme, T. & Baker, D. A simple physical model for binding energy hot spots in protein-protein complexes. *Proc Natl Acad Sci USA* 99, 14116-14121, doi:10.1073/pnas.202485799 (2002).
64 Gavenonis, J., Sheneman, B. A., Siegert, T. R., Eshelman, M. R. & Kritzer, J. A. Comprehensive analysis of loops at protein-protein interfaces for macrocycle design. *Nat Chem Biol* 10, 716-722, doi:10.1038/nchembio.1580 (2014).

ADDITIONAL REFERENCES:

1. Conrad T M, Joyce A R, Applebee M K, Barrett C L, Xie B, Gao Y, Palsson B O: Whole-genome resequencing of *Escherichia coli* K-12 MG1655 undergoing short-term laboratory evolution in lactate minimal media reveals flexible selection of adaptive mutations. Genome Biol 2009, 10(10):R118.
2. Jensen K F: The *Escherichia coli* K-12 "wild types" W3110 and MG1655 have an rph frameshift mutation that leads to pyrimidine starvation due to low pyrE expression levels. J Bacteriol 1993, 175(11):3401-3407.
3. Kuznedelov K, Minakhin L, Niedziela-Majka A, Dove S L, Rogulja D, Nickels B E, Hochschild A, Heyduk T, Severinov K: A role for interaction of the RNA polymerase flap domain with the sigma subunit in promoter recognition. Science 2002, 295(5556):855-857.
4. Bukhari A I, Shapiro J A, Adhya S L, Cold Spring Harbor Laboratory.: DNA insertion elements, plasmids, and episomes. Cold Spring Harbor, N.Y.: Cold Spring Harbor Laboratory; 1977.
5. Barker C S, Pruss B M, Matsumura P: Increased motility of Escherichia coli by insertion sequence element integration into the regulatory region of the flhD operon. J Bacteriol 2004, 186(22):7529-7537.
6. Hall B G: Transposable elements as activators of cryptic genes in E. coli. Genetica 1999, 107(1-3):181-187.
7. Umeda M, Ohtsubo E: Mapping of insertion elements IS1, IS2 and IS3 on the Escherichia coli K-12 chromosome. Role of the insertion elements in formation of Hfrs and F' factors and in rearrangement of bacterial chromosomes. J Mol Biol 1989, 208(4):601-614.
8. Riley M, Abe T, Arnaud M B, Berlyn M K, Blattner F R, Chaudhuri R R, Glasner J D, Horiuchi T, Keseler I M, Kosuge T et al: Escherichia coli K-12: a cooperatively developed annotation snapshot—2005. Nucleic Acids Res 2006, 34(1):1-9.
9. Ishino Y, Shinagawa H, Makino K, Amemura M, Nakata A: Nucleotide sequence of the iap gene, responsible for alkaline phosphatase isozyme conversion in Escherichia coli, and identification of the gene product. J Bacteriol 1987, 169(12):5429-5433.
10. Flamholz A, Noor E, Bar-Even A, Liebermeister W, Milo R: Glycolytic strategy as a tradeoff between energy yield and protein cost. Proc Natl Acad Sci USA 2013, 110(24): 10039-10044.
11. Totemeyer S, Booth N A, Nichols W W, Dunbar B, Booth I R: From famine to feast: the role of methylglyoxal production in Escherichia coli. Mol Microbiol 1998, 27(3):553-562.
12. Cooper S, Helmstetter C E: Chromosome replication and the division cycle of Escherichia coli B/r. J Mol Biol 1968, 31(3):519-540.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A mutant *Escherichia coli* cell comprising SEQ ID NO:3.

2. The mutant of claim 1, wherein said mutant has an increased level of growth in minimal media compared to an *Escherichia coli* that lacks said SEQ ID NO:3.

3. The mutant of claim 1, wherein said mutant has an increased glucose uptake rate in minimal media compared to an *Escherichia coli* that lacks said SEQ ID NO:3.

4. The mutant of claim 1, wherein said mutant has an increased acetate production rate in minimal media compared to an *Escherichia coli* that lacks said SEQ ID NO:3.

5. The mutant of claim 1, wherein said mutant has an increased biomass yield in minimal media compared to an *Escherichia coli* that lacks said SEQ ID NO:3.

6. The mutant of claim 1, wherein said mutant has an increased production rate of one or more desired product as compared to an *Escherichia coli* that lacks said SEQ ID NO:3.

7. A method for increasing the growth rate of *Escherichia coli* in minimal media, comprising producing the mutant *Escherichia coli* cell of claim 1.

8. The method of claim 7, further comprising culturing said mutant in minimal media.

* * * * *

SEQUENCE LISTING

```
<160> NUMBER OF SEQ ID NOS: 30

<210> SEQ ID NO 1
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 1
atggtttact cctataccga gaaaaaacgt attcgtaagg attttggtaa acgtccacaa      60
gttctggatg taccttatct cctttctatc cagcttgact cgtttcagaa atttatcgag     120
caagatcctg aagggcagta tggtctggaa gctgctttcc gttccgtatt cccgattcag     180
agctacagcg gtaattccga gctgcaatac gtcagctacc gccttggcga accggtgttt     240
gacgtccagg aatgtcaaat ccgtggcgtg acctattccg caccgctgcg cgttaaactg     300
cgtctggtga tctatgagcg cgaagcgccg gaaggcaccg taaagacat taagaacaa      360 gaagtctaca tgggcgaaat tccgctcatg acagacaacg gtacctttgt tatcaacggt     420
actgagcgtg ttatcgtttc ccagctgcac cgtagtccgg gcgtcttctt tgactccgac     480
aaaggtaaaa cccactcttc gggtaaagtg ctgtataacg cgcgtatcat cccttaccgt     540
ggttcctggc tggacttcga attcgatccg aaggacaacc tgttcgtacg tatcgaccgt     600
cgccgtaaac tgcctgcgac catcattctg cgcgccctga actacaccac agagcagatc     660
ctcgacctgt tctttgaaaa agttatcttt gaaatccgtg ataacaagct gcagatggaa     720
ctggtgccgg aacgcctgcg tggtgaaacc gcatcttttg acatcgaagc taacggtaaa     780
gtgtacgtag aaaaaggccg ccgtatcact gcgcgccaca ttcgccagct ggaaaaagac     840
gacgtcaaac tgatcgaagt cccggttgag tacatcgcag gtaaagtggt tgctaaagac     900
tatattgatg agtctaccgg cgagctgatc tgcgcagcga acatggagct gagcctggat     960
```

```
ctgctggcta agctgagcca gtctggtcac aagcgtatcg aaacgctgtt caccaacgat    1020
ctggatcacg gcccatatat ctctgaaacc ttacgtgtcg acccaactaa cgaccgtctg    1080
agcgcactgg tagaaatcta ccgcatgatg cgccctggcg agccgccgac tcgtgaagca    1140
gctgaaagcc tgttcgagaa cctgttcttc tccgaagacc gttatgactt gtctgcggtt    1200
ggtcgtatga agttcaaccg ttctctgctg cgcgaagaaa tcgaaggttc cggtatcctg    1260
agcaaagacg acatcattga tgttatgaaa aagctcatcg atatccgtaa cggtaaaggc    1320
gaagtcgatg atatcgacca cctcggcaac cgtcgtatcc gttccgttgg cgaaatggcg    1380
gaaaaccagt tccgcgttgg cctggtacgt gtagagcgtg cggtgaaaga gcgtctgtct    1440
ctgggcgatc tggataccct gatgccacag gatatgatca acgccaagcc gatttccgca    1500
gcagtgaaag agttcttcgg ttccagccag ctgtctcagt ttatggacca gaacaacccg    1560
ctgtctgaga ttacgcacaa acgtcgtatc tccgcactcg gcccaggcgg tctgacccgt    1620
gaacgtgcag gcttcgaagt tcgagacgta cacccgactc actacggtcg cgtatgtcca    1680
atcgaaaccc ctgaaggtcc gaacatcggt ctgatcaact ctctgtccgt gtacgcacag    1740
actaacgaat acggcttcct tgagactccg tatcgtaaag tgaccgacgg tgttgtaact    1800
gacgaaattc actacctgtc tgctatcgaa gaaggcaact acgttatcgc ccaggcgaac    1860
tccaacttgg atgaagaagg ccacttcgta gaagacctgg taacttgccg tagcaaaggc    1920
gaatccagct tgttcagccg cgaccaggtt gactacatgg acgtatccac ccagcaggtg    1980
gtatccgtcg gtgcgtccct gatcccgttc ctgaaacacg atgacgccaa ccgtgcattg    2040
atgggtgcga acatgcaacg tcaggccgtt ccgactctgc gcgctgataa gccgctggtt    2100
ggtactggta tggaacgtgc tgttgccgtt gactccggtg taactgcggt agctaaacgt    2160
ggtggtgtcg ttcagtacgt ggatgcttcc cgtatcgtta tcaaagttaa cgaagacgag    2220
atgtatccgg gtgaagcagg tatcgacatc tacaacctga ccaaatacac ccgttctaac    2280
cagaacacct gtatcaacca gatgccgtgt gtgtctctgg gtgaaccggt tgaacgtggc    2340
gacgtgctgg cagacggtcc gtccaccgac ctcggtgaac tggcgcttgg tcagaacatg    2400
cgcgtagcgt tcatgccgtg gaatggttac aacttcgaag actccatcct cgtatccgag    2460
cgtgttgttc aggaagaccg tttcaccacc atccacattc aggaactggc gtgtgtgtcc    2520
cgtgacacca agctgggtcc ggaagagatc accgctgaca tcccgaacgt gggtgaagct    2580
gcgctctcca aactggatga atccggtatc gtttacattg gtgcggaagt gaccggtggc    2640
gacattctgg ttggtaaggt aacgccgaaa ggtgaaactc agctgacccc agaagaaaaa    2700
ctgctgcgtg cgatcttcgg tgagaaagcc tctgacgtta agactcttc tctgcgcgta    2760 ccaaacggtg tatccggtac ggttatcgac gttcaggtct ttactcgcga tggcgtagaa    2820
aaagacaaac gtgcgctgga atcgaagaa atgcagctca acaggcgaa gaaagacctg    2880 tctgaagaac tgcagatcct cgaagcgggt ctgttcagcc gtatccgtgc tgtgctggta    2940
gccggtggcg ttgaagctga aagctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaacgcc gcaaaatcac ccagggcgac    3120
gatctggcac cgggcgtgct gaagattgtt aaggtatatc tggcggttaa cgccgtatc    3180 cagcctggtg acaagatggc aggtcgtcac ggtaacaagg gtgtaatttc taagatcaac    3240
ccgatcgaag atatgcctta cgatgaaaac ggtacgccgg tagacatcgt actgaacccg    3300
```

| | |
|---|---|
| ctgggcgtac cgtctcgtat gaacatcggt cagatcctcg aaacccacct gggtatggct | 3360 |
| gcgaaaggta tcggcgacaa gatcaacgcc atgctgaaac agcagcaaga agtcgcgaaa | 3420 |
| ctgcgcgaat tcatccagcg tgcgtacgat ctgggcgctg acgttcgtca gaaagttgac | 3480 |
| ctgagtacct tcagcgatga agaagttatg cgtctggctg aaaacctgcg caaaggtatg | 3540 |
| ccaatcgcaa cgccggtgtt cgacggtgcg aaagaagcag aaattaaaga gctgctgaaa | 3600 |
| cttggcgacc tgccgacttc cggtcagatc cgcctgtacg atggtcgcac tggtgaacag | 3660 |
| ttcgagcgtc cggtaaccgt tggttacatg tacatgctga aactgaacca cctggtcgac | 3720 |
| gacaagatgc acgcgcgttc caccggttct tacagcctgg ttactcagca gccgctgggt | 3780 |
| ggtaaggcac agttcggtgg tcagcgtttc ggggagatga agtgtgggc gctggaagca | 3840 |
| tacggcgcag catacaccct gcaggaaatg ctcaccgtta agtctgatga cgtgaacggt | 3900 |
| cgtaccaaga tgtataaaaa catcgtggac ggcaaccatc agatggagcc gggcatgcca | 3960 |
| gaatccttca acgtattgtt gaaagagatt cgttcgctgg gtatcaacat cgaactggaa | 4020 |
| gacgagtaa | 4029 |

<210> SEQ ID NO 2
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 2

| | |
|---|---|
| atggtttact cctataccga gaaaaaacgt attcgtaagg attttggtaa acgtccacaa | 60 |
| gttctggatg taccttatct cctttctatc cagcttgact cgtttcagaa atttatcgag | 120 |
| caagatcctg aagggcagta tggtctggaa gctgctttcc gttccgtatt cccgattcag | 180 |
| agctacagcg gtaattccga gctgcaatac gtcagctacc gccttggcga accggtgttt | 240 |
| gacgtccagg aatgtcaaat ccgtggcgtg acctattccg caccgctgcg cgttaaactg | 300 |
| cgtctggtga tctatgagcg cgaagcgccg gaaggcaccg taaaagacat taagaacaa | 360 |
| gaagtctaca tggcgaaat tccgctcatg acagacaacg gtacctttgt tatcaacggt | 420 |
| actgagcgtg ttatcgtttc ccagctgcac cgtagtccgg gcgtcttctt tgactccgac | 480 |
| aaaggtaaaa cccactcttc gggtaaagtg ctgtataacg cgcgtatcat cccttaccgt | 540 |
| ggttcctggc tggacttcga attcgatccg aaggacaacc tgttcgtacg tatcgaccgt | 600 |
| cgccgtaaac tgcctgcgac catcattctg cgcgccctga actacaccac agagcagatc | 660 |
| ctcgacctgt tctttgaaaa agttatcttt gaaatccgtg ataacaagct gcagatggaa | 720 |
| ctggtgccgg aacgcctgcg tggtgaaacc gcatcttttg acatcgaagc taacggtaaa | 780 |
| gtgtacgtag aaaaaggccg ccgtatcact gcgcgccaca ttcgccagct ggaaaaagac | 840 |
| gacgtcaaac tgatcgaagt cccggttgag tacatcgcag gtaaagtggt tgctaaagac | 900 |
| tatattgatg agtctaccgg cgagctgatc tgcgcagcga acatggagct gagcctggat | 960 |
| ctgctggcta agctgagcca gtctggtcac aagcgtatcg aaacgctgtt caccaacgat | 1020 |
| ctggatcacg gccatatat ctctgaaacc ttacgtgtcg acccaactaa cgaccgtctg | 1080 |
| agcgcactgg tagaaatcta ccgcatgatg cgccctggcg agccgccgac tcgtgaagca | 1140 |
| gctgaaagcc tgttcgagaa cctgttcttc tccgaagacc gttatgactt gtctgcggtt | 1200 |
| ggtcgtatga gttcaaccg ttctctgctg cgcgaagaaa tcgaaggttc cggtatcctg | 1260 |
| agcaaagacg acatcattga tgttatgaaa aagctcatcg atatccgtaa cggtaaaggc | 1320 |

```
gaagtcgatg atatcgacca cctcggcaac cgtcgtatcc gttccgttgg cgaaatggcg    1380
gaaaaccagt tccgcgttgg cctggtacgt gtagagcgtg cggtgaaaga gcgtctgtct    1440
ctgggcgatc tggatacccT gatgccacag gatatgatca acgccaagcc gatttccgca    1500
gcagtgaaag agttcttcgg ttccagccag ctgtctcagt ttatggacca gaacaacccg    1560
ctgtctgaga ttacgcacaa acgtcgtatc tccgcactcg gcccaggcgg tctgacccgt    1620
gaacgtgcag gcttcgaagt tcgagacgta cacccgactc actacggtcg cgtatgtcca    1680
atcgaaaccc ctgaaggtcc gaacatcggt ctgatcaact ctctgtccgt gtacgcacag    1740
actaacgaat acggcttcct tgagactccg tatcgtaaag tgaccgacgg tgttgtaact    1800
gacgaaattc actacctgtc tgctatcgaa gaaggcaact acgttatcgc ccaggcgaac    1860
tccaacttgg atgaagaagg ccacttcgta gaagacctgg taacttgccg tagcaaaggc    1920
gaatccagct tgttcagccg cgaccaggtt gactacatgg acgtatccac ccagcaggtg    1980
gtatccgtcg gtgcgtccct gatcccgttc tggaacacg atgacgccaa ccgtgcattg    2040
atgggtgcga acatgcaacg tcaggccgtt ccgactctgc gcgctgataa gccgctggtt    2100
ggtactggta tggaacgtgc tgttgccgtt gactccggtg taactgcggt agctaaacgt    2160
ggtggtgtcg ttcagtacgt ggatgcttcc cgtatcgtta tcaaagttaa cgaagacgag    2220
atgtatccgg gtgaagcagg tatcgacatc tacaacctga ccaaatacac ccgttctaac    2280
cagaacacct gtatcaacca gatgccgtgt gtgtctctgg gtgaaccggt tgaacgtggc    2340
gacgtgctgg cagacggtcc gtccaccgac ctcggtgaac tggcgcttgg tcagaacatg    2400
cgcgtagcgt tcatgccgtg gaatggttac aacttcgaag actccatcct cgtatccgag    2460
cgtgttgttc aggaagaccg tttcaccacc atccacattc aggaactggc gtgtgtgtcc    2520
cgtgacacca agctgggtcc ggaagagatc accgctgaca tcccgaacgt gggtgaagct    2580
gcgctctcca aactggatga atccggtatc gtttacattg gtgcggaagt gaccggtggc    2640
gacattctgg ttggtaaggt aacgccgaaa ggtgaaactc agctgacccc agaagaaaaa    2700
ctgctgcgtg cgatcttcgg tgagaaagcc tctgacgtta agactcttc tctgcgcgta    2760 ccaaacggtg tatccggtac ggttatcgac gttcaggtct ttactcgcga tggcgtagaa    2820
aaagacaaac gtcgcgctgga aatcgaagaa atgcagctca acaggcgaa gaaagacctg    2880 tctgaagaac tgcagatcct cgaagcgggt ctgttcagcc gtatccgtgc tgtgctggta    2940
gccggtggcg ttgaagctga gaagctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaacgcc gcaaaatcac ccagggcgac    3120
gatctggcac cgggcgtgct gaagattgtt aaggtatatc tggcggttaa cgccgtatc    3180 cagcctggtg acaagatggc aggtcgtcac ggtaacaagg gtgtaatttc taagatcaac    3240
ccgatcgaag atatgcctta cgatgaaaac ggtacgccgg tagacatcgt actgaaccag    3300
ctgggcgtac cgtctcgtat gaacatcggt cagatcctcg aaacccacct gggtatggct    3360
gcgaaaggta tcggcgacaa gatcaacgcc atgctgaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaacctgcg caaaggtatg    3540
ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
```

-continued

| | |
|---|---|
| ttcgagcgtc cggtaaccgt tggttacatg tacatgctga aactgaacca cctggtcgac | 3720 |
| gacaagatgc acgcgcgttc caccggttct tacagcctgg ttactcagca gccgctgggt | 3780 |
| ggtaaggcac agttcggtgg tcagcgtttc ggggagatgg aagtgtgggc gctggaagca | 3840 |
| tacggcgcag catacaccct gcaggaaatg ctcaccgtta agtctgatga cgtgaacggt | 3900 |
| cgtaccaaga tgtataaaaa catcgtggac ggcaaccatc agatggagcc gggcatgcca | 3960 |
| gaatccttca acgtattgtt gaaagagatt cgttcgctgg gtatcaacat cgaactggaa | 4020 |
| gacgagtaa | 4029 |

<210> SEQ ID NO 3
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 3

| | |
|---|---|
| atggtttact cctataccga gaaaaaacgt attcgtaagg attttggtaa acgtccacaa | 60 |
| gttctggatg taccttatct cctttctatc cagcttgact cgtttcagaa atttatcgag | 120 |
| caagatcctg aagggcagta tggtctggaa gctgctttcc gttccgtatt cccgattcag | 180 |
| agctacagcg gtaattccga gctgcaatac gtcagctacc gccttggcga accggtgttt | 240 |
| gacgtccagg aatgtcaaat ccgtggcgtg acctattccg caccgctgcg cgttaaactg | 300 |
| cgtctggtga tctatgagcg cgaagcgccg gaaggcaccg taaaagacat taagaacaa | 360 |
| gaagtctaca tgggcgaaat tccgctcatg acagacaacg gtacctttgt tatcaacggt | 420 |
| actgagcgtg ttatcgtttc ccagctgcac cgtagtccgg gcgtcttctt tgactccgac | 480 |
| aaaggtaaaa cccactcttc gggtaaagtg ctgtataacg cgcgtatcat cccttaccgt | 540 |
| ggttcctggc tggacttcga attcgatccg aaggacaacc tgttcgtacg tatcgaccgt | 600 |
| cgccgtaaac tgcctgcgac catcattctg cgcgccctga actacaccac agagcagatc | 660 |
| ctcgacctgt tctttgaaaa agttatcttt gaaatccgtg ataacaagct gcagatggaa | 720 |
| ctggtgccgg aacgcctgcg tggtgaaacc gcatcttttg acatcgaagc taacggtaaa | 780 |
| gtgtacgtag aaaaaggccg ccgtatcact gcgcgccaca ttcgccagct ggaaaaagac | 840 |
| gacgtcaaac tgatcgaagt cccggttgag tacatcgcag gtaaagtggt tgctaaagac | 900 |
| tatattgatg agtctaccgg cgagctgatc tgcgcagcga catggagct gagcctggat | 960 |
| ctgctggcta agctgagcca gtctggtcac aagcgtatcg aaacgctgtt caccaacgat | 1020 |
| ctggatcacg gcccatatat ctctgaaacc ttacgtgtcg acccaactaa cgaccgtctg | 1080 |
| agcgcactgg tagaaatcta ccgcatgatg cgccctggcg agccgccgac tcgtgaagca | 1140 |
| gctgaaagcc tgttcgagaa cctgttcttc tccgaagacc gttatgactt gtctgcggtt | 1200 |
| ggtcgtatga gttcaaccg ttctctgctg cgcgaagaaa tcgaaggttc cggtatcctg | 1260 |
| agcaaagacg acatcattga tgttatgaaa aagctcatcg atatccgtaa cggtaaaggc | 1320 |
| gaagtcgatg atatcgacca cctcggcaac cgtcgtatcc gttccgttgg cgaaatggcg | 1380 |
| gaaaaccagt tccgcgttgg cctggtacgt gtagagcgtg cggtgaaaga gcgtctgtct | 1440 |
| ctgggcgatc tggataccct gatgccacag gatatgatca acgccaagcc gatttccgca | 1500 |
| gcagtgaaag agttcttcgg ttccagccag ctgtctcagt ttatggacca gaacaacccg | 1560 |
| ctgtctgaga ttacgcacaa acgtcgtatc tccgcactcg gccaggcgg tctgacccgt | 1620 |
| gaacgtgcag gcttcgtagt tcgagacgta caccgactc actacggtcg cgtatgtcca | 1680 |

```
atcgaaaccc ctgaaggtcc gaacatcggt ctgatcaact ctctgtccgt gtacgcacag    1740
actaacgaat acggcttcct tgagactccg tatcgtaaag tgaccgacgg tgttgtaact    1800
gacgaaattc actacctgtc tgctatcgaa gaaggcaact acgttatcgc ccaggcgaac    1860
tccaacttgg atgaagaagg ccacttcgta gaagacctgg taacttgccg tagcaaaggc    1920
gaatccagct tgttcagccg cgaccaggtt gactacatgg acgtatccac ccagcaggtg    1980
gtatccgtcg gtgcgtccct gatcccgttc ctggaacacg atgacgccaa ccgtgcattg    2040
atgggtgcga acatgcaacg tcaggccgtt ccgactctgc gcgctgataa gccgctggtt    2100
ggtactggta tggaacgtgc tgttgccgtt gactccggtg taactgcggt agctaaacgt    2160
ggtggtgtcg ttcagtacgt ggatgcttcc cgtatcgtta tcaaagttaa cgaagacgag    2220
atgtatccgg gtgaagcagg tatcgacatc tacaacctga ccaaatacac ccgttctaac    2280
cagaacacct gtatcaacca gatgccgtgt gtgtctctgg gtgaaccggt tgaacgtggc    2340
gacgtgctgg cagacggtcc gtccaccgac ctcggtgaac tggcgcttgg tcagaacatg    2400
cgcgtagcgt tcatgccgtg gaatggttac aacttcgaag actccatcct cgtatccgag    2460
cgtgttgttc aggaagaccg tttcaccacc atccacattc aggaactggc gtgtgtgtcc    2520
cgtgacacca agctgggtcc ggaagagatc accgctgaca tcccgaacgt gggtgaagct    2580
gcgctctcca aactggatga atccggtatc gtttacattg gtgcggaagt gaccggtggc    2640
gacattctgg ttggtaaggt aacgccgaaa ggtgaaactc agctgacccc agaagaaaaa    2700
ctgctgcgtg cgatcttcgg tgagaaagcc tctgacgtta agactcttc tctgcgcgta    2760 ccaaacggtg tatccggtac ggttatcgac gttcaggtct ttactcgcga tggcgtagaa    2820
aaagacaaac gtcgcctgga atcgaagaa atgcagctca acaggcgaa gaaagacctg    2880 tctgaagaac tgcagatcct cgaagcgggt ctgttcagcc gtatccgtgc tgtgctggta    2940
gccggtggcg ttgaagctga aagctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaaacgcc gcaaaatcac ccagggcgac    3120
gatctggcac cgggcgtgct gaagattgtt aaggtatatc tggcggttaa acgccgtatc    3180
cagcctggtg acaagatggc aggtcgtcac ggtaacaagg gtgtaatttc taagatcaac    3240
ccgatcgaag atatgcctta cgatgaaaac ggtacgccgg tagacatcgt actgaacccg    3300
ctgggcgtac cgtctcgtat gaacatcggt cagatcctcg aaacccacct gggtatggct    3360
gcgaaaggta tcggcgacaa gatcaacgcc atgctgaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaaacctgcg caaaggtatg    3540 ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
ttcgagcgtc cggtaaccgt tggttacatg tacatgctga aactgaacca cctggtcgac    3720
gacaagatgc acgcgcgttc caccggttct tacagcctgg ttactcagca gccgctgggt    3780
ggtaaggcac agttcggtgg tcagcgtttc ggggagatga agtgtgggc gctgaagca    3840 tacggcgcag catacaccct gcaggaaatg ctcaccgtta agtctgatga cgtgaacggt    3900
cgtaccaaga tgtataaaaa catcgtggac ggcaaccatc agatggagcc gggcatgcca    3960
gaatccttca cgtattgtt gaaagagatt cgttcgctgg gtatcaacat cgaactggaa    4020
```

-continued

```
gacgagtaa                                                          4029

<210> SEQ ID NO 4
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 4
atggtttact cctataccga gaaaaaacgt attcgtaagg attttggtaa acgtccacaa      60
gttctggatg taccttatct cctttctatc cagcttgact cgtttcagaa atttatcgag     120
caagatcctg aagggcagta tggtctggaa gctgctttcc gttccgtatt cccgattcag     180
agctacagcg gtaattccga gctgcaatac gtcagctacc gccttggcga accggtgttt     240
gacgtccagg aatgtcaaat ccgtggcgtg acctattccg caccgctgcg cgttaaactg     300
cgtctggtga tctatgagcg cgaagcgccg gaaggcaccg taaaagacat taaagaacaa     360
gaagtctaca tgggcgaaat tccgctcatg acagacaacg gtacctttgt tatcaacggt     420
actgagcgtg ttatcgtttc ccagctgcac cgtagtccgg cgtcttcttt tgactccgac     480
aaaggtaaaa cccactcttc gggtaaagtg ctgtataacg cgcgtatcat cccttaccgt     540
ggttcctggc tggacttcga attcgatccg aaggacaacc tgttcgtacg tatcgaccgt     600
cgccgtaaac tgcctgcgac catcattctg cgcgccctga actacaccac agagcagatc     660
ctcgacctgt tctttgaaaa agttatcttt gaaatccgtg ataacaagct gcagatggaa     720
ctggtgccgg aacgcctgcg tggtgaaacc gcatcttttg catcgaagc taacggtaaa     780 gtgtacgtag aaaaaggccg ccgtatcact gcgcgccaca ttcgccagct ggaaaaagac     840
gacgtcaaac tgatcgaagt cccggttgag tacatcgcag gtaaagtggt tgctaaagac     900
tatattgatg agtctaccgg cgagctgatc tgcgcagcga catggagct gagcctggat     960 ctgctggcta agctgagcca gtctggtcac aagcgtatcg aaacgctgtt caccaacgat    1020
ctggatcacg gcccatatat ctctgaaacc ttacgtgtcg acccaactaa cgaccgtctg    1080
agcgcactgg tagaaatcta ccgcatgatg cgccctggcg agccgccgac tcgtgaagca    1140
gctgaaagcc tgttcgagaa cctgttcttc tccgaagacc gttatgactt gtctgcggtt    1200
ggtcgtatga gttcaaccg ttctctgctg cgcgaagaaa tcgaaggttc cggtatcctg    1260
agcaaagacg acatcattga tgttatgaaa aagctcatcg atatccgtaa cggtaaaggc    1320
gaagtcgatg atatcgacca cctcggcaac cgtcgtatcc gttccgttgg cgaaatggcg    1380
gaaaaccagt tccgcgttgg cctggtacgt gtagagcgtg cggtgaaaga gcgtctgtct    1440
ctgggcgatc tggataccct gatgccacag gatatgatca cgccaagcc gatttccgca    1500 gcagtgaaag agttcttcgg ttccagccag ctgtctcagt ttatggacca gaacaacccg    1560
ctgtctgaga ttacgcacaa acgtcgtatc tccgcactcg gcccaggcgg tctgacccgt    1620
gaacgtgcag gcttcgaagt tcgagacgta cacccgactc actacggtcg cgtatgtcca    1680
atcgaaaccc ctgaaggtcc gaacatcggt ctgatcaact ctctgtccgt gtacgcacag    1740
actaacgaat acggcttcct tgagactccg atcgtaaag tgaccgacgg tgttgtaact    1800
gacgaaattc actacctgtc tgctatcgaa gaaggcaact acgttatcgc ccaggcgaac    1860
tccaacttgg atgaagaagg ccacttcgta gaagacctgg taacttgccg tagcaaaggc    1920
gaatccagct tgttcagccg cgaccaggtt gactacatga cgtatccac ccagcaggtg    1980 gtatccgtcg gtgcgtccct gatcccgttc ctggaatacg atgacgccaa ccgtgcattg    2040
```

```
atgggtgcga acatgcaacg tcaggccgtt ccgactctgc gcgctgataa gccgctggtt    2100
ggtactggta tggaacgtgc tgttgccgtt gactccggtg taactgcggt agctaaacgt    2160
ggtggtgtcg ttcagtacgt ggatgcttcc cgtatcgtta tcaaagttaa cgaagacgag    2220
atgtatccgg gtgaagcagg tatcgacatc tacaacctga ccaaatacac ccgttctaac    2280
cagaacacct gtatcaacca gatgccgtgt gtgtctctgg gtgaaccggt gaacgtggc    2340
gacgtgctgg cagacggtcc gtccaccgac ctcggtgaac tggcgcttgg tcagaacatg    2400
cgcgtagcgt tcatgccgtg gaatggttac aacttcgaag actccatcct cgtatccgag    2460
cgtgttgttc aggaagaccg tttcaccacc atccacattc aggaactggc gtgtgtgtcc    2520
cgtgacacca agctgggtcc ggaagagatc accgctgaca tcccgaacgt gggtgaagct    2580
gcgctctcca aactggatga atccggtatc gtttacattg gtgcggaagt gaccggtggc    2640
gacattctgg ttggtaaggt aacgccgaaa ggtgaaactc agctgacccc agaagaaaaa    2700
ctgctgcgtg cgatcttcgg tgagaaagcc tctgacgtta agactcttc tctgcgcgta    2760
ccaaacggtg tatccggtac ggttatcgac gttcaggtct ttactcgcga tggcgtagaa    2820
aaagacaaac gtcgcgctgga atcgaagaa atgcagctca acaggcgaa gaaagacctg    2880
tctgaagaac tgcagatcct cgaagcgggt ctgttcagcc gtatccgtgc tgtgctggta    2940
gccggtggcg ttgaagctga agctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaaacgcc gcaaaatcac ccagggcgac    3120
gatctggcac cgggcgtgct gaagattgtt aaggtatatc tggcggttaa acgccgtatc    3180
cagcctggtg acaagatggc aggtcgtcac ggtaacaagg gtgtaatttc taagatcaac    3240
ccgatcgaag atatgccta cgatgaaaac ggtacgccgg tagacatcgt actgaacccg    3300
ctgggcgtac cgtctcgtat gaacatcggt cagatcctcg aaacccacct gggtatggct    3360
gcgaaaggta tcggcgacaa gatcaacgcc atgctgaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaacctgcg caaaggtatg    3540
ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
ttcgagcgtc cggtaaccgt tggttacatg tacatgctga actgaacca cctggtcgac    3720
gacaagatgc acgcgcgttc caccggttct tacagcctgg ttactcagca gccgctgggt    3780
ggtaaggcac agttcggtgg tcagcgtttc ggggagatgg aagtgtgggc gctggaagca    3840
tacgcgcag catacaccct gcaggaaatg ctcaccgtta agtctgatga cgtgaacggt    3900
cgtaccaaga tgtataaaaa catcgtggac ggcaaccatc agatggagcc gggcatgcca    3960
gaatccttca acgtattgtt gaaagagatt cgttcgctgg gtatcaacat cgaactggaa    4020
gacgagtaa                                                            4029
```

<210> SEQ ID NO 5
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 5

```
atggtttact cctataccga gaaaaaacgt attcgtaagg attttggtaa acgtccacaa    60
gttctggatg taccttatct cctttctatc cagcttgact cgtttcagaa atttatcgag   120
caagatcctg aagggcagta tggtctggaa gctgctttcc gttccgtatt cccgattcag   180
agctacagcg gtaattccga gctgcaatac gtcagctacc gccttggcga accggtgttt   240
gacgtccagg aatgtcaaat ccgtggcgtg acctattccg caccgctgcg cgttaaactg   300
cgtctggtga tctatgagcg cgaagcgccg gaaggcaccg taaaagacat taaagaacaa   360
gaagtctaca tgggcgaaat tccgctcatg acagacaacg gtacctttgt tatcaacggt   420
actgagcgtg ttatcgtttc ccagctgcac cgtagtccgg cgtcttctt  tgactccgac   480
aaaggtaaaa cccactcttc gggtaaagtg ctgtataacg cgcgtatcat cccttaccgt   540
ggttcctggc tggacttcga attcgatccg aaggacaacc tgttcgtacg tatcgaccgt   600
cgccgtaaac tgcctgcgac catcattctg cgcgccctga actacaccac agagcagatc   660
ctcgacctgt tctttgaaaa agttatcttt gaaatccgtg ataacaagct gcagatggaa   720
ctggtgccgg aacgcctgcg tggtgaaacc gcatcttttg catcgaagc  taacggtaaa   780
gtgtacgtag aaaaaggccg ccgtatcact gcgcgccaca ttcgccagct ggaaaaagac   840
gacgtcaaac tgatcgaagt cccggttgag tacatcgcag gtaaagtggt tgctaaagac   900
tatattgatg agtctaccgg cgagctgatc tgcgcagcga acatggagct gagcctggat   960
ctgctggcta agctgagcca gtctggtcac aagcgtatcg aaacgctgtt caccaacgat  1020
ctggatcacg gccatatat ctctgaaacc ttacgtgtcg acccaactaa cgaccgtctg  1080
agcgcactgg tagaaatcta ccgcatgatg cgccctggcg agccgccgac tcgtgaagca  1140
gctgaaagcc tgttcgagaa cctgttcttc tccgaagacc gttatgactt gtctgcggtt  1200
ggtcgtatga gttcaaccg ttctctgctg cgcgaagaaa tcgaaggttc cggtatcctg  1260
agcaaagacg acatcattga tgttatgaaa aagctcatcg atatccgtaa cggtaaaggc  1320
gaagtcgatg atatcgacca cctcggcaac cgtcgtatcc gttccgttgg cgaaatggcg  1380
gaaaaccagt tccgcgttgg cctggtacgt gtagagcgtg cggtgaaaga gcgtctgtct  1440
ctgggcgatc tggataccct gatgccacag gatatgatca cgccaagcc  gatttccgca  1500
gcagtgaaag agttcttcgg ttccagccag ctgtctcagt ttatggacca gaacaacccg  1560
ctgtctgaga ttacgcacaa acgtcgtatc tccgcactcg gcccaggcgg tctgacccgt  1620
gaacgtgcag gcttcgaagt tcgagacgta caccgactc actacggtcg cgtatgtcca  1680
atcgaaaccc ctgaaggtcc gaacatcggt ctgatcaact ctctgtccgt gtacgcacag  1740
actaacgaat acggcttcct tgagactccg tatcgtaaag tgaccgacgg tgttgtaact  1800
gacgaaattc actacctgtc tgctatcgaa gaaggcaact acgttatcgc ccaggcgaac  1860
tccaacttgg atgaagaagg ccacttcgta gaagacctgg taacttgccg tagcaaaggc  1920
gaatccagct tgttcagccg cgaccaggtt gactacatgg acgtatccac ccagcaggtg  1980
gtatccgtcg gtgcgtccct gatcccgttc ccggaacacg atgacgccaa ccgtgcattg  2040
atgggtgcga acatgcaacg tcaggccgtt ccgactctgc gcgctgataa gccgctggtt  2100
ggtactggta tggaacgtgc tgttgccgtt gactccggtg taactgcggt agctaaacgt  2160
ggtggtgtcg ttcagtacgt ggatgcttcc cgtatcgtta tcaaagttaa cgaagacgag  2220
atgtatccgg gtgaagcagg tatcgacatc tacaacctga ccaaatacac ccgttctaac  2280
cagaacacct gtatcaacca gatgccgtgt gtgtctctgg gtgaaccggt tgaacgtggc  2340
gacgtgctgg cagacggtcc gtccaccgac ctcggtgaac tggcgcttgg tcagaacatg  2400
```

```
cgcgtagcgt tcatgccgtg gaatggttac aacttcgaag actccatcct cgtatccgag    2460
cgtgttgttc aggaagaccg tttcaccacc atccacattc aggaactggc gtgtgtgtcc    2520
cgtgacacca agctgggtcc ggaagagatc accgctgaca tcccgaacgt gggtgaagct    2580
gcgctctcca aactgatgga atccggtatc gtttacattg gtgcggaagt gaccggtggc    2640
gacattctgg ttggtaaggt aacgccgaaa ggtgaaactc agctgacccc agaagaaaaa    2700
ctgctgcgtg cgatcttcgg tgagaaagcc tctgacgtta agactcttc tctgcgcgta    2760 ccaaacggtg tatccggtac ggttatcgac gttcaggtct ttactcgcga tggcgtagaa    2820
aaagacaaac gtgcgctgga aatcgaagaa atgcagctca acaggcgaa gaaagacctg    2880 tctgaagaac tgcagatcct cgaagcgggt ctgttcagcc gtatccgtgc tgtgctggta    2940
gccggtggcg ttgaagctga aagctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaacgcc gcaaaatcac ccagggcgac    3120
gatctggcac cgggcgtgct gaagattgtt aaggtatatc tggcggttaa cgccgtatc    3180 cagcctggtg acaagatggc aggtcgtcac ggtaacaagg gtgtaatttc taagatcaac    3240
ccgatcgaag atatgcctta cgatgaaaac ggtacgccgg tagacatcgt actgaacccg    3300
ctgggcgtac cgtctcgtat gaacatcggt cagatcctcg aaacccacct gggtatggct    3360
gcgaaaggta tcggcgacaa gatcaacgcc atgctgaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaacctgcg caaaggtatg    3540
ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
ttcgagcgtc cggtaaccgt tggttacatg tacatgctga aactgaacca cctggtcgac    3720
gacaagatgc acgcgcgttc caccggttct tacagcctgg ttactcagca gccgctgggt    3780
ggtaaggcac agttcggtgg tcagcgtttc ggggagatgg aagtgtgggc gctgaagca    3840 tacggcgcag catacaccct gcaggaaatg ctcaccgtta agtctgatga cgtgaacggt    3900
cgtaccaaga tgtataaaaa catcgtggac ggcaaccatc agatggagcc gggcatgcca    3960
gaatccttca acgtattgtt gaaagagatt cgttcgctgg gtatcaacat cgaactggaa    4020
gacgagtaa                                                           4029
```

<210> SEQ ID NO 6
<211> LENGTH: 4029
<212> TYPE: DNA
<213> ORGANISM: Artificial Sequence
<220> FEATURE:
<223> OTHER INFORMATION: Mutant Escherichia coli

<400> SEQUENCE: 6

```
atggtttact cctataccga gaaaaaacgt attcgtaagg attttggtaa acgtccacaa     60
gttctggatg taccttatct cctttctatc cagcttgact cgtttcagaa atttatcgag    120
caagatcctg aagggcagta tggtctggaa gctgctttcc gttccgtatt cccgattcag    180
agctacagcg gtaattccga gctgcaatac gtcagctacc gccttggcga accggtgttt    240
gacgtccagg aatgtcaaat ccgtggcgtg acctattccg caccgctgcg cgttaaactg    300
cgtctggtga tctatgagcg cgaagcgccg gaaggcaccg taaagacat taagaacaa    360
```

-continued

```
gaagtctaca tgggcgaaat tccgctcatg acagacaacg gtacctttgt tatcaacggt    420
actgagcgtg ttatcgtttc ccagctgcac cgtagtccgg gcgtcttctt tgactccgac    480
aaaggtaaaa cccactcttc gggtaaagtg ctgtataacg cgcgtatcat cccttaccgt    540
ggttcctggc tggacttcga attcgatccg aaggacaacc tgttcgtacg tatcgaccgt    600
cgccgtaaac tgcctgcgac catcattctg cgcgccctga actacaccac agagcagatc    660
ctcgacctgt tctttgaaaa agttatcttt gaaatccgtg ataacaagct gcagatggaa    720
ctggtgccgg aacgcctgcg tggtgaaacc gcatcttttg acatcgaagc taacggtaaa    780
gtgtacgtag aaaaaggccg ccgtatcact gcgcgccaca ttcgccagct ggaaaaagac    840
gacgtcaaac tgatcgaagt cccggttgag tacatcgcag gtaaagtggt tgctaaagac    900
tatattgatg agtctaccgg cgagctgatc tgcgcagcga acatggagct gagcctggat    960
ctgctggcta agctgagcca gtctggtcac aagcgtatcg aaacgctgtt caccaacgat   1020
ctggatcacg gcccatatat ctctgaaacc ttacgtgtcg acccaactaa cgaccgtctg   1080
agcgcactgg tagaaatcta ccgcatgatg cgccctggcg agccgccgac tcgtgaagca   1140
gctgaaagcc tgttcgagaa cctgttcttc tccgaagacc gttatgactt gtctgcggtt   1200
ggtcgtatga agttcaaccg ttctctgctg cgcgaagaaa tcgaaggttc cggtatcctg   1260
agcaaagacg acatcattga tgttatgaaa aagctcatcg atatccgtaa cggtaaaggc   1320
gaagtcgatg atatcgacca cctcggcaac cgtcgtatcc gttccgttgg cgaaatggcg   1380
gaaaaccagt tccgcgttgg cctggtacgt gtagagcgtg cggtgaaaga gcgtctgtct   1440
ctgggcgatc tggataccct gatgccacag gatatgatca cgccaagcc gatttccgca   1500 gcagtgaaag agttcttcgg ttccagccag ctgtctcagt ttatggacca gaacaacccg   1560
ctgtctgaga ttacgcacaa acgtcgtatc tccgcactcg gcccaggcgg tctgacccgt   1620
gaacgtgcag gcttcgaagt tcgagacgta cacccgactc actacggtcg cgtatgtcca   1680
atcgaaaccc ctgaaggtcc gaacatcggt ctgatcaact ctctgtccgt gtacgcacag   1740
actaacgaat acggcttcct tgagactccg tatcgtaaag tgaccgacgg tgttgtaact   1800
gacgaaattc actacctgtc tgctatcgaa gaaggcaact acgttatcgc ccaggcgaac   1860
tccaacttgg atgaagaagg ccacttcgta aagacctgg taacttgccg tagcaaaggc   1920
gaatccagct tgttcagccg cgaccaggtt gactacatgg acgtatccac ccagcaggtg   1980
gtatccgtcg gtgcgtccct gatcccgttc ctggaacacg atgacgccaa ccgtgcattg   2040
atgggtgcga acatgcaacg tcaggccgtt ccgactctgc gcgctgataa gccgctggtt   2100
ggtactggta tggaacgtgc tgttgccgtt gactccggtg taactgcggt agctaaacgt   2160
ggtggtgtcg ttcagtacgt ggatgcttcc cgtatcgtta tcaaagttaa cgaagacgag   2220
atgtatccgg gtgaagcagg tatcgacatc tacaacctga ccaaatacac ccgttctaac   2280
cagaacacct gtatcaacca gatgccgtgt gtgtctctgg gtgaaccggt tgaacgtggc   2340
gacgtgctgg catacggtcc gtccaccgac ctcggtgaac tggcgcttgg tcagaacatg   2400
cgcgtagcgt tcatgccgtg gaatggttac aacttcgaag actccatcct cgtatccgag   2460
cgtgttgttc aggaagaccg tttcaccacc atccacattc aggaactggc gtgtgtgtcc   2520
cgtgacacca gctgggtccc ggaagagatc accgctgaca tcccgaacgt gggtgaagct   2580
gcgctctcca actgtgatga atccggtatc gtttacattg gtgcggaagt gaccggtggc   2640
gacattctgt tggtaaggt aacgccgaaa ggtgaaactc agctgacccc agaagaaaaa   2700
ctgctgcgtg cgatcttcgg tgagaaagcc tctgacgtta agactcttc tctgcgcgta   2760
```

```
ccaaacggtg tatccggtac ggttatcgac gttcaggtct ttactcgcga tggcgtagaa    2820
aaagacaaac gtgcgctgga aatcgaagaa atgcagctca acaggcgaa gaaagacctg    2880 tctgaagaac tgcagatcct cgaagcgggt ctgttcagcc gtatccgtgc tgtgctggta   2940
gccggtggcg ttgaagctga aagctcgac aaactgccgc gcgatcgctg gctggagctg    3000
ggcctgacag acgaagagaa acaaaatcag ctggaacagc tggctgagca gtatgacgaa   3060
ctgaaacacg agttcgagaa gaaactcgaa gcgaaacgcc gcaaaatcac ccagggcgac   3120
gatctggcac cgggcgtgct gaagattgtt aaggtatatc tggcggttaa cgccgtatc    3180 cagcctggtg acaagatggc aggtcgtcac ggtaacaagg gtgtaatttc taagatcaac   3240
ccgatcgaag atatgcctta cgatgaaaac ggtacgccgg tagacatcgt actgaacccg   3300
ctgggcgtac cgtctcgtat gaacatcggt cagatcctcg aaacccacct gggtatggct   3360
gcgaaaggta tcggcgacaa gatcaacgcc atgctgaaac agcagcaaga gtcgcgaaa    3420 ctgcgcgaat tcatccagcg tgcgtacgat ctgggcgctg acgttcgtca gaaagttgac   3480
ctgagtacct tcagcgatga agaagttatg cgtctggctg aaaacctgcg caaaggtatg   3540
ccaatcgcaa cgccggtgtt cgacggtgcg aaagaagcag aaattaaaga gctgctgaaa   3600
cttggcgacc tgccgacttc cggtcagatc cgcctgtacg atggtcgcac tggtgaacag   3660
ttcgagcgtc cggtaaccgt tggttacatg tacatgctga aactgaacca cctggtcgac   3720
gacaagatgc acgcgcgttc caccggttct tacagcctgg ttactcagca gccgctgggt   3780
ggtaaggcac agttcggtgg tcagcgtttc ggggagatgg aagtgtgggc gctggaagca   3840
tacggcgcag catacaccct gcaggaaatg ctcaccgtta agtctgatga cgtgaacggt   3900
cgtaccaaga tgtataaaaa catcgtggac ggcaaccatc agatggagcc gggcatgcca   3960
gaatccttca acgtattgtt gaaagagatt cgttcgctgg gtatcaacat cgaactggaa   4020
gacgagtaa                                                           4029
```

<210> SEQ ID NO 7
<211> LENGTH: 2053
<212> TYPE: DNA
<213> ORGANISM: Artificial Sequence
<220> FEATURE:
<223> OTHER INFORMATION: Mutant Escherichia coli

<400> SEQUENCE: 7

```
ttgtagtaat ctcaaactta tattggggtg gtttgttgag gtaataatag agccttaaat     60
tcagttgtgc aatagccagg aatgtaagga attcaaaatt gttctttatt ttgtgccgcg    120
attccactaa tttattccat gtcacacttt tcgcatcttt gttatgctat ggttatttca    180
tacctggatt tgcccctata tttccagaca tctgttatcc cttaacccat tacaagcccg    240
ctgccgcaga tattcccgtg gcgagcgata acccagcgca ctatgcggat gccattcgtt    300
ataatgctcg aacgcctctg caaggttctt tgctgccgtt aacccgtctg gtttgggcat    360
gatactgatg tagtcacgct ttatcgtttt cacgaagctc tctgctattc cgttactctc    420
cggactccgc accgccgtgt tcttcggttc aagtcccaac atccgggcga actggcgtgt    480
ttcattagcc cggtagcatg aaccattatc cgtcagccac tccactggag acgacggaag    540
atcgttgccg aagcggcgtt ccaccgctcc cagcatgacg tcctgtactg tttcactgtt    600
gaagccgccg gtagtgaccg cccagtgcag tgcctcacga tcacagcagt ccagcgcgaa    660
cgtgacacgc agtctctctc cgttatcaca gcagaactcg aacccgtcag agcaccatcg    720
```

```
ctgattgctt tctttcacgg ccactctgcc tgtatgtgcc cgtttcgatg gcggtacagc    780
aggttttcgc tcaagcaaca gcgcattctg gcgcatgatc cggtaaacac gtttggcatt    840
gatcgcaggc ataccatcaa gttctgcctg tctgcgaagc agcgcccata cccgacgata    900
accatacgtt ggcagctctc cgataacatg gtgtatacgg agaagcacat ccgtatcatc    960
agtgtgacga ctgcggcggc catccatcca gtcatcggtt cgtctgagaa tgacgtgcaa   1020
ctgcgcacgc gacacccgga gacaacggct gactaagctt actccccatc ccgggcaat    1080 aagggcgcgt gcgctatcca cttttttgcc cgtccatatt caacggcttc tttgaggagt   1140
tcattttcca tcgttttctt gccgagcagg cgctggagtt ctttaatctg cttcatggcg   1200
gcagcaagtt cagaggcagg aacaacctgt tctccggcgg cgacagcagt aagacttcct   1260
tcctggtatt gcttacgcca gagaaataac tggctggctg ctacaccatg ttgccgggca   1320
acgagggaga ccgtcatccc cggttcaaag ctctgctgaa caattgcgat cttttcctgt   1380
gtggtacgcc gtctgcgttt ctccggccct aagacatcaa tcatctgttc tccaatgact   1440
agtctaaaaa ctagtattaa gactatcact tatttaagtg atattggttg tctggagatt   1500 caggggggcca gtctaatacc ataagcctaa tggagcgaat tatgagagtt ctggttaccg   1560
ggccgccaat aaatatcttt tcataaaatt agccagaaaa gacgcggcat atagccctat   1620
ttacaccgat gatttcgcag cacgtgaggt taaaacttcc tgattcatgt cacattttat   1680
ggggagatta tcgtaggctg acgacctttc agtcttctgt attagttgtg tttacgagaa   1740
ttccctatta agcgaatgat gaaaagtaga acagtcgcaa taagagcatg gacttagtat   1800
tgcactatct cctggaggtc aacagagggc tattacttgc gcaacaggtt aaagattgtg   1860
aatagttacc agcagtcatt tacccgctta taacaagcga ggcagttgta atgatagctc   1920
agaaggatta tgcaaggctt cgtaagggag aacgcatata cccacttctg tgcatactgt   1980
tgagctgaaa aactgacgaa ttatgataaa ctccagccaa ctttatttca tatcattgag   2040
ggcctgtggc tga                                                      2053

<210> SEQ ID NO 8
<211> LENGTH: 1516
<212> TYPE: DNA
<213> ORGANISM: Artificial Sequence
<220> FEATURE:
<223> OTHER INFORMATION: Mutant Escherichia coli

<400> SEQUENCE: 8
ttgtagtaat ctcaaactta tattggggtg gtttgttgag gtaataatag agccttaaat     60
tcagttgtgc aatagccagg aatgtaagga attcaaaatt gttctttatt ttgtgccgaa    120
taaatagagg aatctgatta cttccttcat ggggatgctg aaaagagtag taattgctgg    180
taatgactcc aacttattga tagtgtttta tgttcagata atgcccgatg actttgtcat    240
gcagctccac cgattttgag aacgacagcg acttccgtcc cagccgtgcc aggtgctgcc    300
tcagattcag gttatgccgc tcaattcgct gcgtatatcg cttgctgatt acgtgcagct    360
ttcccttcag gcgggattca tacagcggcc agccatccgt catccatatc accacgtcaa    420
agggtgacag caggctcata agacgcccca gcgtcgccat agtgcgttca ccgaatacgt    480
gcgcaacaac cgtcttccgg agactgtcat acgcgtaaaa cagccagcgc tggcgcgatt    540 tagcccccgac atagcccac tgttcgtcca tttccgcgca gacgatgacg tcactgcccg    600
gctgtatgcg cgaggttacc gactgcggcc tgagtttttt aagtgacgta aaatcgtgtt    660
gaggccaacg cccataatgc gggctgttgc ccggcatcca acgccattca tggccatatc    720
```

```
aatgattttc tggtgcgtac cgggttgaga agcggtgtaa gtgaactgca gttgccatgt    780
tttacggcag tgagagcaga gatagcgctg atgtccggcg gtgcttttgc cgttacgcac    840 cacccegtca gtagctgaac aggagggaca gctgatagaa acagaagcca ctggagcacc    900
tcaaaaacac catcatacac taaatcagta agttggcagc atcacctacc tcaatgtgta    960
tcacaatatc catattcttt gtggggagt ctggagattg agtagatatt cttgttcaga    1020
ttgtgccgcc aataaatatc ttttcataaa attagccaga aaagacgcgg catatagccc    1080
tatttacacc gatgatttcg cagcacgtga ggttaaaact tcctgattca tgtcacattt    1140
tatggggaga ttatcgtagg ctgacgacct ttcagtcttc tgtattagtt gtgtttacga    1200
gaattcccta ttaagcgaat gatgaaaagt agaacagtcg caataagagc atggacttag    1260
tattgcacta tctcctggag gtcaacagag ggctattact tgcgcaacag gttaaagatt    1320
gtgaatagtt accagcagtc atttacccgc ttataacaag cgaggcagtt gtaatgatag    1380
ctcagaagga ttatgcaagg cttcgtaagg gagaacgcat atacccactt ctgtgcatac    1440
tgttgagctg aaaaactgac gaattatgat aaactccagc caactttatt tcatatcatt    1500
gagggcctgt ggctga                                                   1516

<210> SEQ ID NO 9
<211> LENGTH: 1809
<212> TYPE: DNA
<213> ORGANISM: Artificial Sequence
<220> FEATURE:
<223> OTHER INFORMATION: Mutant Escherichia coli

<400> SEQUENCE: 9
ttgtagtaat ctcaaactta tattggggtg gtttgttgag gtaataatag agccttaaat    60
tcagttgtgc aatagccagg aatgtaagga attcaaaatt gttctttatt ttgtgccgcc    120
aataaatatc ttttcataaa attagccaga aaagacgcgg catatagccc tatttacacc    180
gatgatttcg cagcacgtga ggttaaaact tcctgattca tgtcacattt tatggggaga    240
ttatcgtagg ctgacgacct ttcagtcttc tgtattaggg aaggtgcgaa taagcgggga    300
aattcttctc ggctgactca gtcatttcat ttcttcatgt ttgagccgat ttttttctccc    360 gtaaatgcct tgaatcagcc tatttagacc gttttcttcgc catttaaggc gttatcccca    420 gttttttagtg agatctctcc cactgacgta tcatttggtc cgcccgaaac aggttggcca    480
gcgtgaataa catcgccagt tggttatcgt ttttcagcaa ccccttgtat ctggctttca    540
cgaagccgaa ctgtcgcttg atgatgcgaa atgggtgctc caccctggcc cggatgctgg    600
ctttcatgta ttcgatgttg atggccgttt tgttcttgcg tggatgctgt ttcaaggttc    660
ttaccttgcc ggggcgctcg gcgatcagcc agtccacatc cacctcggcc agctcctcgc    720
gctgtggcgc cccttggtag ccggcatcgg ctgagacaaa ttgctcctct ccatgcagca    780
gattacccag ctgattgagg tcatgctcgt tggccgcgt ggtgaccagg ctgtgggtca    840
ggccactctt ggcatcgaca ccaatgtggg ccttcatgcc aaagtgccac tgattgcctt    900
tcttggtctg atgcatctcc ggatcgcgtt gctgctcttt gttcttggtc gagctgggtg    960
cctcaatgat ggtggcatcg accaaggtgc cttgagtcat catgacgcct gcttcggcca    1020
gccagcgatt gatggtcttg aacaattggc gggccagttg atgctgctcc agcaggtggc    1080
ggaaattcat gatggtggtg cggtccggca aggcgctatc cagggataac cgggcaaaca    1140
gacgcatgga ggcgatttcg tacagagcat cttccatcgc gccatcgctc aggttgtacc    1200
```

| | |
|---|---|
| aatgctgcat gcagtgaatg cgtagcatgg tttccagcgg ataaggtcgc cggccattac | 1260 |
| cagccttggg gtaaaacggc tcgatgactt ccaccatgtt ttgccatggc agaatctgct | 1320 |
| ccatgcggga caagaaaatc tctttcctgg tctgacggcg cttactgctg aattcactgt | 1380 |
| cggcgaaggt aagttgatga ctcatgatga accctgttct atggctccag atgacaaaca | 1440 |
| tgatctcata tcagggactt gttcgcacct tccttagtta gttgtgttta cgagaattcc | 1500 |
| ctattaagcg aatgatgaaa agtagaacag tcgcaataag agcatggact tagtattgca | 1560 |
| ctatctcctg gaggtcaaca gagggctatt acttgcgcaa caggttaaag attgtgaata | 1620 |
| gttaccagca gtcatttacc cgcttataac aagcgaggca gttgtaatga tagctcagaa | 1680 |
| ggattatgca aggcttcgta agggagaacg catataccca cttctgtgca tactgttgag | 1740 |
| ctgaaaaact gacgaattat gataaactcc agccaacttt atttcatatc attgagggcc | 1800 |
| tgtggctga | 1809 |

<210> SEQ ID NO 10
<211> LENGTH: 1517
<212> TYPE: DNA
<213> ORGANISM: Artificial Sequence
<220> FEATURE:
<223> OTHER INFORMATION: Mutant Escherichia coli

<400> SEQUENCE: 10

| | |
|---|---|
| ttgtagtaat ctcaaactta tattggggtg gtttgttgag gtaataatag agccttaaat | 60 |
| tcagttgtgc aatagccagg aatgtaagga attcaaataa atagaggaat ctgattactt | 120 |
| ccttcatggg gatgctgaaa agagtagtaa ttgctggtaa tgactccaac ttattgatag | 180 |
| tgttttatgt tcagataatg cccgatgact ttgtcatgca gctccaccga ttttgagaac | 240 |
| gacagcgact tccgtcccag ccgtgccagg tgctgcctca gattcaggtt atgccgctca | 300 |
| attcgctgcg tatatcgctt gctgattacg tgcagctttc ccttcaggcg ggattcatac | 360 |
| agcggccagc catccgtcat ccatatcacc acgtcaaagg gtgacagcag gctcataaga | 420 |
| cgccccagcg tcgccatagt gcgttcaccg aatacgtgcg caacaaccgt cttccggaga | 480 |
| ctgtcatacg cgtaaaacag ccagcgctgg cgcgatttag ccccgacata gccccactgt | 540 |
| tcgtccattt ccgcgcagac gatgacgtca ctgcccggct gtatgcgcga ggttaccgac | 600 |
| tgcggcctga gtttttttaag tgacgtaaaa tcgtgttgag gccaacgccc ataatgcggg | 660 |
| ctgttgcccg gcatccaacg ccattcatgg ccatatcaat gattttctgg tgcgtaccgg | 720 |
| gttgagaagc ggtgtaagtg aactgcagtt gccatgtttt acggcagtga gagcagagat | 780 |
| agcgctgatg tccggcggtg cttttgccgt tacgcaccac cccgtcagta gctgaacagg | 840 |
| agggacagct gatagaaaca gaagccactg gagcacctca aaaacaccat catacactaa | 900 |
| atcagtaagt tggcagcatc acctacctca atgtgtatca caatatccat attctttgtg | 960 |
| ggggagtctg gagattgagt agatattctt gttcagaagg aattcaaaat tgttctttat | 1020 |
| tttgtgccgc caataaatat cttttcataa aattagccag aaaagacgcg gcatatagcc | 1080 |
| ctatttacac cgatgatttc gcagcacgtg aggttaaaac ttcctgattc atgtcacatt | 1140 |
| ttatggggag attatcgtag gctgacgacc tttcagtctt ctgtattagt tgtgtttacg | 1200 |
| agaattccct attaagcgaa tgatgaaaag tagaacagtc gcaataagag catggactta | 1260 |
| gtattgcact atctcctgga ggtcaacaga gggctattac ttgcgcaaca ggttaaagat | 1320 |
| tgtgaatagt taccagcagt catttacccg cttataacaa gcgaggcagt tgtaatgata | 1380 |
| gctcagaagg attatgcaag gcttcgtaag ggagaacgca tatacccact tctgtgcata | 1440 |

```
ctgttgagct gaaaaactga cgaattatga taaactccag ccaactttat ttcatatcat    1500
tgagggcctg tggctga                                                   1517

<210> SEQ ID NO 11
<211> LENGTH: 1516
<212> TYPE: DNA
<213> ORGANISM: Artificial Sequence
<220> FEATURE:
<223> OTHER INFORMATION: Mutant Escherichia coli

<400> SEQUENCE: 11
ttgtagtaat ctcaaactta tattggggtg gtttgttgag gtaataatag agccttaaat      60
tcagttgtgc aatagaataa atagaggaat ctgattactt ccttcatggg gatgctgaaa     120
agagtagtaa ttgctggtaa tgactccaac ttattgatag tgttttatgt tcagataatg     180
cccgatgact ttgtcatgca gctccaccga ttttgagaac gacagcgact tccgtcccag     240
ccgtgccagg tgctgcctca gattcaggtt atgccgctca attcgctgcg tatatcgctt     300
gctgattacg tgcagctttc ccttcaggcg ggattcatac agcggccagc catccgtcat     360
ccatatcacc acgtcaaagg gtgacagcag gctcataaga cgcccagcg tcgccatagt      420 gcgttcaccg aatacgtgcg caacaaccgt cttccggaga ctgtcatacg cgtaaaacag     480
ccagcgctgg cgcgatttag ccccgacata gccccactgt tcgtccattt ccgcgcagac    540
gatgacgtca ctgcccggct gtatgcgcga ggttaccgac tgcggcctga gttttttaag    600
tgacgtaaaa tcgtgttgag gccaacgccc ataatgcggg ctgttgcccg gcatccaacg    660
ccattcatgg ccatatcaat gatttttctgg tgcgtaccgg gttgagaagc ggtgtaagtg   720
aactgcagtt gccatgtttt acggcagtga gagcagagat agcgctgatg tccggcggtg    780
cttttgccgt tacgcaccac cccgtcagta gctgaacagg agggacagct gatagaaaca    840
gaagccactg gagcacctca aaaacaccat catacactaa atcagtaagt tggcagcatc    900
acctacctca atgtgtatca caatatccat attctttgtg ggggagtctg gagattgagt    960
agatattctt gttcagatgc aatagccagg aatgtaagga attcaaaatt gttctttatt   1020
ttgtgccgcc aataaatatc ttttcataaa attagccaga aaagacgcgg catatagccc   1080
tatttacacc gatgatttcg cagcacgtga ggttaaaact tcctgattca tgtcacattt   1140
tatgggagta ttatcgtagg ctgacgacct ttcagtcttc tgtattagtt gtgtttacga   1200
gaattcccta ttaagcgaat gatgaaaagt agaacagtcg caataagagc atggacttag   1260
tattgcacta tctcctggag gtcaacagag ggctattact tgcgcaacag gttaaagatt   1320
gtgaatagtt accagcagtc atttacccgc ttataacaag cgaggcagtt gtaatgatag   1380
ctcagaagga ttatgcaagg cttcgtaagg gagaacgcat atacccactt ctgtgcatac    1440
tgttgagctg aaaaactgac gaattatgat aaactccagc caactttatt tcatatcatt   1500
gagggcctgt ggctga                                                   1516

<210> SEQ ID NO 12
<211> LENGTH: 1813
<212> TYPE: DNA
<213> ORGANISM: Artificial Sequence
<220> FEATURE:
<223> OTHER INFORMATION: Mutant Escherichia coli

<400> SEQUENCE: 12
ttgtagtaat ctcaaactta tattggggtg gtttgttgag gtaataatag agccttaaat      60
```

```
tcagttgtgc aataqccagg aatgtaagga attcaaaatt gggaaggtgc gaataagcgg      120
ggaaattctt ctcggctgac tcagtcattt catttcttca tgtttgagcc gattttttct      180
cccgtaaatg ccttgaatca gcctatttag accgtttctt cgccatttaa ggcgttatcc      240
ccagttttta gtgagatctc tcccactgac gtatcatttg gtccgcccga acaggttgg       300
ccagcgtgaa taacatcgcc agttggttat cgttttttcag caacccttg tatctggctt      360
tcacgaagcc gaactgtcgc ttgatgatgc gaaatgggtg ctccaccctg cccggatgc       420
tggctttcat gtattcgatg ttgatggccg ttttgttctt gcgtggatgc tgtttcaagg      480
ttcttacctt gccggggcgc tcggcgatca gccagtccac atccacctcg gccagctcct      540
cgcgctgtgg cgccccttgg tagccggcat cggctgagac aaattgctcc tctccatgca     600
gcagattacc cagctgattg aggtcatgct cgttggccgc ggtggtgacc aggctgtggg      660
tcaggccact cttggcatcg acaccaatgt gggccttcat gccaaagtgc cactgattgc      720
ctttcttggt ctgatgcatc tccggatcgc gttgctgctc tttgttcttg gtcgagctgg      780
gtgcctcaat gatggtggca tcgaccaagg tgccttgagt catcatgacg cctgcttcgg      840
ccagccagcg attgatggtc ttgaacaatt ggcgggccag ttgatgctgc tccagcaggt      900
ggcggaaatt catgatggtg gtgcggtccg gcaaggcgct atccagggat aaccgggcaa      960
acagacgcat ggaggcgatt tcgtacagag catcttccat cgcgccatcg ctcaggttgt     1020
accaatgctg catgcagtga atgcgtagca tggtttccag cggataaggt cgccggccat     1080
taccagcctt ggggtaaaac ggctcgatga cttccaccat gttttgccat ggcagaatct     1140
gctccatgcg ggacaagaaa atctcttttc tggtctgacg gcgcttactg ctgaattcac     1200
tgtcggcgaa ggtaagttga tgactcatga tgaaccctgt tctatggctc cagatgacaa     1260
acatgatctc atatcaggga cttgttcgca ccttccttag caaaattgtt ctttattttg     1320
tgccgccaat aaatatcttt tcataaaatt agccagaaaa gacgcggcat atagccctat     1380
ttacaccgat gatttcgcag cacgtgaggt taaaacttcc tgattcatgt cacattttat     1440
ggggagatta tcgtaggctg acgacctttc agtcttctgt attagttgtg tttacgagaa     1500
ttccctatta agcgaatgat gaaaagtaga acagtcgcaa taagagcatg acttagtat     1560
tgcactatct cctggaggtc aacagagggc tattacttgc gcaacaggtt aaagattgtg     1620
aatagttacc agcagtcatt tacccgctta taacaagcga ggcagttgta atgatagctc     1680
agaaggatta tgcaaggctt cgtaagggag aacgcatata cccacttctg tgcatactgt     1740
tgagctgaaa aactgacgaa ttatgataaa ctccagccaa cttatttca tatcattgag      1800
ggcctgtggc tga                                                         1813
```

<210> SEQ ID NO 13
<211> LENGTH: 1809
<212> TYPE: DNA
<213> ORGANISM: Artificial Sequence
<220> FEATURE:
<223> OTHER INFORMATION: Mutant Escherichia coli

<400> SEQUENCE: 13

```
ttgtagtaat ctcaaactta tattggggtg gtttgttgag gtaataatag agccttaaat       60
tcagttgtgc aatagccagg aatgtaagga attcaaaatt gttctttatt ttgtgccgcc     120
aataaatatc ttttcataaa attagccaga aaagacgcgg catatagccc tatttacacc     180
gatgatttcg cagcacgtga ggttaaaact tcctgattca tgtcacattt tatggggaga     240
ttatcgtagg ctgacgacct ttggaaggtg cgaataagcg gggaaattct ctcggctga     300
```

```
ctcagtcatt tcatttcttc atgtttgagc cgatttttc tcccgtaaat gccttgaatc      360
agcctattta gaccgttct tcgccattta aggcgttatc cccagttttt agtgagatct      420
ctcccactga cgtatcattt ggtccgcccg aaacaggttg ccagcgtga ataacatcgc      480 cagttggtta tcgtttttca gcaacccctt gtatctggct ttcacgaagc cgaactgtcg      540
cttgatgatg cgaaatgggt gctccaccct ggcccggatg ctggctttca tgtattcgat      600
gttgatggcc gttttgttct tgcgtggatg ctgtttcaag gttcttacct tgccggggcg      660
ctcggcgatc agccagtcca catccacctc ggccagctcc tcgcgctgtg cgccccttg       720 gtagccggca tcggctgaga caaattgctc tctccatgc agcagattac ccagctgatt       780
gaggtcatgc tcgttggccg cggtggtgac caggctgtgg gtcaggccac tcttggcatc      840
gacaccaatg tgggccttca tgccaaagtg ccactgattg cctttcttgg tctgatgcat      900
ctccggatcg cgttgctgct ctttgttctt ggtcgagctg ggtgcctcaa tgatggtggc      960
atcgaccaag gtgccttgag tcatcatgac gcctgcttcg gccagccagc gattgatggt     1020
cttgaacaat tggcgggcca gttgatgctg ctccagcagg tggcggaaat tcatgatggt     1080
ggtgcggtcc ggcaaggcgc tatccaggga taaccgggca aacagacgca tggaggcgat     1140 tcgtacaga gcatcttcca tcgcgccatc gctcaggttg taccaatgct gcatgcagtg      1200
aatgcgtagc atggtttcca gcggataagg tcgccggcca ttaccagcct tggggtaaaa     1260
cggctcgatg acttccacca tgttttgcca tggcagaatc tgctccatgc gggacaagaa     1320
aatctctttt ctggtctgac ggcgcttact gctgaattca ctgtcggcga aggtaagttg     1380
atgactcatg atgaaccctg ttctatggct ccagatgaca aacatgatct catatcaggg     1440
acttgttcgc accttcctta gctttcagtc ttctgtatta gttgtgttta cgagaattcc     1500
ctattaagcg aatgatgaaa agtagaacag tcgcaataag agcatggact tagtattgca     1560
ctatctcctg gaggtcaaca gagggctatt acttgcgcaa caggttaaag attgtgaata     1620
gttaccagca gtcatttacc cgcttataac aagcgaggca gttgtaatga tagctcagaa     1680
ggattatgca aggcttcgta agggagaacg catatacccca cttctgtgca tactgttgag     1740
ctgaaaaact gacgaattat gataaactcc agccaacttt atttcatatc attgagggcc     1800
tgtggctga                                                             1809
```

<210> SEQ ID NO 14
<211> LENGTH: 948
<212> TYPE: DNA
<213> ORGANISM: Artificial Sequence
<220> FEATURE:
<223> OTHER INFORMATION: Mutant Escherichia coli

<400> SEQUENCE: 14

```
atgctgagcg catttcaact ggaaaataac cgactgaccc ggctggaagt cgaagagtca       60
caaccccttg taaatgcagt atggattgat cttgtcgaac cggacgacga cgagcgactg      120
cgcgtacaat ctgaacttgg ccagagcctg gcaacccgcc cggaactgga agacatcgaa      180
gcatcggcac gtttctttga agacgacgac ggcctgcata ttcactcctt cttcttcttt      240
gaaagatgcg aagatcacgc cggtaactcc actgtggcat ttaccatccg tgatggtcgt      300
ctgtttactc tgcgtgagcg tgaactgccc gcttttcgtc tgtatcgtat gcgtgcccgt      360
agccagtcga tggtagacgg taacgcctac gagttgctgc tggatctgtt cgaaaccaaa      420
atcgaacagt tggcagatga aattgaaaat atctatagcg acctggagca gttgagccgg      480
```

```
gtgattatgg aagggcatca gggcgatgag tacgacgagg cgctctccac tctggcggaa    540
ctggaagata tcggctggaa agttcgcctg tgtctgatgg atacccagcg cgcgctcaac    600
ttcctggtgc gtaaagcgcg tttaccgggt gggcaactgg agcaggcgcg tgaaatcctg    660
cgagatatcg aatccctgct gccgcataac gaatccctgt tccagaaggt gaacttcctg    720
atgcaggcaa tgggttttat caacatcgag cagaaccgca tcatcaaaat cttctcggtg    780
gtatccgtgg tattcctgcc gccgacgctc gttgcttcca gctatggcat gaactttgag    840
tttatgccag aactgaagtg gagcttcggc taccctggcg cgattatctt tatgatcctc    900
gcgggcctgg caccgtatct gtactttaag cggaagaact ggttgtaa                 948
```

<210> SEQ ID NO 15
<211> LENGTH: 946
<212> TYPE: DNA
<213> ORGANISM: Artificial Sequence
<220> FEATURE:
<223> OTHER INFORMATION: Mutant Escherichia coli

<400> SEQUENCE: 15

```
atgctgagcg catttcaact ggaaaataac cgactgaccc ggctggaagt cgaagagtca    60
caaccccttg taaatgcagt atggattgat cttgtcgaac cggacgacga cgagcgactg    120
cgcgtacaat ctgaacttgg ccagagcctg caacccgcc cggaactgga agacatcgaa     180
gcatcggcac gtttctttga agacgacgac ggcctgcatc tccttcttct ctttgaaga    240 tgcggaagat cacgccggta actccactgt ggcatttacc atccgtgatg gtcgtctgtt    300
tactctgcgt gagcgtgaac tgcccgcttt tcgtctgtat cgtatgcgtg cccgtagcca    360
gtcgatggta gacggtaacg cctacgagtt gctgctggat ctgttcgaaa ccaaaatcga    420
acagttggca gatgaaattg aaaatatcta tagcgacctg gagcagttga gccgggtgat    480
tatggaaggg catcagggcg atgagtacga cgaggcgctc tccactctgg cggaactgga    540
agatatcggc tggaaagttc gcctgtgtct gatggatacc cagcgcgcgc tcaacttcct    600
ggtgcgtaaa gcgcgtttac cgggtgggca actggagcag gcgcgtgaaa tcctgcgaga    660
tatcgaatcc ctgctgccgc ataacgaatc cctgttccag aaggtgaact tcctgatgca    720
ggcggcaatg ggttttatca acatcgagca gaaccgcatc atcaaaatct ctcggtggt    780 atccgtggta ttcctgccgc cgacgctcgt tgcttccagc tatggcatga actttgagtt    840
tatgccagaa ctgaagtgga gcttcggcta ccctggcgcg attatcttta tgatcctcgc    900
gggcctggca ccgtatctgt actttaagcg gaagaactgg ttgtaa                   946
```

<210> SEQ ID NO 16
<211> LENGTH: 951
<212> TYPE: DNA
<213> ORGANISM: Artificial Sequence
<220> FEATURE:
<223> OTHER INFORMATION: Mutant Escherichia coli

<400> SEQUENCE: 16

```
atgctgagcg catttcaact ggaaaataac cgactgaccc ggctggaagt cgaagagtca    60
caaccccttg taaatgcagt atggattgat cttgtcgaac cggacgacga cgagcgactg    120
cgcgtacaat ctgaacttgg ccagagcctg caacccgcc cggaactgga agacatcgaa     180
gcatcggcac gtttctttga agacgacgac ggcctgcata ttcactcctt cttcttcttt    240
gaagatgcgc aagatcacgc cggtaactcc actgtggcat ttaccatccg tgatggtcgt    300
ctgtttactc tgcgtgagcg tgaactgccc gcttttcgtc tgtatcgtat gcgtgcccgt    360
```

```
agccagtcga tggtagacgg taacgcctac gagttgctgc tggatctgtt cgaaaccaaa    420
atcgaacagt tggcagatga aattgaaaat atctatagcg acctggagca gttgagccgg    480
gtgattatgg aagggcatca gggcgatgag tacgacgagg cgctctccac tctggcggaa    540
ctggaagata tcggctggaa agttcgcctg tgtctgatgg atacccagcg cgcgctcaac    600
ttcctggtgc gtaaagtgcg tttaccgggt gggcaactgg agcaggcgcg tgaaatcctg    660
cgagatatcg aatccctgct gccgcataac gaatccctgt tccagaaggt gaacttcctg    720
atgcaggcgg caatgggttt tatcaacatc gagcagaacc gcatcatcaa aatcttctcg    780
gtggtatccg tggtattcct gccgccgacg ctcgttgctt ccagctatgg catgaacttt    840
gagtttatgc cagaactgaa gtggagcttc ggctaccctg cgcgattat ctttatgatc    900 ctcgcgggcc tggcaccgta tctgtacttt aagcggaaga actggttgta a            951

<210> SEQ ID NO 17
<211> LENGTH: 852
<212> TYPE: DNA
<213> ORGANISM: Artificial Sequence
<220> FEATURE:
<223> OTHER INFORMATION: Mutant Escherichia coli

<400> SEQUENCE: 17
atgctgagcg catttcaact ggaaaataac cgactgaccc ggctggaagt cgaagagtca     60 caacccttg taaatgcagt atggattgat cttgtcgaac cggacgacga cggcctgcat    120
attcactcct tcttcttctt tgaagatgcg gaagatcacg ccgtaactc cactgtggca    180 tttaccatcc gtgatggtcg tctgtttact ctgcgtgagc gtgaactgcc cgcttttcgt    240
ctgtatcgta tgcgtgcccg tagccagtcg atggtagacg gtaacgccta cgagttgctg    300
ctggatctgt tcgaaaccaa aatcgaacag ttggcagatg aaattgaaaa tatctatagc    360
gacctggagc agttgagccg ggtgattatg aagggcatc agggcgatga gtacgacgag    420
gcgctctcca ctctggcgga actggaagat atcggctgga agttcgcct gtgtctgatg    480 gatacccagc gcgcgctcaa cttcctggtg cgtaaagcgc gtttaccggg tgggcaactg    540
gagcaggcgc gtgaaatcct gcgagatatc gaatccctgc tgccgcataa cgaatccctg    600
ttccagaagg tgaacttcct gatgcaggcg gcaatgggtt ttatcaacat cgagcagaac    660
cgcatcatca aaatcttctc ggtggtatcc gtggtattcc tgccgccgac gctcgttgct    720
tccagctatg gcatgaactt tgagtttatg ccagaactga gtggagctt cggctaccct    780 ggcgcgatta tctttatgat cctcgcgggc ctggcaccgt atctgtactt taagcggaag    840
aactggttgt aa                                                        852

<210> SEQ ID NO 18
<211> LENGTH: 972
<212> TYPE: DNA
<213> ORGANISM: Artificial Sequence
<220> FEATURE:
<223> OTHER INFORMATION: Mutant Escherichia coli

<400> SEQUENCE: 18
atgctgagcg catttcaact ggaaaataac cgactgaccc ggctggaagt cgaagagtca     60 caacccttg taaatgcagt atggattgat cttgtcgaac cggacgacga cgagcgactg    120
cgcgtacaat ctgaacttgg ccagagcctg caacccgcc cggaactgga agacatcgaa    180
gcatcggcac gtttctttga agacgacgac ggcctgcata ttcactcctt cttcttcttt    240
```

| | |
|---|---|
| gaagatgcgg aagatcacgc cggtaactcc actgtggcat ttaccatccg tgatggtcgt | 300 |
| ctgtttactc tgcgtgagcg tgaactgccc gcttttcgtc tgtatcgtat gcgtgcccgt | 360 |
| agccagtcga tggtagacgg taacgcctac gagttgctgc tggatctgtt cgaaaccaaa | 420 |
| atcgaacagt tggcagatga aattgaaaat atctatagcg acctggagca gttgagccgg | 480 |
| gtgattatgg aagggcatca gggcgatgag tacgacgagg cgctctccac tctggcggaa | 540 |
| ctggaagata tcggctggaa agttcgcctg tgtctgatgg atacccagcg cgcgctcaac | 600 |
| ttcctggtgc gtaaagcgcg tttaccgggt gggcaactgg agcaggcgcg tgaaatcctg | 660 |
| cgagatatcg aatccctgct gccgcataac gaatccctgc tgccgcataa cgaatccctg | 720 |
| ttccagaagg tgaacttcct gatgcaggcg gcaatgggtt ttatcaacat cgagcagaac | 780 |
| cgcatcatca aaatcttctc ggtggtatcc gtggtattcc tgccgccgac gctcgttgct | 840 |
| tccagctatg gcatgaactt tgagtttatg ccagaactga agtggagctt cggctaccct | 900 |
| ggcgcgatta tctttatgat cctcgcgggc ctggcaccgt atctgtactt taagcggaag | 960 |
| aactggttgt aa | 972 |

<210> SEQ ID NO 19
<211> LENGTH: 1941
<212> TYPE: DNA
<213> ORGANISM: Artificial Sequence
<220> FEATURE:
<223> OTHER INFORMATION: Mutant Escherichia coli

<400> SEQUENCE: 19

| | |
|---|---|
| atggaaagcc ctactccaca gcctgctcct ggttcggcga ccttcatgga aggatgcaaa | 60 |
| gacagtttac cgattgttat tagttatatt ccggtggcct ttgcgttcgg tctgaatgcg | 120 |
| acccgtctgg gattctctcc tctcgaaagc gttttttct cctgcatcat ttatgcaggc | 180 |
| gcgagccagt tcgtcattac cgcgatgctg gcagccggga gtagtttgtg gattgctgca | 240 |
| ctgaccgtca tggcaatgga tgttcgccat gtgttgtatg gcccgtcact gcgtagccgt | 300 |
| attattcagc gtctgcaaaa atcgaaaacc gccctgtggg cgtttggcct gacggatgag | 360 |
| gttttttgccg ccgcaaccgc aaaactggta cgcaataatc gccgctggag cgagaactgg | 420 |
| atgatcggca ttgccttcag ttcatggtca tcgtgggtat ttggtacggt aataggggca | 480 |
| ttctccggca gcggcttgct gcaaggttat cccgccgttg aagctgcatt agggaaggtg | 540 |
| cgaataagcg gggaaattct tctcggctga ctcagtcatt tcatttcttc atgtttgagc | 600 |
| cgatttttc tcccgtaaat gccttgaatc agcctatta gaccgtttct tcgccattta | 660 |
| aggcgttatc cccagttttt agtgagatct ctcccactga cgtatcattt ggtccgcccg | 720 |
| aaacaggttg gccagcgtga ataacatcgc cagttggtta tcgttttca gcaacccctt | 780 |
| gtatctggct ttcacgaagc cgaactgtcg cttgatgatg cgaaatgggt gctccaccct | 840 |
| ggcccggatg ctggctttca tgtattcgat gttgatggcc gttttgttct tgcgtggatg | 900 |
| ctgtttcaag gttcttacct tgccggggcg ctcggcgatc agccagtcca catccacctc | 960 |
| ggccagctcc tcgcgctgtg gcgccccttg gtagccggca tcggctgaga caaattgctc | 1020 |
| ctctccatgc agcagattac ccagctgatt gaggtcatgc tcgttggccg cggtggtgac | 1080 |
| caggctgtgg gtcaggccac tcttggcatc gacaccaatg tgggccttca tgccaaagtg | 1140 |
| ccactgattg cctttcttgg tctgatgcat ctccggatcg cgttgctgct ctttgttctt | 1200 |
| ggtcgagctg ggtgcctcaa tgatggtggc atcgaccaag gtgccttgag tcatcatgac | 1260 |
| gcctgcttcg gccagccagc gattgatggt cttgaacaat tggcgggcca gttgatgctg | 1320 |

```
ctccagcagg tggcggaaat tcatgatggt ggtgcggtcc ggcaaggcgc tatccaggga   1380
taaccgggca aacagacgca tggaggcgat ttcgtacaga gcatcttcca tcgcgccatc   1440
gctcaggttg taccaatgct gcatgcagtg aatgcgtagc atggtttcca gcggataagg   1500
tcgccggcca ttaccagcct tggggtaaaa cggctcgatg acttccacca tgttttgcca   1560
tggcagaatc tgctccatgc gggacaagaa aatctctttt ctggtctgac ggcgcttact   1620
gctgaattca ctgtcggcga aggtaagttg atgactcatg atgaaccctg ttctatggct   1680
ccagatgaca aacatgatct catatcaggg acttgttcgc accttcctta gttaggtttt   1740
atgcttccgg cactctttat gagtttcctg ctcgcctctt tccagcgcaa acaatctctt   1800
tgcgttaccg cagcgttagt tggtgcccctt gcaggcgtaa cgctatttc tattcccgtc    1860 gccattctgg caggcattgt ctgtggctgc ctcactgcgt taatccaggc attctggcaa   1920
ggagcgcccg atgagctatg a                                              1941

<210> SEQ ID NO 20
<211> LENGTH: 728
<212> TYPE: DNA
<213> ORGANISM: Artificial Sequence
<220> FEATURE:
<223> OTHER INFORMATION: Mutant Escherichia coli

<400> SEQUENCE: 20
atggaaagcc ctactccaca gcctgctcct ggttcggcga ccttcatgga aggatgcaaa     60
gacagtttac cgattgttat tagttatatt ccggtggcct ttgcgttcgg tctgaatgcg    120
acccgtctgg gattctctcc tctcgaaagc gtttttttct cctgcatcat ttatgcaggc    180
gcgagccagt tcgtcattac cgcgatgctg cagccggga gtagtttgtg gattgctgca    240
ctgaccgtca tggcaatgga tgttcgccat gtgttgtatg gcccgtcact gcgtagccgt    300
attattaaaa atcgaaaacc gccctgtggg cgtttggcct gacggatgag gttttttgccg   360 ccgcaaccgc aaaactggta cgcaataatc gccgctggag cgagaactgg atgatcggca    420
ttgccttcag ttcatggtca tcgtgggtat ttggtacggt aatagggggca ttctccggca   480 gcggcttgct gcaaggttat cccgccgttg aagctgcatt aggttttatg cttccggcac    540
tctttatgag tttcctgctc gcctcttttcc agcgcaaaca atctctttgc gttaccgcag    600
cgttagttgg tgcccttgca ggcgtaacgc tattttctat tccccgtcgcc attctggcag    660 gcattgtctg tggctgcctc actgcgttaa tccaggcatt ctggcaagga cgcccgatg    720 agctatga                                                            728

<210> SEQ ID NO 21
<211> LENGTH: 738
<212> TYPE: DNA
<213> ORGANISM: Artificial Sequence
<220> FEATURE:
<223> OTHER INFORMATION: Mutant Escherichia coli

<400> SEQUENCE: 21
atggaaagcc ctactccaca gcctgctcct ggttcggcga ccttcatgga aggatgcaaa     60
gacagtttac cgattgttat tagttatatt ccggtggcct ttgcgttcgg tctgaatgcg    120
acccgtctgg gattctctcc tctctaaagc gtttttttct cctgcatcat ttatgcaggc    180
gcgagccagt tcgtcattac cgcgatgctg cagccggga gtagtttgtg gattgctgca    240
ctgaccgtca tggcaatgga tgttcgccat gtgttgtatg gcccgtcact gcgtagccgt    300
```

```
attattcagc gtctgcaaaa atcgaaaacc gccctgtggg cgtttggcct gacggatgag      360 gttttttgccg ccgcaaccgc aaaactggta cgcaataatc gccgctggag cgagaactgg     420
atgatcggca ttgccttcag ttcatggtca tcgtgggtat ttggtacggt aatagggggca    480 ttctccggca gcggcttgct gcaaggttat cccgccgttg aagctgcatt aggttttatg    540
cttccggcac tctttatgag tttcctgctc gcctcttttcc agcgcaaaca atctctttgc   600
gttaccgcag cgttagttgg tgcccttgca ggcgtaacgc tatttttctat tcccgtcgcc   660 attctggcag gcattgtctg tggctgcctc actgcgttaa tccaggcatt ctggcaagga    720
gcgcccgatg agctatga                                                   738
```

```
<210> SEQ ID NO 22
<211> LENGTH: 757
<212> TYPE: DNA
<213> ORGANISM: Artificial Sequence
<220> FEATURE:
<223> OTHER INFORMATION: Mutant Escherichia coli

<400> SEQUENCE: 22
atggaaagcc ctactccaca gcctgctcct ggttcggcga ccttcatgga aggatgcaaa      60
gacagtttac cgattgttat tagttatatt ccggtggcct ttgcgttcgg tctgaatgcg     120
acccgtctgg gattctctcc tctcgaaagc gttttttttct cctgcatcat ttatgcaggc    180
gcgagccagt tcgtcattac cgcgatgctg gcagccggga gtagtttgtg gattgctgca    240
ctgaccgtca tggcaatgga tgttcgccat gtgttgtatg gttcgccatg tgttgtatgg    300
cccgtcactg cgtagccgta ttattcagcg tctgcaaaaa tcgaaaaccg ccctgtgggc    360
gtttggcctg acggatgagg ttttttgccgc cgcaaccgca aaactggtac gcaataatcg   420
ccgctggagc gagaactgga tgatcggcat tgccttcagt tcatggtcat cgtgggtatt    480
tggtacggta ataggggcat tctccggcag cggcttgctg caaggttatc cgccgttga     540 agctgcatta ggttttatgc ttccggcact ctttatgagt ttcctgctcg cctcttttcca   600 gcgcaaacaa tctctttgcg ttaccgcagc gttagttggt gcccttgcag gcgtaacgct    660
attttctatt cccgtcgcca ttctggcagg cattgtctgt ggctgcctca ctgcgttaat    720
ccaggcattc tggcaaggag cgcccgatga gctatga                             757
```

```
<210> SEQ ID NO 23
<211> LENGTH: 2241
<212> TYPE: DNA
<213> ORGANISM: Artificial Sequence
<220> FEATURE:
<223> OTHER INFORMATION: Mutant Escherichia coli

<400> SEQUENCE: 23
atgttttccg cattgcgcca ccgtaccgct gccctggcgc tcggcgtatg ctttattctc      60
cccgtacacg cctcgtcacc taaacctggc gattttgcta aggaaggtgc gaataagcgg    120
ggaaattctt ctcggctgac tcagtcattt catttcttca tgtttgagcc gattttttct    180
cccgtaaatg ccttgaatca gcctatttag accgtttctt cgccatttaa ggcgttatcc    240
ccagttttta gtgagatctc tcccactgac gtatcatttg gtccgcccga aacaggttgg    300
ccagcgtgaa taacatcgcc agttggttat cgttttttcag caacccccttg tatctggctt   360 tcacgaagcc gaactgtcgc ttgatgatgc gaaatgggtg ctccaccctg gcccggatgc    420
tggctttcat gtattcgatg ttgatggccg ttttgttctt gcgtggatgc tgtttcaagg    480
ttcttacctt gccggggcgc tcggcgatca gccagtccac atccacctcg gccagctcct    540
```

```
cgcgctgtgg cgccccttgg tagccggcat cggctgagac aaattgctcc tctccatgca    600
gcagattacc cagctgattg aggtcatgct cgttggccgc ggtggtgacc aggctgtggg    660
tcaggccact cttggcatcg acaccaatgt gggccttcat gccaaagtgc cactgattgc    720
ctttcttggt ctgatgcatc tccgatcgc gttgctgctc tttgttcttg gtcgagctgg    780
gtgcctcaat gatggtggca tcgaccaagg tgccttgagt catcatgacg cctgcttcgg    840
ccagccagcg attgatggtc ttgaacaatt ggcgggccag ttgatgctgc tccagcaggt    900
ggcggaaatt catgatggtg gtgcggtccg gcaaggcgct atccagggat aaccgggcaa    960
acagacgcat ggaggcgatt tcgtacagag catcttccat cgcgccatcg ctcaggttgt    1020
accaatgctg catgcagtga atgcgtagca tggtttccag cggataaggt cgccggccat    1080
taccagcctt ggggtaaaac ggctcgatga cttccaccat gttttgccat ggcagaatct    1140
gctccatgcg ggacaagaaa atctctttc tggtctgacg gcgcttactg ctgaattcac    1200
tgtcggcgaa ggtaagttga tgactcatga tgaaccctgt tctatggctc agatgacaa    1260 acatgatctc atatcaggga cttgttcgca ccttccttag ctaatactca ggcacgacat    1320
attgctactt tctttccggg acgcatgacc ggaactcctg cagaaatgtt atctgccgat    1380
tatattcgcc aacagtttca gcaaatgggt tatcgcagtg atattcggac atttaatagt    1440
cggtatattt ataccgcccg cgataatcgt aagagctggc ataacgtgac gggaagtacg    1500
gtgattgccg ctcatgaagg caaagcgccg cagcagatca tcattatggc gcatctggat    1560
acttacgccc cgctgagcga tgctgacgcc gatgccaatc tcggcgggct gacgttacaa    1620
ggaatggatg ataacgccgc aggtttaggt gtcatgctgg aattggcaga acgcctgaaa    1680
aatacgccta ccgagtatgg tattcgattt gtggcgacca gcggcgaaga ggaagggaaa    1740
ttaggcgctg agaatttact caagcggatg agtgacaccg aaaagaaaaa tacgctgctg    1800
gtgattaatc tcgataactt aattgttggc gataaattgt atttcaacag cggtgtaaaa    1860
acccctgagg cagtaaggaa attaacgcgc gacagggcgc tggcaattgc gcgcagtcac    1920
ggaatagccg caacgaccaa tccgggtttg aataaaaatt atccgaaagg cactgggtgt    1980
tgtaatgacg cagaaatatt cgacaaagcg ggcattgctg tactttcggt ggaagcgact    2040
aactggaatc ttgggaataa ggatggttat cagcaacgcg caaaaacacc tgccttcccg    2100
gcgggaaata gctggcatga cgtaagactg gataatcacc aacatattga taaggctctt    2160
cctggaagaa tagaacgtcg ctgccgtgac gttatgcgga taatgctacc tctggtgaag    2220
gagttggcga aggcgtcttg a                                              2241
```

<210> SEQ ID NO 24
<211> LENGTH: 2432
<212> TYPE: DNA
<213> ORGANISM: Artificial Sequence
<220> FEATURE:
<223> OTHER INFORMATION: Mutant Escherichia coli

<400> SEQUENCE: 24

```
atgagtgtga ttgcgcaggc aggggcgaaa ggtcgtcagc tgcataaatt tggtggcagt    60
agtctggctg atgtgaagtg ttatttgcgt gtcgcgggca ttatggcgga gtactctcag    120
cctgacgata tgatggtggt ttccgccgcc ggtagcacca ctaaccagtt gattaactgg    180
ttgaaactaa gccagaccga tcgtctctct gcgcatcagg ttcaacaaac gctgcgtcgc    240
tatcagtgcg atctgattag cggtctgcta cccgctgaag aagccgatag cctcattagc    300
```

```
gcttttgtca gcgaccttga gcgcctggcg gcgctgctcg acagcggtat taacgacgca    360
gtgtatgcgg aagtggtggg ccacggggaa gtatggtcgg cacgtctgat gtctgcggta    420
cttaatcaac aagggctgcc agcggcctgg cttgatgccc gcgagttttt acgcgctgaa    480
cgcgccgcac aaccgcaggt tgatgaaggg ctttcttacc cgttgctgca acagctgctg    540
gtgcaacatc cgggcaaacg tctggtggtg accggattta tcagccgcaa caacgccggt    600
gaaacggtgc tgctggggcg taacggttcc gactattccg cgacacaaat cggtgcgctg    660
gcgggtgttt ctcgcgtaac catctggagc gacgtcgccg gggtatacag tgccgacccg    720
cgtaaagtga aagatgcctg cctgctgccg ttgctgcgtc tggatgaggc cagcgaactg    780
gcgcgcctgg cggctcccgt tcttcacgcc cgtactttac agccggtttc tggcagcgaa    840
atcgacctgc aactgcgctg tagctacacg ccggatcaag gttccacgcg cattgaacgc    900
gtgctggcct ccggtactgg tgcgcgtatt gtcaccagcc acgatgatgt ctgtttgatt    960
gagtttcagg tgcccgccag tcaggatttc aaactggcgc ataaagagat cgaccaaatc   1020
ctgaaacgcg cgcaggtacg cccgctggcg gttggcgtac ataacgatcg ccagttgctg   1080
caattttgct acacctcaga agtggccgac agtgcgctga aaatcctcga cgaagcggga   1140
ttacctggcg aactgcgcct gcgtcagggg ctggcgctgg tggcgatggt cggtgcaggc   1200
gtcacccgta accgctgcca ttgccaccgc ttctggcagc aactgaaagg ccagccggtc   1260
gaatttacct ggcagtccga tgacggcatc agcctggtgg cagtactgcg caccggcccg   1320
accgaaagcc tgattcaggg ctgcatcagt ccgtcttccg cgcagaaaaa cgcatcggcc   1380
tggtattgtt cggtaagggc aatatcggtt cccgttggct ggaactgttc gcccgtgagc   1440
agagcacgct ttcggcacgt accggctttg agtttgtgct ggcaggtgtg gtggacagcc   1500
gccgcagcct gttgagctat gacgggctgg acgccagccg cgcgttagcc ttcttcaacg   1560
atgaagcggt tgagcaggat gaagagtcgt tgttcctgtg gatgcgcgcc catccgtatg   1620
atgatttagt ggtgctggac gttaccgcca gccagcagct tgctgatcag tatcttgatt   1680
tcgccagcca cggttttcca gttatcagcg ccaacaaact ggcgggagcc agcgacagca   1740
ataaatatcg ccagatccac gacgccttcg aaaaaaccgg gcgtcactgg ctgtacaatg   1800
ccaccgtcgg tgcgggcttg ccgatcaacc acaccgtgcg cgatctgatc gacagcggcg   1860
atactatttt gtcgatcagc gggatcttct ccggcacgct ctcctggctg ttcctgcaat   1920
tcgacggtag cgtgccgttt accgagctgg tggatcaggc gtggcagcag ggcttaaccg   1980
aacctgaccc gcgtgacgat ctctctggca aagacgtgat gcgcaagctg gtgattctgg   2040
cgcgtgaagc aggttacaac atcgaaccgg atcaggtacg tgtggaatcg ctggtgcctg   2100
ctcattgcga aggcggcagc atcgaccatt tctttgaaaa tggcgatgaa ctgaacgagc   2160
agatggtgca acggctggaa gcggcccgcg aaatggggct ggtgctgcgc tacgtggcgc   2220
gtttcgatgc caacggtaaa gcgcgtgtag gcgtggaagc ggtgcgtgaa gatcatccgt   2280
tggcatcact gctgccgtgc gataacgtct ttgccatcga aagccgctgg tatcgcgata   2340
accctctggt gatccgcgga cctggcgctg ggcgcgacgt caccgccggg gcgattcagt   2400
cggatatcaa ccggctggca cagttgttgt aa                                 2432
```

<210> SEQ ID NO 25
<211> LENGTH: 2433
<212> TYPE: DNA
<213> ORGANISM: Artificial Sequence
<220> FEATURE:
<223> OTHER INFORMATION: Mutant Escherichia coli -continued

<400> SEQUENCE: 25

```
atgagtgtga ttgcgcaggc aggggcgaaa ggtcgtcagc tgcataaatt tggtggcagt      60
agtctggctg atgtgaagtg ttatttgcgt gtcgcgggca ttatggcgga gtactctcag     120
cctgacgata tgatggtggt ttccgccgcc ggtagcacca ctaaccagtt gattaactgg     180
ttgaaactaa gccagaccga tcgtctctct gcgcatcagg ttcaacaaac gctgcgtcgc     240
tatcagtgcg atctgattag cggtctgcta cccgctgaag aagccgatag cctcattagc     300
gcttttgtca gcgaccttga gcgcctggcg gcgctgctcg acagcggtat taacgacgca     360
gtgtatgcgg aagtggtggg ccacggggaa gtatggtcgg cacgtctgat gtctgcggta     420
cttaatcaac aagggctgcc agcggcctgg cttgatgccc gcgagttttt acgcgctgaa     480
cgcgccgcac aaccgcaggt tgatgaaggg ctttcttacc cgttgctgca cagctgctg     540
gtgcaacatc cgggcaaacg tctggtggtg accggattta tcagccgcaa caacgccggt     600
gaaacggtgc tgctggggcg taacggttcc gactattccg cgacacaaat cggtgcgctg     660
gcgggtgttt ctcgcgtaac catctggagc gacgtcgccg gggtatacag tgccgacccg     720
cgtaaagtga agatgcctg cctgctgccg ttgctgcgtc tggatgaggc cagcgaactg     780
gcgcgcctgg cggctcccgt tcttcacgcc cgtactttac agccggtttc tggcagcgaa     840
atcgacctgc aactgcgctg tagctacacg ccggatcaag gttccacgcg cattgaacgc     900
gtgctggcct ccggtactgg tgcgcgtatt gtcaccagcc acgatgatgt ctgtttgatt     960
gagtttcagg tgcccgccag tcaggatttc aaactggcgc ataaagagat cgaccaaatc    1020
ctgaaacgcg cgcaggtacg cccgctggcg gttggcgtac ataacgatcg ccagttgctg    1080
caattttgct acacctcaga agtggccgac agtgcgctga aaatcctcga cgaagcggga    1140
ttacctggcg aactgcgcct gcgtcagggg ctggcgctgg tggcgatggt cggtgcaggc    1200
gtcacccgta accgctgca ttgccaccgc ttctggcagc aactgaaagg ccagccggtc    1260
gaatttacct ggcagtccga tgacggcatc agcctggtgg cagtactgcg caccggcccg    1320
accgaaagcc tgattcaggg gctgcatcag tccgtcttcc gcgcagaaaa acgcatcggc    1380
ctggtattgt tcggtaaggg caatatcggt tcccgttggc tggaactgtt cgcccgtgag    1440
cagagcacgc tttcggcacg taccggcttt gagtttgtgc tggcaggtgt ggtggacagc    1500
cgccgcagcc tgttgagcta tgacgggctg acgccagcc gcgcgttagc cttcttcaac    1560
gatgaagcgg ttgagcagga tgaagagtcg ttgttcctgt ggatgcgcgc ccatccgtat    1620
gatgatttag tggtgctgga cgttaccgcc agccagcagc ttgctgatca gtatcttgat    1680
ttcgccagcc acggtttcca cgttatcagc gccaacaaac tggcgggagc cagcgacagc    1740
aataaatatc gccagatcca cgacgccttc gaaaaaaccg gcgtcactg gctgtacaat    1800
gccaccgtcg gtgcgggctt gccgatcaac cacaccgtgc gcgatctgat cgacagcggc    1860
gatactattt tgtcgatcag cgggatcttc tccggcacgc tctcctggct gttcctgcaa    1920
ttcgacggta gcgtgccgtt taccgagctg gtggatcagg cgtggcagca gggcttaacc    1980
gaacctgacc cgcgtgacga tctctctggc aaagacgtga tgcgcaagct ggtgattctg    2040
gcgcgtgaag caggttacaa catcgaaccg gatcaggtac gtgtggaatc gctggtgcct    2100
gctcattgcg aaggcggcag catcgaccat ttctttgaaa atggcgatga actgaacgag    2160
cagatggtgc aacggctgga agcggcccgc gaaatgggc tggtgctgcg ctacgtggcg    2220
cgtttcgatg ccaacggtaa agcgcgtgta ggcgtggaag cggtgcgtga agatcatccg    2280
```

```
ttggcatcac tgctgccgtg cgataacgtc tttgccatcg aaagccgctg gtatcgcgat   2340
aaccctctgg tgatccgcgg acctggcgct gggcgcgacg tcaccgccgg ggagattcag   2400
tcggatatca accggctggc acagttgttg taa                                 2433
```

<210> SEQ ID NO 26
<211> LENGTH: 1191
<212> TYPE: DNA
<213> ORGANISM: Artificial Sequence
<220> FEATURE:
<223> OTHER INFORMATION: Mutant Escherichia coli

<400> SEQUENCE: 26

```
atgatgaaaa ctgttaatga gctgattaag gatatcaatt cgctgacctc tcaccttcac     60
gagaaagatt ttttgttaac gtgggaacag acgccagatg aactgaaaca agtactggac    120
gttgccgcag cattaaaagc actgcgtgct gaaaacatct caaccaaagt ctttaatagt    180
ggattaggta tttccgtatt ccgcgacaac tccacccgta cccgcttctc ttatgcttcc    240
gcgcttaacc tgctcggcct tgcacaacaa gatctcgacg aaggcaaatc acaaatcgct    300
cacggcgaaa ccgtgcgtga accgccaat atgatctcct tctgcgccga cgctattggt    360
attcgcgacg atatgtatct gggcgcaggc aacgcctata tgcgtgaagt tggcgctgca    420
cttgatgacg gttacaagca gggtgtactg ccacagcgtc cggctttagt gaacctgcaa    480
tgcgatattg accacccgac tcagtcaatg gctgacctcg cgtggttacg tgaacacttt    540
ggttcactgg aaaacctgaa aggtaaaaaa atcgccatga cctgggccta ctctccaagc    600
tatggcaaac cgctctctgt accacaaggc atcatcggtc tgatgactcg cttcggtatg    660
gatgtcaccc tggcccatcc ggaaggctac gacctgatcc cggatgtggt tgaagtggcg    720
aaaaacaatg ctaaagcctc cggtggtagc ttccgtcagg tcaccagcat ggaagaagcc    780
ttcaaagacg cagacatcgt ttatccgaag tcatgggcac cttacaaagt gatggaagag    840
cgtactgaat tgctgcgtgc gaacgatcac gaaggcttaa aagcactgga aaaacagtgt    900
ctggcacaga acgcgcaaca caaagactgg cattgtactg aagagatgat ggaactgacc    960
cgtgatggcg aagccctgta catgcactgc ctgccagctg atatcagcgg cgtatcctgt   1020
aaagaaggtg aagtgactga aggcgtattc gaaaaatacc gtatcgctac ctacaaagaa   1080
gccagctgga agccttatat catcgccgcg atgatcctgt cccgtaaata cgccaaacca   1140
ggtgcactgc tcgagcaact gctgaaagaa gcgcaagaac gcgtgaaata a            1191
```

<210> SEQ ID NO 27
<211> LENGTH: 700
<212> TYPE: DNA
<213> ORGANISM: Artificial Sequence
<220> FEATURE:
<223> OTHER INFORMATION: Mutant Escherichia coli

<400> SEQUENCE: 27

```
tgccttcgct cctcatctta cttttctaca gacaaaaaaa aggcgactca tcagtcgcct     60
taaaaatcag tttgccagcg ccgccttctg ccgtcccctg cacttcaatg atgcgcccgt    120
cttcggtcat cactacgttc atgtcggtct ctgcggcaga gtcttcaacg tattccagat    180
cgcaaaccgc ttcgccgttc acaattccga cagaaactgc ggctaccatc cctttcatcg    240
gattggtttt cagcttgccg ttttccacca gcttctgtag cgcatctacc agcgccacgc    300
aggcacccgt aatcgacgcg gtacgcgtgc caccatcagc ctgaagcacg tcgcagtcca    360
gcgtaatggt gaactcaccc agcgctttca aatctactgc cgcgcgaaga gcacgggcga    420
```

```
tcagacgctg gatttccatt gtgcgtccac cctgcttacc tttcgccgct tcacgagcgt    480
tacgggtgtg ggtagaacgt ggcagcatgc cgtactctgc ggtgatccag ccctggccct    540
gacctttcag gaagcgcggc acgccttctt caatagaggc ggtacacaac actttggtat    600
cgccaaattc gaccagcacc gagccttctg catgttttgt atagttacga gtcagggtaa    660
cgggacgcac ctgattattg ctacggcctg ctggacgcat                          700
```

<210> SEQ ID NO 28
<211> LENGTH: 902
<212> TYPE: DNA
<213> ORGANISM: Artificial Sequence
<220> FEATURE:
<223> OTHER INFORMATION: Mutant Escherichia coli

<400> SEQUENCE: 28

```
aataaataga ggaatctgat tacttccttc atggggatgc tgaaaagagt agtaattgct     60
ggtaatgact ccaacttatt gatagtgttt tatgttcaga taatgcccga tgactttgtc    120
atgcagctcc accgattttg agaacgacag cgacttccgt cccagccgtg ccaggtgctg    180
cctcagattc aggttatgcc gctcaattcg ctgcgtatat cgcttgctga ttacgtgcag    240
cttttccttc aggcgggatt catacagcgg ccagccatcc gtcatccata tcaccacgtc    300
aaagggtgac agcaggctca taagacgccc cagcgtcgcc atagtgcgtt caccgaatac    360
gtgcgcaaca accgtcttcc ggagactgtc atacgcgtaa acagccagc gctggcgcga     420 tttagccccg acatagcccc actgttcgtc catttccgcg cagacgatga cgtcactgcc    480
cggctgtatg cgcgaggtta ccgactgcgg cctgagtttt ttaagtgacg taaaatcgtg    540
ttgaggccaa cgcccataat gcgggctgtt gcccggcatc aacgccatt catggccata     600 tcaatgattt tctggtgcgt accggggtga gaagcggtgt aagtgaactg cagttgccat    660
gttttacggc agtgagagca gagatagcgc tgatgtccgg cggtgctttt gccgttacgc    720
accaccccgt cagtagctga acaggaggga cagctgatag aaacagaagc cactggagca    780
cctcaaaaac accatcatac actaaatcag taagttggca gcatcaccta cctcaatgtg    840
tatcacaata tccatattct ttgtggggga gtctggagat tgagtagata ttcttgttca    900
ga                                                                   902
```

<210> SEQ ID NO 29
<211> LENGTH: 1442
<212> TYPE: DNA
<213> ORGANISM: Artificial Sequence
<220> FEATURE:
<223> OTHER INFORMATION: Mutant Escherichia coli

<400> SEQUENCE: 29

```
gattccacta atttattcca tgtcacactt ttcgcatctt tgttatgcta tggttatttc     60
atacctggat tgcccctat atttccagac atctgttatc acttaaccca ttacaagccc     120
gctgccgcag atattcccgt ggcgagcgat aacccagcgc actatgcgga tgccattcgt    180
tataatgctc gaacgcctct gcaaggttct ttgctgccgt taacccgtct ggtttgggca    240
tgatactgat gtagtcacgc tttatcgttt tcacgaagct ctctgctatt ccgttactct    300
ccggactccg caccgccgtg ttcttcggtt caagtcccaa catccgggcg aactggcgtg    360
tttcattagc ccggtagcat gaaccattat ccgtcagcca ctccactgga gacgacggaa    420
gatcgttgcc gaagcggcgt tccaccgctc ccagcatgac gtcctgtact gtttcactgt    480
```

```
tgaagccgcc ggtagtgacc gcccagtgca gtgcctcacg atcacagcag tccagcgcga        540
acgtgacacg cagtctctct ccgttatcac agcagaactc gaacccgtca gagcaccatc        600
gctgattgct ttctttcacg gccactctgc ctgtatgtgc ccgtttcgat ggcggtacag        660
caggttttcg ctcaagcaac agcgcattct ggcgcatgat ccgtaaaca cgtttggcat         720 tgatcgcagg cataccatca agttctgcct gtctgcgaag cagcgcccat acccgacgat        780
aaccatacgt tggcagctct ccgataacat ggtgtatacg gagaagcaca tccgtatcat        840
cagtgtgacg actgcggcgg ccatccatcc agtcatcggt tcgtctgaga atgacgtgca       900
actgcgcacg cgacacccgg agacaacggc tgactaagct tactccccat ccccgggcaa       960
taagggcgcg tgcgctatcc actttttgc ccgtccatat tcaacggctt ctttgaggag       1020 ttcatttttcc atcgttttct tgccgagcag gcgctggagt tctttaatct gcttcatggc     1080
ggcagcaagt tcagaggcag gaacaacctg ttctccggcg gcgacagcag taagacttcc     1140
ttcctggtat tgcttacgcc agagaaataa ctggctggct gctacaccat gttgccgggc     1200
aacgagggag accgtcatcc ccggttcaaa gctctgctga acaattgcga tcttttcctg      1260
tgtggtacgc cgtctgcgtt tctccggccc taagacatca atcatctgtt ctccaatgac      1320
tagtctaaaa actagtatta agactatcac ttatttaagt gatattggtt gtctggagat      1380
tcagggggcc agtctaatac cataagccta atggagcgaa ttatgagagt tctggttacc     1440
gg                                                                      1442

<210> SEQ ID NO 30
<211> LENGTH: 1199
<212> TYPE: DNA
<213> ORGANISM: Artificial Sequence
<220> FEATURE:
<223> OTHER INFORMATION: Mutant Escherichia coli

<400> SEQUENCE: 30
ggaaggtgcg aataagcggg gaaattcttc tcggctgact cagtcatttc atttcttcat       60
gtttgagccg attttttctc ccgtaaatgc cttgaatcag cctatttaga ccgtttcttc      120
gccatttaag gcgttatccc cagttttttag tgagatctct cccactgacg tatcatttgg    180
tccgcccgaa acaggttggc cagcgtgaat aacatcgcca gttggttatc gttttttcagc     240 aaccccttgt atctggcttt cacgaagccg aactgtcgct tgatgatgcg aaatgggtgc     300 tccacccctgg cccggatgct ggctttcatg tattcgatgt tgatggccgt tttgttcttg     360
cgtggatgct gtttcaaggt tcttaccttg ccggggcgct cggcgatcag ccagtccaca    420
tccacctcgg ccagctcctc gcgctgtggc gccccttggt agccggcatc ggctgagaca    480
aattgctcct ctccatgcag cagattaccc agctgattga ggtcatgctc gttgccgcg      540 gtggtgacca ggctgtgggt caggccactc ttggcatcga caccaatgtg ggccttcatg   600
ccaaagtgcc actgattgcc tttcttggtc tgatgcatct ccggatcgcg ttgctgctct     660
ttgttcttgg tcgagctggg tgcctcaatg atggtggcat cgaccaaggt gccttgagtc    720
atcatgacgc ctgcttcggc cagccagcga ttgatggtct tgaacaattg gcgggccagt    780
tgatgctgct ccagcaggtg gcggaaattc atgatggtgg tgcggtccgg caaggcgcta   840
tccagggata accgggcaaa cagacgcatg gaggcgattt cgtacagagc atcttccatc    900
gcgccatcgc tcaggttgta ccaatgctgc atgcagtgaa tgcgtagcat ggtttccagc   960
ggataaggtc gccggccatt accagccttg gggtaaaacg gctcgatgac ttccaccatg   1020
ttttgccatg gcagaatctg ctccatgcgg gacaagaaaa tctcttttct ggtctgacgg   1080
```

-continued

```
cgcttactgc tgaattcact gtcggcgaag gtaagttgat gactcatgat gaaccctgtt    1140
ctatggctcc agatgacaaa catgatctca tatcagggac ttgttcgcac cttccttag    1199
```